United States Patent
Schneider et al.

(10) Patent No.: US 9,321,771 B2
(45) Date of Patent: Apr. 26, 2016

(54) 5-ALKYNYL-PYRIMIDINES

(71) Applicants: Siegfried Schneider, Vienna (AT); Dirk Kessler, Vienna (AT); Lars van der Veen, Alsbach-Haehnlein (DE); Tobias Wunberg, Hinterbruehl (AT)

(72) Inventors: Siegfried Schneider, Vienna (AT); Dirk Kessler, Vienna (AT); Lars van der Veen, Alsbach-Haehnlein (DE); Tobias Wunberg, Hinterbruehl (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/087,179

(22) Filed: Nov. 22, 2013

(65) Prior Publication Data

US 2014/0073621 A1     Mar. 13, 2014

Related U.S. Application Data

(62) Division of application No. 13/012,082, filed on Jan. 24, 2011, now Pat. No. 8,633,183.

(30) Foreign Application Priority Data

Jan. 26, 2010 (EP) .................................. 10151723

(51) Int. Cl.
| | |
|---|---|
| A61K 31/495 | (2006.01) |
| C07D 239/26 | (2006.01) |
| C07D 471/10 | (2006.01) |
| C07D 239/48 | (2006.01) |
| C07D 401/06 | (2006.01) |
| C07D 401/14 | (2006.01) |
| C07D 405/14 | (2006.01) |
| C07D 409/14 | (2006.01) |
| C07D 413/14 | (2006.01) |
| C07D 471/04 | (2006.01) |
| C07D 487/08 | (2006.01) |

(52) U.S. Cl.
CPC ............ C07D 471/10 (2013.01); A61K 31/495 (2013.01); C07D 239/26 (2013.01); C07D 239/48 (2013.01); C07D 401/06 (2013.01); C07D 401/14 (2013.01); C07D 405/14 (2013.01); C07D 409/14 (2013.01); C07D 413/14 (2013.01); C07D 471/04 (2013.01); C07D 487/08 (2013.01)

(58) Field of Classification Search
CPC ... A61K 31/495; C07D 239/26; C07D 239/48
USPC ......... 514/211.15, 217.06, 218, 228.8, 235.8, 514/249, 252.18, 256; 540/544, 575, 600; 544/60, 63, 122, 295, 333
See application file for complete search history.

(56) References Cited

U.S. PATENT DOCUMENTS

| | | |
|---|---|---|
| 5,091,386 A | 2/1992 | Kesseler et al. |
| 5,622,954 A | 4/1997 | Henrie, II et al. |
| 8,633,183 B2 * | 1/2014 | Schneider ............ C07D 239/26 514/211.15 |
| 2011/0281838 A1 | 11/2011 | Wunberg et al. |
| 2012/0028952 A1 | 2/2012 | Schneider et al. |

FOREIGN PATENT DOCUMENTS

| | | |
|---|---|---|
| EP | 0361273 A2 | 4/1990 |
| JP | 2006044823 A | 2/2006 |
| WO | 9414780 A1 | 7/1994 |
| WO | 9820878 A1 | 5/1998 |
| WO | 0162233 A2 | 8/2001 |
| WO | 0208205 A1 | 1/2002 |
| WO | 2005016914 A1 | 2/2005 |
| WO | 2005060969 A1 | 7/2005 |
| WO | 2006044823 A2 | 4/2006 |
| WO | 2006082371 A1 | 8/2006 |
| WO | 2006082373 A1 | 8/2006 |
| WO | 2006103449 A2 | 10/2006 |
| WO | 2006106721 A1 | 10/2006 |
| WO | 2008023180 A1 | 2/2008 |
| WO | 2008067389 A2 | 6/2008 |
| WO | 2008080965 A2 | 7/2008 |
| WO | 2008155140 A1 | 12/2008 |
| WO | WO 2010/012740 | * 2/2010 |

OTHER PUBLICATIONS

Pearce et al., Failure modes in anticancer drug discovery and development, Cancer Drug Design and Discovery Edited by Stephen Neidle, Chapter 18, pp. 424-435 (2008).*

(Continued)

*Primary Examiner* — Deepak Rao
(74) *Attorney, Agent, or Firm* — Michael P. Morris; Usha R. Patel

(57) ABSTRACT

The present invention encompasses compounds of general formula (1)

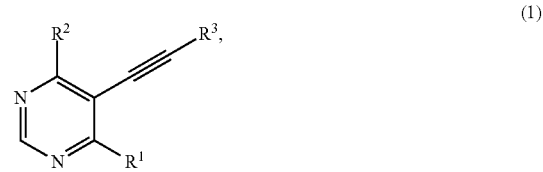

(1)

wherein $R^1$ to $R^3$ are defined as in claim 1, which are suitable for the treatment of diseases characterized by excessive or abnormal cell proliferation, and the use thereof for preparing a medicament having the above-mentioned properties.

2 Claims, No Drawings

(56) References Cited

OTHER PUBLICATIONS

Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Matulenko et al., 4-Amino-5-aryl-6-arylethynylpyrimidines: Structure-activity relationships of non-nucleoside adenosine kinase inhibitors, Bioorganic & Medicinal Chemistry 15 (2007), pp. 1586-1605.*
Fry, Phosphoinoditide 3-Kinase signalling in breast cancer: how big a role might it play?, Breast Cancer Research, vol. 3, No. 5, pp. 304-312, 2001.*
Bundgaard, Design of Prodrugs, p. 1, 1985.*
Wolff, Some consideration for prodrug design, Burger's Medicinal Chemistry and Drug Discovery, 5th Edition, vol. I Principles and Practice, pp. 975-977, 1995.*
Banker et al., Prodrugs, Modern Pharmaceutics, Third Edition and Expanded, pp. 451 and 596 (1996).*
Douglas, Jr., Introduction to Viral Diseases, Cecil Textbook of Medicine, 20th Edition, vol. 2, pp. 1739-1742, 1996.*
Silverman, Prodrugs and Drug Delivery Systems, The Organic Chemistry of Drug Design and Drug Action, pp. 352-399, 1992.*
Diaz-Padilla, Ivan et al. "Biologic rationale and clinical activity of mTOR inhibitors in gynecological cancer" Cancer Treatment Review (2012) 9 pgs.
Hannah, Duncan R. et al. "Structural Studies on Bioactive Compounds. Part 29: Palladium Catalysed Arylations and Alkynylations of Sterically Hindered Immunomodulatory 2-Amino-5-halo-4,6-(disubstituted) pyrimidines" Bioorganic & Medicinal Chemistry (2000) vol. 8, pp. 739-750.
Hisamatsu, Takeshi et al. "Potential Role of mTORC2 as a Therapeutic Target in Clear Cell Carcinoma of the Ovary" Molecular Cancer Therapeutics (2013) vol. 12(7) pp. 1367-1377.
International Search Report for PCT/EP2011/051061 mailed on Mar. 22, 2011.
International Search Report PCT/EP2011/051060 mailed Apr. 26, 2011.
International Search Report, Form PCT/ISA/210, for corresponding PCT/EP2009/059114; date of mailing: Oct. 2, 2009.
Janku, Filip et al. "PI3K/AKT/mTOR Inhibitors in Patients with Breast and Gynecologic Malignancies Harboring PIK3CA Mutations" Journal of Clincal Oncology (2012) pp. 1-7.
Jones, Michael L. et al. "Inhibitors of Dihydrofolate Reductase: Design, Synthesis and Antimicrobial Activities of 2,4-Diamino-6-methyl-5-ethynylpyrimidines" Journal of Heterocylic Chemistry (1999) vol. 36, pp. 145-148.
Liu, Pixu et al. "Targeting the phosphoinositide 3-kinase pathway in cancer" (2009) Nature Reviews vol. 8, pp. 627-644.
Pal, Manojit et al. "Alkynylation of halo pyrimidines under Pd/C-copper catalysis: regioselective synthesis of 4- and 5-alkynylpyrimidines" Tetrahedron Letters (2006) vol. 47, pp. 3923-3928.
Pelphrey, Phillip M. et al. "Highly Efficient Ligands for Dihydrofolate Reductase from Cryptosporidium hominis and Toxoplasma gondii Inspired by Structural Analysis" Journal of Medicinal Chemistry (2007) vol. 50 pp. 940-950.
Petricci, Elena et al. "Microwave-enhanced Sonogashira coupling reaction of substituted pyrimidinones and pyrimidine nucleosides" Tetrahedron Letters, (2003) vol. 44, pp. 9181-9184.
Rodriguez, Alain Louis et al. "Verstile Indole Synthesis by a 5-endo-dig Cyclization Mediated by Potassium or Cesium Bases" Angew Chem. Int. Ed. (2000) vol. 39, No. 14 pp. 2488-2490.
Schmid, Bernd C. et al. "New perspectives in ovarian cancer treatment" Maturitas (2013) 9 pgs.
Testa, Bernard et al. "Prodrug Design" Encyclopedia of Pharmaceutical Technology, (J Swarbrick ed., 3rd ed, 2007) pp. 3008-3014.
Wiberg, Kenneth et al. "Substituent Effects. 3. A Comparison of Ethyl, Vinyl, Isopropyl, and Cyclopropyl Derivatives" J. Org. Chem. (1992) 57, pp. 5092-5101.

* cited by examiner

5-ALKYNYL-PYRIMIDINES

The present invention relates to new 5-alkynyl-pyrimidines of general formula (1)

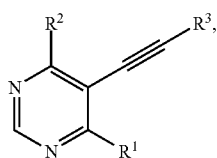

(1)

wherein the groups $R^1$ to $R^3$ have the meanings given in the claims and specification, the isomers thereof, processes for preparing these alkynyl-pyrimidines and their use as medicaments.

BACKGROUND TO THE INVENTION

A number of protein kinases have already proved to be suitable target molecules for therapeutic intervention in a variety of indications, e.g. cancer and inflammatory and autoimmune diseases. Since a high percentage of the genes involved in the development of cancer which have been identified thus far encode kinases, these enzymes are attractive target molecules for the therapy of cancer in particular.

The phosphoinositide 3-kinase (PI3K) pathway is activated in a broad spectrum of human cancers. This may occur either via mutation of PI3K resulting in activation of the kinase, or indirectly via inactivation of the phosphatase and tensin homologue (PTEN) suppressor. In both cases, an activation of the signalling cascade is induced that promotes transformation of cells both in vitro and in vivo. Within the cascade, the Pi3K family of enzymes and the kinase mTOR play a pivotal role. The PI3K family comprises 15 lipid kinases with distinct substrate specificities, expression pattern and modes of regulation. They play an important role in numerous cell processes such as e.g. cell growth and differentiation processes, the control of cytoskeletal changes and the regulation of intracellular transport processes. On the basis of their in vitro specificity for certain phosphoinositide substrates the PI3-kinases can be divided into different categories. The mammalian target of rapamycin (mTOR) is a serine/threonine kinase related to the lipide kinases of the PI3-kinase family. It exists in two complexes, mTORC1 and mTORC2, which are differentially regulated, have distinct substrate specificities, and are differentially sensitive to rapamycin. The central role of mTOR in controlling key cellular growth and survival pathways has sparked interest in discovering mTOR inhibitors that bind to the ATP site and therefore target both mTORC2 and mTORC1. As a consequence, inhibition of the PI3K pathway, particularly mediated via Pi3Kα and mTOR, has emerged as an attractive target for cancer therapeutics.

5-Alkynyl-pyrimidines are described for example as protein kinases inhibiting compounds in WO2006044823.

DETAILED DESCRIPTION OF THE INVENTION

It has now surprisingly been found that compounds of general formula (1), wherein the groups $R^1$ to $R^4$ have the meanings given below, act as inhibitors of kinases. In particular, the compounds of the invention inhibit PI3Kα and mTOR kinases. Thus, the compounds according to the invention may be used for example for the treatment of diseases connected with the activity of kinases and characterised by excessive or abnormal cell proliferation, like for example cancer.

The present invention relates to compounds of general formula (1)

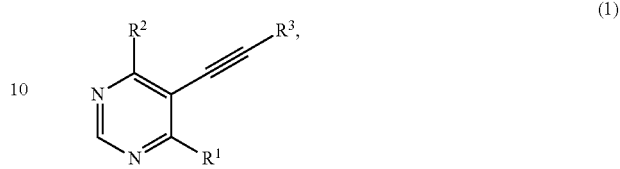

(1)

wherein
$R^3$ denotes a group selected from among 3-8 membered heterocycloalkyl, $C_{6-10}$aryl and 5-12 membered heteroaryl, optionally substituted by one or more identical or different $R^4$; and
$R^1$ denotes a group selected from among $C_{6-10}$aryl and 5-12 membered heteroaryl, optionally substituted by one or more identical or different $R^5$ and
$R^2$ denotes a group selected from among hydrogen, $C_{1-4}$alkyl, $C_{3-8}$cycloalkyl, 3-8 membered heteroalkyl, 3-8 membered heterocycloalkyl, $OR^v$, $NR^vR^{v1}$, —$SR^v$, $CF_3$, —CN, —NC and —$NO_2$, and
each $R^4$ denotes a group selected from among $R^a$ and $R^b$; and
each $R^a$ independently of one another denotes hydrogen or a group selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, $R^a$ optionally being substituted by one or more identical or different $R^b$ and/or $R^{c4}$,
each $R^b$ denotes a suitable group and is selected independently of one another from among =O, —$OR^c$, $C_{1-3}$haloalkyloxy, —$OCF_3$, —$OCHF_2$, =S, —$SR^c$, =$NR^c$, =$NOR^c$, =$NNR^cR^{c1}$, =$NN(R^g)C(O)NR^cR^{c1}$, —$NR^cR^{c1}$, —$ONR^cR^{c1}$, —$N(OR^c)R^{c1}$, —$N(R^g)NR^cR^{c1}$, halogen, —$CF_3$, —CN, —NC, —OCN, —SCN, —NO, —$NO_2$, =$N_2$, —$N_3$, —$S(O)R^c$, —$S(O)OR^c$, —$S(O)_2R^c$, —$S(O)_2OR^c$, —$S(O)NR^cR^{c1}$, —$S(O)_2NR^cR^{c1}$, —$OS(O)R^c$, —$OS(O)_2R^c$, —$OS(O)_2OR^c$, —$OS(O)NR^cR^{c1}$, —$OS(O)_2NR^cR^{c1}$, —$C(O)R^c$, —$C(O)OR^c$, —$C(O)SR^c$, —$C(O)NR^cR^{c1}$, —$C(O)N(R^g)NR^cR^{c1}$, —$C(O)N(R^g)OR^c$, —$C(NR^g)NR^cR^{c1}$, —$C(NOH)R^c$, —$C(NOH)NR^cR^{c1}$, —$OC(O)R^c$, —$OC(O)OR^c$, —$OC(O)SR^c$, —$OC(O)NR^cR^{c1}$, —$OC(NR^g)NR^cR^{c1}$, —$SC(O)R^c$, —$SC(O)OR^c$, —$SC(O)NR^cR^{c1}$, —$SC(NR^g)NR^cR^{c1}$, —$N(R^g)C(O)R^c$, —$N[C(O)R^c][C(O)R^{c1}]$, —$N(OR^g)C(O)R^c$, —$N(R^g)C(NR^{g1})R^c$, —$N(R^g)N(R^{g1})C(O)R^c$, —$N[C(O)R^{c2}]NR^cR^{c1}$, —$N(R^g)C(S)R^c$, —$N(R^g)S(O)R^c$, —$N(R^g)S(O)OR^c$, —$N(R^g)S(O)_2R^c$, —$N[S(O)_2R^c][S(O)_2R^{c1}]$, —$N(R^g)S(O)_2OR^c$, —$N(R^g)S(O)_2NR^cR^{c1}$, —$N(R^g)[S(O)_2]_2R^c$, —$N(R^g)C(O)OR^c$, —$N(R^g)C(O)SR^c$, —$N(R^g)C(O)NR^cR^{c1}$, —$N(R^g)C(O)NR^{g1}NR^cR^{c1}$, —$N(R^g)N(R^{g1})C(O)NR^cR^{c1}$, —$N(R^g)C(S)NR^cR^{c1}$, —$[N(R^g)C(O)]_2R^c$, —$N(R^g)[C(O)]_2R^c$, —$N\{[C(O)]_2R^c\}\{[C(O)]_2R^{c1}\}$, —$N(R^g)[C(O)]_2OR^c$, —$N(R^g)[C(O)]_2NR^cR^{c1}$, —$N\{[C(O)]_2OR^c\}\{[C(O)]_2OR^{c1}\}$, —$N\{[C(O)]_2NR^cR^{c1}\}\{[C(O)]_2NR^{c2}R^{c3}\}$, —$[N(R^g)C(O)]_2OR^c$, —$N(R^g)C(NR^{g1})OR^c$, —$N(R^g)C(NOH)R^c$, —$N(R^g)C(NR^{g1})SR^c$, —$N(R^g)C(NR^{g1})NR^cR^{c1}$, —$N(R^g)C(=N—CN)NR^cR^{c1}$ and —$N=C(R^g)NR^cR^{c1}$ and
each $R^c$, $R^{c1}$, $R^{c2}$, $R^{c3}$ and $R^{c4}$ independently of one another denotes hydrogen or a group selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered hetero-aryl, 6-18 membered heteroarylalkyl, 3-14 membered heterocycloalkyl and 4-14 membered heterocyloalkylalkyl, $R^c$, $R^{c1}$, $R^{c2}$, $R^{c3}$ and $R^{c4}$ independently optionally being substituted by one or more identical or different $R^d$ and/or $R^{e4}$, where $R^c$ together with $R^g$ and/or $R^{c1}$ and/or $R^{c2}$ and/or $R^{c3}$ or $R^{c2}$ together with $R^{c3}$ may form a 3-8 membered heterocyclalkyl residue via a shared C-, N-, O- or S-atom, and each $R^d$ denotes a suitable group and is selected independently of one another from among $=$O, —OR$^e$, $C_{1-3}$haloalkyloxy, —OCF$_3$, —OCHF2, $=$S, —SR$^e$, $=$NR$^e$, $=$NOR$^e$, $=$NNR$^e$R$^{e1}$, $=$NN(R$^{g2}$)C(O)NR$^e$R$^{e1}$, —NR$^e$R$^{e1}$, —ONR$^e$R$^{e1}$, —N(R$^{g2}$)NR$^e$R$^{e1}$, halogen, —CF$_3$, —CN, —NC, —OCN, —SCN, —NO, —NO$_2$, $=$N$_2$, —N$_3$, —S(O)R$^e$, —S(O)OR$^e$, —S(O)$_2$R$^e$, —S(O)$_2$OR$^e$, —S(O)NR$^e$R$^{e1}$, —S(O)$_2$NR$^e$R$^{e1}$, —OS(O)R$^e$, —OS(O)$_2$R$^e$, —OS(O)$_2$OR$^e$, —OS(O)NR$^e$R$^{e1}$, —OS(O)$_2$NR$^e$R$^{e1}$, —C(O)R$^e$, —C(O)OR$^e$, —C(O)SR$^e$, —C(O)NR$^e$R$^{e1}$, —C(O)N(R$^{g2}$)NR$^e$R$^{e1}$, —C(O)N(R$^{g2}$)OR$^e$, —C(NR$^{g2}$)NR$^e$R$^{e1}$, —C(NOH)R$^e$, —C(NOH)NR$^e$R$^{e1}$, —OC(O)R$^e$, —OC(O)OR$^e$, —OC(O)SR$^e$, —OC(O)NR$^e$R$^{e1}$, —OC(NR$^{g2}$)NR$^e$R$^{e1}$, —SC(O)R$^e$, —SC(O)OR$^e$, —SC(O)NR$^e$R$^{e1}$, —SC(NR$^{g2}$)NR$^e$R$^{e1}$, —N(R$^{g2}$)C(O)R$^e$, —N[C(O)R$^e$][C(O)R$^{e1}$], —N(OR$^{g2}$)C(O)R$^e$, —N(R$^{g2}$)C(O)R$^e$, —N(R$^{g2}$)C(NR$^{g3}$)R$^e$, —N(R$^{g2}$)N(R$^{g3}$)C(O)R$^e$, —N[C(O)R$^{e2}$]NR$^e$R$^{e1}$, —N(R$^{g2}$)C(S)R$^e$, —N(R$^{g2}$)S(O)R$^e$, —N(R$^{g2}$)S(O)OR$^e$ —N(R$^{g2}$)S(O)$_2$R$^e$, —N[S(O)$_2$R$^e$][S(O)$_2$R$^{e1}$], —N(R$^{g2}$)S(O)$_2$OR$^e$, —N(R$^{g2}$)S(O)$_2$NR$^e$R$^{e1}$, —N(R$^{g2}$)[S(O)$_2$]$_2$R$^e$, —N(R$^{g2}$)C(O)OR$^e$, —N(R$^{g2}$)C(O)SR$^e$, —N(R$^{g2}$)C(O)NR$^e$R$^{e1}$, —N(R$^{g2}$)C(O)NR$^{g3}$NR$^e$R$^{e1}$, —N(R$^{g2}$)N(R$^{g3}$)C(O)NR$^e$R$^{e1}$, —N(R$^{g2}$)C(S)NR$^e$R$^{e1}$, —[N(R$^{g2}$)C(O)][N(R$^{g3}$)C(O)]R$^e$, —N(R$^{g2}$)[C(O)]$_2$R$^e$, —N{[C(O)]$_2$R$^e$}{[C(O)]$_2$R$^{e1}$}, —N(R$^{g2}$)[C(O)]$_2$OR$^e$, —N(R$^{g2}$)[C(O)]$_2$NR$^e$R$^{e1}$, —N{[C(O)]$_2$OR$^e$}{[C(O)]$_2$OR$^e$}, —N{[C(O)]$_2$NR$^e$R$^{e1}$}{[C(O)]$_2$NR$^{e2}$R$^{e3}$}, —[N(R$^{g3}$)C(O)][N(R$^{g3}$)C(O)]OR$^e$, —N(R$^{g2}$)C(NR$^{g3}$)OR$^e$, —N(R$^{g2}$)C(NOH)R$^e$, —N(R$^{g2}$)C(NR$^{g3}$)SR$^e$, —N(R$^{g2}$)C(NR$^{g3}$)NR$^e$R$^{e1}$, —N(R$^{g2}$)C($=$N—CN)NR$^e$R$^{e1}$ and —N$=$C(R$^{g2}$)NR$^e$R$^{e1}$ each $R^e$, $R^{e1}$, $R^{e2}$, $R^{e3}$ and $R^{e4}$ independently of one another denotes hydrogen or a group selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered hetero-aryl, 6-18 membered heteroarylalkyl, 3-14 membered heterocycloalkyl and 4-14 membered heterocyloalkylalkyl, where $R^e$ together with $R^{g2}$ and/or $R^{e1}$ and/or $R^{e2}$ and/or $R^{e3}$ or $R^{e2}$ together with $R^{e3}$ may form a 3-8 membered heterocyclalkyl residue via a shared C-, N-, O- or S-atom, and where $R^e$, $R^{e1}$, $R^{e2}$, $R^{e3}$ and $R^{e4}$ independently optionally being substituted by one or more identical or different $R^f$ and/or $R^{g6}$, and each $R^f$ denotes a suitable group and in each case is selected independently of one another from among $=$O, —OR$^g$, $C_{1-3}$haloalkyloxy, —OCF$_3$, —OCHF$_2$, $=$S, —SR$^g$, $=$NR$^{g4}$, $=$NOR$^{g4}$, $=$NNR$^{g4}$R$^{g5}$, $=$NN(R$^h$)C(O)NR$^{g4}$R$^{g5}$, —NR$^{g4}$R$^{g5}$, —ONR$^{g4}$R$^{g5}$, —N(R$^h$)NR$^{g4}$R$^{g5}$, halogen, —CF$_3$, —CN, —NC, —OCN, —SCN, —NO, —NO$_2$, $=$N$_2$, —N$_3$, —S(O)R$^{g4}$, —S(O)OR$^{g4}$, —S(O)$_2$R$^{g4}$, —S(O)$_2$OR$^{g4}$, —S(O)NR$^{g4}$R$^{g5}$, —S(O)$_2$NR$^{g4}$R$^{g5}$, —OS(O)R$^{g4}$, —OS(O)$_2$R$^{g4}$, —OS(O)$_2$OR$^{g4}$, —OS(O)NR$^{g4}$R$^{g5}$, —OS(O)$_2$NR$^{g4}$R$^{g5}$, —C(O)R$^{g4}$, —C(O)OR$^{g4}$, —C(O)SR$^{g4}$, —C(O)NR$^{g4}$R$^{g5}$, C(O)N(R$^h$)NR$^{g4}$R$^{g5}$, —C(O)N(R$^h$)OR$^{g4}$, —C(NR$^h$)NR$^{g4}$R$^{g5}$, —C(NOH)R$^{g4}$, —C(NOH)NR$^{g4}$R$^{g5}$, —OC(O)R$^{g4}$, —OC(O)OR$^{g4}$, —OC(O)SR$^{g4}$, —OC(O)NR$^{4}$R$^{g5}$, —OC(NR$^h$)NR$^{g4}$R$^{g5}$, —SC(O)R$^{g4}$, —SC(O)OR$^{g4}$, —SC(O)NR$^{g4}$R$^{g5}$, —SC(NR$^h$)NR$^{g4}$R$^{g5}$, —N(R$^h$)C(O)R$^{g4}$, —N[C(O)R$^{g4}$]$_2$, —N(OR$^h$)C(O)R$^{g4}$, —N(R$^h$)C(NR$^{h1}$)R$^{g4}$, —N(R$^h$)N(R$^{h1}$)C(O)R$^{g4}$, —N[C(O)R$^{g6}$]

NR$^{g4}$R$^{g5}$, —N(R$^h$)C(S)R$^{g4}$, —N(R$^h$)S(O)R$^{g4}$, —N(R$^h$)S(O)OR$^{g4}$, —N(R$^h$)S(O)$_2$R$^{g4}$, —N[S(O)$_2$R$^{g4}$][S(O)$_2$R$^{g5}$], —N(R$^h$)S(O)$_2$OR$^{g4}$, —N(R$^h$)S(O)$_2$NR$^{g4}$R$^{g5}$, —N(R$^h$)[S(O)$_2$]$_2$R$^{g4}$, —N(R$^h$)C(O)OR$^{g4}$, —N(R$^h$)C(O)SR$^{g4}$, —N(R$^h$)C(O)NR$^{g4}$R$^{g5}$, —N(R$^h$)C(O)NR$^{h1}$NR$^{g4}$R$^{g5}$, —N(R$^h$)N(R$^{h1}$)C(O)NR$^{g4}$R$^{g5}$, —N(R$^h$)C(S)NR$^{g4}$R$^{g5}$, —[N(R$^h$)C(O)][N(R$^{h1}$)C(O)]R$^{g4}$, —N(R$^h$)[C(O)]$_2$R$^{g4}$, —N{[C(O)]$_2$R$^{g4}$}{[C(O)]$_2$R$^{g5}$}, —N(R$^h$)[C(O)]$_2$OR$^{g4}$, —N(R$^h$)[C(O)]$_2$NR$^{g4}$R$^{g5}$, —N{[C(O)]$_2$OR$^{g4}$}{[C(O)]$_2$OR$^{g4}$}, —N{[C(O)]$_2$NR$^{g4}$R$^{g5}$}{[C(O)]$_2$NR$^{g4}$R$^{g5}$}, —[N(R$^h$)C(O)][N(R$^{h1}$)C(O)]OR$^{g4}$, —N(R$^h$)C(NR$^{h1}$)OR$^{g4}$, —N(R$^h$)C(NOH)R$^{g4}$, —N(R$^h$)C(NR$^{h1}$)SR$^{g4}$, —N(R$^h$)C(NR$^{h1}$)NR$^{g4}$R$^{g5}$, —N(R$^h$)C($=$N—CN)NR$^{g4}$R$^{g5}$ and —N$=$C(R$^h$)NR$^{g4}$R$^{g5}$; and each $R^g$, $R^{g1}$, $R^{g2}$, $R^{g3}$, $R^{g4}$, $R^{g5}$ and $R^{g6}$ independently of one another denotes hydrogen or a group selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered hetero-aryl, 6-18 membered heteroarylalkyl, 3-14 membered heterocycloalkyl and 4-14 membered heterocycloalkylalkyl, where $R^g$ together with $R^{g1}$ and/or $R^h$ may form a 3-8 membered cycloalkyl or a 3-8 membered heterocyclalkyl residue via a shared C—, N—O- or S-atom, and where $R^g$, $R^{g1}$, $R^{g2}$, $R^{g3}$, $R^{g4}$, $R^{g5}$ and $R^{g6}$ independently optionally being substituted by one or more identical or different $R^{h2}$; and each $R^h$, $R^{h1}$ and $R^{h2}$ is selected independently of one another from among hydrogen, $C_{1-6}$ alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$ arylalkyl, 5-12 membered heteroaryl, 6-18 membered heteroarylalkyl, 3-14 membered heterocycloalkyl and 4-14 membered heterocycloalkylalkyl, where $R^h$ together with $R^{h1}$ may form a 3-8 membered cycloalkyl or a 3-8 membered heterocyclalkyl residue via a shared C-, N- O- or S-atom, and each $R^5$ denotes a group selected from among $R^m$ and $R^n$; and each $R^m$ independently of one another denotes hydrogen or a group selected from among $C_{1-6}$ alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$ arylalkyl, 5-12 membered heteroaryl, 6-18 membered heteroarylalkyl, 3-14 membered heterocycloalkyl and 4-14 membered heterocycloalkylalkyl, and $R^m$ optionally substituted by one or more identical or different $R^n$ and/or $R^{o4}$, each $R^n$ denotes a suitable group and is selected independently of one another from among $=$O, —OR$^o$, $C_{1-3}$haloalkyloxy, —OCF$_3$, —OCHF$_2$, $=$S, —SR$^o$, $=$NR$^o$, $=$NOR$^o$, $=$NNR$^o$R$^{o1}$, $=$NN(R$^s$)C(O)NR$^o$R$^{o1}$, —NR$^o$R$^{o1}$, —ONR$^o$R$^{o1}$, —N(OR$^s$)R$^{o1}$, —N(R$^s$)NR$^o$R$^{o1}$, halogen, —CF$_3$, —CN, —NC, —OCN, —SCN, —NO, —NO$_2$, $=$N$_2$, —N$_3$, —S(O)R$^o$, —S(O)OR$^o$, —S(O)$_2$R$^o$, —S(O)$_2$OR$^o$, —S(O)NR$^o$R$^{o1}$, —S(O)$_2$NR$^o$R$^{o1}$, —OS(O)R$^o$, —OS(O)$_2$R$^o$, —OS(O)$_2$OR$^o$, —OS(O)NR$^o$R$^{o1}$, —OS(O)$_2$NR$^o$R$^{o1}$, —C(O)R$^o$, —C(O)OR$^o$, —C(O)SR$^o$, —C(O)NR$^o$R$^{o1}$, —C(O)N(R$^s$)NR$^o$R$^{o1}$, —C(O)N(R$^s$)OR$^o$, —C(NR$^s$)NR$^o$R$^{o1}$, —C(NOH)R$^o$, —C(NOH)NR$^o$R$^{o1}$, —OC(O)R$^o$, —OC(O)OR$^o$, —OC(O)SR$^o$, —OC(O)NR$^o$R$^{o1}$, —OC(NR$^s$)NR$^o$R$^{o1}$, —SC(O)R$^o$, —SC(O)OR$^o$, —SC(O)NR$^o$R$^{o1}$, —SC(NR$^s$)NR$^o$R$^{o1}$, —N(R$^s$)C(O)R$^o$, —N[C(O)R$^o$][C(O)R$^{o1}$], —N(OR$^s$)C(O)R$^o$, —N(R$^s$)C(NR$^{s1}$)R$^o$, —N(R$^s$)N(R$^{s1}$)C(O)R$^o$, —N[C(O)R$^{o2}$]NR$^o$R$^{o1}$, —N(R$^s$)C(S) R$^o$, —N(R$^s$)S(O)R$^o$, —N(R$^s$)S(O)OR$^o$, —N(R$^s$)S(O)$_2$R$^o$, —N[S(O)$_2$R$^o$][S(O)$_2$R$^{o1}$], —N(R$^s$)S(O)$_2$OR$^o$, —N(R$^s$)S(O)$_2$NR$^o$R$^{o1}$, —N(R$^s$)[S(O)$_2$]$_2$R$^o$, —N(R$^s$)C(O)OR$^o$, —N(R$^s$)C(O)SR$^o$, —N(R$^s$)C(O)NR$^o$R$^{o1}$, —N(R$^s$)C(O)NR$^{s1}$NR$^o$R$^{o1}$, —N(R$^s$)N(R$^{s1}$)C(O)NR$^o$R$^{o1}$, —N(R$^s$)C(S)NR$^o$R$^{o1}$, —[N(R$^s$)C(O)][N(R$^{s1}$)C(O)]R$^o$, —N(R$^s$)[C(O)]$_2$R$^o$, —N{[C(O)]$_2$R$^o$}{[C(O)]$_2$R$^{o1}$}, —N(R$^s$)[C(O)]$_2$OR$^o$, —N(R$^s$)[C(O)]$_2$NR$^o$R$^{o1}$, —N{[C(O)]$_2$OR$^o$}{[C(O)]$_2$OR$^{o1}$}, —N{[C(O)]$_2$NR$^o$R$^{o1}$}{[C(O)]$_2$ NR$^{o2}$R$^{o3}$}, —[N(R$^s$)C(O)]$_2$OR$^o$, —N(R$^s$)C(NR$^{s1}$)OR$^o$, —N(R$^s$)C(NOH)R$^o$, —N(R$^s$)C(NR$^{s1}$)SR$^o$, —N(R$^s$)C(NR$^{s1}$) NR$^o$R$^{o1}$ and —N=C(R$^s$)NR$^o$R$^{o1}$ and each R$^o$, R$^{o1}$, R$^{o2}$ and R$^{o3}$ independently of one another denotes hydrogen or a group selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered hetero-aryl, 6-18 membered heteroarylalkyl, 3-14 membered heterocycloalkyl and 4-14 membered heterocycloalkylalkyl, where R$^o$ together with R$^s$ and/or R$^{o1}$ and/or R$^{o2}$ and/or R$^{o3}$ or R$^{o2}$ together with R$^{o3}$ may form a 3-8 membered heterocyclalkyl residue via a shared C-, N-, O- or S-atom, and where R$^o$, R$^{o1}$, R$^{o2}$ and R$^{o3}$ independently optionally being substituted by one or more identical or different R$^p$ and/or R$^{q4}$, and each R$^p$ denotes a suitable group and is selected independently of one another from among =O, —OR$^q$, C$_{1-3}$haloalkyloxy, —OCF$_3$, —OCHF$_2$, =S, —SR$^q$, =NR$^q$, =NOR$^q$, =NNR$^q$R$^{q1}$, =NN(R$^s$)C(O)NR$^q$R$^{q1}$, —NR$^q$R$^{q1}$, —ONR$^q$R$^{q1}$, —N(R$^s$)NR$^q$R$^{q1}$, halogen, —CF$_3$, —CN, —NC, —OCN, —SCN, —NO, —NO$_2$, =N$_2$, —N$_3$, —S(O)R$^q$, —S(O)OR$^q$, —S(O)$_2$R$^q$, —S(O)$_2$OR$^q$, S(O)NR$^q$R$^{q1}$, —S(O)$_2$NR$^q$R$^{q1}$, —OS(O)R$^q$, —OS(O)$_2$R$^q$, —OS(O)$_2$OR$^q$, —OS(O)NR$^q$R$^{q1}$, —OS(O)$_2$NR$^q$R$^{q1}$, —C(O)R$^q$, —C(O)OR$^q$, —C(O)SR$^q$, —C(O)NR$^q$R$^{q1}$, —C(O)N(R$^s$)NR$^q$R$^{q1}$, —C(O)N(R$^s$)OR$^q$, —C(NR$^s$)NR$^q$R$^{q1}$, —C(NOH)R$^q$, —C(NOH)NR$^q$R$^{q1}$, —OC(O)R$^q$, —OC(O)OR$^q$, —OC(O)SR$^q$, —OC(O)NR$^q$R$^{q1}$, —OC(NR$^s$)NR$^q$R$^{q1}$, —SC(O)R$^q$, —SC(O)OR$^q$, —SC(O)NR$^q$R$^{q1}$, —SC(NR$^s$)NR$^q$R$^{q1}$, —N(R$^s$)C(O)R$^q$, —N[C(O)R$^q$][C(O)R$^{q1}$], —N(OR$^s$)C(O)R$^q$, —N(R$^s$)C(R$^{s1}$)R$^q$, —N(R$^s$)N(R$^{s1}$)C(O)R$^q$, —N[C(O)R$^{q2}$]NR$^q$R$^{q1}$, —N(R$^s$)C(S)R$^q$, —N(R$^s$)S(O)R$^q$, —N(R$^s$)S(O)OR$^q$, —N(R$^s$)S(O)$_2$R$^q$, —N[S(O)$_2$R$^q$][S(O)$_2$R$^{q1}$], —N(R$^s$)S(O)$_2$OR$^q$, —N(R$^s$)S(O)$_2$NR$^q$R$^{q1}$, —N(R$^s$)[S(O)$_2$]$_2$R$^q$, —N(R$^s$)C(O)OR$^q$, —N(R$^s$)C(O)SR$^q$, —N(R$^s$)C(O)NR$^q$R$^{q1}$, —N(R$^s$)C(O)NR$^{s1}$NR$^q$R$^{q1}$, —N(R$^s$)N(R$^{s1}$)C(O)NR$^q$R$^{q1}$, —N(R$^s$)C(S)NR$^{q1}$, —[N(R$^s$)C(O)][N(R$^{g1}$)C(O)]R$^q$, —N(R$^s$)[C(O)]$_2$R$^q$, —N{[C(O)]$_2$R$^q$}{[C(O)]$_2$R$^{q1}$}, —N(R$^s$)[C(O)]$_2$OR$^q$, —N(R$^s$)[C(O)]$_2$NR$^q$R$^{q1}$, —N{[C(O)]$_2$OR$^q$}{[C(O)]$_2$OR$^q$}, —N{[C(O)]$_2$NR$^q$R$^{q1}$}{[C(O)]$_2$NR$^{q2}$R$^{q3}$}, —[N(R$^s$)C(O)][N(R$^{s1}$)C(O)]OR$^q$, —N(R$^s$)C(NR$^{s1}$)OR$^q$, —N(R$^s$)C(NOH)R$^q$, —N(R$^s$)C(NR$^{s1}$)SR$^q$, —N(R$^s$)C(NR$^{s1}$)NR$^q$R$^{q1}$, —N(R$^s$)C(=N—CN)NR$^q$R$^{q1}$ and —N=C(R$^s$)NR$^q$R$^{q1}$, and each R$^q$, R$^{q1}$, R$^{q2}$, R$^{q3}$ and R$^{q4}$ independently of one another denotes hydrogen or a group selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered hetero-aryl, 6-18 membered heteroarylalkyl, 3-14 membered heterocycloalkyl and 4-14 membered heterocycloalkylalkyl, where R$^q$ together with R$^{q1}$ and/or R$^{q2}$ and/or R$^{q3}$ and/or R$^s$ may form a 3-8 membered heterocyclalkyl residue via a shared C—, N—O- or S-atom, wherein R$^q$, R$^{q1}$, R$^{q2}$, R$^{q3}$ and R$^{q4}$ are optionally independently substituted by one or more identical or different R$^a$ and/or R$^{s4}$, and each R$^r$ denotes a suitable group and in each case is selected independently of one another from among =O, —OR$^s$, C$_{1-3}$haloalkyloxy, —OCF$_3$, —OCHF$_2$, =S, —SR$^s$, =NR$^s$, =NOR$^s$, =NNR$^s$R$^{s1}$, =NN(R$^t$)C(O)NR$^s$R$^{s1}$, —NR$^s$R$^{s1}$, —ONR$^s$R$^{s1}$, —N(R$^h$)NR$^s$R$^{s1}$, halogen, —CF$_3$, —CN, —NC, —OCN, —SCN, —NO, —NO$_2$, =N$_2$, —N$_3$, —S(O)R$^s$, —S(O)OR$^s$, —S(O)$_2$R$^s$, —S(O)$_2$OR$^s$, —S(O)NR$^s$, —S(O)$_2$NR$^s$R$^{s1}$, —OS(O)R$^s$, —OS(O)$_2$R$^s$, —OS(O)$_2$OR$^s$, —OS(O)NR$^s$R$^{s1}$, —OS(O)$_2$NR$^s$R$^{s1}$, —C(O)R$^s$, —C(O)OR$^s$, —C(O)SR$^s$, —C(O)NR$^s$R$^{s1}$, —C(O)N(R$^t$)NR$^s$R$^{s1}$, —C(O)N(R$^t$)OR$^s$, —C(NR$^t$)NR$^s$R$^{s1}$, —C(NOH)R$^s$, —C(NOH)NR$^s$R$^{s1}$, —OC(O)R$^s$, —OC(O)OR$^s$, —OC(O)SR$^s$, —OC(O)NR$^s$R$^{s1}$, —OC(NR$^t$)NR$^s$R$^{s1}$, —SC(O)R$^s$, —SC(O)OR$^s$, —SC(O)NR$^s$R$^{s1}$, —SC(NR$^t$)NR$^s$R$^{s1}$, —N(R$^t$)C(O)R$^s$, —N[C(O)R$^s$][C(O)R$^{s1}$], —N(OR$^t$)C(O)R$^s$, —N(R$^t$)C(NR$^{t1}$)R$^s$, —N(R$^t$)N(R$^{t1}$)C(O)R$^s$, —N[C(O)R$^{g2}$]NR$^s$R$^{s1}$, —N(R$^t$)C(S)R$^s$, —N(R$^t$)S(O)R$^s$, —N(R$^t$)S(O)OR$^s$, —N(R$^t$)S(O)$_2$R$^s$, —N[S(O)$_2$R][S(O)$_2$R$^{s1}$], —N(R$^t$)S(O)$_2$OR$^s$, —N(R$^t$)S(O)$_2$NR$^s$R$^{s1}$, —N(R$^t$)[S(O)$_2$]$_2$R$^s$, —N(R$^t$)C(O)OR$^s$, —N(R$^t$)C(O)SR$^s$, —N(R$^t$)C(O)NR$^s$R$^{s1}$, —N(R$^t$)C(O)NR$^{t1}$NR$^s$R$^{s1}$, —N(R$^t$)N(R$^{t1}$)C(O)NR$^s$R$^{s1}$, —N(R$^t$)C(S)NR$^s$R$^{s1}$, —[N(R$^t$)C(O)][N(R$^{h1}$)C(O)]R$^s$, —N(R$^t$)[C(O)]$_2$R$^s$, —N{[C(O)]$_2$R$^s$}{[C(O)]$_2$R$^{s1}$}, —N(R$^t$)[C(O)]$_2$OR$^s$, —N(R$^t$)[C(O)]$_2$NR$^{s2}$R$^{s1}$, —N{[C(O)]$_2$OR$^s$}{[C(O)]$_2$OR$^{s1}$}, —N{[C(O)]$_2$NR$^s$R$^{s1}$}{[C(O)]$_2$NR$^{s2}$R$^{s3}$}, —[N(R$^t$)C(O)][N(R$^{t1}$)C(O)]OR$^s$, —N(R$^t$)C(NR$^{t1}$)OR$^s$, —N(R$^t$)C(NOH)R$^s$, —N(R$^t$)C(NR$^{t1}$)SR$^s$, —N(R$^t$)C(NR$^{t1}$)NR$^s$R$^{s1}$; and —N=C(R$^t$)NR$^s$R$^{s1}$; and each R$^s$, R$^{s1}$, R$^{s2}$, R$^{s3}$ and R$^{s4}$ independently of one another denotes hydrogen or a group selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered hetero-aryl, 6-18 membered heteroarylalkyl, 3-14 membered heterocycloalkyl and 4-14 membered heterocycloalkylalkyl, where R$^s$ together with R$^{s1}$ and/or R$^{s2}$ and/or R$^{s3}$ and/or R$^t$ may form a 3-8 membered heterocyclalkyl residue via a shared C-, N- O- or S-atom, R$^s$, R$^{s1}$, R$^{s2}$, R$^{s3}$ and R$^{s4}$ independently optionally being substituted by one or more identical or different R$^{t2}$; and each R$^t$, R$^{t1}$ and R$^{t2}$ is selected independently of one another from among hydrogen, C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl, where R$^t$ together with R$^{t1}$ may form a 3-8 membered heterocyclalkyl residue via a shared C-, N- O- or S-atom, and each R$^v$ and R$^{v1}$ is selected independently of one another from among hydrogen, C$_{1-6}$alkyl, 2-6 membered heteroalkyl, C$_{1-6}$haloalkyl, where R$^v$ together with R$^{v1}$ may form a 3-8 membered heterocyclalkyl residue via a shared C-, N-, O- or S-atom, optionally in the form of the prodrugs, the tautomers, the racemates, the enantiomers, the diastereomers, the prodrugs and the mixtures thereof, and optionally the pharmacologically acceptable salts thereof.

In a preferred embodiment R$^2$ denotes a group selected from among C$_{3-8}$cycloalkyl, 3-8 membered heteroalkyl, 3-8 membered heterocycloalkyl, —OR$^v$, NR$^v$R$^{v1}$, CF$_3$, —CN, —NC and —NO$_2$.

In another preferred embodiment R$^2$ denotes C$_{1-4}$-alkyl.

In another preferred embodiment R$^2$ denotes —CH$_3$ or —C$_2$H$_5$.

In another preferred embodiment R$^1$ denotes phenyl or pyridyl, optionally substituted by one or more identical or different R$^5$.

In another preferred embodiment R$^5$ denotes a group selected from among R$^m$, R$^n$; and each R$^m$ independently of one another denotes hydrogen or a group selected from among C$_{1-4}$alkyl, C$_{4-6}$cycloalkyl, methoxyethyl, cyclopropylmethyl, phenyl, naphthyl, benzyl, 5-6 membered heteroaryl, 4-6 membered heterocycloalkyl, wherein R$^m$ is optionally independently substituted by one or more identical or different R$^n$ and/or R$^{o4}$, and each R$^n$ denotes a suitable group and is selected independently of one another from among =O, —OH, —OCH$_3$, —OC$_2$H$_5$, OCF$_3$, —OCHF$_2$, =SCH$_3$, =NOH, =NOCH$_3$, —NR$^o$R$^{o1}$, —F, —Cl, —Br, —CF$_3$, —CN, —NO$_2$, —N$_3$, —S(O)R$^o$, —S(O)$_2$R$^o$, —C(O)R$^o$, —C(O)OR$^o$, —C(O)NR$^o$R$^{o1}$, —OC(O)R$^o$, —OC(O)OR$^o$, —OC(O)NR$^o$R$^{o1}$, —N(R$^s$)C(O)R$^o$, —N(R$^s$)S(O)R$^o$, —N(R$^s$)S(O)$_2$R$^o$, —N(R$^s$)S(O)$_2$NR$^o$R$^{o1}$, —N(R$^s$)C(O)OR$^o$, —N(R$^s$)C(O)NR$^o$R$^{o1}$, and each R$^o$, R$^{o1}$ and R$^{o4}$ independently of one another denotes hydrogen or a group selected from among C$_{1-4}$alkyl, 2-6 membered heteroalkyl, C$_{3-6}$cycloalkyl, C$_{4-10}$cycloalkylalkyl, phenyl, benzyl, 5-6 membered heteroaryl, C$_{4-6}$heterocycloalkyl, where R$^o$ together with R$^{o1}$ or R$^s$ may form a 3-8 membered heterocyclalkyl residue via a shared C-, N-, O- or S-atom, wherein R$^o$, R$^{o1}$ and R$^{o4}$ is optionally independently substituted by one or more identical or different R$^q$ and/or R$^{q4}$, and each R$^p$ denotes a suitable group and is selected independently of one another from among =O, —OH, methoxy, ethoxy, isopropoxy, —OCF$_3$, —OCHF$_2$, —SCH$_3$, amino, methylamino, dimethylamino, ethylamino, isopropylamino, morpholine, piperidine, pyrrolidine, piperazine, N-methylpiperazine, acetyl, methylsulfonyl, ethylsulfonyl, isopropylsulfonyl, methoxycarbonyl, ethoxycarbonyl, —F, —Cl, —Br, —CF$_3$, —CN, —S(O)$_2$C$_2$H$_5$, —S(O)$_2$CH$_3$, and each R$^{q4}$ denotes a suitable group and is independently of one another selected from among C$_{1-4}$alkyl, 4-6 membered heteroalkyl, C$_{4-6}$cycloalkyl, C$_{4-7}$cycloalkylalkyl, phenyl, benzyl, 5-6 membered heteroaryl, 6-8 membered heteroarylalkyl, 4-6 membered heterocycloalkyl and 4-7 membered heterocycloalkylalkyl, and each R$^s$ independently of one another denotes hydrogen or a group selected from among C$_{1-4}$alkyl, 2-6 membered heteroalkyl, C$_{3-8}$cycloalkyl, C$_{4-10}$cycloalkylalkyl, phenyl, benzyl, 5-6 membered heteroaryl, 6-12 membered heteroarylalkyl, 3-8 membered heterocycloalkyl and 4-10 membered heterocycloalkylalkyl.

In another preferred embodiment R$^{q4}$ denotes a suitable group and is independently of one another selected from among methyl, ethyl, 1-propyl, 2-propyl, 1-butyl, tert-butyl, oxetanyl, tetrahydrofuranyl, tetrahydropyranyl, cyclobutyl, cyclopentyl, cyclohexyl, cyclopropylmethyl, methoxyethyl, phenyl, benzyl, pyridyl, pyrimidinyl, pyridazinyl, imidazolyl, pyrazolyl, thiazolyl.

In another preferred embodiment R$^5$ denotes a group selected from among R$^n$, and each R$^n$ denotes a suitable group and is selected independently of one another from among methoxy, ethoxy, —F, —Cl, C(O)R$^o$, —C(O)NR$^o$R$^{o1}$, and each R$^o$ and R$^{o1}$ independently of one another denotes hydrogen or a group selected from among methyl, ethyl, prop-2-yl, prop-1-yl, methoxyethyl, cyclopropyl, cyclobutyl, cyclopentyl, cyclohexyl, cyclopropylmethyl, morpholine, piperidine, pyrrolidine, piperazine, or where R$^o$ and R$^{o1}$ form a cyclic amine, selected from morpholine, piperazine, homomorpholine, homopiperazine, piperidine, pyrrolidine, wherein R$^o$ and R$^{o1}$ are independently optionally substituted by one or more identical or different R$^p$ and/or R$^{q4}$, and each R$^p$ denotes a suitable group and is selected independently of one another from among =O, —OH, methoxy, ethoxy, isopropoxy, amino, methylamino, dimethylamino, ethylamino, isopropylamino, acetyl, methylsulfonyl, ethylsulfonyl, isopropylsulfonyl, methoxycarbonyl, ethoxycarbonyl, —F, —Cl, —Br, CF$_3$, CN, and each R$^{q4}$ denotes a suitable group and is independently of one another selected from among methyl, ethyl, 1-propyl, 2-propyl, 1-butyl, 2-butyl, tert-butyl, morpholinyl, piperidinyl, pyrrolidinyl, piperazinyl, N-methylpiperazinyl, oxetanyl, tetrahydrofuranyl, tetrahydropyranyl, tetrahydrothiophenyl, 1,1-dioxo-tetrahydrothiophenyl, cyclopropyl, cyclobutyl, cyclopentyl, cyclohexyl, cyclopropylmethyl, methoxyethyl, phenyl, benzyl, pyridyl, pyrimidinyl, pyridazinyl, imidazolyl, pyrazolyl, thiazolyl.

In another preferred embodiment R$^1$ denotes pyridyl, and wherein R$^5$ and R$^5$ are selected from among methyl, ethyl, n-propyl, isopropyl, cyclopropyl, methoxy, —CF$_3$.

In another preferred embodiment R$^1$ denotes phenyl, and wherein R$^5$ wherein R$^5$ are selected from among R$^n$, and each R$^n$ denotes a suitable group and is selected independently of one another from among methyl, methoxy, ethoxy, —F, —Cl, C(O)R$^o$, —C(O)NR$^o$R$^{o1}$, and each R$^o$ and R$^{o1}$ independently of one another denotes hydrogen or a group optionally substituted by one or more identical or different R$^p$ and/or R$^{q4}$, selected from among methyl, ethyl, prop-2-yl, prop-1-yl, methoxyethyl, cyclopropyl, cyclobutyl, cyclopentyl, cyclohexyl, cyclopropylmethyl, morpholine, piperidine, pyrrolidine, piperazine, or where R$^o$ and R$^{o1}$ form a cyclic amine, selected from morpholine, piperazine, homomorpholine, homopiperazine, piperidine, pyrrolidine, optionally substituted by one or more identical or different R$^p$ and/or R$^{q4}$, and each R$^p$ denotes a suitable group and is selected independently of one another from among =O, —OH, methoxy, ethoxy, isopropoxy, amino, methylamino, dimethylamino, ethylamino, isopropylamino, acetyl, methylsulfonyl, ethylsulfonyl, isopropylsulfonyl, methoxycarbonyl, ethoxycarbonyl, —F, —Cl, —Br, —CF$_3$, —CN, and each R$^{q4}$ denotes a suitable group and is independently of one another selected from among methyl, ethyl, 1-propyl, 2-propyl, 1-butyl, 2-butyl, tert-butyl, morpholinyl, piperidinyl, pyrrolidinyl, piperazinyl, N-methylpiperazinyl, oxetanyl, tetrahydrofuranyl, tetrahydropyranyl, tetrahydrothiophenyl, 1,1-dioxo-tetrahydrothiophenyl, cyclopropyl, cyclobutyl, cyclopentyl, cyclohexyl, cyclopropylmethyl, methoxyethyl, phenyl, benzyl, pyridyl, pyrimidinyl, pyridazinyl, imidazolyl, pyrazolyl, thiazolyl.

In another preferred embodiment R$^3$ denotes phenyl or pyridyl, optionally substituted by one or more identical or different R$^4$.

In another preferred embodiment R$^4$ denotes a group selected from among R$^a$, R$^b$ and R$^a$ substituted by one or more identical or different R$^b$ and/or R$^c$; and each R$^a$ independently of one another is selected from among hydrogen, methyl, ethyl, and each R$^b$ denotes a suitable group and is selected independently of one another from among —OCH$_3$, —NH$_2$, —NHCH$_3$, —NHC$_2$H$_5$, —F, —Cl, —Br, —CF$_3$, —CN.

In another preferred embodiment R$^3$ denotes pyridyl, optionally substituted by one or more identical or different R$^4$.

In another preferred embodiment R$^3$ denotes pyridyl and wherein R$^4$ and R$^4$ are selected from among methyl, ethyl, amino, methylamino, ethylamino. The compounds, or the pharmacologically effective salts thereof, according to the present invention can be used as medicaments.

The compounds, or the pharmacologically effective salts thereof, according to the present invention can be used for preparing a medicament with an antiproliferative activity.

The present invention also relates to pharmaceutical preparations, containing as active substance one or more compounds of general formula (1) according to the present invention or the pharmacologically effective salts thereof, optionally in combination with conventional excipients and/or carriers.

The present invention also relates to compounds according to formula (1) for use in the treatment and/or prevention of cancer, infections, inflammatory and autoimmune diseases.

The present invention also relates to the use of compounds of general formula (1) according to the present invention for preparing a medicament for the treatment and/or prevention of cancer, infections, inflammatory and autoimmune diseases.

The present invention also relates to pharmaceutical preparation comprising a compound of general formula (1) according to the present invention and at least one other cytostatic or cytotoxic active substance, different from formula (1), optionally in the form of the tautomers, the racemates, the enantiomers, the diastereomers and the mixtures thereof, as well as optionally the pharmacologically acceptable salts thereof.

DEFINITIONS

As used herein the following definitions apply, unless stated otherwise.

By alkyl substituents are meant in each case saturated, unsaturated, straight-chain or branched aliphatic hydrocarbon groups (alkyl group) and this includes both saturated alkyl groups and unsaturated alkenyl and alkynyl groups. Alkenyl substituents are in each case straight-chain or branched, unsaturated alkyl groups, which have at least one double bond. By alkynyl substituents are meant in each case straight-chain or branched, unsaturated alkyl groups, which have at least one triple bond.

The term heteroalkyl refers to groups which can be derived from alkyl as defined above in to its broadest sense by replacing one or more of the groups —$CH_3$ in the hydrocarbon chains independently of one another by the groups —OH, —SH or —$NH_2$, one or more of the groups —$CH_2$— independently of one another by the groups —O—, —S— or —NH—, one or more of the groups

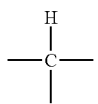

by the group

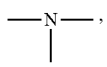

one or more of the groups =CH— by the group =N—, one or more of the groups =$CH_2$ by the group =NH or one or more of the groups ≡CH by the group ≡N, while in all only a maximum of three heteroatoms may be present in a heteroalkyl, there must be at least one carbon atom between two oxygen and between two sulphur atoms or between one oxygen and one sulphur atom and the group as a whole must have chemical stability.

It flows from the indirect definition/derivation from alkyl that heteroalkyl is made up of the sub-groups of saturated hydrocarbon chains with hetero-atom(s), heteroalkenyl and heteroalkynyl, while further subdivision into straight-chain (unbranched) and branched may be carried out. If a heteroalkyl is supposed to be substituted, the substitution may take place independently of one another, in each case mono- or polysubstituted, at all the hydrogen-carrying oxygen, sulphur, nitrogen and/or carbon atoms. Heteroalkyl itself may be linked to the molecule as substituent both through a carbon atom and through a heteroatom.

By way of example, the following representative compounds are listed: dimethylaminomethyl; dimethylaminoethyl (1-dimethylaminoethyl; 2-dimethyl-aminoethyl); dimethylaminopropyl (1-dimethylaminopropyl, 2-dimethylaminopropyl, 3-dimethylaminopropyl); diethylaminomethyl; diethylaminoethyl (1-diethylaminoethyl, 2-diethylaminoethyl); diethylaminopropyl (1-diethylaminopropyl, 2-diethylamino-propyl, 3-diethylaminopropyl); diisopropylaminoethyl (1-diisopropylaminoethyl, 2-di-isopropylaminoethyl); bis-2-methoxyethylamino; [2-(dimethylamino-ethyl)-ethyl-amino]-methyl; 3-[2-(dimethylamino-ethyl)-ethyl-amino]-propyl; hydroxymethyl; 2-hydroxyethyl; 3-hydroxypropyl; methoxy; ethoxy; propoxy; methoxymethyl; 2-methoxyethyl etc.

Haloalkyl relates to alkyl groups, wherein one or more hydrogen atoms are replaced by halogen atoms. Haloalkyl includes both saturated alkyl groups and unsaturated alkenyl and alkynyl groups, such as for example —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —CI=$CH_2$, —C≡C—$CF_3$, —$CHFCH_2CH_3$ and —$CHFCH_2CF_3$.

Halogen refers to fluorine, chlorine, bromine and/or iodine atoms.

$C_{1-3}$haloalkoxy is meant to be $C_{1-3}$haloalkyl-O—.

By cycloalkyl is meant a mono, bicyclic or spirocyclic ring, while the ring system may be a saturated ring or, however, an unsaturated, non-aromatic ring, which may optionally also contain double bonds, such as for example cyclopropyl, cyclopropenyl, cyclobutyl, cyclobutenyl, cyclopentyl, cyclopentenyl, cyclohexyl, cyclohexenyl, norbornyl and norbornenyl.

Cycloalkylalkyl includes a non-cyclic alkyl group wherein a hydrogen atom bound to a carbon atom, usually to a terminal C atom, is replaced by a cycloalkyl group.

Aryl relates to monocyclic or bicyclic aromatic rings with 6-10 carbon atoms such as phenyl and naphthyl, for example.

Arylalkyl includes a non-cyclic alkyl group wherein a hydrogen atom bound to a carbon atom, usually to a terminal C atom, is replaced by an aryl group.

By heteroaryl are meant mono- or bicyclic aromatic rings, which instead of one or more carbon atoms contain one or more, identical or different hetero atoms, such as e.g. nitrogen, sulphur or oxygen atoms. Examples include furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl. Examples of bicyclic heteroaryl groups are indolyl, isoindolyl, benzofuryl, benzothienyl, benzoxazolyl, benzothiazolyl, benzisoxazolyl, benzisothiazolyl, benzimidazolyl, benzopyrazolyl, indazolyl, isoquinolinyl, quinolinyl, quinoxalinyl, cinnolinyl, phthalazinyl, quinazolinyl and benzotriazinyl, indolizinyl, oxazolopyridyl, imidazopyridyl, naphthyridinyl, indolinyl, isochromanyl, chromanyl, tetrahydroisoquinolinyl, isoindolinyl, isobenzotetrahydrofuryl, isobenzotetrahydrothienyl, isobenzothienyl, benzoxazolyl, pyridopyridyl, benzotetrahydrofuryl, benzotetrahydrothienyl, purinyl, benzodioxolyl, triazinyl, phenoxazinyl, phenothiazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridyl-N-oxide tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl-N-oxide, pyrimidinyl-N-oxide, pyridazinyl-N-oxide, pyrazinyl-N-oxide, quinolinyl-N-oxide, indolyl-N-oxide, indolinyl-N-oxide, isoquinolyl-N-oxide, quinazolinyl-N-oxide, quinoxalinyl-N-oxide, phthalazinyl-N-oxide, imidazolyl-N-oxide, isoxazolyl-N-oxide, oxazolyl-N-oxide, thiazolyl-N-oxide, indolizinyl-N-oxide, indazolyl-N-oxide, benzothiazolyl-N- oxide, benzimidazolyl-N-oxide, pyrrolyl-N-oxide, oxadiazolyl-N-oxide, thiadiazolyl-N-oxide, triazolyl-N-oxide, tetrazolyl-N-oxide, benzothiopyranyl-5-oxide and benzothiopyranyl-S,S-dioxide.

Heteroarylalkyl encompasses a non-cyclic alkyl group wherein a hydrogen atom bound to a carbon atom, usually to a terminal C atom, is replaced by a heteroaryl group.

Heterocycloalkyl relates to saturated or unsaturated, non-aromatic mono-, bicyclic, spirocyclic or bridged bicyclic rings comprising 3-14 carbon atoms, which instead of one or more carbon atoms carry heteroatoms, such as nitrogen, oxygen or sulphur. Examples of such heterocyloalkyl groups are tetrahydrofuryl, pyrrolidinyl, pyrrolinyl, imidazolidinyl, imidazolinyl, pyrazolidinyl, pyrazolinyl, piperidinyl, piperazinyl, indolinyl, isoindolinyl, morpholinyl, thiomorpholinyl, homomorpholinyl, homopiperidinyl, homopiperazinyl, homothiomorpholinyl, thiomorpholinyl-5-oxide, thiomorpholinyl-S,S-dioxide, tetrahydropyranyl, tetrahydrothienyl, homothiomorpholinyl-S,S-dioxide, oxazolidinonyl, dihydropyrazolyl, dihydropyrrolyl, dihydropyrazinyl, dihydropyridyl, dihydropyrimidinyl, dihydrofuryl, dihydropyranyl, tetrahydrothienyl-5-oxide, tetrahydrothienyl-S,S-dioxide, homothiomorpholinyl-5-oxide, 2-oxa-5-azabicyclo[2,2,1]heptane, 8-oxa-3-aza-bicyclo[3.2.1]octane, 3.8-diaza-bicyclo[3.2.1]octane, 2,5-diaza-bicyclo[2.2.1]heptane, 3.8-diaza-bicyclo[3.2.1]octane, 3.9-diaza-bicyclo[4.2.1]nonane and 2.6-diaza-bicyclo[3.2.2]nonane, 3,9-diaza-spiro[5.5]undecane, 2,9-diaza-spiro[5.5]undecane, 2,8-diaza-spiro[4.5]decane, 1,8-diaza-spiro[4.5]decane, 3-aza-spiro[5.5]undecane, 1,5-dioxa-9-aza-spiro[5.5]undecane, 2-oxa-9-aza-spiro[5.5]undecane, 3-oxa-9-aza-spiro[5.5]undecane, 8-aza-spiro[4.5]decane, 2-oxa-8-aza-spiro[4.5]decane, 1,4-dioxa-8-aza-spiro[4.5]decane, 3-aza-spiro[5.6]dodecane, 3,9-diaza-spiro[5.6]dodecane, 9-oxa-3-aza-spiro[5.6]dodecane and 1,3,8-triaza-spiro[4.5]decane.

Heterocycloalkylalkyl relates to a non-cyclic alkyl group wherein a hydrogen atom bound to a carbon atom, usually to a terminal C atom, is replaced by a heterocycloalkyl group.

The following Examples illustrate the present invention without restricting its scope.

General Procedure 1 (GP1): Iodination of Pyrimidines or Pyridines

A solution of the pyrimidine or pyridine (1.0 eq.) in acetic acid is cooled to 0° C. and NIS (1.0 eq.) is added in one portion. The reaction mixture is stirred at RT until conversion of the starting material is completed (2-6 h). The mixture is poured on ice-cooled water and treated with a mixture of 5% $Na_2S_2O_3$ and 10% $NaHCO_3$. The precipitate is filtered off, intensely washed with water and dried under vacuum at 40° C. The crude product can be used without further purification or is further purified by chromatography on silica gel using a $CH_2Cl_2$/MeOH gradient.

General Procedure 2 (GP2): Sonogashira Reaction
Method 1:

The halide (1.0 eq.) is dissolved in DMF or THF and 0.1 eq. Pd-catalyst (e.g. $PdCl_2(PPh_3)_2$ or $Pd(PPh_3)_4$) and CuI (0.1 eq.) are added. Subsequently, triethylamine (10.0 eq.) and finally the alkyne (1.5 eq.) are added and the reaction mixture is stirred at 65° C. The reaction is monitored by LC-MS. If the iodide is not completed converted after 4 h, additional amounts of alkyne are added in small portions. The product either precipitates from the reaction mixture (and is filtered off and if necessary re-crystallized) and/or, after removal of the solvent, is purified by preparative RP-HPLC or chromatography on silica gel.

Method 2:

The halide (1.0 eq.) is dissolved in DMSO and $Pd(PPh_3)_4$ (0.1 eq.) and CuI (0.1 eq.) are added. Subsequently, diisopropylamine (0.9 eq.) and finally the alkyne (1.2 eq.) are added. The reaction mixture is put on a pre-heated hot plate and stirred at 80° C. The reaction is monitored by LC-MS. If the halide is not completed converted after 4 h, additional amounts of alkyne are added in small portions. The product either precipitates from the reaction mixture (and is filtered off and if necessary re-crystallized) and/or, after removal of the solvent, is purified by preparative RP-HPLC or flash chromatography on silica gel.

General Procedure 3 (GP3): Desilylation of Alkynes

The TMS-alkyne (1.0 eq.) is dissolved in MeOH, $K_2CO_3$ (0.5 eq.) is added in one portion and the reaction mixture is stirred at RT until conversion is complete (3-16 h). The solvent is removed in vaccuo, the crude product is dissolved in ethyl acetate and the organic phase is extracted with water. The organic phase is dried, filtered off and the solvent removed in vaccuo. The product is either used without further purification or purified by chromatography on silica gel using a DCM/MeOH or (cyclo-)hexane/ethyl acetate.

General Procedure 4 (GP4): Suzuki Coupling

The 4-chloropyrimidine (1.0 eq.) is dissolved in DME/water (20:1 v/v), boronic acid (1.3 eq.), $K_2CO_3$ (2.0 eq.) and $Pd(PPh_3)_4$ (0.2 eq.) are added and the reaction mixture is stirred for 4 h under reflux. In case the conversion of the starting material is not complete, additional amounts of boronic acid and Pd-catalyst are added and the reaction is run over night under reflux. After cooling to RT water is added. The precipitate is filtered off. In cases where the product is not precipitated it is extracted with diethylether, the organic phase is dried, filtered off, and the solvent removed under reduced pressure. The obtained product can either be used without further purification or is purified by chromatography.

General Procedure 8 (GP8): Saponification of Esters

The ester is taken up in either THF or dioxane, 1.1-1.5 eq. of 1 N NaOH are added and the mixture is heated under reflux until reaction control shows complete conversion of the starting material. The product either precipitates from the reaction mixture and is used without additional purification steps or can further be purified by chromatography.

General Procedure 9 (GP9): Amide Formation with Amines

A mixture of 0.21 mmol starting material, 0.31 mmol TBTU or HATU and 0.42 mmol Huenig's base in 2 mL DMSO is stirred for 5 min Subsequently 0.31 mmol of amine is added and the resultant mixture is stirred at RT over night. Purification is performed via preparative RP-HPLC yielding after evaporation of the solvent the desired product.

General Procedure 10 (GP10) Amide Formation with Acid Chlorides

To a mixture of 0.13 mmol of starting material and 67 µL Huenig's base in 2 mL THF is added 0.26 mmol acid chloride. The reaction mixture is stirred over night at RT. The solvent is evaporated and the residue is taken up in 1 mL DMSO. Insoluble material is filtered off and the resulting solution is purified via preparative RP-HPLC yielding after evaporation of the solvent the desired product.

General Procedure 11 (GP11): Urea Formation with Isocyanates

To a mixture of 0.16 mmol of starting material and 64.4 µL Huenig's base in 2 mL THF is added 0.49 mmol isocyanate. The reaction mixture is stirred over night at RT. The solvent is evaporated and the residue is taken up in 1 mL DMSO. Insoluble material is filtered off and the resulting solution is purified via preparative RP-HPLC yielding after evaporation of the solvent the desired product.

General Procedure 12 (GP12): Urea Formation via Pre-activation of the Amine.

A mixture of 0.34 mmol amine and 0.34 mmol N,N'-carbonyldiimidazole and 0.34 mmol 1,8-diazabicyclo[5.4.0]undec-7-ene is stirred for 10 min at RT. Then 0.32 mmol of starting material is added in one portion. The reaction mixture is heated at 100° C. for 1 h in the microwave. The solvent is evaporated and the residue is taken up in 1 mL DMSO. Insoluble material is filtered off and the resulting solution is purified via preparative RP-HPLC yielding the desired product.

General Procedure 13 (GP13): Amide formation with carbonic acids

A mixture of 0.62 mmol carbonic acid, 0.93 mmol TBTU and 1.2 mmol Huenig's base in 2 mL DMSO is stirred for 5 min. Subsequently 0.31 mmol of starting material is added and the resultant mixture is stirred at RT over night. Purification is performed via preparative RP-HPLC yielding after evaporation of the solvent the desired product.

Intermediates A

A-1a) 6-Methyl-3H-pyrimidin-4-one

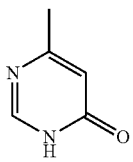

100 g (0.70 mol) 4-Hydroxy-2-mercapto-6-methylpyrimidine and 300 g Raney-Nickel are suspended in water (1000 mL) and the suspension is heated and stirred under reflux over night. Full conversion is detected by TLC (10% MeOH in DCM). The catalyst is filtered off over celite and the filtrate is evaporated to give crude product as a pale green solid. The product is used without further purification for the next step.

A-1b) 5-Iodo-6-methyl-3H-pyrimidin-4-one

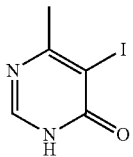

To a stirred solution of 70 g (0.64 mol) 4-hydroxy-6-methylpyrimidine in acetic acid is added 127 g (0.56 mol) NIS portion wise at RT within 15 min. The reaction is stirred for 30 h at RT until all starting material is consumed. The reaction mixture is diluted with water and the solid product is filtered off and washed with sodium thiosulfate solution to remove excess iodine. After drying, the desired product is obtained as a pale brown solid (90 g; 60%) which is used without further purification.

A-1) 4-Chloro-5-iodo-6-methyl-pyrimidin

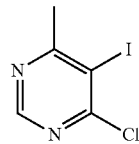

A suspension of 90 g (0.38 mol) 4-hydroxy-5-iodo-6-methylpyrimidine in 600 mL POCl₃ is heated for 1 h at 90° C. The reaction mixture is concentrated under reduced pressure and the residue is poured into crushed ice. The precipitated solid is collected by filtration and washed with water. After drying, the desired product is obtained as a solid (90 g; 93%).

A-2a) 6-Ethyl-3H-pyrimidin-4-one

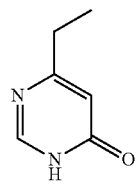

90 g (0.58 mol) 4-Hydroxy-2-mercapto-6-ethyl pyrimidine and 270 g Raney-Nickel are suspended in water (1000 mL). The suspension is heated and stirred under reflux over night. Full conversion is detected by TLC (10% MeOH in DCM). The catalyst is filtered off over celite and the filtrate is evaporated to give crude product as a pale green solid (70.0 g; 98%). The product is used without further purification for the next step.

A-2b) 6-Ethyl-5-iodo-3H-pyrimidin-4-one

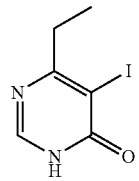

To a stirred solution of 70 g (0.56 mol) 4-hydroxy-6-ethyl pyrimidine in acetic acid is added 127 g (0.56 mol) NIS portion wise at RT within 15 min. The reaction is stirred for 30 h at RT until all starting material is consumed. The reaction mixture is diluted with water and the solid product is filtered off and washed with sodium thiosulfate solution to remove excess iodine. After drying, the desired product is obtained as a solid (90 g; 64%) which is used without further purification.

A-2c) 4-Chloro-5-iodo-6-ethyl-pyrimidin

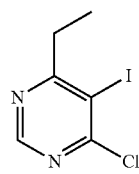

A suspension of 90 g (0.36 mol) 4-hydroxy-5-iodo-6-ethyl pyrimidine in 600 mL POCl₃ is heated for 1 h at 90° C. The reaction mixture is concentrated under reduced pressure and the residue is poured into crushed ice. The precipitated solid is collected by filtration and washed with water. After drying, the desired product is obtained as a solid (65 g; 67%).

A-2) 5-Iodo-3-trifluoromethyl-pyridin-2-ylamine

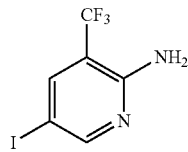 [SMILES: Nc1ncc(I)cc1C(F)(F)F]

The title compound is synthesized according to general procedure GP1 starting from 5.0 g (31 mmol) 3-trifluoropyridin-2-ylamine and 6.9 g (31 mmol) NIS. Yield after precipitation from the reaction mixture: 6.78 g (76%).

A-3) 6-Trifluoromethyl-5-iodo-pyridin-2-ylamine

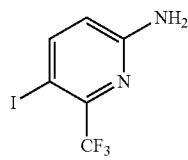 [SMILES: Nc1ccc(I)c(C(F)(F)F)n1]

The title compound is synthesized according to general procedure GP1 starting from 4.8 g (30 mmol) 6-trifluoromethyl-pyridin-2-ylamine and 6.7 g (30 mmol) NIS. Yield after precipitation from the reaction mixture and isolation of additional product from the mother liquid by chromatography in silica gel: 5.73 g (67%).

A-4) 5-Iodo-6-methyl-pyridin-2-ylamine

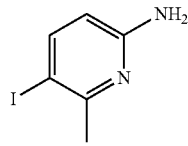

The title compound is synthesized according to general procedure GP1 starting from 2.7 g (25 mmol) 6-methyl-pyridin-2-ylamine and 5.6 g (25 mmol) NIS. Small amounts of the corresponding bis-iodopyridine are formed during the reaction (LC-MS). The reaction mixture is poured into ice upon which the bis-iodo product precipitated. The mother liquid is treated with a mixture of 5% $Na_2S_2O_3$ and 10% $NaHCO_3$ and is subsequently neutralized by addition of 4 N NaOH. The precipitated product is collected by filtration and washed with water. Yield: 4.95 g (85%).

A-5) 6-Ethyl-5-iodo-pyridin-2-ylamine

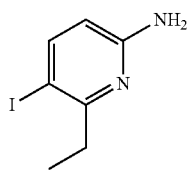

The title compound is synthesized according to general procedure GP1 starting from 10.0 g (83 mmol) 6-ethyl-pyridin-2-ylamine and 18.4 g (83 mmol) NIS. Yield after precipitation from the reaction mixture: 18.0 g (89%).

A-6) 5-Iodo-4-methyl-pyridin-2-ylamine

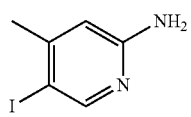

The title compound is synthesized according to general procedure GP1 starting from 2.0 g (18 mmol) 4-methyl-pyridin-2-ylamine and 4.2 g (18 mmol) NIS. Yield after precipitation from the reaction mixture: 3.6 g (83%).

A-7) 4-Ethyl-5-iodo-pyridin-2-ylamine

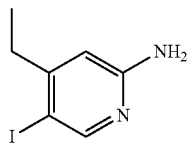

The title compound is synthesized according to general procedure GP1 starting from 5.0 g (41 mmol) 4-ethyl-pyridin-2-ylamine and 9.2 g (41 mmol) NIS. Yield after precipitation from the reaction mixture and isolation of additional product from the mother liquid by chromatography using silica gel: 10.3 g (100%).

A-8) 4-Trifluoromethyl-5-iodo-pyridin-2-ylamine

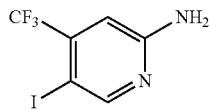

The title compound is synthesized according to general procedure GP1 starting from 20.0 g (123 mmol) 4-trifluoromethyl-pyridin-2-ylamine and 27.8 g (123 mmol) NIS. Yield after precipitation from the reaction mixture and isolation of additional product from the mother liquid by chromatography in silica gel: 20.3 g (57%).

A-9) 3-Fluoro-5-iodo-pyridin-2-ylamine

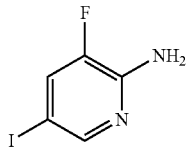

The title compound is synthesized according to general procedure GP1 starting from 200 mg (1.78 mmol) 3-fluoro-pyridin-2-ylamine and 401 mg (1.78 mmol) NIS. Yield after precipitation from the reaction mixture: 380 mg (90%).

A-10) 2-Methyl-5-trimethylsilanylethynyl-pyridine

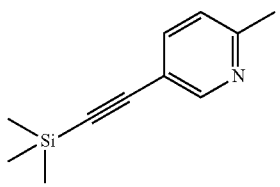

The title compound is synthesized according to general procedure GP2 starting from 2.0 g (11.6 mmol) 5-bromo-pyridin-2-ylamine and 2.3 mL (16.3 mmol) 1-trimethylsilyl-ethyne using 68 mg (0.36 mmol) CuI, 305 mg (1.2 mmol) triphenylphosphine, 213 mg (0.30 mmol) $PdCl_2(PPh_3)_2$ and 18 mL (127 mmol) triethylamine in 18 mL dry THF. For the work-up the reaction mixture is diluted with ethyl acetate, the organic phase is extracted with water and brine. The product is purified by chromatography on silica gel using a hexane/ethyl acetate gradient. Yield: 1.5 g (68%).

A-11) 5-Trimethylsilanylethynyl-pyridin-2-ylamine

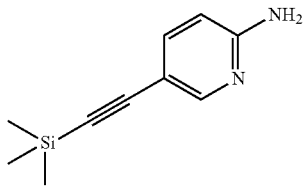

The title compound is synthesized according to general procedure GP2 starting from 5.0 g (28.9 mmol) 5-bromo-pyridin-2-ylamine and 5.7 mL (40.5 mmol) 1-trimethylsilyl-ethyne using 168 mg (0.88 mmol) CuI, 758 mg (2.9 mmol) triphenylphosphine, 533 mg (0.76 mmol) $PdCl_2(PPh_3)_2$ and 40 mL (288 mmol) triethylamine in 40 mL dry THF. For the work-up the reaction mixture is diluted with ethyl acetate and small amounts of cyclohexane, the organic phase is extracted with water and brine. The product is purified by chromatography on silica gel using hexane/ethyl acetate (10/1 v/v). Yield: 5.0 g (91%).

A-12) Methyl-(5-trimethylsilanylethynyl-pyridin-2-yl)-amine

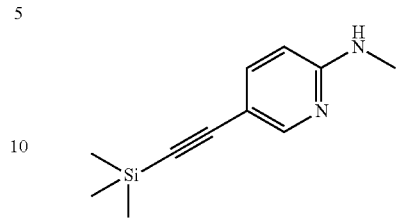

The title compound is synthesized according to general procedure GP2 starting from 4.3 g (23.0 mmol) 5-bromo-2-methylamino-pyridine and 4.5 mL (32.2 mmol) 1-trimethylsilyl-ethyne using 134 mg (0.71 mmol) CuI, 601 mg (2.3 mmol) triphenylphosphine, 420 mg (0.60 mmol) $PdCl_2$ $(PPh_3)_2$ and 32 mL (101 mmol) triethylamine in 40 mL dry THF. For the work-up the reaction mixture is diluted with ethyl acetate and small amounts of cyclohexane, the organic phase is extracted with water and brine. The product is purified by chromatography on silica gel using a hexane/ethyl acetate gradient. Yield: 4.0 g (85%).

A-13) Ethyl-(5-trimethylsilanylethynyl-pyridin-2-yl)-amine

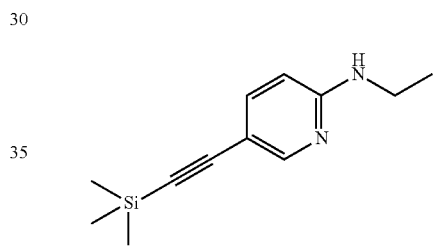

The title compound is synthesized according to general procedure GP2 starting from 909 mg (4.5 mmol) 5-bromo-2-ethylamino-pyridine and 0.89 mL (6.3 mmol) 1-trimethylsilyl-ethyne using 26 mg (0.13 mmol) CuI, 118 mg (0.45 mmol) triphenylphosphine, 82 mg (0.12 mmol) $PdCl_2(PPh_3)_2$ and 6.3 mL (45.0 mmol) triethylamine in 7 mL dry THF. For the work-up the reaction mixture is diluted with ethyl acetate and small amounts of cyclohexane, the organic phase is extracted with water and brine. The product is purified by chromatography on silica gel using a hexane/ethyl acetate gradient. Yield: 980 mg (99%).

A-14) 4-Trifluoromethyl-5-trimethylsilanylethynyl-pyridin-2-ylamine

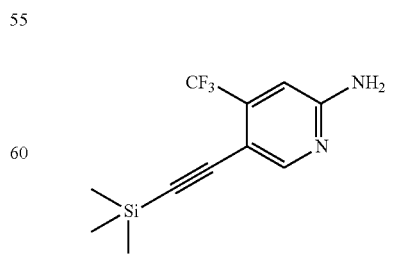

The title compound is synthesized according to general procedure GP2 starting from 12.8 g (44 mmol) 4-trifluoromethyl-5-iodo-pyridin-2-ylamine and 8.8 mL (62 mmol) 1-trimethyl-silyl-ethyne using 844 mg (4.4 mmol) CuI, 3.1 g (4.4 mmol) PdCl$_2$(PPh$_3$)$_2$ and 62 mL (443 mmol) triethylamine in 80 mL dry THF. For the work-up the solvent is removed under reduced pressure, the crude product is taken up in ethyl acetate and the organic phase is extracted with water. The product is purified twice by chromatography on silica gel using a DCM/MeOH gradient. Yield: 5.85 g (51%).

A-15) 6-Trifluoromethyl-5-trimethylsilanylethynyl-pyridin-2-ylamine

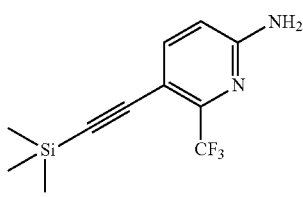 [SMILES: C[Si](C)(C)C#Cc1ccc(N)nc1C(F)(F)F]

The title compound is synthesized according to general procedure GP2 starting from 5.7 g (20 mmol) 6-trifluoromethyl-5-iodo-pyridin-2-ylamine and 3.9 mL (28 mmol) 1-trimethyl-silyl-ethyne using 379 mg (2.0 mmol) CuI, 1.4 g (2.0 mmol) PdCl$_2$(PPh$_3$)$_2$ and 28 mL (199 mmol) triethylamine in 30 mL dry THF. For the work-up the solvent is removed under reduced pressure, the crude product is taken up in ethyl acetate and the organic phase is extracted with water. The product is purified by chromatography on silica gel using a DCM/MeOH gradient. Yield: 2.83 g (55%).

A-16) 4-Methyl-5-trimethylsilanylethynyl-pyridin-2-ylamine

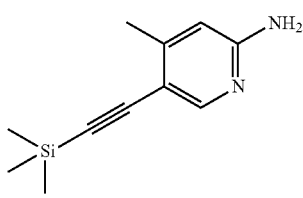

The title compound is synthesized according to general procedure GP2 starting from 3.3 g (14.1 mmol) 4-methyl-5-iodo-pyridin-2-ylamine and 2.8 mL (19.7 mmol) 1-trimethyl-silyl-ethyne using 81 mg (1.4 mmol) CuI, 296 mg (0.42 mmol) PdCl$_2$(PPh$_3$)$_2$, 370 mg (1.4 mmol) triphenylphosphine and 20 mL (141 mmol) triethylamine in 25 mL dry THF. After cooling to RT, the mixture is filtered and the product is isolated from the filtrate by chromatography on silica gel using a DCM/MeOH gradient. Yield: 2.75 g (95%).

A-17) 6-Methyl-5-trimethylsilanylethynyl-pyridin-2-ylamine

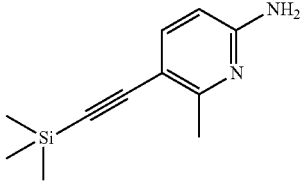

The title compound is synthesized according to general procedure GP2 starting from 5.0 g (21.4 mmol) 6-methyl-5-iodo-pyridin-2-ylamine and 4.5 mL (32 mmol) 1-trimethyl-silyl-ethyne using 407 mg (2.1 mmol) CuI, 2.0 g (2.1 mmol) Pd(PPh$_3$)$_4$ and 30 mL (214 mmol) triethylamine in 40 mL dry DMF. For the work-up the solvent is removed under reduced pressure and the product is purified twice by chromatography on silica gel using a DCM/MeOH gradient. Yield: 4.2 g (96%).

A-18) 4-Ethyl-5-trimethylsilanylethynyl-pyridin-2-ylamine

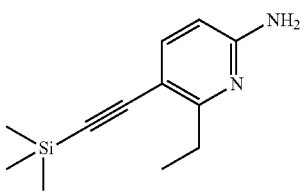

The title compound is synthesized according to general procedure GP2 starting from 10.3 g (41.6 mmol) 4-ethyl-5-iodo-pyridin-2-ylamine and 8.2 mL (58.2 mmol) 1-trimethyl-silyl-ethyne using 792 mg (4.2 mmol) CuI, 2.9 g (4.2 mmol) PdCl$_2$(PPh$_3$)$_2$ and 58 mL (416 mmol) triethylamine in 140 mL dry THF. For the work-up the solvent is removed under reduced pressure, the crude product is taken up in ethyl acetate and the organic phase is extracted with water. The product is purified twice by chromatography on silica gel using a cyclohexane/ethyl acetate gradient. Yield: 9.08 g (100%).

A-19) 6-Ethyl-5-trimethylsilanylethynyl-pyridin-2-ylamine

The title compound is synthesized according to general procedure GP2 starting from 18 g (72.6 mmol) 6-ethyl-5-iodo-pyridin-2-ylamine and 14.4 mL (102 mmol) 1-trimethyl-silyl-ethyne using 1.38 g (7.3 mmol) CuI, 5.1 g (7.3 mmol) PdCl$_2$(PPh$_3$)$_2$ and 101 mL (726 mmol) triethylamine in 100 mL dry THF. For the work-up the solvent is removed under reduced pressure, the crude product is taken up in ethyl acetate and the organic phase is extracted with water. The product is purified twice by chromatography on silica gel using a cyclohexane/ethyl acetate gradient. Yield: 12.73 g (80%).

A-20) 5-Trimethylsilanylethynyl-pyridin-3-ol

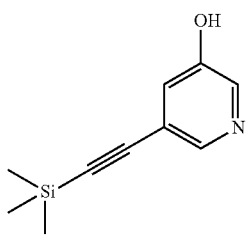

The title compound is synthesized according to general procedure GP2 starting from 2.0 g (11.6 mmol) 5-bromo-3-hydroxy-pyridine and 2.3 mL (16.2 mmol) 1-trimethylsilyl-ethyne to using 66 mg (0.3 mmol) CuI, 303 mg (1.2 mmol) triphenylphosphine, 243 mg (0.3 mmol) PdCl$_2$(PPh$_3$)$_2$ and 19 mL (139 mmol) triethylamine in 20 mL dry THF. For the work-up the reaction mixture is diluted with ethyl acetate and small amounts of cyclohexane, the organic phase is extracted with water and brine. The product is purified by chromatography on silica gel using a DCM/MeOH gradient. Yield: 2.0 g (91%).

A-21) 5-Trimethylsilanylethynyl-pyridin-3-ylamine

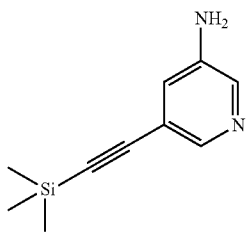

The title compound is synthesized according to general procedure GP2 starting from 2.0 g (11.6 mmol) 5-bromo-pyridin-3-ylamine and 2.3 mL (16.2 mmol) 1-trimethylsilyl-ethyne using 66 mg (0.3 mmol) CuI, 303 mg (1.2 mmol) triphenylphosphine, 243 mg (0.3 mmol) PdCl$_2$(PPh$_3$)$_2$ and 19 mL (139 mmol) triethylamine in 20 mL dry THF. For the work-up the reaction mixture is diluted with ethyl acetate and small amounts of cyclohexane, the organic phase is extracted with water and brine. The product is purified by chromatography on silica gel using a DCM/MeOH gradient. The product precipitated on the column and was subsequently extracted from the silica gel with pure MeOH. Yield: 2.0 g (91%).

A-22) 5-Trimethylsilanylethynyl-1H-pyrazolo[3,4-b]pyridine

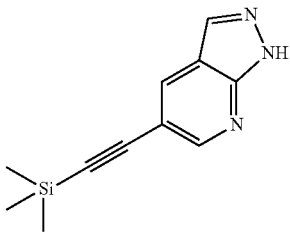

The title compound is synthesized according to general procedure GP2 starting from 1.0 g (5.1 mmol) 5-bromo-1H-pyrazolo[4,5-b]pyridine and 1.0 mL (7.1 mmol) 1-trimethylsilyl-ethyne using 29 mg (0.15 mmol) CuI, 133 mg (0.51 mmol) triphenylphosphine, 106 mg (0.15 mmol) PdCl$_2$(PPh$_3$)$_2$ and 8.4 mL (60.6 mmol) triethylamine in 8 mL dry THF. The formed precipitate is filtered off and the product is purified by RP-HPLC using an ACN/H$_2$O gradient. Yield: 542 mg (50%).

A-23) 5-Trimethylsilanylethynyl-1H-pyrrolo[2,3-b]pyridine

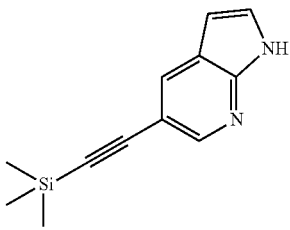

The title compound is synthesized according to general procedure GP2 starting from 3.0 g (15.2 mmol) 5-bromo-1H-pyrrolo[2,3-B]pyridine and 3.0 mL (21.3 mmol) 1-trimethylsilyl-ethyne using 87 mg (0.46 mmol) CuI, 400 mg (1.5 mmol) triphenylphosphine, 312 mg (0.46 mmol) PdCl$_2$(PPh$_3$)$_2$ and 25.4 mL (182 mmol) triethylamine in 25 mL dry THF. The formed precipitate is filtered off and the product is purified by chromatography on silica gel using a DCM/MeOH gradient. Yield: 3.05 g (94%).

A-24) 6-Trimethylsilanylethynyl-3H-imidazo[4,5-b]pyridine

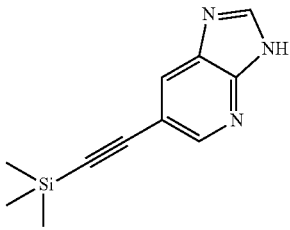

The title compound is synthesized according to general procedure GP2 starting from 1.2 g (6.1 mmol) 5-bromo-3H- imidazol[4,5-b]pyridine and 1.2 mL (8.4 mmol) 1-trimethylsilyl-ethyne using 34 mg (0.18 mmol) CuI, 159 mg (0.61 mmol) triphenylphosphine, 128 mg (0.18 mmol) PdCl$_2$(PPh$_3$)$_2$ and 10.1 mL (72.7 mmol) triethylamine in 10 mL dry THF. The formed precipitate is filtered off and the product is purified by RP-HPLC using an ACN/H$_2$O gradient. Yield: 606 mg (46%).

A-25) 5-Ethynyl-2-methyl-pyridine

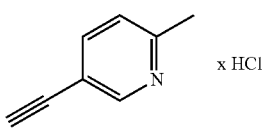

The title compound is synthesized according to general procedure GP3 starting from 2.2 g (12 mmol) 2-methyl-5-trimethylsilanylethynyl-pyridine and 0.80 g (5.8 mmol) K$_2$CO$_3$ in 13 mL MeOH. The crude product is purified by chromatography on silica gel using a cyclohexane/ethyl acetate gradient. The product is extracted from the organic phase with 1 N HCl and isolated as the hydrochloride after lyophilization. Yield: 1.3 g (73%).

A-26) 5-Ethynyl-pyridin-2-ylamine

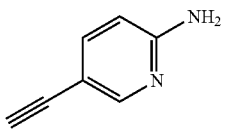

The title compound is synthesized according to general procedure GP3 starting from 5.5 g (29 mmol) 5-trimethylsilanylethynyl-pyridin-2-ylamine and 2.0 g (14 mmol) K$_2$CO$_3$ in 30 mL MeOH. The product is purified by chromatography on silica gel using a hexane/ethyl acetate gradient. Yield: 2.9 g (85%).

A-27) (5-Ethynyl-pyridin-2-yl)-methyl-amine

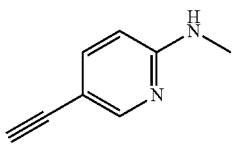

The title compound is synthesized according to general procedure GP3 starting from 1.5 g (7.3 mmol) methyl-(5-trimethylsilanylethynyl-pyridin-2-yl)-amine and 507 mg (3.7 mmol) K$_2$CO$_3$ in 10 mL MeOH. Yield: 698 mg (56%) after chromatography on silica gel.

A-28) (5-Ethynyl-pyridin-2-yl)-ethyl-amine

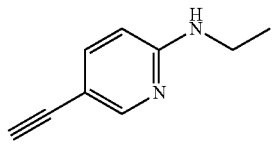

The title compound is synthesized according to general procedure GP3 starting from 980 mg (4.5 mmol) TMS-alkyne and 310 mg (2.3 mmol) K$_2$CO$_3$ in 6 mL MeOH. Yield: 388 mg (59%) after chromatography on silica gel.

A-29) 5-Ethynyl-4-trifluoromethyl-pyridin-2-ylamine

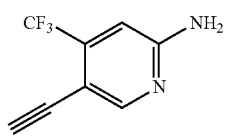

The title compound is synthesized according to general procedure GP3 starting from 5.9 g (22.6 mmol) 4-trifluoromethyl-5-trimethylsilanylethynyl-pyridin-2-ylamine and 1.56 g to (11.3 mmol) K$_2$CO$_3$ in 50 mL MeOH. The product is purified by chromatography on silica gel using a DCM/MeOH gradient. Yield: 2.97 g (71%).

A-30) 5-Ethynyl-6-trifluoromethyl-pyridin-2-ylamine

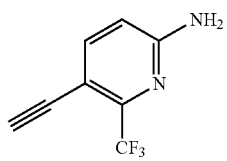

The title compound is synthesized according to general procedure GP3 starting from 2.82 g (11.0 mmol) 6-trifluoromethyl-5-trimethylsilanylethynyl-pyridin-2-ylamine and 757 mg (5.5 mmol) K$_2$CO$_3$ in 25 mL MeOH. The product is purified by chromatography on silica gel using a cyclohexane/ethyl acetate gradient. Yield: 0.9 g (44%).

A-31) 5-Ethynyl-4-methyl-pyridin-2-ylamine

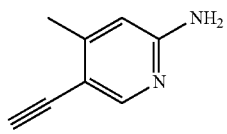

The title compound is synthesized according to general procedure GP3 starting from 1.8 g (8.8 mmol) 4-methyl-5-trimethylsilanylethynyl-pyridin-2-ylamine and 609 mg (4.4 mmol) K₂CO₃ in 315 mL MeOH. The product is purified by chromatography on silica gel using a DCM/MeOH gradient. Yield: 1.0 g (86%).

A-32) 5-Ethynyl-6-methyl-pyridin-2-ylamine

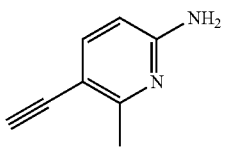

The title compound is synthesized according to general procedure GP3 starting from 4.3 g (21.0 mmol) 6-methyl-5-trimethylsilanylethynyl-pyridin-2-ylamine and 1.5 g (10.5 mmol) K₂CO₃ in 30 mL MeOH. The product is purified by chromatography on silica gel using a DCM/MeOH gradient. Yield: 3.6 g.

A-33) 4-Ethyl-5-ethynyl-pyridin-2-ylamine

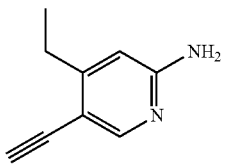

The title compound is synthesized according to general procedure GP3 starting from 3.3 g (15 mmol) 4-ethyl-5-trimethylsilanylethynyl-pyridin-2-ylamine and 1.04 g (7.5 mmol) K₂CO₃ in 30 mL MeOH. The product is purified by chromatography on silica gel using a DCM/MeOH gradient. Yield: 1.78 g (81%).

A-34) 6-Ethyl-5-ethynyl-pyridin-2-ylamine

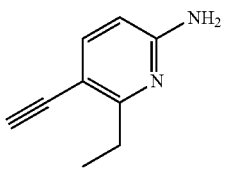

The title compound is synthesized according to general procedure GP3 starting from 12.23 g (56 mmol) 6-ethyl-5-trimethylsilanylethynyl-pyridin-2-ylamine and 3.87 g (28 mmol) K₂CO₃ in 120 mL MeOH. The product is purified by chromatography on silica gel using a DCM/MeOH gradient. Yield: 4.5 g (85%).

A-35) 5-Ethynyl-pyridin-3-ol

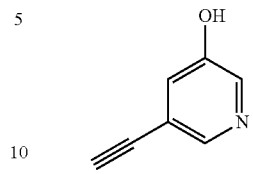

The title compound is synthesized according to general procedure GP3 starting from 2.0 g (10.5 mmol) TMS-alkyne and 722 mg (5.2 mmol) K₂CO₃ in 10 mL MeOH. Yield: 804 mg (49%) after chromatography on silica gel.

A-36) 5-Ethynyl-pyridin-3-ylamine

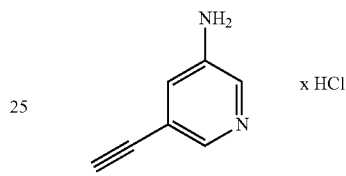

The title compound is synthesized according to general procedure GP3 starting from 2.0 g (11 mmol) TMS-alkyne and 722 mg (5.2 mmol) K₂CO₃ in 10 mL MeOH. Yield: 1.2 g (74%) after chromatography on silica gel and precipitation from dioxane/HCl.

A-37) 5-Ethynyl-1H-pyrazolo[3,4-b]pyridine

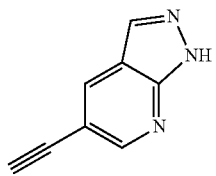

The title compound is synthesized according to general procedure GP3 starting from 542 mg (2.5 mmol) TMS-alkyne and 174 mg (1.3 mmol) K₂CO₃ in 6 mL MeOH. Yield: 330 mg (92%) after extraction.

A-38) 5-Ethynyl-1H-pyrrolo[2,3-b]pyridine

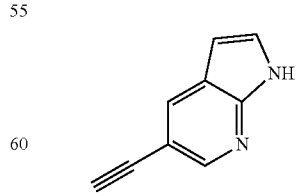

The title compound is synthesized according to general procedure GP3 starting from 3.1 g (14 mmol) TMS-alkyne and 983 mg (7.1 mmol) K₂CO₃ in 15 mL MeOH. Yield: 1.2 g (61%) after chromatography on silica gel.

A-39) 6-Ethynyl-3H-imidazo[4,5-b]pyridine

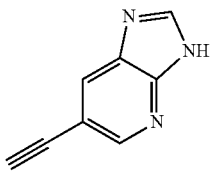

The title compound is synthesized according to general procedure GP3 starting from 706 mg (3.3 mmol) TMS-alkyne and 227 mg (1.6 mmol) K$_2$CO$_3$ in 6 mL MeOH. Yield: 491 mg (94%) after extraction.

A-40) 4-Chloro-6-methyl-5-pyridin-3-ylethynyl-pyrimidine

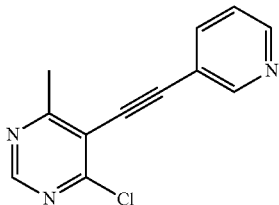 [SMILES: Cc1ncnc(Cl)c1C#Cc1cccnc1]

The title compound is synthesized according to general procedure GP2 starting from 250 mg (1.0 mmol) 4-chloro-5-iodo-6-methyl-pyrimidin using 123 mg (1.2 mmol) 3-ethynyl-pyridine, 18 mg (0.10 mmol) CuI, 34 mg (0.05 mmol) bis-(triphenylphoshine)palladium(II) chloride, 0.5 mL triethylamine in 2 mL DMF. The reaction mixture is stirred for 3 h at 60° C. After removal of the solvent under reduced pressure, the product is purified by PR-HPLC. Yield: 25 mg (11%).

A-41) 5-(6-Amino-pyridin-3-ylethynyl)-4-chloro-6-methyl-pyrimidine

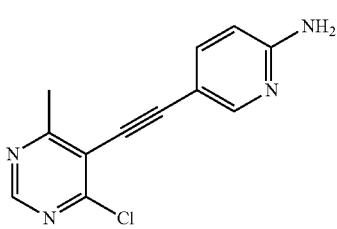 [SMILES: Cc1ncnc(Cl)c1C#Cc1ccc(N)nc1]

The title compound can be synthesized according to general procedure GP2 starting from 30 g (0.11 mol) 4-chloro-5-iodo-6-methyl-pyrimidin (A-1) and 26.4 g (0.22 mol) of 5-ethynyl-pyridin-2-ylamie (A-36) using 2.1 g (11 mmol) copper iodide and 7.9 g (11 mmol) bis(triphenylphosphine) palladium chloride and triethylamine in 600 mL THF. After work up and chromatography (silica, eluent 5% MeOH in DCM) 13 g (45%) of the desired product is obtained.

A-42) 4-Chloro-6-ethyl-5-(6-methyl-pyridin-3-yl-ethynyl)-pyrimidine

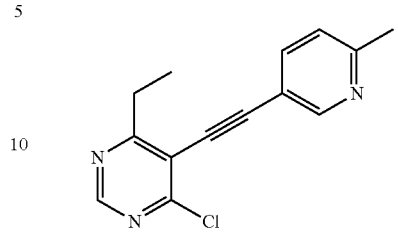

The title compound is synthesized according to general procedure GP2 starting from 250 mg (1.0 mmol) 4-chloro-6-ethyl-5-iodo-pyrimidine using 121.5 mg (1.2 mmol) 5-ethynyl-2-methyl-pyridine, 18 mg (0.10 mmol) CuI, 34 mg (0.05 mmol) bis-(triphenylphoshine)palladium(II) chloride, 0.5 mL triethylamine in 2 mL DMF. The reaction mixture is stirred for 3 h at 60° C. After removal of the solvent under reduced pressure, the product is purified by PR-HPLC. Yield: 25 mg (11%).

A-43) 5-(6-Amino-pyridin-3-ylethynyl)-4-chloro-6-ethyl-pyrimidine

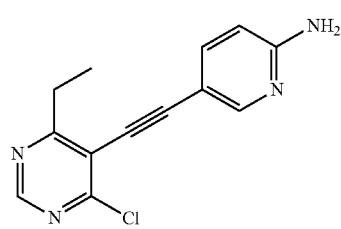 [SMILES: CCc1ncnc(Cl)c1C#Cc1ccc(N)nc1]

To a stirred solution of 60 g (0.22 mol) 4-chloro-5-iodo-6-ethyl-pyrimidin (A-2) in 1200 mL THF under argon is added 4.2 g (22 mmol) CuI and 15.7 g (22 mmol) bis(triphenylphosphine)palladium chloride. The reaction mixture is purged with argon for 30 min 15.7 g (0.22 mol) of 5-ethynyl-pyridin-2-ylamie (A-36) and triethylamine is added and the reaction mixture is heated at 60° C. for 4 h. After work up and chromatography (silica, eluent 5% MeOH in DCM) 26 g (45%) of the desired product is obtained.

A-44) 5-(6-Amino-2-methyl-pyridin-3-ylethynyl)-4-chloro-6-ethyl-pyrimidine

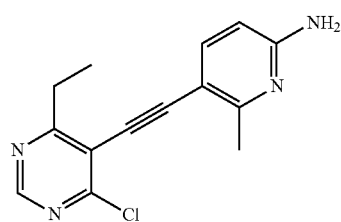 [SMILES: CCc1ncnc(Cl)c1C#Cc1ccc(N)nc1C]

The title compound is synthesized according to general procedure GP2 starting from 6.0 g (22.3 mmol) 4-chloro-6-ethyl-5-iodo-pyrimidine using 3.5 g (26.8 mmol) 5-ethynyl-6-methyl-pyridin-2-ylamine, 213 mg (1.1 mmol) CuI, 1.57 g (2.2 mmol) bis-(triphenyl-phoshine)palladium(II) chloride, 15 mL (112 mmol) triethylamine in 100 mL DME. The reaction mixture is stirred over night at RT. After removal of the solvent under reduced pressure, the residue is taken up in water and ethylacetate and the aqueous phase is extracted twice with ethylacetate. The combined organic phases are dried over MgSO$_4$, filtered over silica and the solvent is removed under reduced pressure. Yield: 2.9 g (64%)

A-45) [5-(4-Chloro-6-ethyl-pyrimidin-5-ylethynyl)-pyridin-2-yl]-methyl-amine

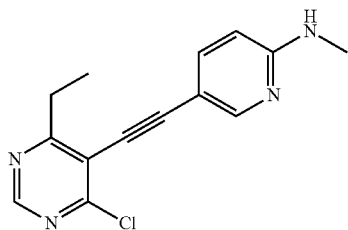 [SMILES: CCc1ncnc(Cl)c1C#Cc1ccc(NC)nc1]

The title compound is synthesized according to general procedure GP2 starting from 0.89 g (2.6 mmol) 4-chloro-6-ethyl-5-iodo-pyrimidine using 0.48 g (3.65 mmol) (5-Ethynyl-pyridin-2-yl)-methyl-amine, 40 mg (0.21 mmol) CuI, 180 mg (0.26 mmol) bis-(triphenyl-phoshine)palladium(II) chloride, 3.6 mL (26.1 mmol) triethylamine in 5.5 mL THF. The reaction mixture is stirred over night at 65° C. After removal of the solvent under reduced pressure, the residue is taken up in water and ethylacetate and the aqueous phase is extracted twice with ethylacetate. The combined organic phases are dried over MgSO$_4$, filtered over silica and the solvent is removed under reduced pressure. Yield: 320 mg (46%).

A-46) [5-(4-Chloro-6-ethyl-pyrimidin-5-ylethynyl)-pyridin-2-yl]-ethyl-amine

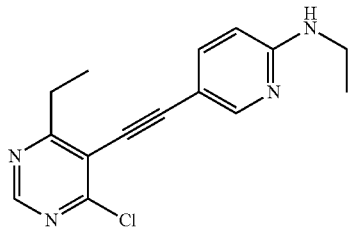 [SMILES: CCNc1ccc(C#Cc2c(Cl)ncnc2CC)cn1]

The title compound is synthesized according to general procedure GP2 starting from 4-chloro-6-ethyl-5-iodo-pyrimidine using 5-Ethynyl-pyridin-2-yl)-ethyl-amine (A-28), CuI, bis-(triphenyl-phoshine)palladium(II) chloride, triethylamine in THF. After work-up the desired compound is obtained in good yield and acceptable purity.

H2) 4-Bromo-2,6-difluorobenzoic acid

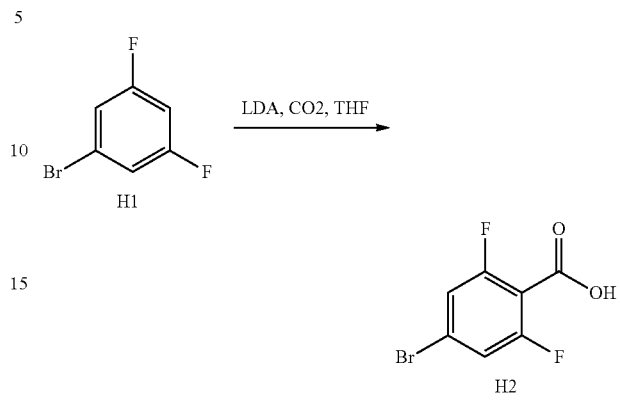

A solution of diisoporpylamine (32 g, 0.31 mol) in THF (170 ml) is added n-BuLi (116 ml, 0.30 mol) drop wise, while keeping inner temperature below −65° C. The mixture is stirred at −50° C. for 1 h to get LDA solution. To a solution of compound III (50 g, 0.26 mol) in THF (170 mL) is added LDA, while keeping inner temperature below −65° C., then stirred for 1.5 h and CO$_2$ is added at −65° C., followed adjusting pH to 2-3 with 1 N HCl, and extracted with EtOAc (3×500 ml). The organic layer is dried by Na$_2$SO$_4$, concentrated in vacuo to get compound H2 (39.0 g, 63.4%).

H3) 4-Bromo-2,6-difluorobenzoic acid methyl ester

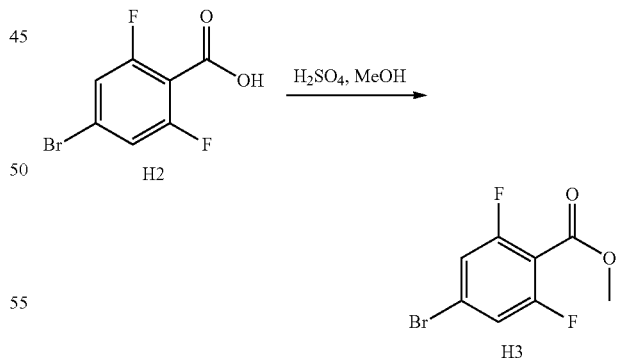

To a suspension of compound H2 (52.5 g, 0.23 mol) in MeOH (320 mL) is added H$_2$SO$_4$ (98%) slowly. The reaction mixture is refluxed until TLC shows the starting material is consumed completely. The solvent is removed and the resulting reside is partioned between saturated NaHCO$_3$ and EtOAc. The organic layer is dried over anhydrous Na$_2$SO$_4$ and concentrated under vacuum to give product 113 (50.0 g, 90.0%).

A-47) 2,6-Difluoro-4-(4,4,5,5-tetramethyl-[1,3,2]dioxaborolan-2-yl)-benzoicacid methyl ester

H6) 4-Bromo-2-chloro-6-fluorobenzoic acid methyl ester

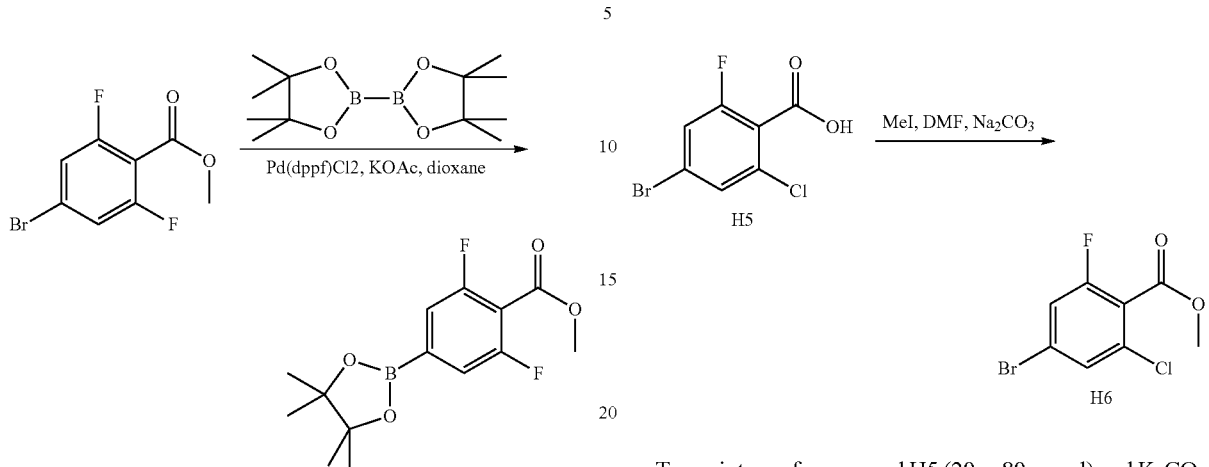

A suspension of compound H3 (50.0 g, 0.20 mol), Bis(pinacolato)diborn (53.3 g, 0.21 mol), Pd(dppf)Cl$_2$ (15.0 g, 0.02 mol) and KOAc (61.5 g, 0.6 mol) in dixoane (400 mL) is heated to 70° C. quickly for 2 h. The dixoane is evaporated in vacuo and the resulting reside is washed with PE. The collected organic solution is concentrated in vacuo. The crude product is crystallized from PE to give A-47 (52.76 g, 89.0%).

To a mixture of compound H5 (20 g, 80 mmol) and K$_2$CO$_3$ (13.2 g, 96 mmol) in DMF (200 mL) is added methyl iodide (23 g, 160 mmol). The mixture is stirred at ambient temperature for 2 h, poured into water (600 mL) and extracted with DCM (2×200 mL). The combined organic layers are washed with water, brine, dried, and concentrated under reduced pressure to provide a brown oil, purified by chromatography on silica gel (PE: EtOAc=100:1) to give compound H6 (isomer, 8 g, 49% for 2 steps) as a light yellow oil.

H5) 4-Bromo-2-chloro-6-fluorobenzoic acid

A-48) 2-Chloro 6-fluoro-4-(4,4,5,5-tetramethyl-[1,3,2]dioxaborolan-2-yl)-benzoicacid methyl ester

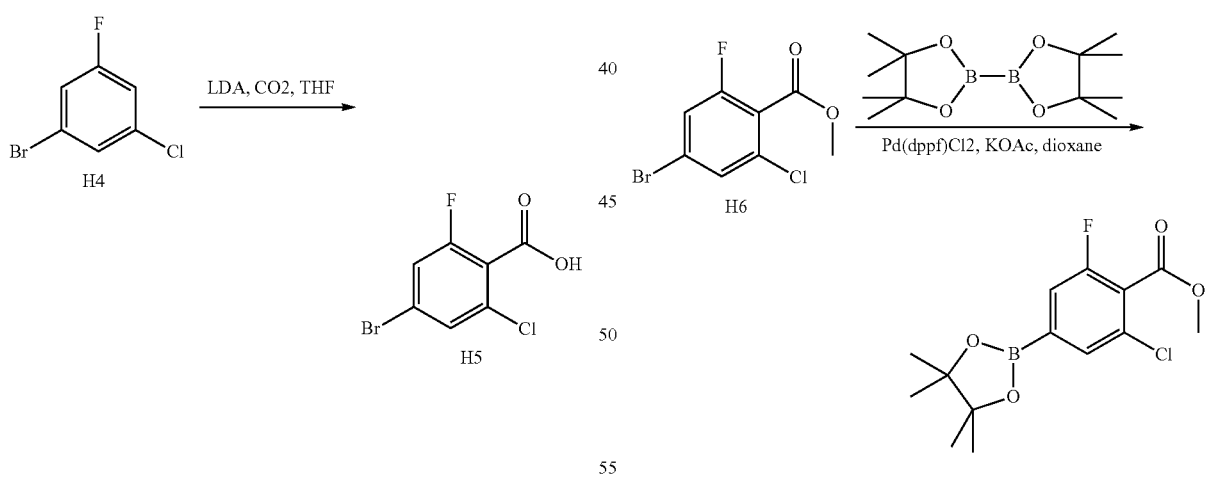

To a solution of diisopropylamine (2.4 g, 24 mmol) in THF (40 mL) is added n-BuLi (8.8 mL, 22 mmol) dropwise at −78° C. The mixture is stirred at −78° C. for 1 h, and then allowed to warm to 0° C. The resulting solution is transferred to a solution of compound H4 (4.16 g, 20 mmol) in THF (60 mL) at −78° C. and stirred for 1 h, followed bubbling with dry CO$_2$ for another 1 h. The obtained solution is quenched with 1 N HCl (50 mL) at 0° C. and extracted with EtOAc (2×50 mL). The organic layers are washed with saturated aq. NaHCO$_3$ and brine, dried and concentrated to afford a crude product 115 (isomer, 5 g, crude) as a brown oil, used for the next step directly.

A mixture of compound H6 (18 g, 68 mmol), bis(pinacolato)diboron (17.3 g, 68 mmol), Pd(dppf)Cl$_2$ (2.5 g, 3.4 mmol) and KOAc (20 g, 0.2 mol) in dioxane (300 mL) is heated to 80° C. for 2 h, and concentrated to dryness under reduced pressure. The resulting residue is purified by chromatography on silica gel (PE: EtOAc=150:1) to give crude product as a clear oil, followed recrystallization with hexane to give A-48 (5.5 g, 35.7%) as a white solid.

H8) 2,6-Dichloro-benzoic acid methyl ester

H10) 4-Bromo-2-trifluoromethyl-benzoic acid methyl ester

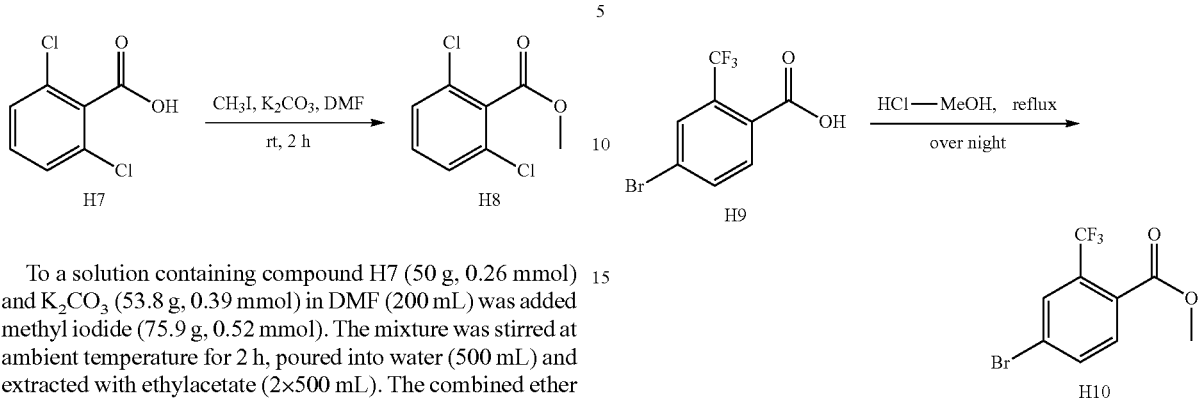

To a solution containing compound H7 (50 g, 0.26 mmol) and K₂CO₃ (53.8 g, 0.39 mmol) in DMF (200 mL) was added methyl iodide (75.9 g, 0.52 mmol). The mixture was stirred at ambient temperature for 2 h, poured into water (500 mL) and extracted with ethylacetate (2×500 mL). The combined ether layers were washed with water, brine, dried, filtered, and concentrated under reduced pressure to provide compound H8 (45 g, 83%) as a yellow oil, $R_f$=0.8 (petrolether:ethylacetate=10:1).

A-49A) 2,6-Dichloro-4-(4,4,5,5-tetramethyl-[1,3,2]dioxaborolan-2-yl)-benzoicacid methyl ester A solution of compound H9 (25.0 g, 94 mmol) in HCl-MeOH (250 mL) was refluxed overnight. TLC showed the starting material was consumed completely. The MeOH was evaporated in vacuo. And the resulting reside was partitioned between saturated NaHCO₃ and EtOAc. The organic layer was dried over anhydrous Na₂SO₄ and concentrated under vacuum to give product H10 (23.5 g; 90.0%).

A-49B) 2-Trifluoromethyl-4-(4,4,5,5-tetramethyl-[1,3,2]dioxaborolan-2-yl)-benzoicacid methyl ester

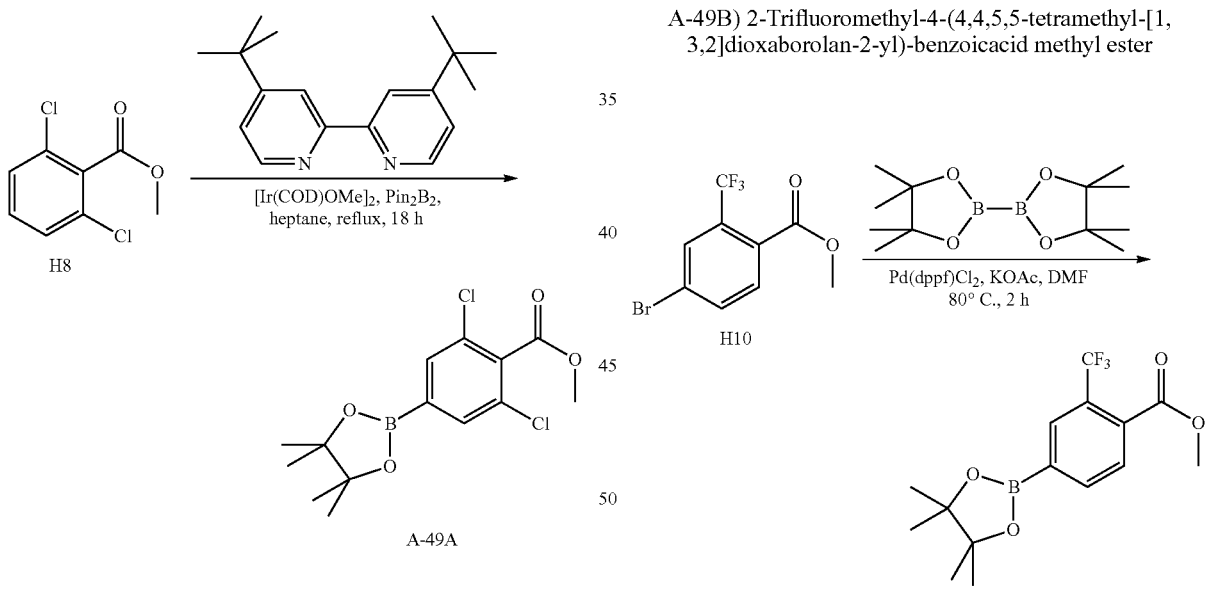

Bis(pinacolato)diboron [Pin₂B₂] (44.8 g, 176 mmol), 4,4'-Di-tert-butyl-[2,2]bipyridinyl (120 mg, 0.44 mmol), and [Ir(COD)(OMe)]₂ (147 mg, 0.22 mmol) were added to a solution of compound H8 (45 g, 0.22 mol) in heptane (500 mL). The reaction mixture turned from yellow to forest green to brick red within the first minute. The reaction mixture was heated to reflux for 18 h and then partitioned between ethyl acetate and water. The organic extracts were combined, dried over Na₂SO₄ and concentrated under reduced pressure. The solid residue was purified by chromatography on silica gel (PE: EtOAc=50:1, detected by boric indicator) to afford the title compound (A-49A) as a white solid (41.0 g, 53%). $R_f$=0.4 (petrolether: ethylacetate=20:1).

A suspension of compound H10 (23.5 g, 83.3 mmol), Bis(pinacolato)diboron (21 g, 83.3 mmol), Pd(dppf)Cl₂ (6 g, 8.3 mmol) and KOAc (24 g, 25 mmol) in DMF (400 mL) was heated to 80° C. quickly for 2 h. The solvent was evaporated in vacuo. The resulting residue was dissolved in PE, filtered and the filtrate was collected. The resulting filtrate was concentrated in vacuo to give crude product, crystallized in petrolether to give A-49B (10.8 g; 40%).

H12) 4-Bromo-2-trifluoromethoxy-benzoic acid methyl ester

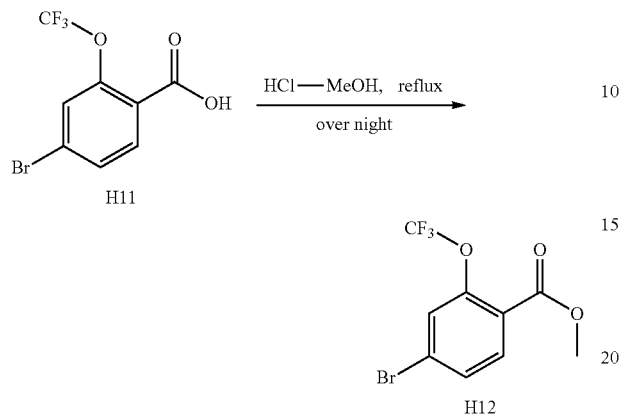

To a suspension of compound H11 (30.0 g, 0.11 mol) in 4 M MeOH—HCl (500 mL) was refluxed overnight. The MeOH was evaporated in vacuo. And the resulting reside was partitioned between saturated $Na_2CO_3$ and EtOAc. The organic layer was dried over anhydrous $Na_2SO_4$ and concentrated under vacuum to give product H12 (24.0 g; 77%).

A-49C) 2-Trifluoromethoxy-4-(4,4,5,5-tetramethyl-[1,3,2]dioxaborolan-2-yl)-benzoicacid methyl ester

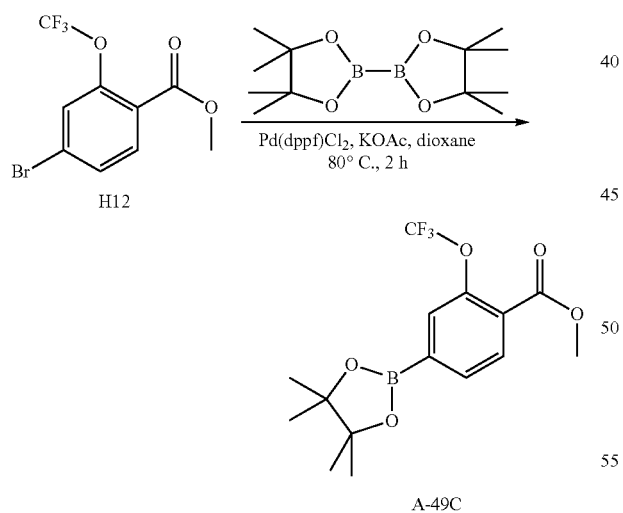

A suspension of compound H12 (24 g, 0.08 mol), Bis(pinacolato)diboron (20.4 g, 0.08 mol) Pd(dppf)$Cl_2$(1.0 g) and KOAc (15.68 g, 0.16 mol) in dixoane (400 mL) was heated to 80° C. quickly for 2 h. The solvent was evaporated in vacuo and the resulting residue was dissolved in petrolether, filtered and the filtrate was collected. The resulting filtrate was concentrated in vacuo to give crude product, crystallized in petrolether to give A-49C (15.0 g; 63.2%).

A-50) 4-[5-(6-Amino-2-methyl-pyridin-3-ylethynyl)-6-ethyl-pyrimidin-4-yl]-2-fluoro-benzoic acid methyl ester

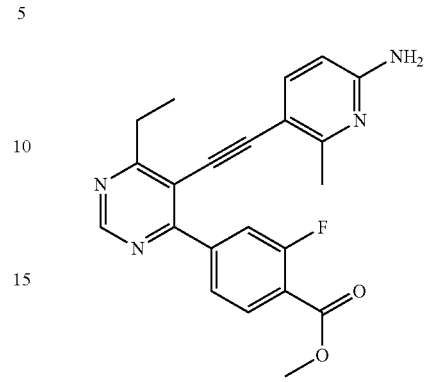

The title compound is synthesized in analogy to general procedure GP4 starting from 3.9 g (14.3 mmol) 5-(6-Amino-2-methyl-pyridin-3-ylethynyl)-4-chloro-6-ethyl-pyrimidine using 3.7 g (18.6 mmol) 3-fluoro-4-methoxycarbonylphenyl boronic acid, 502 g (0.71 mmol) bis-(triphenylphoshine)palladium(II) chloride, 10.7 mL (21.5 mmol) of an aqueous 2 M $Cs_2CO_3$ and 10 mL EtOH in 100 mL DME. The reaction mixture is stirred over night at 80° C. The reaction mixture is filtered over celite and the solvent is removed under reduced pressure. The crude product is triturated with water and ethylacetate. The phases are separated and the aqueous is extracted twice with ethylacetate. The combined organic layers are dried over Mg2SO$_4$ and the solvent is evaporated under reduced pressure. The crude is stirred with cyclohexane and filtered off. After drying 4.0 g (72%) of the desired product is obtained as solid material, which is used without further purification in the next step.

A-51) 4-[5-(6-Amino-2-methyl-pyridin-3-ylethynyl)-6-ethyl-pyrimidin-4-yl]-2-fluoro-benzoic acid

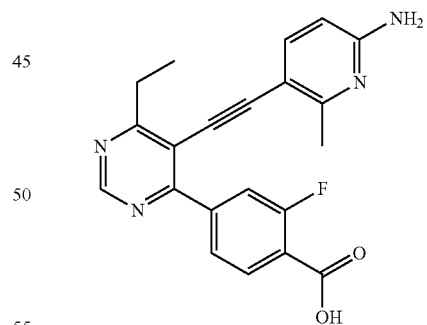

The title compound is synthesized according to general procedure GP8 starting from 4.0 g (10.3 mmol) 4-[5-(6-Amino-2-methyl-pyridin-3-ylethynyl)-6-ethyl-pyrimidin-4-yl]-2-fluoro-benzoic acid methyl ester using 1.29 g (30.7 mmol.) LiOH in 40 mL water and 200 mL THF. The reaction mixture is stirred over night at 50° C. The solvent is removed under reduced pressure and the residie is taken up in water. Aqueous 1 M HCl is added until pH 5 is reached. The precipitated product is filtered off and washed with ACN. After drying 1.3 g (32%) of the desired product are obtained a solid material.

A-52) 5-[5-(6-Amino-pyridin-3-ylethynyl)-6-ethyl-pyrimidin-4-yl]-pyridine-2-carboxylic acid

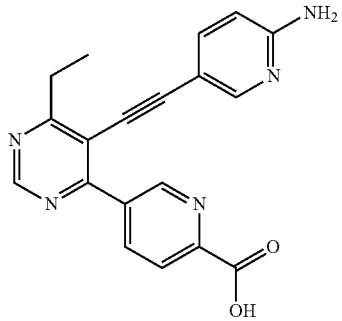 [SMILES: CCc1ncnc(-c2ccc(C(=O)O)nc2)c1C#Cc1ccc(N)nc1]

The title compound is synthesized in analogy to general procedure GP4 starting from 1.2 g (4.63 mmol) 4-chloro-6-ethyl-5-(6-amino-pyridin-3-ylethynyl)-pyrimidine using 1.0 g (5.6 mmol) 4-methoxycarbonyl-3-pyridyl boronic acid, 163 mg (0.23 mmol) bis-(triphenylphoshine)palladium(II) chloride, 7.0 mL (13.9 mmol) of an aqueous 2 M $Cs_2CO_3$ and 2 mL MeOH in 10 mL DME. The reaction mixture is stirred over night at 80° C. The reaction mixture is poured on water and washed with DCM. Aqueous 1 M HCl is added to the aqueous phase until pH 5 is reached. The precipitated product is filtered off and washed with water and methanol. After drying 290 mg (13%) of the desired product are obtained a solid material which is used for the next step without further purification.

A-72) 4-[5-(6-Amino-pyridin-3-ylethynyl)-6-ethyl-pyrimidin-4-yl]-2-fluoro-benzoic acid methyl ester

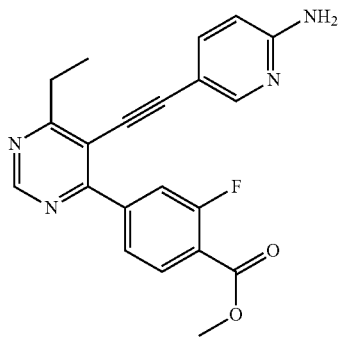

The title compound is synthesized in analogy to general procedure GP4 starting from 15 g (58.06 mmol) 4-chloro-6-ethyl-5-(6-amino-pyridin-3-ylethynyl)-pyrimidine using 13.8 g (69.6 mmol) 3-fluoro-4-methoxycarbonylphenyl boronic acid, 1.51 g (2.15 mmol) bis-(triphenylphoshine)palladium(II) chloride, 43.5 mL (87.0 mmol) of an aqueous 2 M $Cs_2CO_3$ and 20 mL EtOH in 200 mL DME. The reaction mixture is stirred over night at 80° C. The reaction mixture is filtered over celite and the solvent is removed under reduced pressure. The crude product is triturated with water and sonicated for 30 min. The precipitated product is filtered off, washed with ACN and a small amount of MeOH. After drying 14.8 g (6.8%) of the desired product is obtained as solid material.

A-73) 4-[5-(6-Amino-pyridin-3-ylethynyl)-6-ethyl-pyrimidin-4-yl]-2-fluoro-benzoic acid

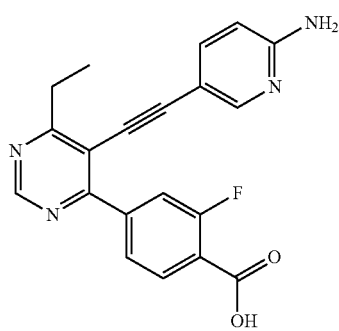

The title compound is synthesized according to general procedure GP8 starting from 17.8 g (47.3 mmol) 4-[5-(6-amino-pyridin-3-ylethynyl)-6-ethyl-pyrimidin-4-yl]-2-fluoro-benzoic acid methyl ester using 3.97 g (94.6 mmol.) LiOH in 30 mL water and 300 mL THF. The reaction mixture is stirred over night at RT. The solvent is removed under reduced pressure and the residie is taken up in water. Aqueous 1 M HCl is added until pH 5 is reached. The precipitated product is filtered off and washed with ACN. After drying 17.1 g (85%) of the desired product are obtained a solid material.

A-74) 4-[5-(6-Amino-pyridin-3-ylethynyl)-6-ethyl-pyrimidin-4-yl]-benzoic acid methyl ester

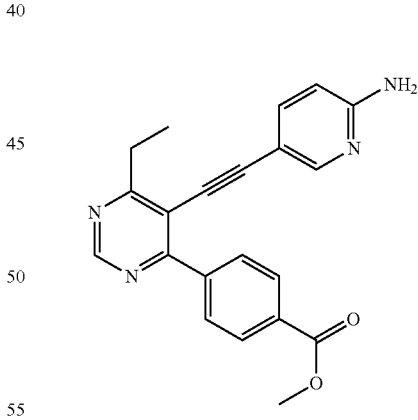

The title compound is synthesized according to general procedure GP4 starting from 2.0 g (7.73 mmol) 4-chloro-6-ethyl-5-(6-amino-pyridin-3-ylethynyl)-pyrimidine using 2.1 g (11.6 mmol) 4-methoxycarbonylphenyl boronic acid, 271.3 mg (0.39 mmol) bis-(triphenylphoshine)palladium(II) chloride, 5.7 mL (11.5 mmol) of an aqueous 2 M $Cs_2CO_3$ solution and 2 mL EtOH in 5 mL DME. The reaction mixture is stirred for 1 h at 130° C. in the microwave. The reaction mixture is suspended in MeOH and the precipitated product is filtered off and washed with MeOH. After drying 2.25 g (81%) of the desired product are obtained as solid material.

A-75) 4-[5-(6-Amino-pyridin-3-ylethynyl)-6-ethyl-pyrimidin-4-yl]-benzoic acid

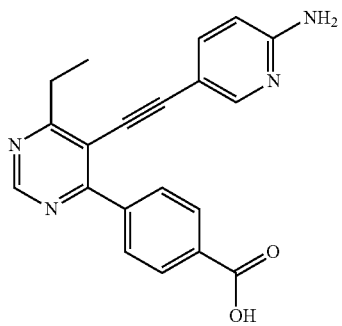 [SMILES: CCc1ncnc(-c2ccc(C(=O)O)cc2)c1C#Cc1ccc(N)nc1]

The title compound is synthesized according to general procedure GP8 starting from 2.25 g (6.28 mmol) 4-[5-(6-amino-pyridin-3-ylethynyl)-6-ethyl-pyrimidin-4-yl]-benzoic acid methyl ester using 1.32 g (31.4 mmol.) LiOH in 5 mL water and 50 mL THF. The reaction mixture is stirred over night at 50° C. The solvent is removed under reduced pressure and the residue is taken up in water. Aqueous 1 M HCl is added until pH 5 is reached. The precipitated product is filtered off and taken up in water. After freeze drying 2.3 g of crude product are obtained which is used for the next step without further purification.

A-76) 4-[5-(6-Amino-pyridin-3-ylethynyl)-6-ethyl-pyrimidin-4-yl]-2-chloro-benzoic acid methyl ester

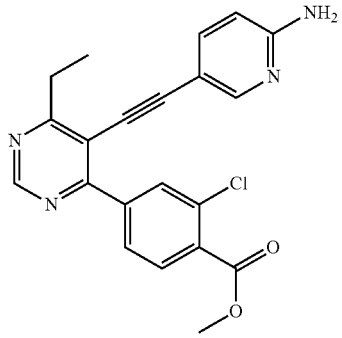 [SMILES: CCc1ncnc(-c2ccc(C(=O)OC)c(Cl)c2)c1C#Cc1ccc(N)nc1]

The title compound is synthesized according to general procedure GP4 starting from 4.0 g (15.5 mmol) 4-chloro-6-ethyl-5-(6-amino-pyridin-3-ylethynyl)-pyrimidine using 4.3 g (20.1 mmol) 3-chloro-4-methoxycarbonylphenyl boronic acid, 543 mg (0.77 mmol) bis-(triphenylphoshine)palladium (II) chloride, 11.6 mL (23.2 mmol) of an aqueous 2 M $Cs_2CO_3$ and 10 mL EtOH in 100 mL DME. The reaction mixture is stirred over night at 80° C. The solvent is removed under reduced pressure and the residue is taken up in water and ethylacetate. The aqueous phase is extracted twice with ethylacetate. The combined organic layers are dried over $MgSO_4$ filtered over celite and the solvent is removed under reduced pressure. After drying 3.3 g (54%) of the desired product is obtained.

A-77) 4-[5-(6-Amino-pyridin-3-ylethynyl)-6-ethyl-pyrimidin-4-yl]-2-chloro-benzoic acid

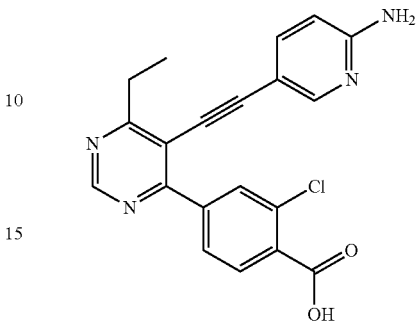

The title compound is synthesized according to general procedure GP8 starting from 3.3 g (8.4 mmol) 4-[5-(6-amino-pyridin-3-ylethynyl)-6-ethyl-pyrimidin-4-yl]-2-chloro-benzoic acid methyl ester using 1.06 g (25.2 mmol.) LiOH in 20 mL water and 100 mL THF. The reaction mixture is stirred over night at 50° C. The solvent is removed under reduced pressure and the residue is taken up in water. Aqueous 1 M HCl is added until pH 5-6 is reached. The precipitated product is filtered off and washed with water and MeOH. After drying 2.5 g (89%) of the desired product are obtained as solid material.

A-78) 4-[5-(6-Amino-pyridin-3-ylethynyl)-6-methyl-pyrimidin-4-yl]-benzoic acid methyl ester The title compound is synthesized according to general procedure GP4 starting from 2.0 g (8.2 mmol) 4-chloro-6-methyl-5-(6-amino-pyridin-3-ylethynyl)-pyrimidine using 2.2 g (12.3 mmol) 4-methoxycarbonylphenyl boronic acid, 240 mg (1.5 mmol) 287 mg (0.41 mmol) bis-(triphenylphoshine)palladium(II) chloride, 6.1 mL (12.3 mmol) of an aqueous 2 M $Cs_2CO_3$ and 2 mL EtOH in 5 mL DME. The reaction mixture is stirred for 1 h at 130° C. in the microwave. The reaction mixture is suspended in MeOH and the precipitated to product is filtered off and washed with MeOH. After drying 2.2 g (77%) of the desired product are obtained as solid material.

A-79) 4-[5-(6-Amino-pyridin-3-ylethynyl)-6-methyl-pyrimidin-4-yl]-benzoic acid

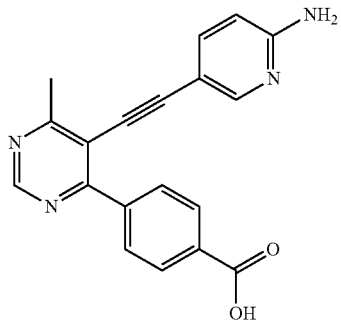 [SMILES: Cc1ncnc(-c2ccc(C(=O)O)cc2)c1C#Cc1ccc(N)nc1]

The title compound is synthesized according to general procedure GP8 starting from 2.2 g (6.3 mmol) 4-[5-(6-amino-pyridin-3-ylethynyl)-6-methyl-pyrimidin-4-yl]-benzoic acid methyl ester using 1.33 g (31.6 mmol.) LiOH in 5 mL water and 50 mL THF. The reaction mixture is stirred over night at 50° C. The solvent is removed under reduced pressure and the residue is taken up in water. Aqueous 1 M HCl is added until pH 5 is reached. The precipitated product is filtered off and taken up in water. After freeze drying 2.7 g of crude product are obtained which is used for the next step without further purification.

A-80) 4-[5-(6-Amino-pyridin-3-ylethynyl)-6-methyl-pyrimidin-4-yl]-2-chloro benzoic acid methyl ester

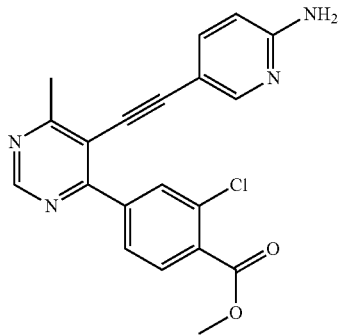 [SMILES: COC(=O)c1ccc(-c2ncnc(C)c2C#Cc2ccc(N)nc2)cc1Cl]

The title compound is synthesized according to general procedure GP4 starting from 10 g (40.9 mmol) 4-chloro-6-methyl-5-(6-amino-pyridin-3-ylethynyl)-pyrimidine using 10.5 g (49.0 mmol) 2-chloro-4-methoxycarbonylphenyl boronic acid, 1.43 g (2.04 mmol) bis-(triphenylphosphine) palladium(II) chloride, 61.3 mL (122 mmol) of an aqueous 2 M $Cs_2CO_3$ solution and 50 mL EtOH in 500 mL DME. The reaction mixture is stirred for 3 h at 80° C. The reaction mixture is filtered over celite and the solvent is removed under reduced to pressure. Water is added and the precipitated product is filtered off and washed with ACN and MeOH. After drying 13.8 g of crude product are obtained which is used in the next step without further purification.

A-81) 4-[5-(6-Amino-pyridin-3-ylethynyl)-6-methyl-pyrimidin-4-yl]-2-chloro benzoic acid

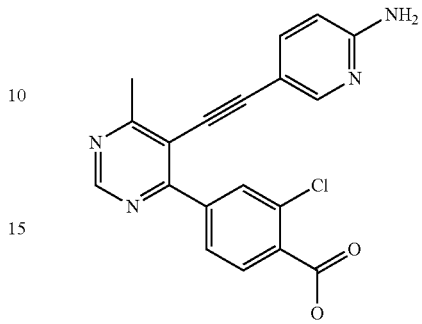

The title compound is synthesized according to general procedure GP8 starting from 13.8 g (36.4 mmol) 4-[5-(6-amino-pyridin-3-ylethynyl)-6-methyl-pyrimidin-4-yl]-2-chloro-benzoic acid methyl ester using 7.64 g (182 mmol.) LiOH in 200 mL water and 400 mL THF. The reaction mixture is stirred over night at 50° C. The solvent is removed under reduced pressure and the residue is taken up in water. Aqueous 1 M HCl is added until pH 5-6 is reached. The precipitated product is filtered off and washed with water and MeOH. After drying 12.1 g of the desired product is obtained, which is used for the next step without further purification.

A-82) 4-[5-(6-amino-pyridin-3-ylethynyl)-6-methyl-pyrimidin-4-yl]-2-fluoro benzoic acid methyl ester (C-45)

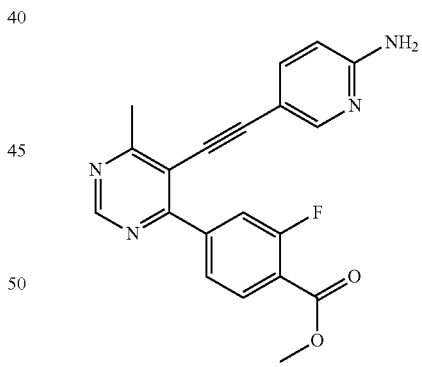

The title compound is synthesized according to general procedure GP4 starting from 2.0 g (8.2 mmol) 4-chloro-6-methyl-5-(6-amino-pyridin-3-ylethynyl)-pyrimidine using 2.9 g (14.7 mmol) 2-fluoro-4-methoxycarbonylphenyl boronic acid, 287 mg (0.41 mmol) bis-(triphenylphoshine) palladium(II) chloride, 6.1 mL (12.3 mmol) of an aqueous 2 M $Cs_2CO_3$ solution and 2 mL EtOH in 5 mL DME. The reaction mixture is stirred for 1 h at 130° C. in the microwave. The reaction mixture is suspended in MeOH and the precipitated product is filtered off and washed with MeOH. After drying, 2.3 g (77%) of the desired product is obtained as solid material.

A-83) 4-[5-(6-Amino-pyridin-3-ylethynyl)-6-methyl-pyrimidin-4-yl]-2-fluoro benzoic acid

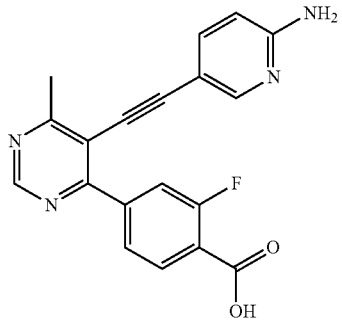 [SMILES: Cc1ncnc(-c2ccc(C(=O)O)c(F)c2)c1C#Cc1ccc(N)nc1]

The title compound is synthesized according to general procedure GP8 starting from 2.28 g (6.29 mmol) 4-[5-(6-amino-pyridin-3-ylethynyl)-6-methyl-pyrimidin-4-yl]-2-fluoro benzoic acid methyl ester using 1.32 g (31.5 mmol.) LiOH in 5 mL water and 50 mL THF. The reaction mixture is stirred over night at 50° C. The solvent is removed under reduced pressure and the residue is taken up in water. Aqueous 1 M HCl is added until pH 5 is reached. The precipitated product is filtered off and taken up in water. After freeze drying 2.7 g of crude product is obtained which is used for the next step without further purification.

A-84) 5-[5-(6-Amino-pyridin-3-ylethynyl)-6-ethyl-pyrimidin-4-yl]-2-fluoro-benzoic acid methyl ester

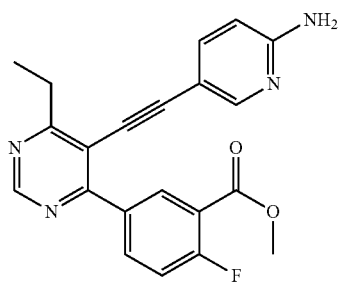 [SMILES: CCc1ncnc(-c2ccc(F)c(C(=O)OC)c2)c1C#Cc1ccc(N)nc1]

The title compound is synthesized according to general procedure GP4 starting from 1.5 g (5.8 mmol) 4-chloro-6-ethyl-5-(6-amino-pyridin-3-ylethynyl)-pyrimidine using 1.7 g (8.7 mmol) (4-fluoro-3-methoxycarbonyl)phenyl boronic acid, 203 mg (0.29 mmol) bis-(triphenylphoshine)palladium (II) chloride, 1.94 g (13.9 mmol) $K_2CO_3$ in 18 mL DME/$H_2O$/EtOH (10:5:1 v/v/v). The reaction mixture is stirred for 3 h at 80° C. The mixture is filtered over celite and the solvent is removed under reduced pressure. Water is added and the precipitated product is filtered off and washed with ACN and MeOH. After drying 1.5 g (68%) of crude product is obtained which is used for the next step without further purification.

A-85) 5-[5-(6-Amino-pyridin-3-ylethynyl)-6-ethyl-pyrimidin-4-yl]-2-fluoro-benzoic acid

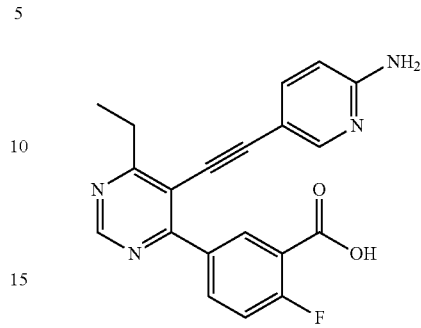

The title compound is synthesized according to general procedure GP8 starting from 1.5 g (3.98 mmol) 5-[5-(6-amino-pyridin-3-ylethynyl)-6-ethyl-pyrimidin-4-yl]-2-fluoro-benzoic acid methyl ester using 334 mg (7.97 mmol) LiOH in 20 mL THF and 5 mL water. The reaction mixture is stirred over night at 50° C. Aqueous 1 M HCl is added until pH 5 is reached. The solvent is removed under reduced pressure and the residue is stirred in MeOH. After drying the crude product (0.8 g) is used in the next step without further purification.

A-86) 4-[5-(6-Amino-2-methyl-pyridin-3-ylethynyl)-6-ethyl-pyrimidin-4-yl]-2-fluoro-benzoic acid methyl ester

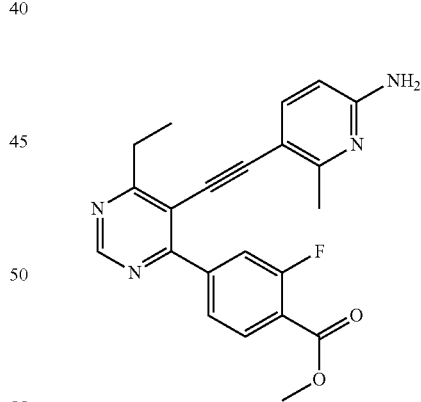

The title compound is synthesized according to general procedure GP4 starting from 3.90 g (14.3 mmol) 4-chloro-6-ethyl-5-(6-amino-2-methyl-pyridin-3-ylethynyl)-pyrimidine using 3.38 g (18.6 mmol) 3-fluoro-4-methoxycarbonylphenyl boronic acid, 502 mg (0.71 mmol) bis-(triphenylphoshine) palladium(II) chloride, 10.7 mL (21.5 mmol) of an aqueous 2 M $Cs_2CO_3$ solution and 10 mL EtOH in 100 mL DME. The reaction mixture is stirred over night at 80° C. The solvent is removed under reduced pressure and the residue is taken up in water and ethylacetate. The aqueous phase is extracted twice with ethylacetate. The combined organic layers are dried over MgSO₄ filtered over celite and the solvent is removed under reduced pressure. After drying 4.0 g (72%) of the desired product is obtained.

A-87) 4-[5-(6-Amino-2-methyl-pyridin-3-ylethynyl)-6-ethyl-pyrimidin-4-yl]-2-fluoro-benzoic acid

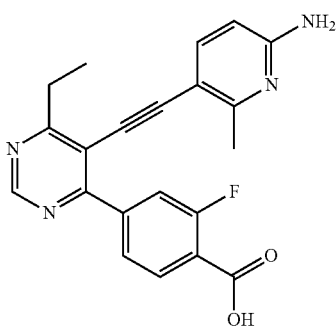 [SMILES: CCc1ncnc(-c2ccc(C(=O)O)c(F)c2)c1C#Cc1ccc(N)nc1C]

The title compound is synthesized according to general procedure GP8 starting from 4.0 g (10.2 mmol) 4-[5-(6-amino-2-methyl-pyridin-3-ylethynyl)-6-ethyl-pyrimidin-4-yl]-2-fluoro-benzoic acid methyl ester using 1.29 g (30.7 mmol.) LiOH in 40 mL water and 200 mL THF. The reaction mixture is stirred over night at 50° C. The THF is removed under reduced pressure and the residue is taken up in water. Aqueous 1 M HCl is added until pH 5-6 is reached. The precipitated product is filtered off and washed with water and MeOH. After drying 1.25 g (32%) of the desired product is obtained a solid material.

A-92) 4-[5-(6-Amino-pyridin-3-ylethynyl)-6-ethyl-pyrimidin-4-yl]-2-methoxy-benzoic acid methyl ester

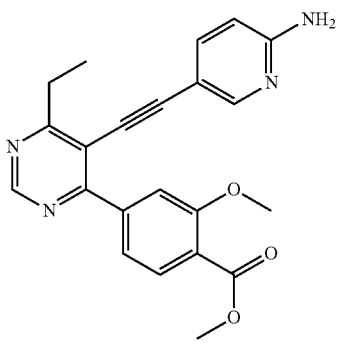 [SMILES: CCc1ncnc(-c2ccc(C(=O)OC)c(OC)c2)c1C#Cc1ccc(N)nc1]

The title compound is synthesized according to general procedure GP4 starting from 2.5 g (9.7 mmol) 4-chloro-6-ethyl-5-(6-amino-pyridin-3-ylethynyl)-pyrimidine using 2.4 g (11.6 mmol) 3-methoxy-4-methoxycarbonylphenyl boronic acid, 339 mg (0.48 mmol) bis-(triphenylphoshine) palladium(II) chloride, 14 mL (28.2 mmol) of an aqueous 2 M Cs₂CO₃ and 5 mL MeOH in 50 mL DME. The reaction mixture is stirred for 2 hours at 90° C. The solvent is removed under reduced pressure and the residue is taken up in water and ethylacetate. The aqueous phase is extracted twice with ethylacetate. The combined organic layers are dried over MgSO₄ filtered over celite and the solvent is removed under reduced pressure. After drying 3.3 g (89%) of the desired product is obtained.

A-93) 4-[5-(6-Amino-pyridin-3-ylethynyl)-6-ethyl-pyrimidin-4-yl]-2-methoxy-benzoic acid

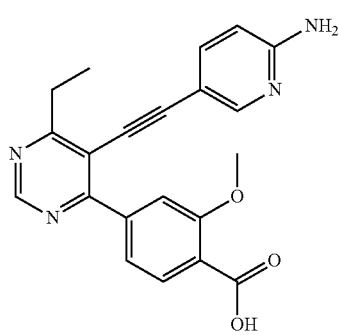 [SMILES: CCc1ncnc(-c2ccc(C(=O)O)c(OC)c2)c1C#Cc1ccc(N)nc1]

The title compound is synthesized according to general procedure GP8 starting from 7.5 g (19.3 mmol) 4-[5-(6-amino-pyridin-3-ylethynyl)-6-ethyl-pyrimidin-4-yl]-2-methoxy-benzoic acid methyl ester using 4.05 g (96.5 mmol.) LiOH in 100 mL water and 200 mL THF. The reaction mixture is stirred over night at room temperature. The solvent is removed under reduced pressure and the residue is taken up in water. Aqueous 1 M HCl is added until pH 5-6 is reached. The precipitated product is filtered off and washed with water and Acetonitrile. After drying 6.5 g (89%) of the desired product is obtained as solid material.

Intermediates A-94 to A-96G can be synthesized according to the general procedure GP4 (Suzuki reaction) outlined above. The appropriate halides required for synthesis can be deduced from the table of examples.

TABLE 1A

Examples A-94-A-96G

| Nr. | Structure | Int. 1 | Int. 2 | MW | MW [M + H] |
|---|---|---|---|---|---|
| A-94 | 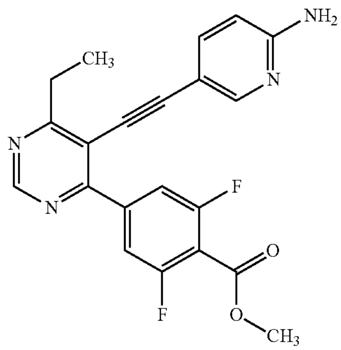 [SMILES: CCc1ncnc(-c2cc(F)c(C(=O)OC)c(F)c2)c1C#Cc1ccc(N)nc1] | A-43 | A-47 | 394.38 | 395 |
| A-95 | 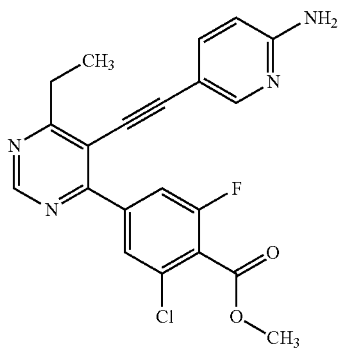 | A-43 | A-48 | 410.84 | 412 |
| A-96 | 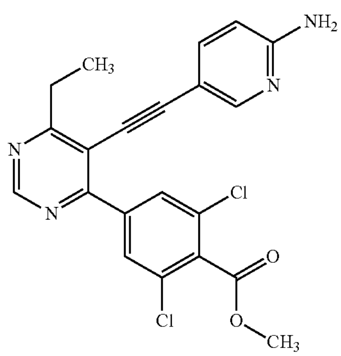 [SMILES: CCc1ncnc(-c2cc(Cl)c(C(=O)OC)c(Cl)c2)c1C#Cc1ccc(N)nc1] | A-43 | 3,5-dichloro-4-methoxycarbonyl-phenyl boronic acid | 427.29 | 428 |
| A-96A | 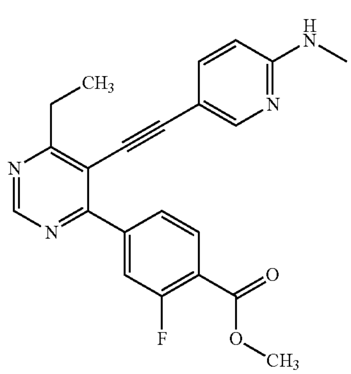 [SMILES: CCc1ncnc(-c2ccc(C(=O)OC)c(F)c2)c1C#Cc1ccc(NC)nc1] | A-45 | A-49A | 390.42 | 392 |

TABLE 1A-continued

Examples A-94-A-96G

| Nr. | Structure | Int. 1 | Int. 2 | MW | MW [M + H] |
|---|---|---|---|---|---|
| A-96B | 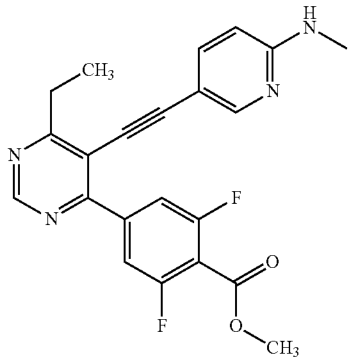 [SMILES: CCc1ncnc(-c2cc(F)c(C(=O)OC)c(F)c2)c1C#Cc1ccc(NC)nc1] | A-45 | A-47 | 408.40 | 410 |
| A-96C | 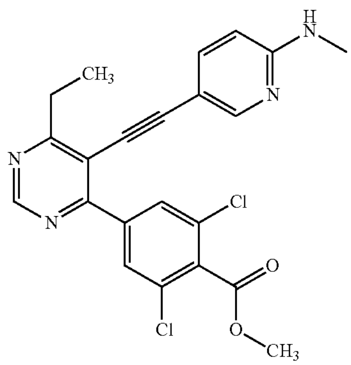 | A-45 | A-49A | 441.32 | 443 |
| A-96D | 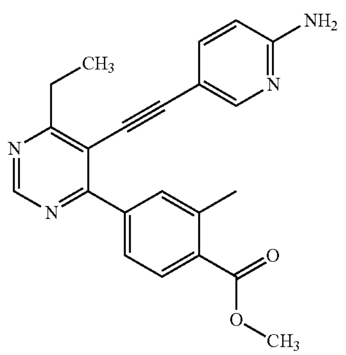 [SMILES: CCc1ncnc(-c2ccc(C(=O)OC)c(C)c2)c1C#Cc1ccc(N)nc1] | A-43 | 3-methyl-4-methoxycarbonyl-phenyl boronic acid | 372.43 | 374 |
| A-96E | 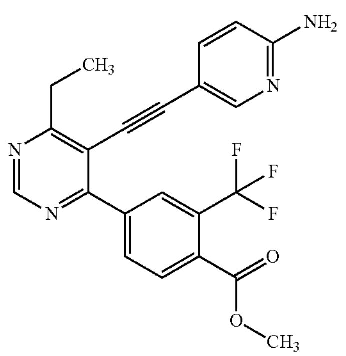 [SMILES: CCc1ncnc(-c2ccc(C(=O)OC)c(C(F)(F)F)c2)c1C#Cc1ccc(N)nc1] | A-43 | A-49B | 426.40 | 428 |

TABLE 1A-continued

Examples A-94-A-96G

| Nr. | Structure | Int. 1 | Int. 2 | MW | MW [M + H] |
|---|---|---|---|---|---|
| A-96F | (structure) | A-43 | A-49C | 442.40 | |
| A-96G | (structure) | A-46 | 3-fluoro-4-methoxycarbonyl-phenyl boronic acid | 404.45 | 406 |

Intermediates A-100 to A-109 can be synthesized according to the general procedure GP8 outlined above. The appropriate methylesters required for synthesis can be deduced from the table of examples.

TABLE 1B

Examples A-100-A-109

| Nr. | Structure | Intermediate 1 | MW | MW [M + H] |
|---|---|---|---|---|
| A-100 | (structure) | A-94 | 380.36 | 382 |

TABLE 1B-continued

Examples A-100-A-109

| Nr. | Structure | Intermediate 1 | MW | MW [M + H] |
|---|---|---|---|---|
| A-101 | | A-95 | 396.81 | 398 |
| A-102 | | A-96 | 413.27 | 415 |
| A-103 | | A-96A | 376.39 | 378 |
| A-104 | | A-96B | 394.38 | 396 |

TABLE 1B-continued

Examples A-100-A-109

| Nr. | Structure | Intermediate 1 | MW | MW [M + H] |
|---|---|---|---|---|
| A-105 | 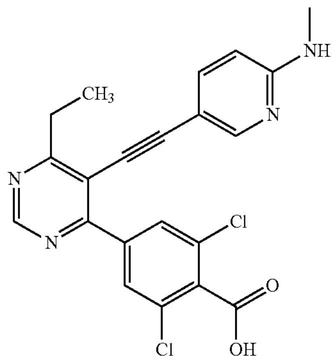 [SMILES: CCc1ncnc(-c2cc(Cl)c(C(=O)O)c(Cl)c2)c1C#Cc1ccc(NC)nc1] | A-96C | 427.29 | 429 |
| A-106 | 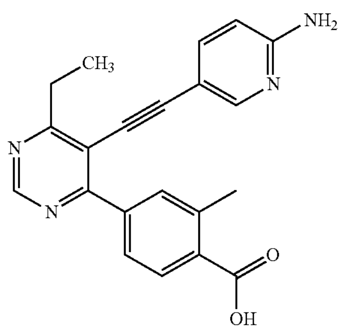 [SMILES: CCc1ncnc(-c2ccc(C(=O)O)c(C)c2)c1C#Cc1ccc(N)nc1] | A-96D | 358.40 | 360 |
| A-107 | 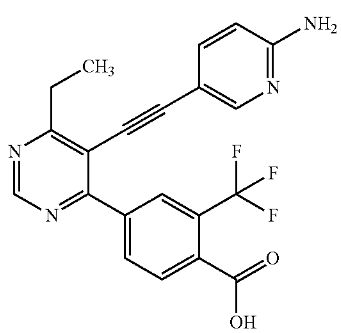 [SMILES: CCc1ncnc(-c2ccc(C(=O)O)c(C(F)(F)F)c2)c1C#Cc1ccc(N)nc1] | A-96E | 412.37 | 414 |
| A-108 | 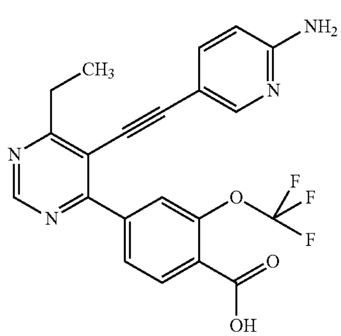 [SMILES: CCc1ncnc(-c2ccc(C(=O)O)c(OC(F)(F)F)c2)c1C#Cc1ccc(N)nc1] | A-96F | 428.37 | 430 |

TABLE 1B-continued

Examples A-100-A-109

| Nr. | Structure | Intermediate 1 | MW | MW [M + H] |
|---|---|---|---|---|
| A-109 | 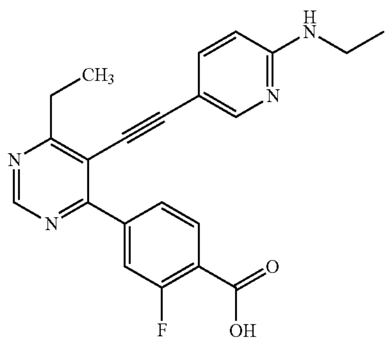 [SMILES: CCNc1ccc(C#Cc2c(CC)ncnc2-c2ccc(C(=O)O)c(F)c2)cn1] | A-96G | 390.42 | 392 |

Examples C

Examples C-1 to C-50 can be synthesized according to the general procedures GP4 (Suzuki reaction) outlined above. The appropriate halides required for synthesis can be deduced from the table of examples.

TABLE 2

Examples C-1-C-53

| Nr. | Structure | Int. | MW | MW [M + H] | $t_R$ [min] | $EC_{50}$ PC3 [nM] |
|---|---|---|---|---|---|---|
| C-1 | 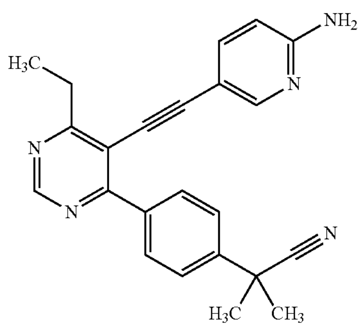 [SMILES: CCc1ncnc(-c2ccc(C(C)(C)C#N)cc2)c1C#Cc1ccc(N)nc1] | A-43 | 367.45 | 368 | 1.78 | 49 |
| C-2 | 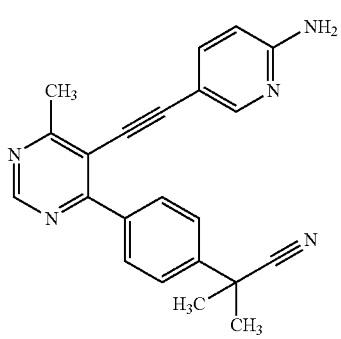 [SMILES: Cc1ncnc(-c2ccc(C(C)(C)C#N)cc2)c1C#Cc1ccc(N)nc1] | A-41 | 353.43 | 354 | 1.65 | 85 |

TABLE 2-continued

| | Examples C-1-C-53 | | | | | |
|---|---|---|---|---|---|---|
| Nr. | Structure | Int. | MW | MW [M + H] | $t_R$ [min] | $EC_{50}$ PC3 [nM] |
| C-3 | | A-43 | 329.41 | 330 | 1.57 | 78 |
| C-4 | | A-43 | 329.41 | 330 | 1.54 | 60 |
| C-5 | | A-41 | 377.83 | 378 | 1.32 | 50 |
| C-6 | | A-41 | 357.42 | 358 | 1.34 | 77 |

TABLE 2-continued

Examples C-1-C-53

| Nr. | Structure | Int. | MW | MW [M + H] | $t_R$ [min] | EC$_{50}$ PC3 [nM] |
|---|---|---|---|---|---|---|
| C-7 | 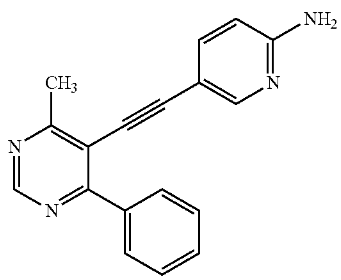 [SMILES: Cc1ncnc(-c2ccccc2)c1C#Cc1ccc(N)nc1] | A-41 | 286.34 | 287 | 1.47 | 163 |
| C-8 | 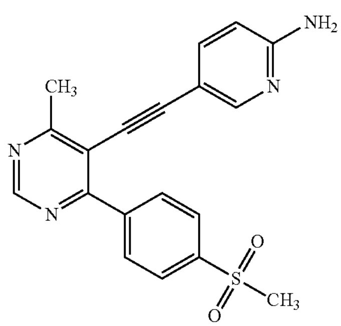 [SMILES: Cc1ncnc(-c2ccc(S(C)(=O)=O)cc2)c1C#Cc1ccc(N)nc1] | A-41 | 364.43 | 365 | 1.3 | 173 |
| C-9 | 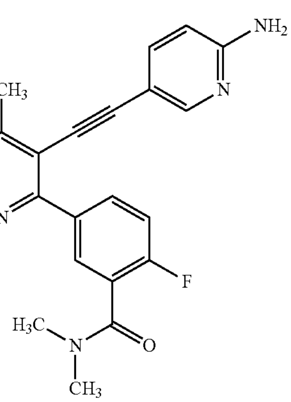 | A-41 | 375.41 | 376 | 1.39 | 275 |
| C-10 | 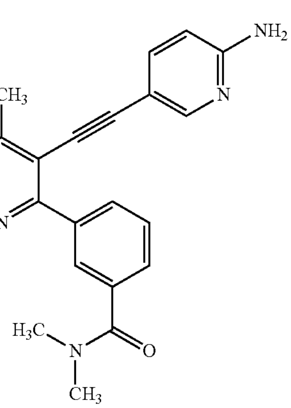 | A-41 | 357.42 | 358 | 1.35 | 134 |

TABLE 2-continued

Examples C-1-C-53

| Nr. | Structure | Int. | MW | MW [M + H] | $t_R$ [min] | $EC_{50}$ PC3 [nM] |
|---|---|---|---|---|---|---|
| C-11 | 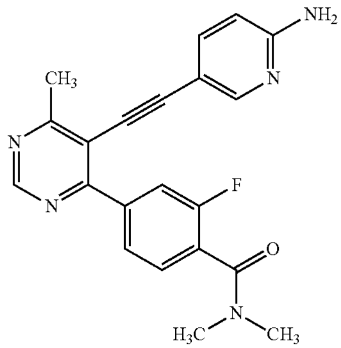 [SMILES: Cc1ncnc(-c2ccc(C(=O)N(C)C)c(F)c2)c1C#Cc1ccc(N)nc1] | A-41 | 375.41 | 376 | 1.38 | 67 |
| C-12 | 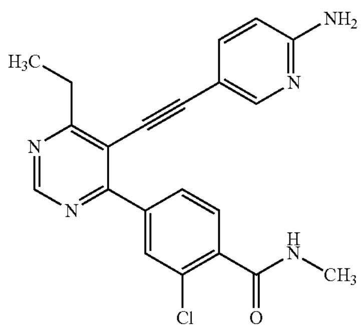 [SMILES: CCc1ncnc(-c2ccc(C(=O)NC)c(Cl)c2)c1C#Cc1ccc(N)nc1] | A-43 | 391.86 | 392 | 1.45 | 46 |
| C-13 | 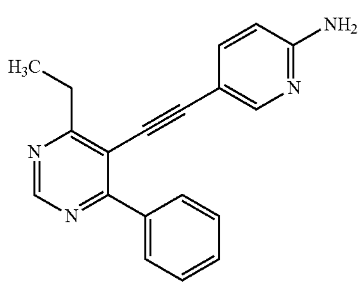 [SMILES: CCc1ncnc(-c2ccccc2)c1C#Cc1ccc(N)nc1] | A-43 | 300.36 | 301 | 1.63 | 170 |
| C-14 | 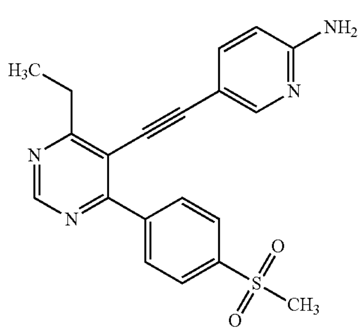 [SMILES: CCc1ncnc(-c2ccc(S(C)(=O)=O)cc2)c1C#Cc1ccc(N)nc1] | A-43 | 378.45 | 379 | 1.47 | 100 |

TABLE 2-continued

Examples C-1-C-53

| Nr. | Structure | Int. | MW | MW [M+H] | $t_R$ [min] | EC$_{50}$ PC3 [nM] |
|---|---|---|---|---|---|---|
| C-15 | 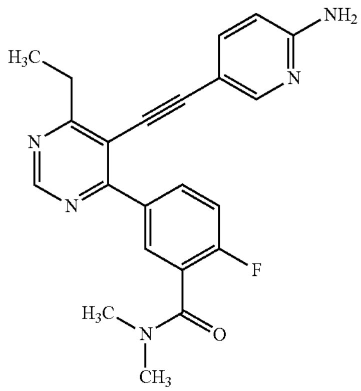 [SMILES: CCc1ncnc(-c2ccc(F)c(C(=O)N(C)C)c2)c1C#Cc1ccc(N)nc1] | A-43 | 389.43 | 390 | 1.53 | 142 |
| C-15A | 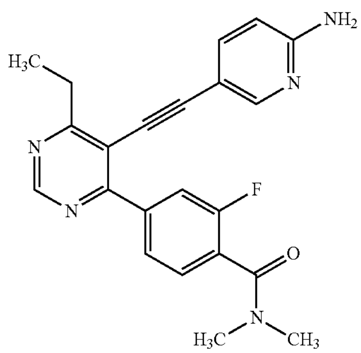 [SMILES: CCc1ncnc(-c2ccc(C(=O)N(C)C)c(F)c2)c1C#Cc1ccc(N)nc1] | A-43 | 389.43 | 390 | 1.55 | 74 |
| C-16 | 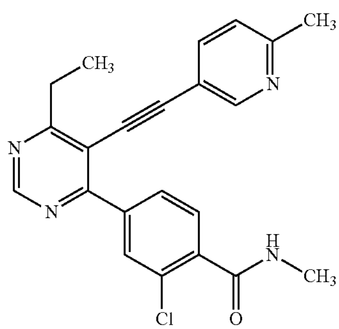 [SMILES: CCc1ncnc(-c2ccc(C(=O)NC)c(Cl)c2)c1C#Cc1ccc(C)nc1] | A-42 | 390.87 | 391/393 | 1.64 | 627 |
| C-17 | 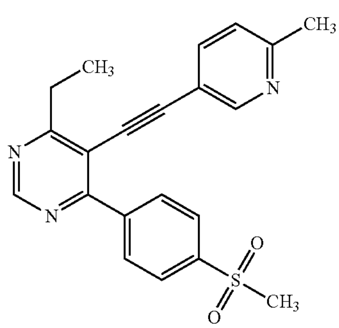 [SMILES: CCc1ncnc(-c2ccc(S(C)(=O)=O)cc2)c1C#Cc1ccc(C)nc1] | A-42 | 377.47 | 378 | 1.63 | 603 |

TABLE 2-continued

Examples C-1-C-53

| Nr. | Structure | Int. | MW | MW [M + H] | $t_R$ [min] | $EC_{50}$ PC3 [nM] |
|---|---|---|---|---|---|---|
| C-18 | 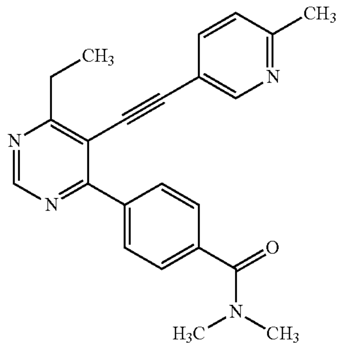 [SMILES: CCc1ncnc(-c2ccc(C(=O)N(C)C)cc2)c1C#Cc1ccc(C)nc1] | A-42 | 370.45 | 371 | 1.64 | 612 |
| C-19 | 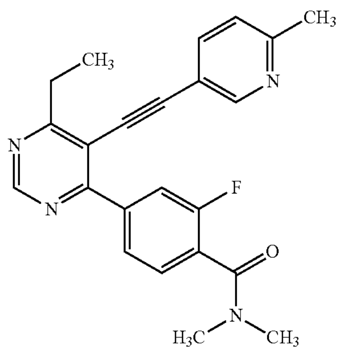 [SMILES: CCc1ncnc(-c2ccc(C(=O)N(C)C)c(F)c2)c1C#Cc1ccc(C)nc1] | A-42 | 388.44 | 289 | 1.71 | 506 |
| C-20 | 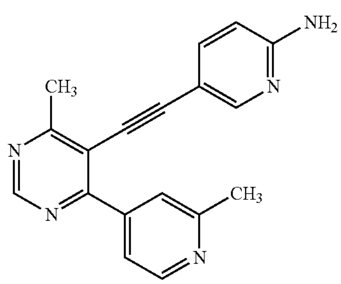 [SMILES: Cc1cc(-c2ncnc(C)c2C#Cc2ccc(N)nc2)ccn1] | A-41 | 301.35 | 302 | 1.33 | 191 |
| C-21 | 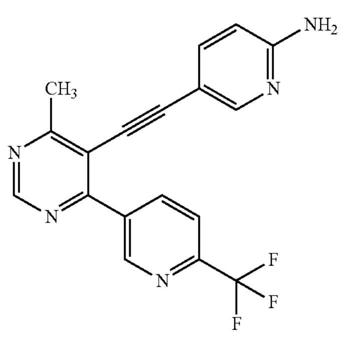 [SMILES: Cc1ncnc(-c2ccc(C(F)(F)F)nc2)c1C#Cc1ccc(N)nc1] | A-41 | 355.32 | 356 (564) | 1.60 (1.70) | 265 |

TABLE 2-continued

Examples C-1-C-53

| Nr. | Structure | Int. | MW | MW [M + H] | $t_R$ [min] | $EC_{50}$ PC3 [nM] |
| --- | --- | --- | --- | --- | --- | --- |
| C-22 | 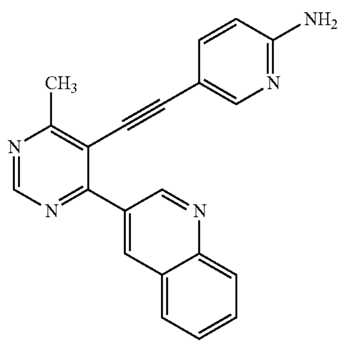 [SMILES: Cc1ncnc(-c2cnc3ccccc3c2)c1C#Cc1ccc(N)nc1] | A-41 | 337.38 | 338 | 1.50 | 163 |
| C-23 | 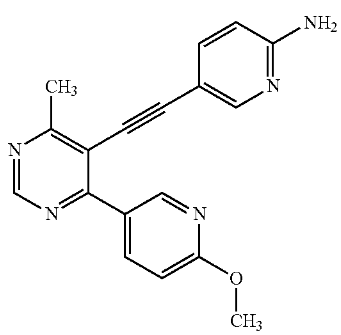 [SMILES: COc1ccc(-c2ncnc(C)c2C#Cc2ccc(N)nc2)cn1] | A-41 | 317.35 | 318 | 1.45 | 245 |
| C-24 | 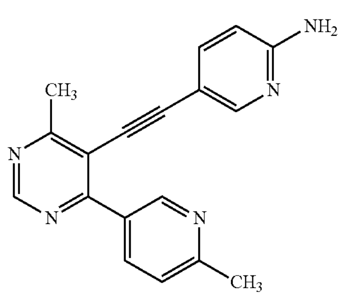 [SMILES: Cc1ccc(-c2ncnc(C)c2C#Cc2ccc(N)nc2)cn1] | A-41 | 301.35 | 302 | 1.34 | 153 |
| C-25 | 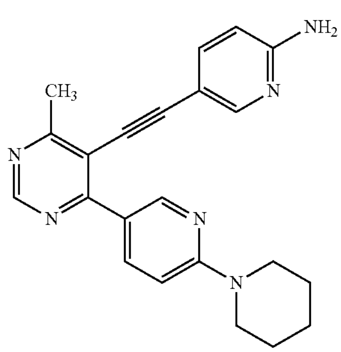 [SMILES: Cc1ncnc(-c2ccc(N3CCCCC3)nc2)c1C#Cc1ccc(N)nc1] | A-41 | 370.46 | 371 | 1.62 | 407 |

TABLE 2-continued

Examples C-1-C-53

| Nr. | Structure | Int. | MW | MW [M + H] | $t_R$ [min] | $EC_{50}$ PC3 [nM] |
|---|---|---|---|---|---|---|
| C-26 | 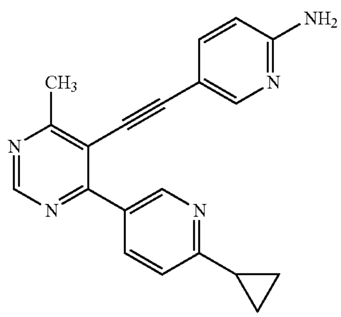 [SMILES: Cc1ncnc(-c2ccc(C3CC3)nc2)c1C#Cc1ccc(N)nc1] | A-41 | 327.39 | 328 | 1.53 | 170 |
| C-27 | 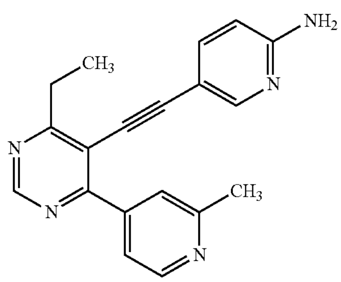 [SMILES: CCc1ncnc(-c2ccnc(C)c2)c1C#Cc1ccc(N)nc1] | A-43 | 315.38 | 316 | 1.47 | 138 |
| C-28 | 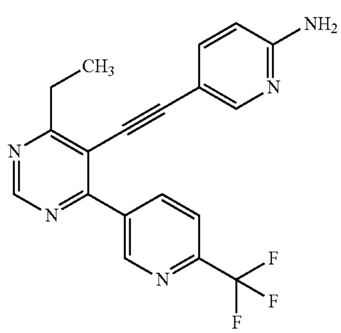 [SMILES: CCc1ncnc(-c2ccc(C(F)(F)F)nc2)c1C#Cc1ccc(N)nc1] | A-43 | 369.35 | 370 | 1.74 | 139 |
| C-29 | 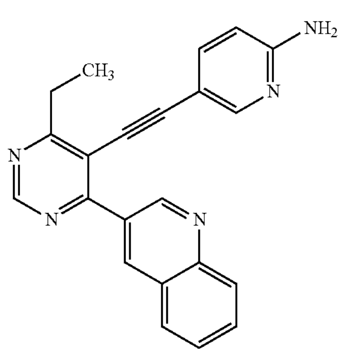 [SMILES: CCc1ncnc(-c2cnc3ccccc3c2)c1C#Cc1ccc(N)nc1] | A-43 | 351.41 | 352 | 1.63 | 123 |

TABLE 2-continued
Examples C-1-C-53
| Nr. | Structure | Int. | MW | MW [M + H] | t$_R$ [min] | EC$_{50}$ PC3 [nM] |
|---|---|---|---|---|---|---|
| C-30 | 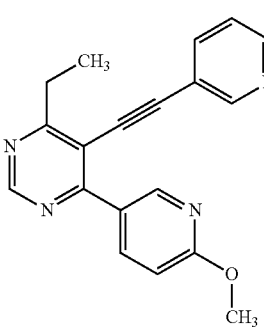 | A-43 | 331.38 | 332 | 1.59 | 178 |
| C-31 | 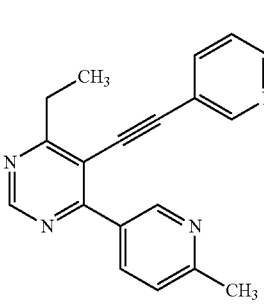 | A-43 | 315.38 | 316 | 1.46 | 133 |
| C-32 | 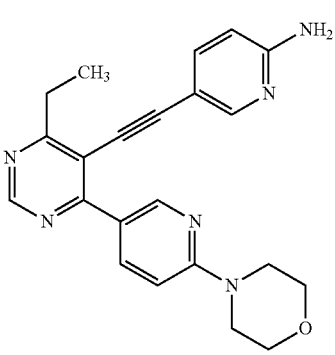 [SMILES: CCc1ncnc(-c2ccc(N3CCOCC3)nc2)c1C#Cc1ccc(N)nc1] | A-43 | 386.46 | 387 | 1.56 | 95 |
| C-33 | 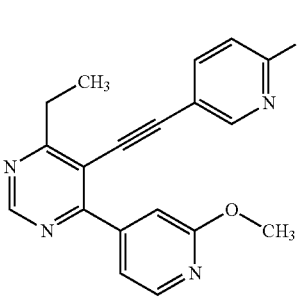 | A-43 | 331.38 | 332 | 1.59 | 106 |

TABLE 2-continued

Examples C-1-C-53

| Nr. | Structure | Int. | MW | MW [M + H] | $t_R$ [min] | $EC_{50}$ PC3 [nM] |
|---|---|---|---|---|---|---|
| C-34 | 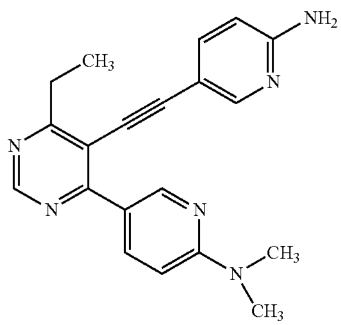 [SMILES: CCc1ncnc(-c2ccc(N(C)C)nc2)c1C#Cc1ccc(N)nc1] | A-43 | 344.42 | 345 | 1.58 | 78 |
| C-35 | 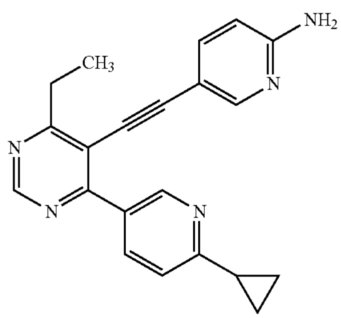 [SMILES: CCc1ncnc(-c2ccc(C3CC3)nc2)c1C#Cc1ccc(N)nc1] | A-43 | 341.42 | 342 | 1.65 | 131 |
| C-36 | 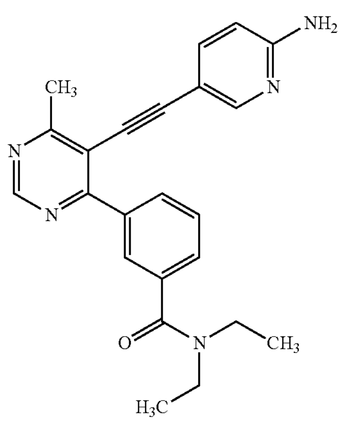 [SMILES: CCN(CC)C(=O)c1cccc(-c2ncnc(C)c2C#Cc2ccc(N)nc2)c1] | A-41 | 385.47 | 386 | 1.53 | 590 |
| C-37 | 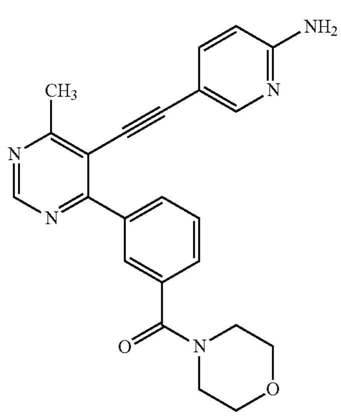 [SMILES: Cc1ncnc(-c2cccc(C(=O)N3CCOCC3)c2)c1C#Cc1ccc(N)nc1] | A-41 | 399.45 | 400 | 1.34 | 644 |

TABLE 2-continued

Examples C-1-C-53

| Nr. | Structure | Int. | MW | MW [M + H] | $t_R$ [min] | $EC_{50}$ PC3 [nM] |
|---|---|---|---|---|---|---|
| C-38 | 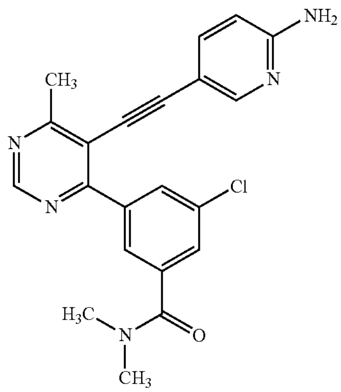 [SMILES: Cc1ncnc(-c2cc(Cl)cc(C(=O)N(C)C)c2)c1C#Cc1ccc(N)nc1] | A-41 | 391.86 | 392 | 1.53 | 245 |
| C-39 | 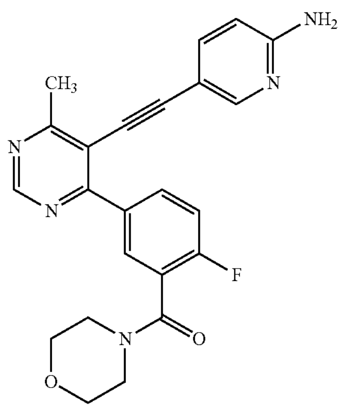 [SMILES: Cc1ncnc(-c2ccc(F)c(C(=O)N3CCOCC3)c2)c1C#Cc1ccc(N)nc1] | A-41 | 417.44 | 418 | 1.23 | 255 |
| C-40 | 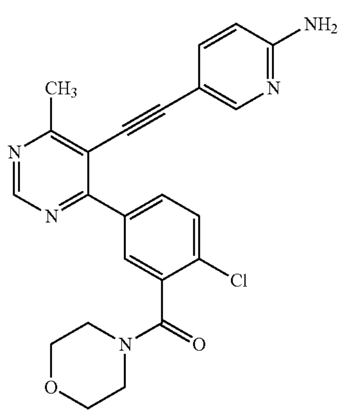 [SMILES: Cc1ncnc(-c2ccc(Cl)c(C(=O)N3CCOCC3)c2)c1C#Cc1ccc(N)nc1] | A-41 | 433.90 | 434 (623) | 1.29 (1.38) | 348 |

TABLE 2-continued

Examples C-1-C-53

| Nr. | Structure | Int. | MW | MW [M + H] | $t_R$ [min] | EC$_{50}$ PC3 [nM] |
|---|---|---|---|---|---|---|
| C-41 | 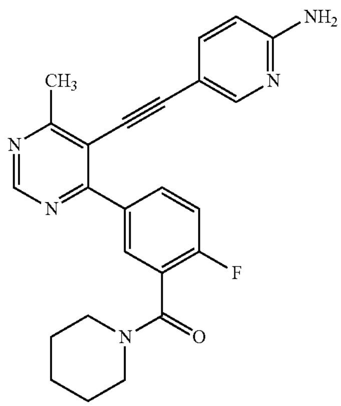 [SMILES: Cc1ncnc(-c2ccc(F)c(C(=O)N3CCCCC3)c2)c1C#Cc1ccc(N)nc1] | A-41 | 415.47 | 416 | 1.46 | 679 |
| C-42 | 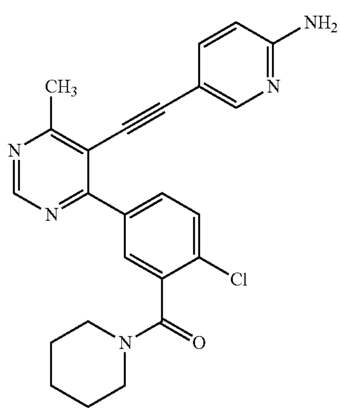 [SMILES: Cc1ncnc(-c2ccc(Cl)c(C(=O)N3CCCCC3)c2)c1C#Cc1ccc(N)nc1] | A-41 | 431.92 | 430 | 1.69 | 503 |
| C-43 | 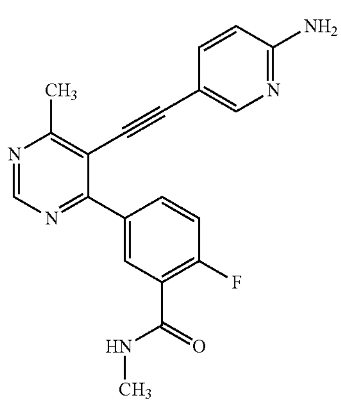 [SMILES: CNC(=O)c1cc(-c2ncnc(C)c2C#Cc2ccc(N)nc2)ccc1F] | A-41 | 361.38 | 362 | 1.30 | 463 |

TABLE 2-continued

Examples C-1-C-53

| Nr. | Structure | Int. | MW | MW [M + H] | $t_R$ [min] | EC$_{50}$ PC3 [nM] |
|---|---|---|---|---|---|---|
| C-44 | 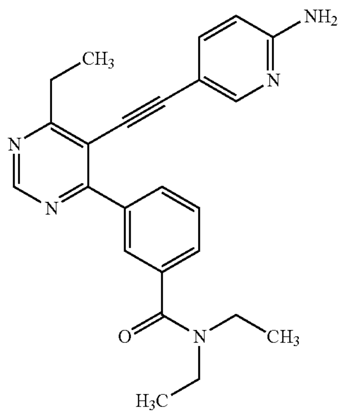 [SMILES: CCc1ncnc(-c2cccc(C(=O)N(CC)CC)c2)c1C#Cc1ccc(N)nc1] | A-43 | 399.50 | 400 | 1.64 | 543 |
| C-45 | 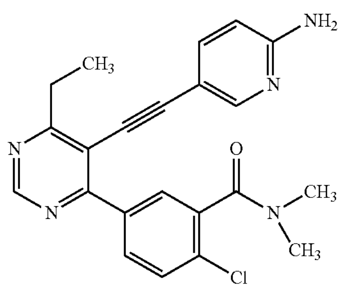 [SMILES: CCc1ncnc(-c2ccc(Cl)c(C(=O)N(C)C)c2)c1C#Cc1ccc(N)nc1] | A-43 | 405.89 | 406 | 1.47 | 90 |
| C-46 | 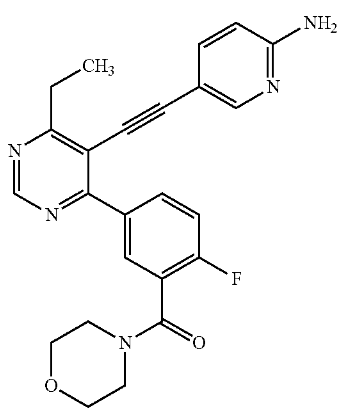 [SMILES: CCc1ncnc(-c2ccc(F)c(C(=O)N3CCOCC3)c2)c1C#Cc1ccc(N)nc1] | A-43 | 431.47 | 432 | 1.51 | 228 |
| C-47 | 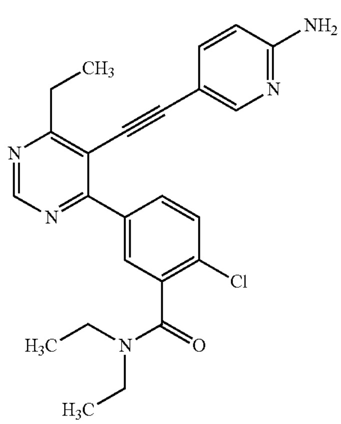 [SMILES: CCc1ncnc(-c2ccc(Cl)c(C(=O)N(CC)CC)c2)c1C#Cc1ccc(N)nc1] | A-43 | 433.94 | 434 | 1.66 | 517 |

TABLE 2-continued

Examples C-1-C-53

| Nr. | Structure | Int. | MW | MW [M + H] | $t_R$ [min] | $EC_{50}$ PC3 [nM] |
|---|---|---|---|---|---|---|
| C-48 | 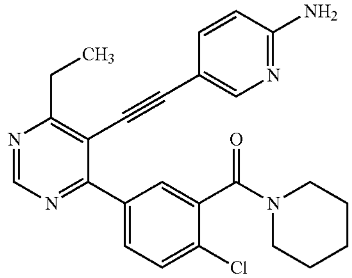 [SMILES: CCc1ncnc(-c2ccc(Cl)c(C(=O)N3CCCCC3)c2)c1C#Cc1ccc(N)nc1] | A-43 | 445.95 | 446 | 1.69 | 747 |
| C-49 | 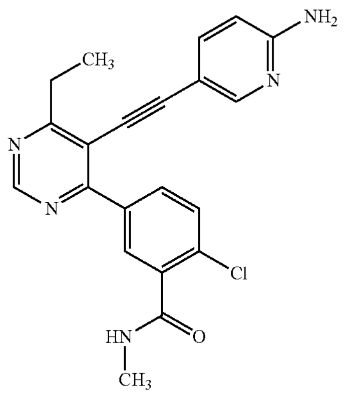 [SMILES: CCc1ncnc(-c2ccc(Cl)c(C(=O)NC)c2)c1C#Cc1ccc(N)nc1] | A-43 | 391.86 | 392 | 1.46 | 506 |
| C-50 | 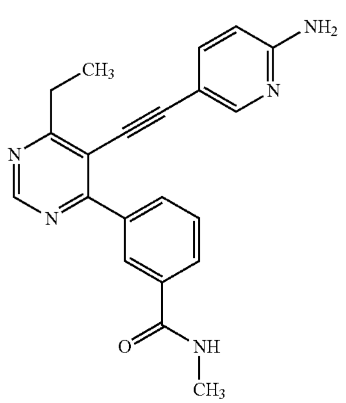 [SMILES: CCc1ncnc(-c2cccc(C(=O)NC)c2)c1C#Cc1ccc(N)nc1] | A-43 | 357.42 | 358 | 1.38 | 212 |

Examples D

Examples D-1 to D-240 can be synthesized according to the general procedures GP9 (amide formation) outlined above. The appropriate intermediates required for synthesis can be deduced from the table of examples.

TABLE 3

Examples D-1-D240

| Nr. | Structure | Int. | MW | MW [M + H] | $t_R$ [min] | $EC_{50}$ PC3 [nM] |
|---|---|---|---|---|---|---|
| D-1 | 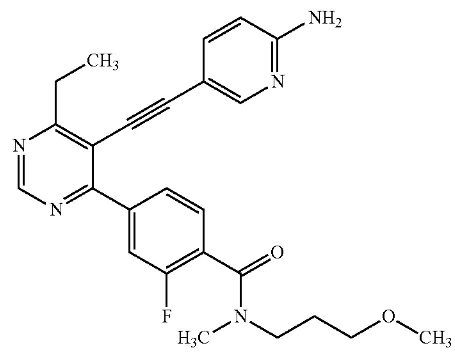 [SMILES: CCc1ncnc(-c2ccc(C(=O)N(C)CCCOC)c(F)c2)c1C#Cc1ccc(N)nc1] | A-73 | 447.51 | 448 | 1.66 | 77 |
| D-2 | 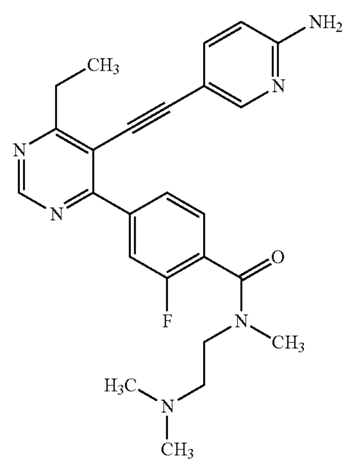 [SMILES: CCc1ncnc(-c2ccc(C(=O)N(C)CCN(C)C)c(F)c2)c1C#Cc1ccc(N)nc1] | A-73 | 446.53 | 447 | 1.62 | 148 |
| D-3 | 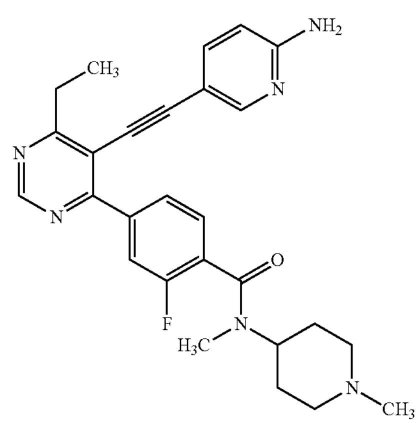 [SMILES: CCc1ncnc(-c2ccc(C(=O)N(C)C3CCN(C)CC3)c(F)c2)c1C#Cc1ccc(N)nc1] | A-73 | 472.57 | 473 | 1.63 | 217 |

TABLE 3-continued
Examples D-1-D240
| Nr. | Structure | Int. | MW | MW [M + H] | $t_R$ [min] | $EC_{50}$ PC3 [nM] |
|---|---|---|---|---|---|---|
| D-4 | 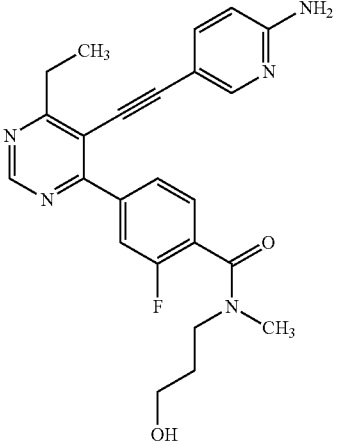 [SMILES: CCc1ncnc(-c2ccc(C(=O)N(C)CCCO)c(F)c2)c1C#Cc1ccc(N)nc1] | A-73 | 433.48 | 434 | 1.49 | 33 |
| D-5 | 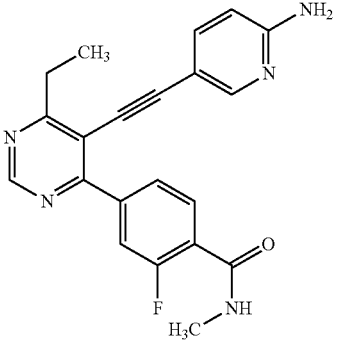 [SMILES: CCc1ncnc(-c2ccc(C(=O)NC)c(F)c2)c1C#Cc1ccc(N)nc1] | A-73 | 375.41 | 376 | 1.50 | 125 |
| D-6 | 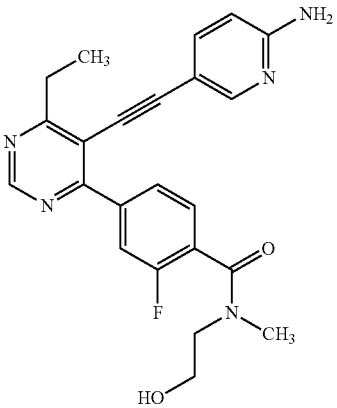 [SMILES: CCc1ncnc(-c2ccc(C(=O)N(C)CCO)c(F)c2)c1C#Cc1ccc(N)nc1] | A-73 | 419.46 | 420 | 1.45 | 32 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-7 | 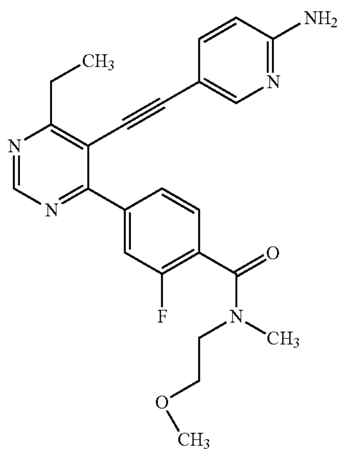 [SMILES: CCc1ncnc(-c2ccc(C(=O)N(C)CCOC)c(F)c2)c1C#Cc1ccc(N)nc1] | A-73 | 433.48 | 434 | 1.63 | 24 |
| D-8 | 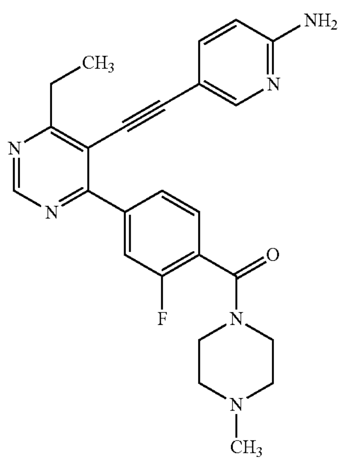 [SMILES: CCc1ncnc(-c2ccc(C(=O)N3CCN(C)CC3)c(F)c2)c1C#Cc1ccc(N)nc1] | A-73 | 444.51 | 445 | 1.57 | 49 |
| D-9 | 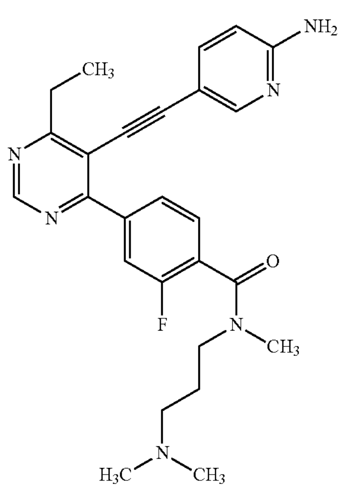 [SMILES: CCc1ncnc(-c2ccc(C(=O)N(C)CCCN(C)C)c(F)c2)c1C#Cc1ccc(N)nc1] | A-73 | 460.55 | 461 | 1.68 | 140 |

TABLE 3-continued

Examples D-1-D240

| Nr. | Structure | Int. | MW | MW [M + H] | $t_R$ [min] | EC$_{50}$ PC3 [nM] |
|---|---|---|---|---|---|---|
| D-10 | 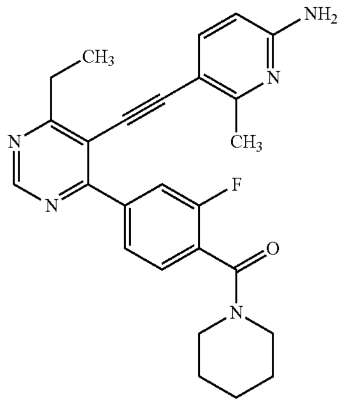 [SMILES: CCc1ncnc(-c2ccc(C(=O)N3CCCCC3)c(F)c2)c1C#Cc1ccc(N)nc1C] | A-87 | 443.52 | 444 | 1.78 | 42 |
| D-11 | 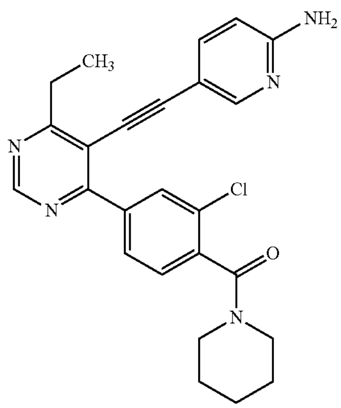 [SMILES: CCc1ncnc(-c2ccc(C(=O)N3CCCCC3)c(Cl)c2)c1C#Cc1ccc(N)nc1] | A-77 | 445.95 | 446 | 1.80 | 51 |
| D-12 | 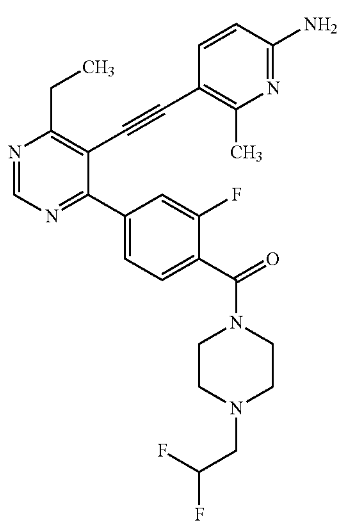 [SMILES: CCc1ncnc(-c2ccc(C(=O)N3CCN(CC(F)F)CC3)c(F)c2)c1C#Cc1ccc(N)nc1C] | A-87 | 508.55 | 509 | 1.74 | 45 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-13 | 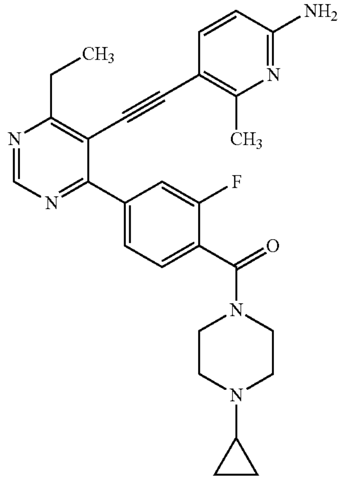 [SMILES: CCc1ncnc(-c2ccc(C(=O)N3CCN(C4CC4)CC3)c(F)c2)c1C#Cc1ccc(N)nc1C] | A-87 | 484.58 | 485 | 1.77 | 53 |
| D-14 | 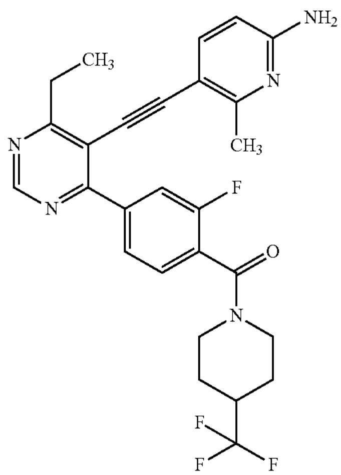 [SMILES: CCc1ncnc(-c2ccc(C(=O)N3CCC(C(F)(F)F)CC3)c(F)c2)c1C#Cc1ccc(N)nc1C] | A-87 | 511.52 | 512 | 1.91 | 72 |
| D-15 | 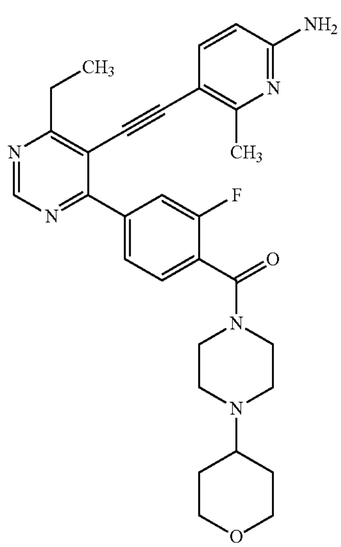 [SMILES: CCc1ncnc(-c2ccc(C(=O)N3CCN(C4CCOCC4)CC3)c(F)c2)c1C#Cc1ccc(N)nc1C] | A-87 | 528.63 | 529 | 1.61 | 51 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-16 | 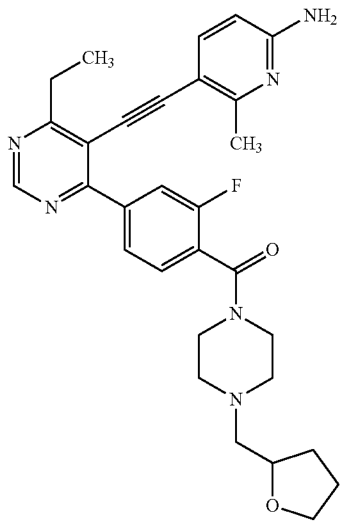 [SMILES: CCc1ncnc(-c2ccc(C(=O)N3CCN(CC4CCCO4)CC3)c(F)c2)c1C#Cc1ccc(N)nc1C] | A-87 | 528.63 | 529 | 1.72 | 67 |
| D-17 | 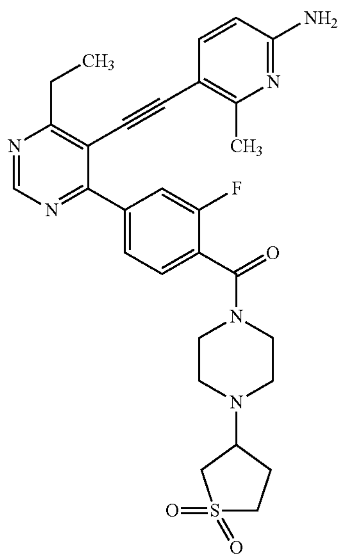 [SMILES: CCc1ncnc(-c2ccc(C(=O)N3CCN(C4CCS(=O)(=O)C4)CC3)c(F)c2)c1C#Cc1ccc(N)nc1C] | A-87 | 562.67 | 563 | 1.53 | 76 |
| D-18 | 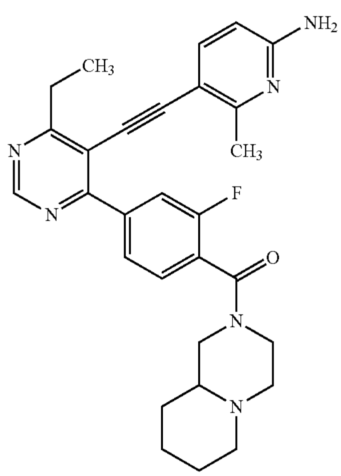 [SMILES: CCc1ncnc(-c2ccc(C(=O)N3CCN4CCCCC4C3)c(F)c2)c1C#Cc1ccc(N)nc1C] | A-87 | 498.60 | 499 | 1.75 | 41 |

TABLE 3-continued

Examples D-1-D240

| Nr. | Structure | Int. | MW | MW [M + H] | $t_R$ [min] | $EC_{50}$ PC3 [nM] |
| --- | --- | --- | --- | --- | --- | --- |
| D-19 | 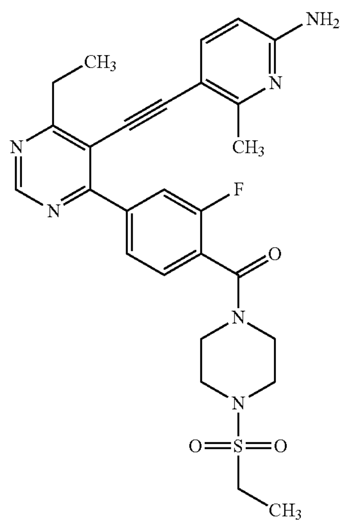 [SMILES: CCc1ncnc(-c2ccc(C(=O)N3CCN(S(=O)(=O)CC)CC3)c(F)c2)c1C#Cc1ccc(N)nc1C] | A-87 | 536.63 | 537 | 1.64 | 30 |
| D-20 | 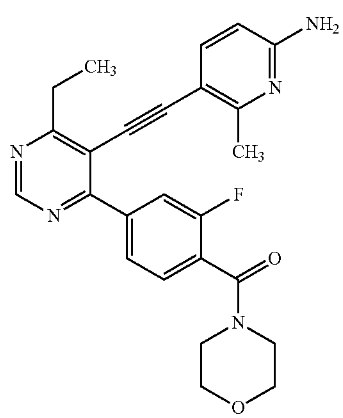 [SMILES: CCc1ncnc(-c2ccc(C(=O)N3CCOCC3)c(F)c2)c1C#Cc1ccc(N)nc1C] | A-87 | 445.50 | 446 | 1.57 | 14 |
| D-21 | 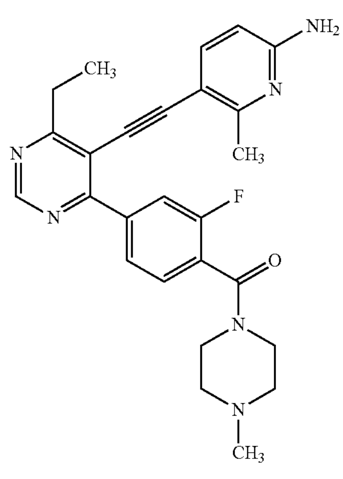 [SMILES: CCc1ncnc(-c2ccc(C(=O)N3CCN(C)CC3)c(F)c2)c1C#Cc1ccc(N)nc1C] | A-87 | 458.54 | 459 | 1.57 | 27 |

TABLE 3-continued
Examples D-1-D240
| Nr. | Structure | Int. | MW | MW [M + H] | $t_R$ [min] | $EC_{50}$ PC3 [nM] |
|---|---|---|---|---|---|---|
| D-22 | 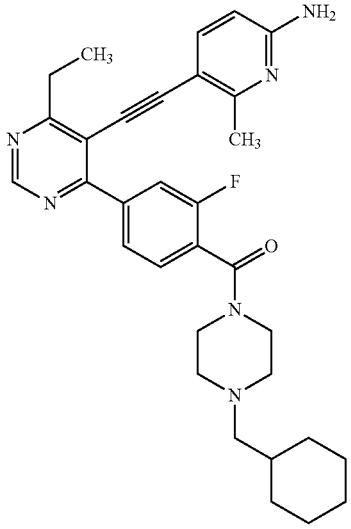 [SMILES: CCc1ncnc(-c2ccc(C(=O)N3CCN(CC4CCCCC4)CC3)c(F)c2)c1C#Cc1ccc(N)nc1C] | A-87 | 540.68 | 541 | 2.23 | 355 |
| D-23 | 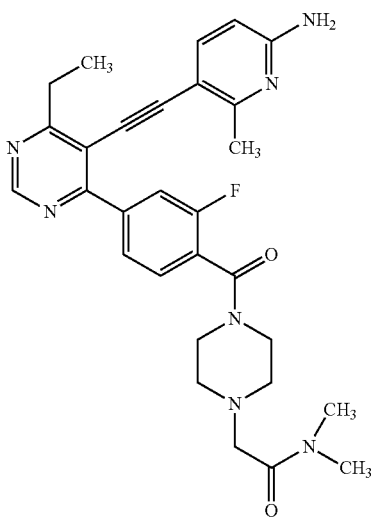 [SMILES: CCc1ncnc(-c2ccc(C(=O)N3CCN(CC(=O)N(C)C)CC3)c(F)c2)c1C#Cc1ccc(N)nc1C] | A-87 | 529.62 | 530 | 1.55 | 41 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-24 | 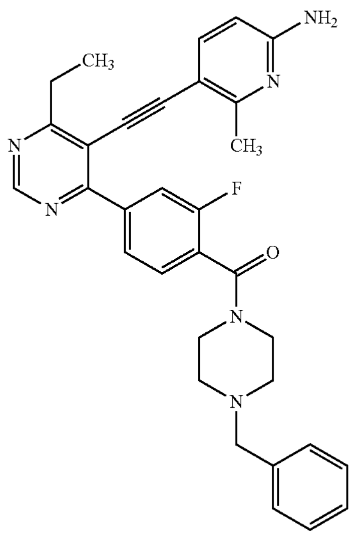 [SMILES: CCc1ncnc(-c2ccc(C(=O)N3CCN(Cc4ccccc4)CC3)c(F)c2)c1C#Cc1ccc(N)nc1C] | A-87 | 534.64 | 535 | 1.96 | 52 |
| D-25 | 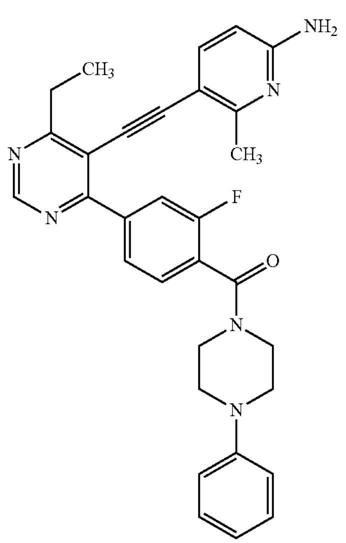 [SMILES: CCc1ncnc(-c2ccc(C(=O)N3CCN(c4ccccc4)CC3)c(F)c2)c1C#Cc1ccc(N)nc1C] | A-87 | 520.61 | 521 | 1.96 | 55 |

TABLE 3-continued
Examples D-1-D240
| Nr. | Structure | Int. | MW | MW [M + H] | $t_R$ [min] | $EC_{50}$ PC3 [nM] |
|---|---|---|---|---|---|---|
| D-26 | 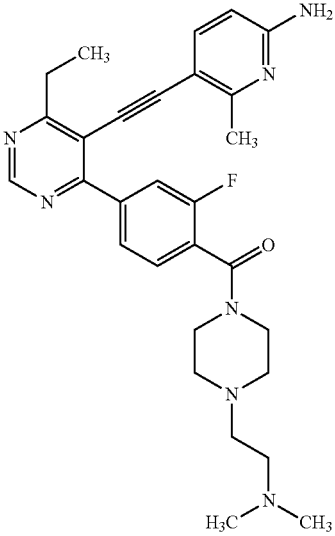 [SMILES: CCc1ncnc(-c2ccc(C(=O)N3CCN(CCN(C)C)CC3)c(F)c2)c1C#Cc1ccc(N)nc1C] | A-87 | 515.63 | 516 | 1.63 | 140 |
| D-27 | 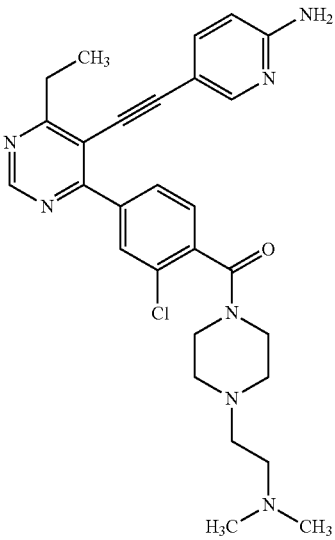 [SMILES: CCc1ncnc(-c2ccc(C(=O)N3CCN(CCN(C)C)CC3)c(Cl)c2)c1C#Cc1ccc(N)nc1] | A-77 | 518.06 | 518 | 1.63 | 96 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-28 | 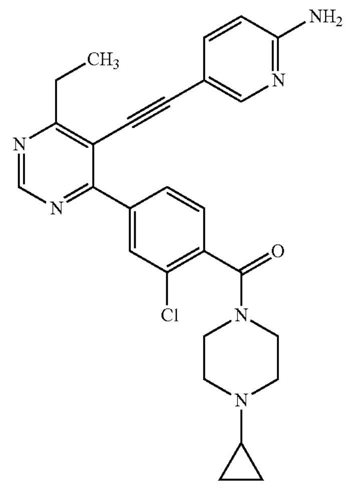 | A-77 | 487.00 | 487/489 | 1.78 | 9 |
| D-29 | 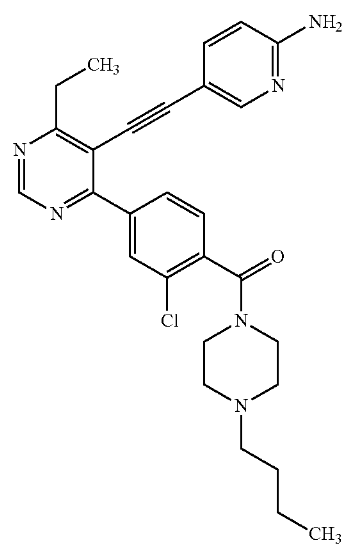 [SMILES: CCCCN1CCN(C(=O)c2ccc(-c3ncnc(CC)c3C#Cc3ccc(N)nc3)cc2Cl)CC1] | A-77 | 503.05 | 503 | 1.93 | 56 |
| D-30 | 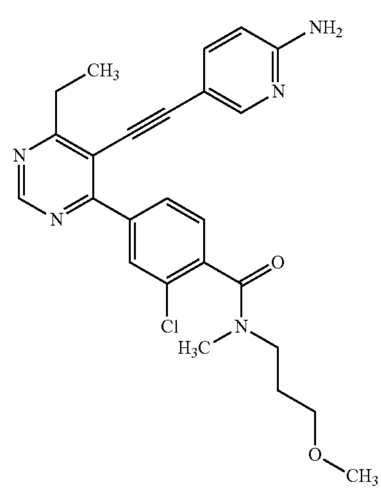 [SMILES: CCc1ncnc(-c2ccc(C(=O)N(C)CCCOC)c(Cl)c2)c1C#Cc1ccc(N)nc1] | A-77 | 463.97 | 464/466 | 1.68 | 71 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-31 | 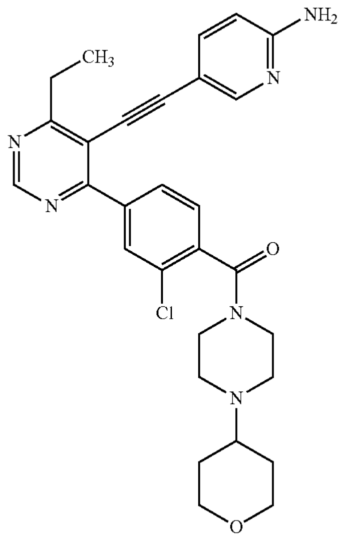 [SMILES: CCc1ncnc(-c2ccc(C(=O)N3CCN(C4CCOCC4)CC3)c(Cl)c2)c1C#Cc1ccc(N)nc1] | A-77 | 531.06 | 531/533 | 1.62 | 23 |
| D-32 | 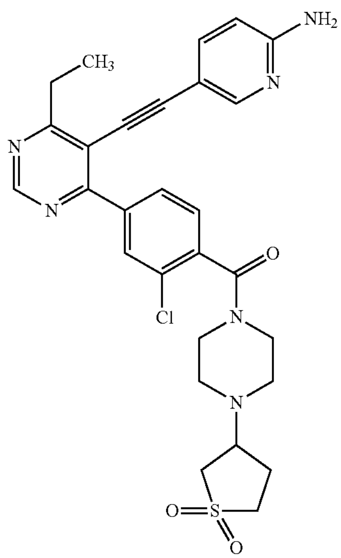 [SMILES: CCc1ncnc(-c2ccc(C(=O)N3CCN(C4CCS(=O)(=O)C4)CC3)c(Cl)c2)c1C#Cc1ccc(N)nc1] | A-77 | 565.10 | 565 | 1.53 | 38 |
| D-33 | 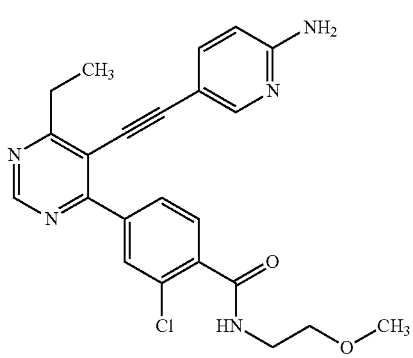 [SMILES: CCc1ncnc(-c2ccc(C(=O)NCCOC)c(Cl)c2)c1C#Cc1ccc(N)nc1] | A-77 | 435.91 | 436/438 | 1.53 | 45 |

TABLE 3-continued

Examples D-1-D240

| Nr. | Structure | Int. | MW | MW [M + H] | $t_R$ [min] | EC$_{50}$ PC3 [nM] |
|---|---|---|---|---|---|---|
| D-34 | 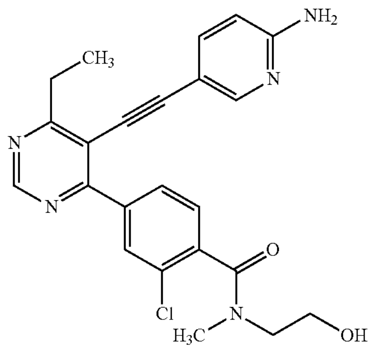 [SMILES: CCc1ncnc(-c2ccc(C(=O)N(C)CCO)c(Cl)c2)c1C#Cc1ccc(N)nc1] | A-77 | 435.91 | 436 | 1.45 | 36 |
| D-35 | 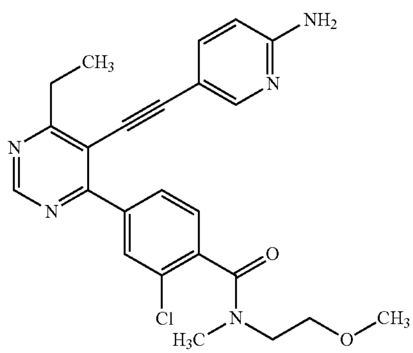 [SMILES: CCc1ncnc(-c2ccc(C(=O)N(C)CCOC)c(Cl)c2)c1C#Cc1ccc(N)nc1] | A-77 | 449.94 | 450/452 | 1.64 | 35 |
| D-36 | 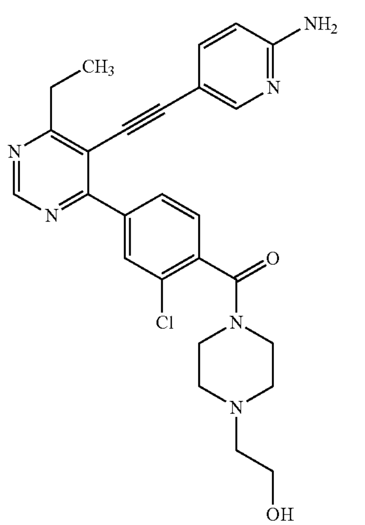 [SMILES: CCc1ncnc(-c2ccc(C(=O)N3CCN(CCO)CC3)c(Cl)c2)c1C#Cc1ccc(N)nc1] | A-77 | 490.99 | 491/493 | 1.47 | 41 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-37 | 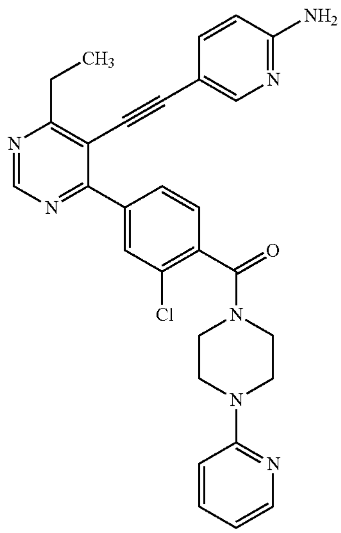 [SMILES: CCc1ncnc(-c2ccc(C(=O)N3CCN(c4ccccn4)CC3)c(Cl)c2)c1C#Cc1ccc(N)nc1] | A-77 | 524.03 | 524 | 1.82 | 38 |
| D-38 | 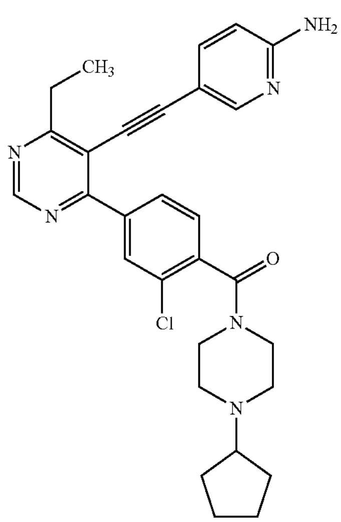 [SMILES: CCc1ncnc(-c2ccc(C(=O)N3CCN(C4CCCC4)CC3)c(Cl)c2)c1C#Cc1ccc(N)nc1] | A-77 | 515.06 | 515 | 1.90 | 65 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-39 | 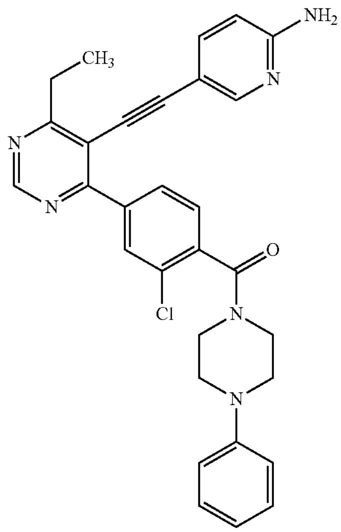 [SMILES: CCc1ncnc(-c2ccc(C(=O)N3CCN(c4ccccc4)CC3)c(Cl)c2)c1C#Cc1ccc(N)nc1] | A-77 | 523.04 | 523 | 1.97 | 67 |
| D-40 | 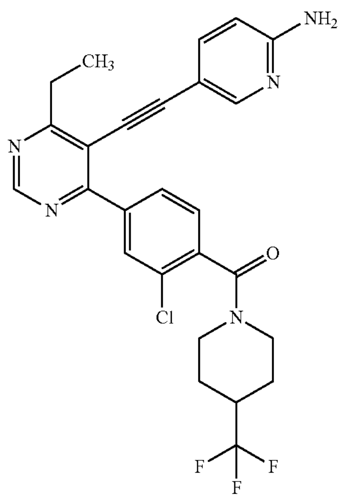 [SMILES: CCc1ncnc(-c2ccc(C(=O)N3CCC(C(F)(F)F)CC3)c(Cl)c2)c1C#Cc1ccc(N)nc1] | A-77 | 513.95 | 514 | 1.93 | 130 |
| D-41 | 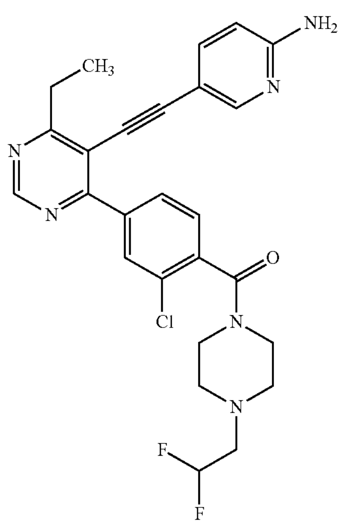 [SMILES: CCc1ncnc(-c2ccc(C(=O)N3CCN(CC(F)F)CC3)c(Cl)c2)c1C#Cc1ccc(N)nc1] | A-77 | 510.97 | 511 | 1.75 | 28 |

TABLE 3-continued

Examples D-1-D240

| Nr. | Structure | Int. | MW | MW [M + H] | $t_R$ [min] | EC$_{50}$ PC3 [nM] |
|---|---|---|---|---|---|---|
| D-42 | 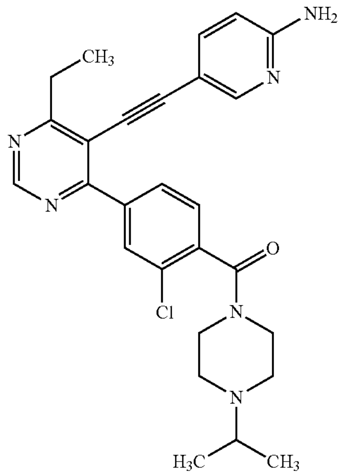 [SMILES: CCc1ncnc(-c2ccc(C(=O)N3CCN(C(C)C)CC3)c(Cl)c2)c1C#Cc1ccc(N)nc1] | A-77 | 489.02 | 487 | 1.78 | 16 |
| D-43 | 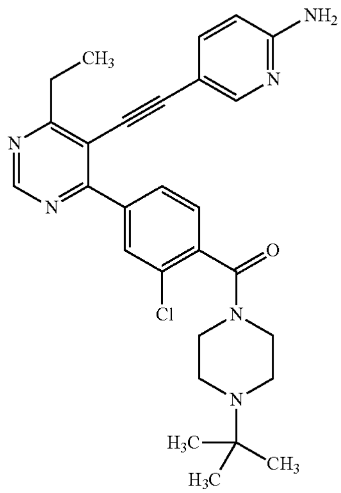 [SMILES: CCc1ncnc(-c2ccc(C(=O)N3CCN(C(C)(C)C)CC3)c(Cl)c2)c1C#Cc1ccc(N)nc1] | A-77 | 503.05 | 503 | 1.86 | 28 |
| D-44 | 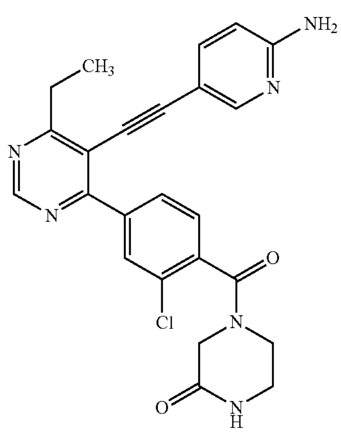 [SMILES: CCc1ncnc(-c2ccc(C(=O)N3CCNC(=O)C3)c(Cl)c2)c1C#Cc1ccc(N)nc1] | A-77 | 460.92 | 461 | 1.43 | 56 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-45 | 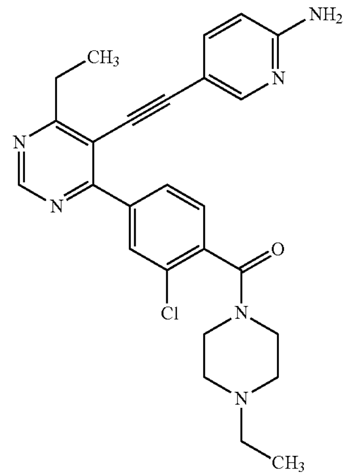 [SMILES: CCc1ncnc(-c2ccc(C(=O)N3CCN(CC)CC3)c(Cl)c2)c1C#Cc1ccc(N)nc1] | A-77 | 474.99 | 475 | 1.68 | 54 |
| D-46 | 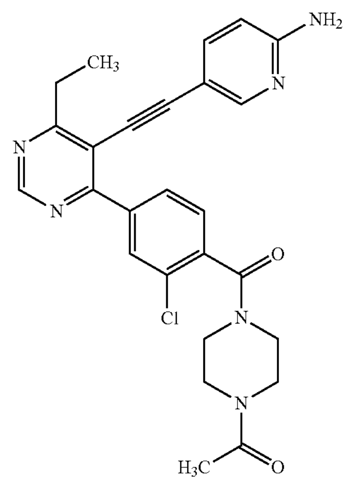 [SMILES: CCc1ncnc(-c2ccc(C(=O)N3CCN(C(C)=O)CC3)c(Cl)c2)c1C#Cc1ccc(N)nc1] | A-77 | 488.98 | 489 | 1.51 | 74 |
| D-47 | 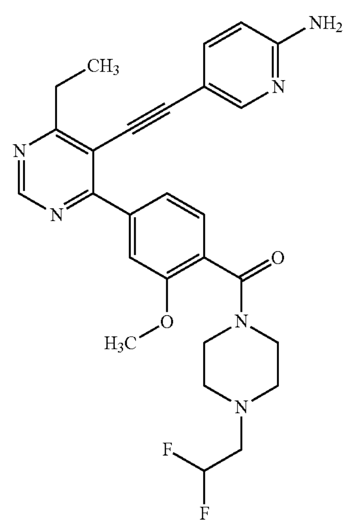 [SMILES: CCc1ncnc(-c2ccc(C(=O)N3CCN(CC(F)F)CC3)c(OC)c2)c1C#Cc1ccc(N)nc1] | A-93 | 506.55 | 507 | 1.64 | 58 |

TABLE 3-continued
Examples D-1-D240
| Nr. | Structure | Int. | MW | MW [M + H] | $t_R$ [min] | $EC_{50}$ PC3 [nM] |
|---|---|---|---|---|---|---|
| D-48 | 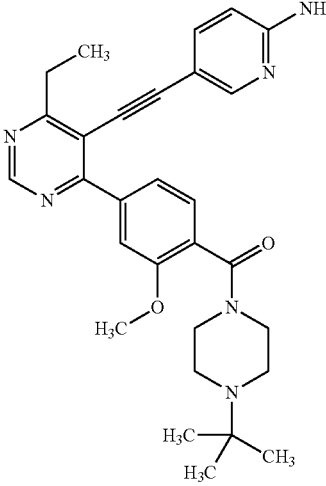 | A-93 | 498.63 | 499 | 1.76 | 58 |
| D-49 | 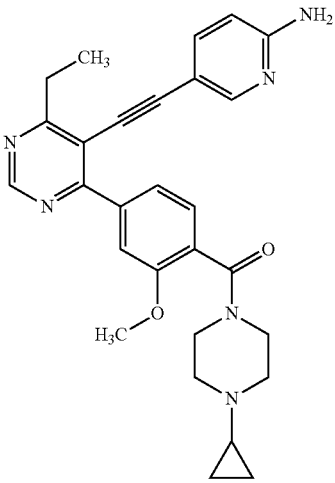 [SMILES: CCc1ncnc(-c2ccc(C(=O)N3CCN(C4CC4)CC3)c(OC)c2)c1C#Cc1ccc(N)nc1] | A-93 | 482.59 | 483 | 1.66 | 43 |
| D-50 | 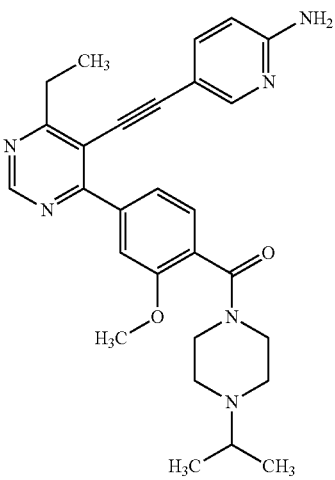 [SMILES: CCc1ncnc(-c2ccc(C(=O)N3CCN(C(C)C)CC3)c(OC)c2)c1C#Cc1ccc(N)nc1] | A-93 | 484.60 | 485 | 1.65 | 80 |

TABLE 3-continued
Examples D-1-D240
| Nr. | Structure | Int. | MW | MW [M + H] | $t_R$ [min] | $EC_{50}$ PC3 [nM] |
|---|---|---|---|---|---|---|
| D-51 | 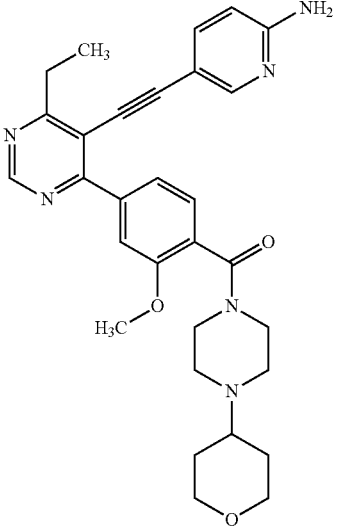 [SMILES: CCc1ncnc(-c2ccc(C(=O)N3CCN(C4CCOCC4)CC3)c(OC)c2)c1C#Cc1ccc(N)nc1] | A-93 | 526.64 | 527 | 1.52 | 30 |
| D-52 | 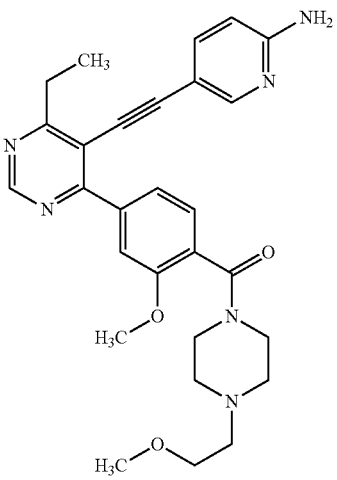 [SMILES: CCc1ncnc(-c2ccc(C(=O)N3CCN(CCOC)CC3)c(OC)c2)c1C#Cc1ccc(N)nc1] | A-93 | 500.60 | 501 | 1.53 | 71 |
| D-53 | 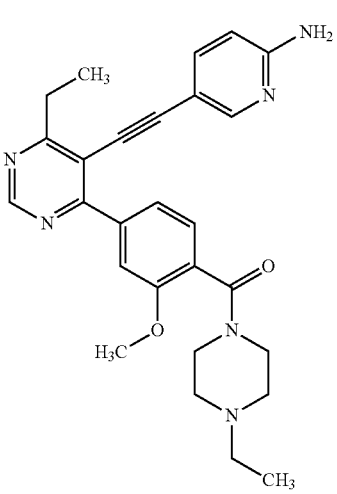 [SMILES: CCc1ncnc(-c2ccc(C(=O)N3CCN(CC)CC3)c(OC)c2)c1C#Cc1ccc(N)nc1] | A-93 | 470.57 | 471 | 1.57 | 67 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-54 | 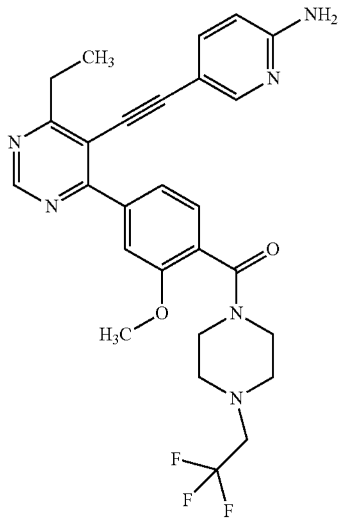 [SMILES: CCc1ncnc(-c2ccc(C(=O)N3CCN(CC(F)(F)F)CC3)c(OC)c2)c1C#Cc1ccc(N)nc1] | A-93 | 524.54 | 525 | 1.77 | 38 |
| D-55 | 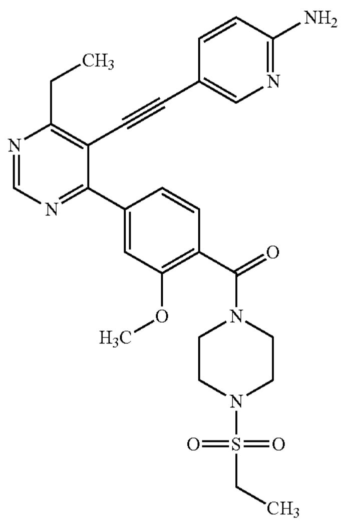 [SMILES: CCc1ncnc(-c2ccc(C(=O)N3CCN(S(=O)(=O)CC)CC3)c(OC)c2)c1C#Cc1ccc(N)nc1] | A-93 | 534.64 | 535 | 1.57 | 36 |
| D-56 | 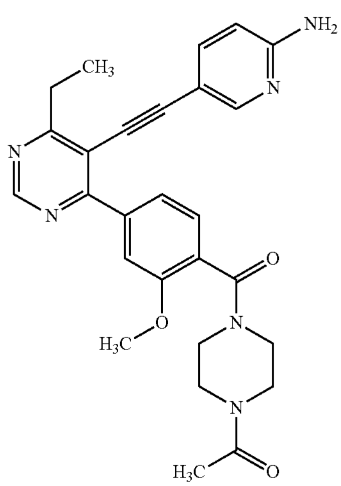 [SMILES: CCc1ncnc(-c2ccc(C(=O)N3CCN(C(C)=O)CC3)c(OC)c2)c1C#Cc1ccc(N)nc1] | A-93 | 484.56 | 485 | 1.42 | 115 |

TABLE 3-continued

Examples D-1-D240

| Nr. | Structure | Int. | MW | MW [M + H] | $t_R$ [min] | EC$_{50}$ PC3 [nM] |
|---|---|---|---|---|---|---|
| D-57 | 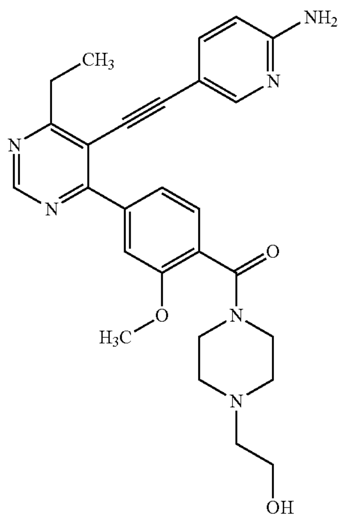 [SMILES: CCc1ncnc(-c2ccc(C(=O)N3CCN(CCO)CC3)c(OC)c2)c1C#Cc1ccc(N)nc1] | A-93 | 486.57 | 487 | 1.39 | 357 |
| D-58 | 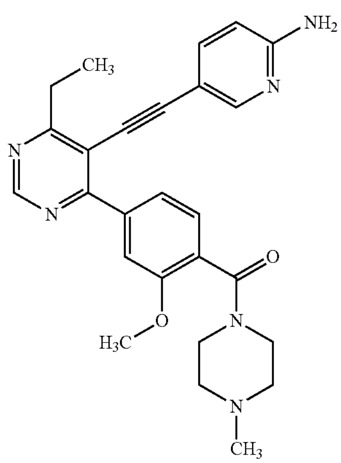 [SMILES: CCc1ncnc(-c2ccc(C(=O)N3CCN(C)CC3)c(OC)c2)c1C#Cc1ccc(N)nc1] | A-93 | 456.55 | 457 | 1.47 | 49 |
| D-59 | 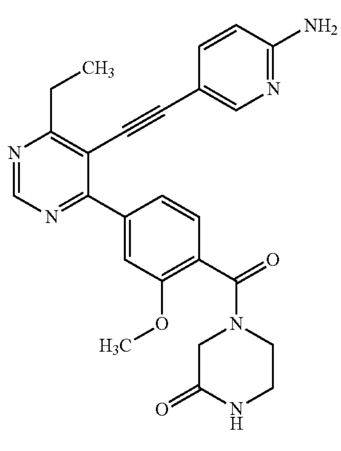 [SMILES: CCc1ncnc(-c2ccc(C(=O)N3CCNC(=O)C3)c(OC)c2)c1C#Cc1ccc(N)nc1] | A-93 | 456.50 | 457 | 1.34 | 248 |

TABLE 3-continued
Examples D-1-D240
| Nr. | Structure | Int. | MW | MW [M + H] | $t_R$ [min] | $EC_{50}$ PC3 [nM] |
|---|---|---|---|---|---|---|
| D-60 | 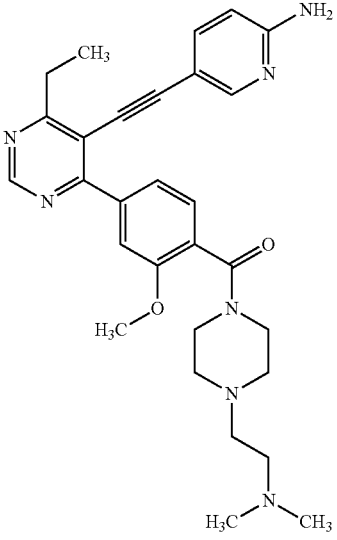 [SMILES: CCc1ncnc(-c2ccc(C(=O)N3CCN(CCN(C)C)CC3)c(OC)c2)c1C#Cc1ccc(N)nc1] | A-93 | 513.64 | 514 | 1.56 | 480 |
| D-61 | 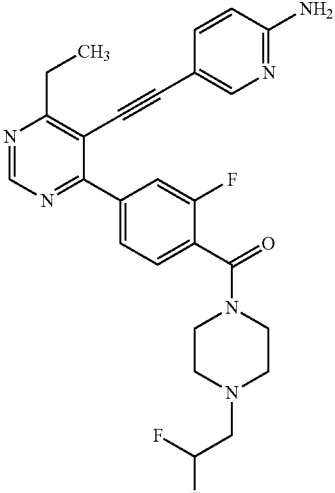 | A-73 | 494.52 | 495 | 1.73 | 22 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-62 | 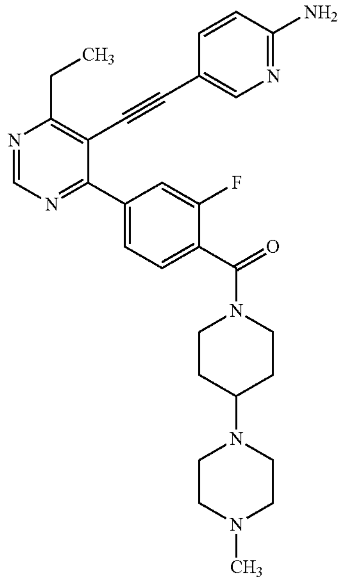 [SMILES: CCc1ncnc(-c2ccc(C(=O)N3CCC(N4CCN(C)CC4)CC3)c(F)c2)c1C#Cc1ccc(N)nc1] | A-73 | 527.64 | 528 | 1.57 | 56 |
| D-63 | 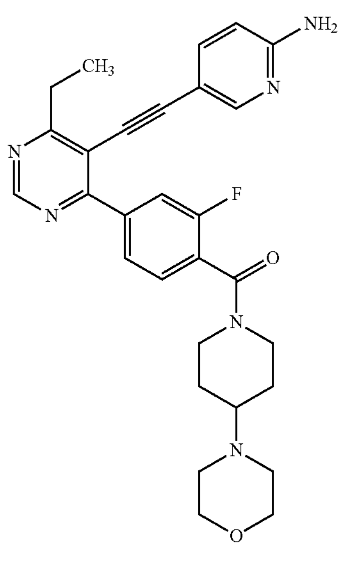 [SMILES: CCc1ncnc(-c2ccc(C(=O)N3CCC(N4CCOCC4)CC3)c(F)c2)c1C#Cc1ccc(N)nc1] | A-73 | 514.60 | 515 | 1.62 | 30 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-64 | 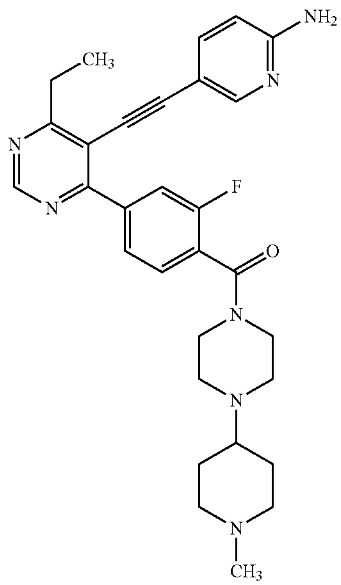 [SMILES: CCc1ncnc(-c2ccc(C(=O)N3CCN(C4CCN(C)CC4)CC3)c(F)c2)c1C#Cc1ccc(N)nc1] | A-73 | 527.64 | 528 | 1.68 | 71 |
| D-65 | 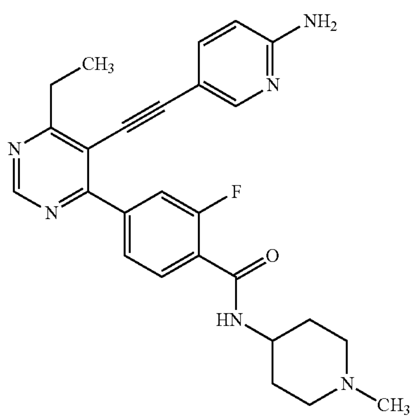 [SMILES: CCc1ncnc(-c2ccc(C(=O)NC3CCN(C)CC3)c(F)c2)c1C#Cc1ccc(N)nc1] | A-73 | 458.54 | 459 | 1.59 | 156 |
| D-66 | 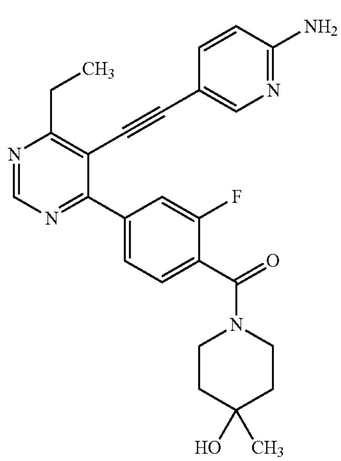 [SMILES: CCc1ncnc(-c2ccc(C(=O)N3CCC(C)(O)CC3)c(F)c2)c1C#Cc1ccc(N)nc1] | A-73 | 459.52 | 460 | 1.54 | 46 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-67 | 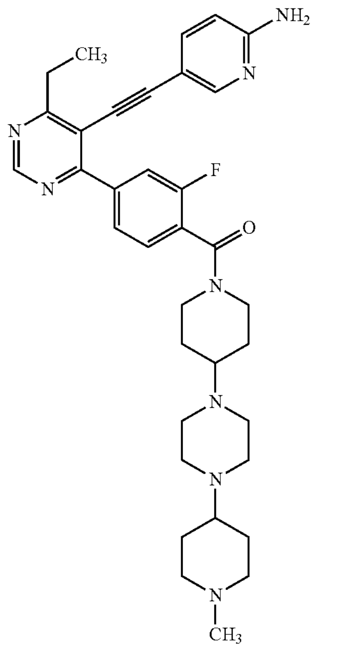 [SMILES: CCc1ncnc(-c2ccc(C(=O)N3CCC(N4CCN(C5CCN(C)CC5)CC4)CC3)c(F)c2)c1C#Cc1ccc(N)nc1] | A-73 | 610.78 | 611 | 1.67 | 105 |
| D-68 | 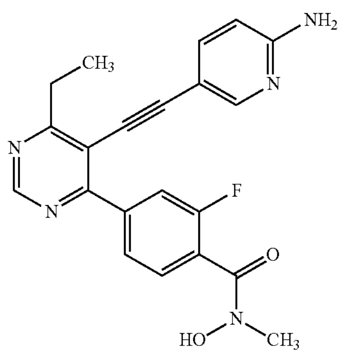 [SMILES: CCc1ncnc(-c2ccc(C(=O)N(C)O)c(F)c2)c1C#Cc1ccc(N)nc1] | A-73 | 391.40 | 392 | 1.11 | 24 |
| D-69 | 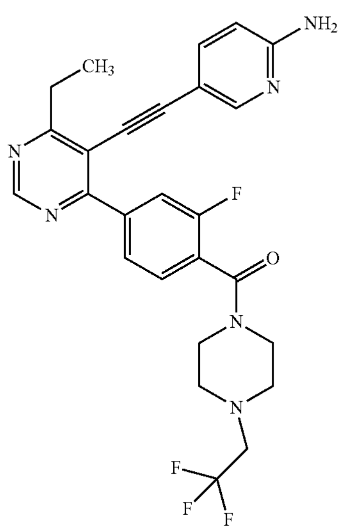 [SMILES: CCc1ncnc(-c2ccc(C(=O)N3CCN(CC(F)(F)F)CC3)c(F)c2)c1C#Cc1ccc(N)nc1] | A-73 | 512.51 | 513 (775) | 1.84 (1.89) | 51 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-70 | 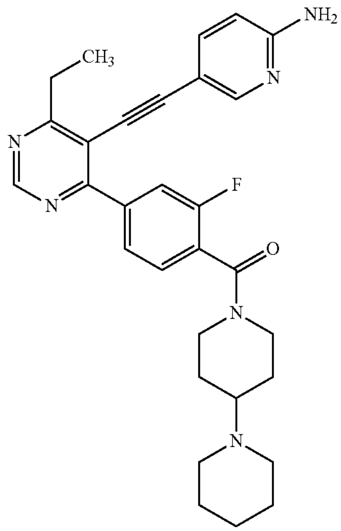 [SMILES: CCc1ncnc(-c2ccc(C(=O)N3CCC(N4CCCCC4)CC3)c(F)c2)c1C#Cc1ccc(N)nc1] | A-73 | 512.63 | 513 | 1.88 | 80 |
| D-71 | 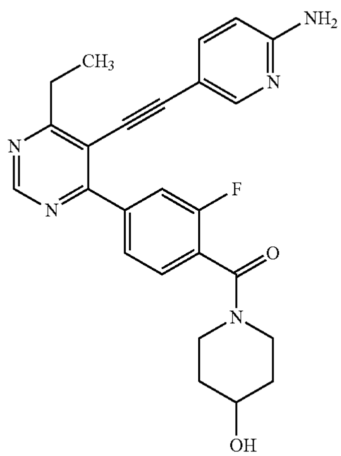 [SMILES: CCc1ncnc(-c2ccc(C(=O)N3CCC(O)CC3)c(F)c2)c1C#Cc1ccc(N)nc1] | A-73 | 445.50 | 446 | 1.45 | 32 |
| D-73 | 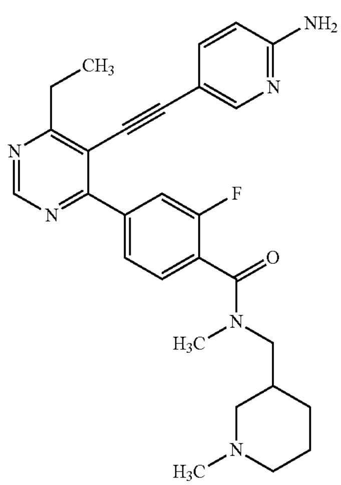 [SMILES: CCc1ncnc(-c2ccc(C(=O)N(C)CC3CCCN(C)C3)c(F)c2)c1C#Cc1ccc(N)nc1] | A-73 | 486.59 | 487 | 1.74 | 179 |

TABLE 3-continued

Examples D-1-D240

| Nr. | Structure | Int. | MW | MW [M + H] | t$_R$ [min] | EC$_{50}$ PC3 [nM] |
|---|---|---|---|---|---|---|
| D-74 | 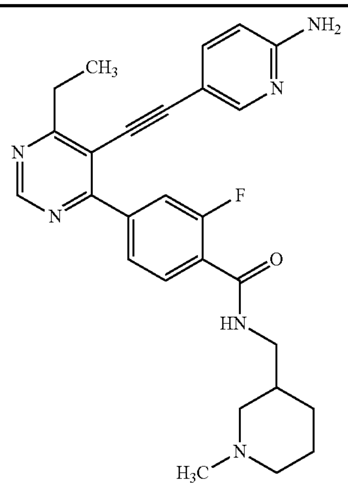 | A-73 | 472.57 | 473 | 1.69 | 128 |
| D-75 | 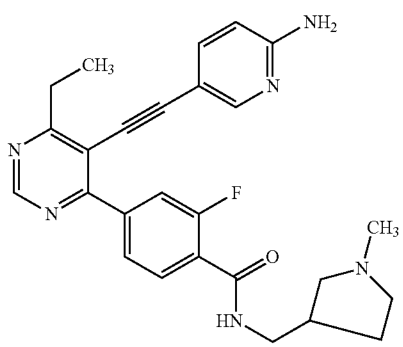 [SMILES: CCc1ncnc(-c2ccc(C(=O)NCC3CCN(C)C3)c(F)c2)c1C#Cc1ccc(N)nc1] | A-73 | 458.54 | 459 | 1.68 | 147 |
| D-76 | 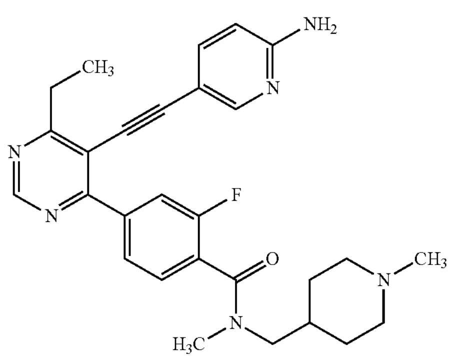 [SMILES: CCc1ncnc(-c2ccc(C(=O)N(C)CC3CCN(C)CC3)c(F)c2)c1C#Cc1ccc(N)nc1] | A-73 | 486.59 | 487 | 1.74 | 93 |
| D-77 | 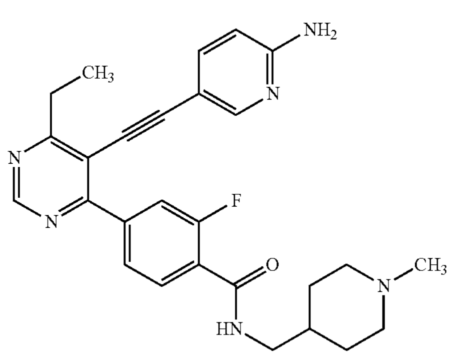 [SMILES: CCc1ncnc(-c2ccc(C(=O)NCC3CCN(C)CC3)c(F)c2)c1C#Cc1ccc(N)nc1] | A-73 | 472.57 | 473 | 1.70 | 80 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-78 | 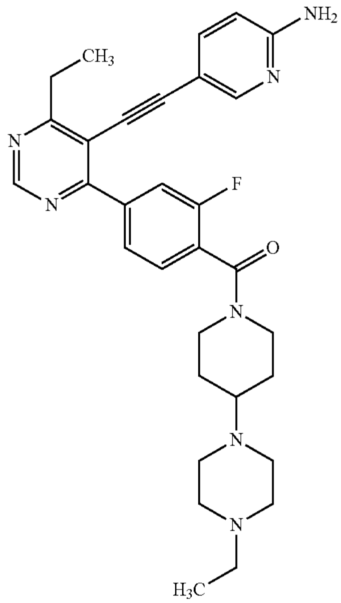 [SMILES: CCc1ncnc(-c2ccc(C(=O)N3CCC(N4CCN(CC)CC4)CC3)c(F)c2)c1C#Cc1ccc(N)nc1] | A-73 | 541.67 | 542 | 1.63 | 53 |
| D-79 | 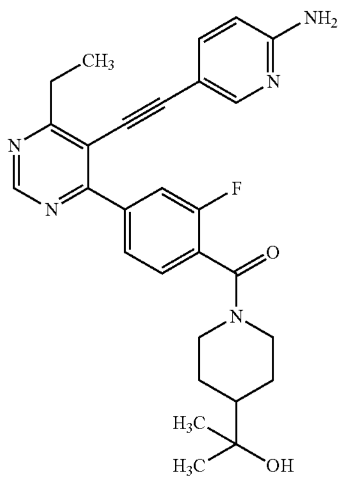 [SMILES: CCc1ncnc(-c2ccc(C(=O)N3CCC(C(C)(C)O)CC3)c(F)c2)c1C#Cc1ccc(N)nc1] | A-73 | 487.58 | 488 | 1.64 | 33 |
| D-80 | 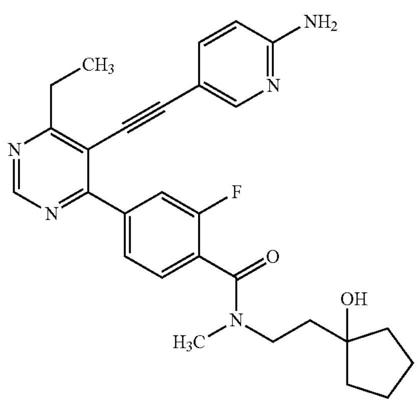 [SMILES: CCc1ncnc(-c2ccc(C(=O)N(C)CCC3(O)CCCC3)c(F)c2)c1C#Cc1ccc(N)nc1] | A-73 | 487.58 | 488 | 1.70 | 53 |

TABLE 3-continued

Examples D-1-D240

| Nr. | Structure | Int. | MW | MW [M + H] | $t_R$ [min] | EC$_{50}$ PC3 [nM] |
|---|---|---|---|---|---|---|
| D-81 | 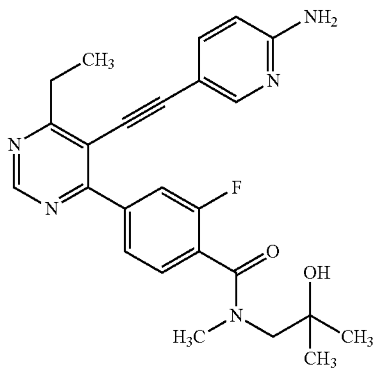 [SMILES: CCc1ncnc(-c2ccc(C(=O)N(C)CC(C)(C)O)c(F)c2)c1C#Cc1ccc(N)nc1] | A-73 | 447.51 | 448 | 1.55 | 72 |
| D-82 | 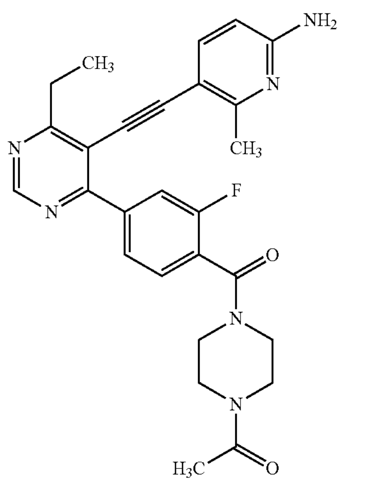 [SMILES: CCc1ncnc(-c2ccc(C(=O)N3CCN(C(C)=O)CC3)c(F)c2)c1C#Cc1ccc(N)nc1C] | A-41 | 486.55 | 487 | 1.52 | 50 |
| D-83 | 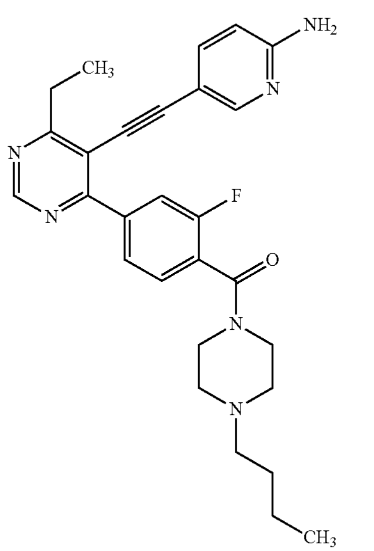 [SMILES: CCCCN1CCN(C(=O)c2ccc(-c3ncnc(CC)c3C#Cc3ccc(N)nc3)cc2F)CC1] | A-73 | 486.59 | 487 | 1.90 | 36 |

TABLE 3-continued

Examples D-1-D240

| Nr. | Structure | Int. | MW | MW [M + H] | $t_R$ [min] | EC$_{50}$ PC3 [nM] |
|---|---|---|---|---|---|---|
| D-84 | 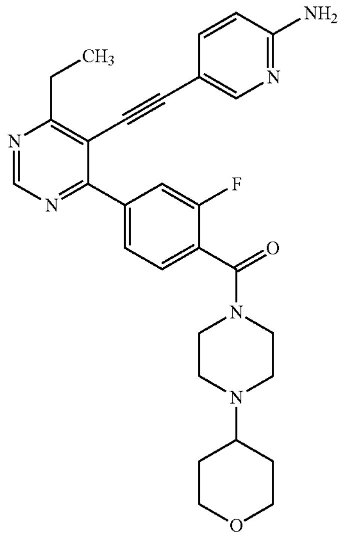 [SMILES: CCc1ncnc(-c2ccc(C(=O)N3CCN(C4CCOCC4)CC3)c(F)c2)c1C#Cc1ccc(N)nc1] | A-73 | 514.60 | 515 | 1.60 | 17 |
| D-85 | 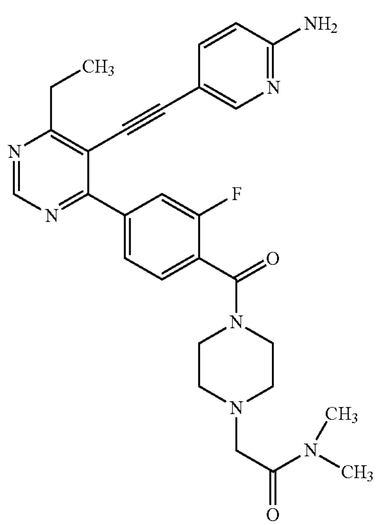 [SMILES: CCc1ncnc(-c2ccc(C(=O)N3CCN(CC(=O)N(C)C)CC3)c(F)c2)c1C#Cc1ccc(N)nc1] | A-73 | 515.59 | 516 | 1.54 | 56 |

TABLE 3-continued

Examples D-1-D240

| Nr. | Structure | Int. | MW | MW [M + H] | $t_R$ [min] | EC$_{50}$ PC3 [nM] |
|---|---|---|---|---|---|---|
| D-86 | 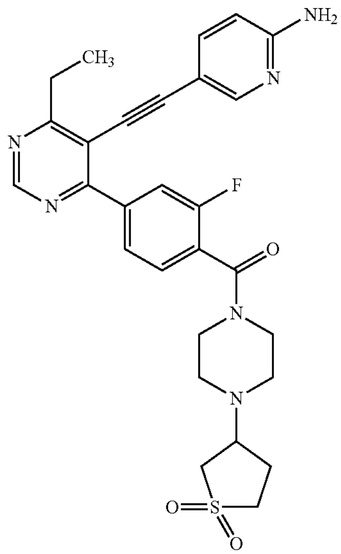 [SMILES: CCc1ncnc(-c2ccc(C(=O)N3CCN(C4CCS(=O)(=O)C4)CC3)c(F)c2)c1C#Cc1ccc(N)nc1] | A-73 | 548.64 | 549 | 1.51 | 39 |
| D-87 | 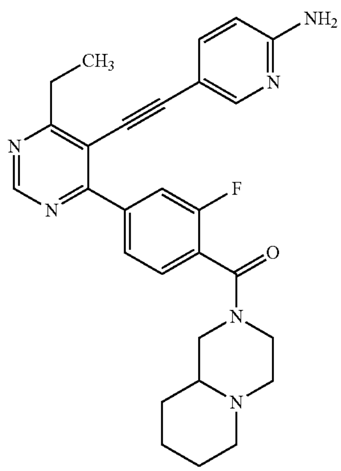 [SMILES: CCc1ncnc(-c2ccc(C(=O)N3CCN4CCCCC4C3)c(F)c2)c1C#Cc1ccc(N)nc1] | A-73 | 484.58 | 485 | 1.73 | 54 |
| D-88 | 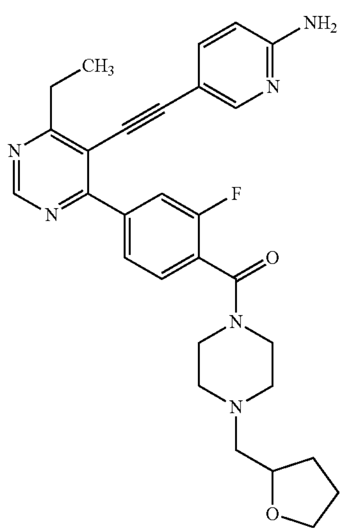 [SMILES: CCc1ncnc(-c2ccc(C(=O)N3CCN(CC4CCCO4)CC3)c(F)c2)c1C#Cc1ccc(N)nc1] | A-73 | 514.60 | 515 | 1.70 | 68 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-89 | 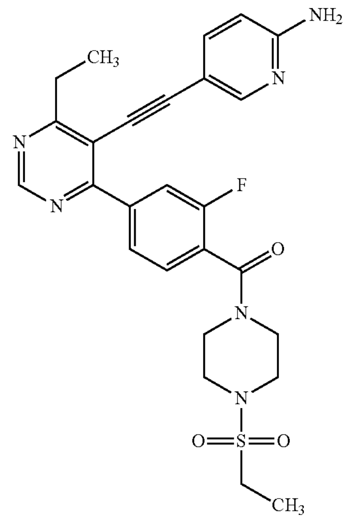 [SMILES: CCc1ncnc(-c2ccc(C(=O)N3CCN(S(=O)(=O)CC)CC3)c(F)c2)c1C#Cc1ccc(N)nc1] | A-73 | 522.60 | 523 | 1.62 | 42 |
| D-90 | 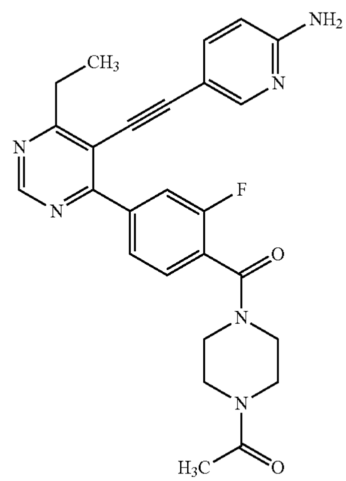 [SMILES: CCc1ncnc(-c2ccc(C(=O)N3CCN(C(C)=O)CC3)c(F)c2)c1C#Cc1ccc(N)nc1] | A-73 | 472.52 | 473 | 1.47 | 48 |
| D-91 | 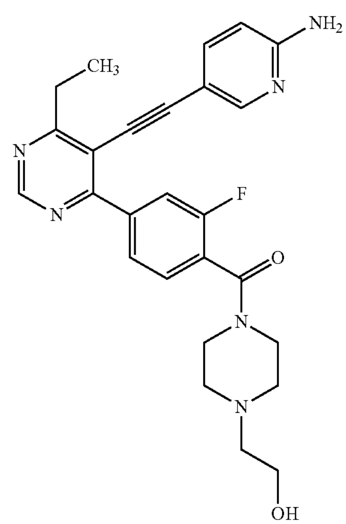 [SMILES: CCc1ncnc(-c2ccc(C(=O)N3CCN(CCO)CC3)c(F)c2)c1C#Cc1ccc(N)nc1] | A-73 | 474.54 | 475 | 1.45 | 44 |

TABLE 3-continued
Examples D-1-D240
| Nr. | Structure | Int. | MW | MW [M + H] | $t_R$ [min] | $EC_{50}$ PC3 [nM] |
|---|---|---|---|---|---|---|
| D-92 | 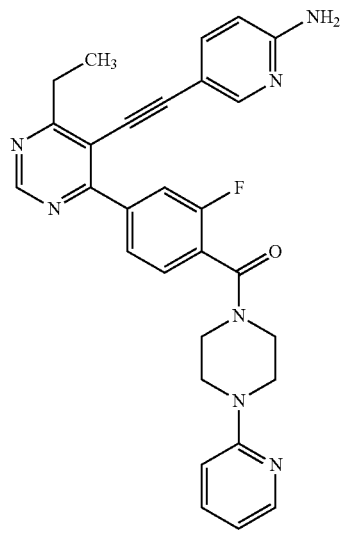 [SMILES: CCc1ncnc(-c2ccc(C(=O)N3CCN(c4ccccn4)CC3)c(F)c2)c1C#Cc1ccc(N)nc1] | A-73 | 507.57 | 508 | 1.8 | 76 |
| D-93 | 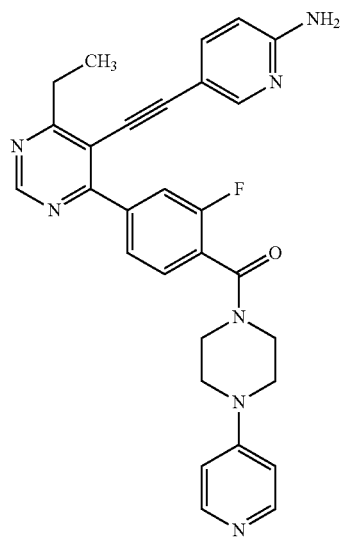 [SMILES: CCc1ncnc(-c2ccc(C(=O)N3CCN(c4ccncc4)CC3)c(F)c2)c1C#Cc1ccc(N)nc1] | A-73 | 507.57 | 508 | 1.62 | 76 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-94 | 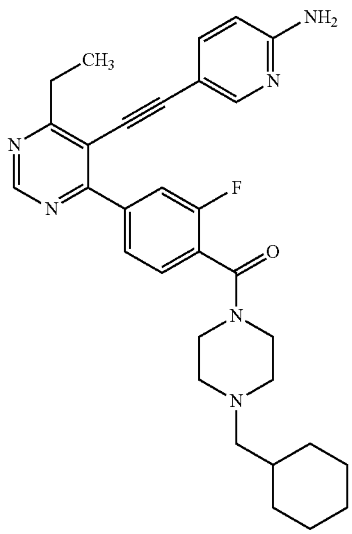 [SMILES: CCc1ncnc(-c2ccc(C(=O)N3CCN(CC4CCCCC4)CC3)c(F)c2)c1C#Cc1ccc(N)nc1] | A-73 | 526.66 | 527 | 2.22 | 602 |
| D-95 | 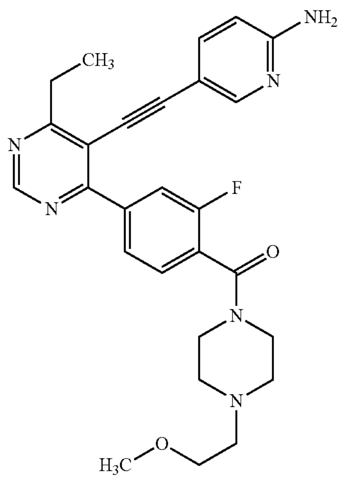 [SMILES: CCc1ncnc(-c2ccc(C(=O)N3CCN(CCOC)CC3)c(F)c2)c1C#Cc1ccc(N)nc1] | A-73 | 488.56 | 489 | 1.6 | 40 |
| D-96 | 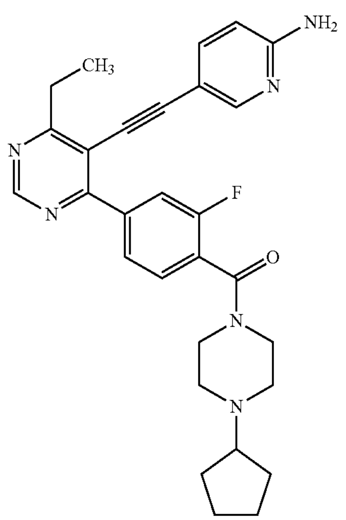 [SMILES: CCc1ncnc(-c2ccc(C(=O)N3CCN(C4CCCC4)CC3)c(F)c2)c1C#Cc1ccc(N)nc1] | A-73 | 498.60 | 499 | 1.87 | 63 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-97 | 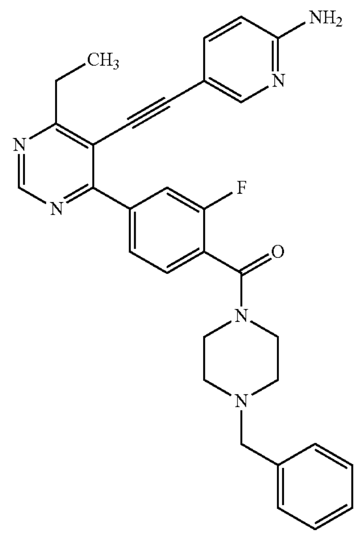 [SMILES: CCc1ncnc(-c2ccc(C(=O)N3CCN(Cc4ccccc4)CC3)c(F)c2)c1C#Cc1ccc(N)nc1] | A-73 | 520.61 | 521 | 1.95 | 151 |
| D-98 | 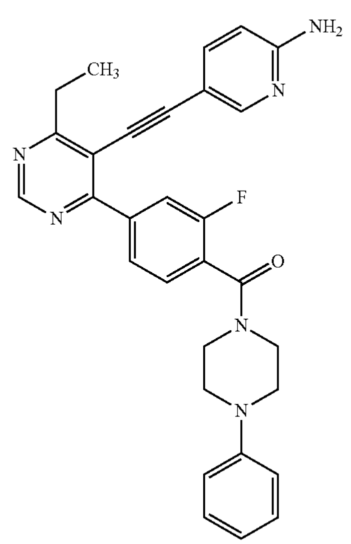 [SMILES: CCc1ncnc(-c2ccc(C(=O)N3CCN(c4ccccc4)CC3)c(F)c2)c1C#Cc1ccc(N)nc1] | A-73 | 506.58 | 507 | 1.95 | 78 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-99 | 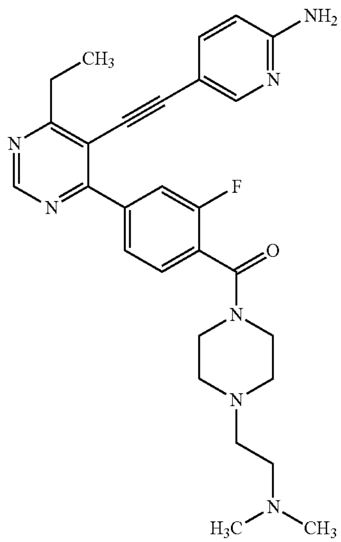 [SMILES: CCc1ncnc(-c2ccc(C(=O)N3CCN(CCN(C)C)CC3)c(F)c2)c1C#Cc1ccc(N)nc1] | A-73 | 501.61 | 502 | 1.62 | 78 |
| D-100 | 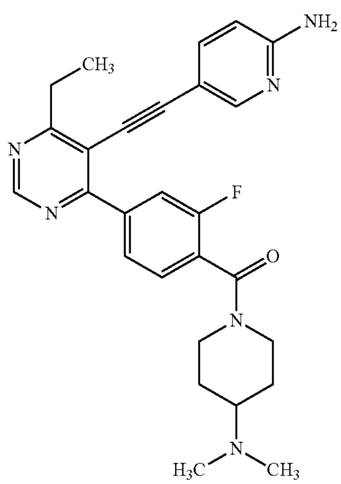 [SMILES: CCc1ncnc(-c2ccc(C(=O)N3CCC(N(C)C)CC3)c(F)c2)c1C#Cc1ccc(N)nc1] | A-73 | 472.57 | 473 | 1.63 | 44 |
| D-101 | 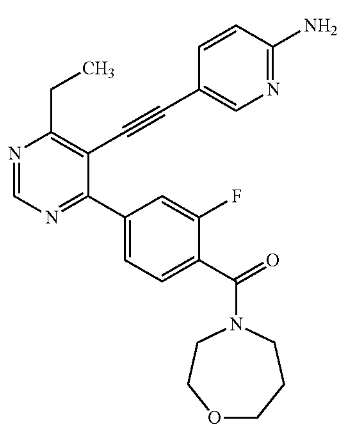 [SMILES: CCc1ncnc(-c2ccc(C(=O)N3CCCOCC3)c(F)c2)c1C#Cc1ccc(N)nc1] | A-73 | 445.50 | 446 | 1.56 | 12 |

TABLE 3-continued

Examples D-1-D240

| Nr. | Structure | Int. | MW | MW [M + H] | $t_R$ [min] | EC$_{50}$ PC3 [nM] |
|---|---|---|---|---|---|---|
| D-103 | 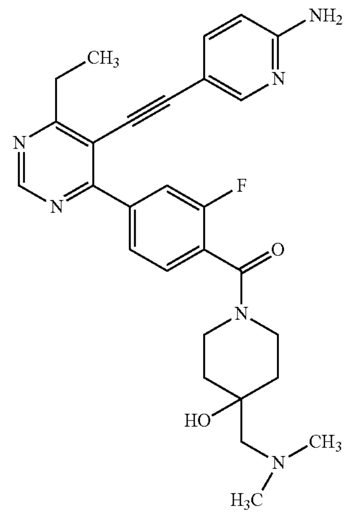 [SMILES: CCc1ncnc(-c2ccc(C(=O)N3CCC(O)(CN(C)C)CC3)c(F)c2)c1C#Cc1ccc(N)nc1] | A-73 | 502.59 | 503 | 1.62 | 58 |
| D-104 | 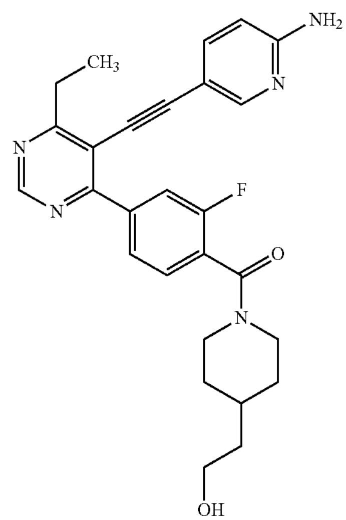 [SMILES: CCc1ncnc(-c2ccc(C(=O)N3CCC(CCO)CC3)c(F)c2)c1C#Cc1ccc(N)nc1] | A-73 | 473.55 | 474 | 1.57 | 62 |
| D-105 | 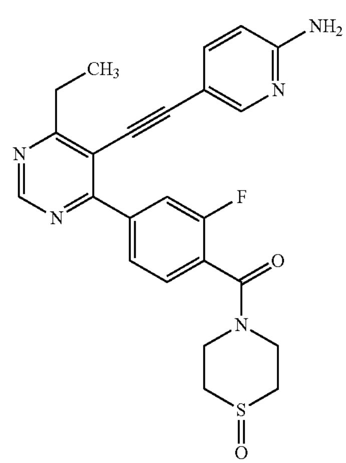 [SMILES: CCc1ncnc(-c2ccc(C(=O)N3CCS(=O)CC3)c(F)c2)c1C#Cc1ccc(N)nc1] | A-73 | 463.53 | 462 | 1.39 | 50 |

TABLE 3-continued
Examples D-1-D240
| Nr. | Structure | Int. | MW | MW [M + H] | $t_R$ [min] | $EC_{50}$ PC3 [nM] |
|---|---|---|---|---|---|---|
| D-106 | 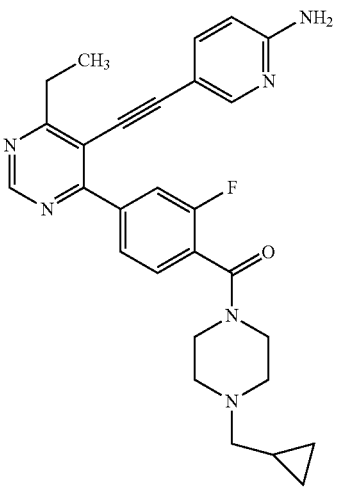 [SMILES: CCc1ncnc(-c2ccc(C(=O)N3CCN(CC4CC4)CC3)c(F)c2)c1C#Cc1ccc(N)nc1] | A-73 | 484.58 | 485 | 1.77 | 42 |
| D-107 | 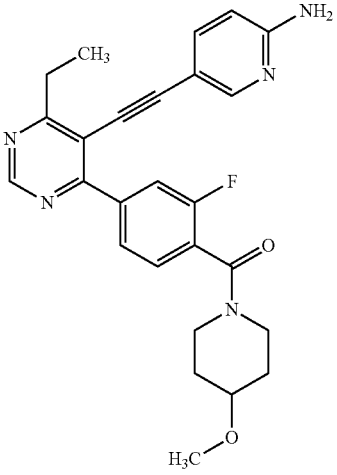 [SMILES: CCc1ncnc(-c2ccc(C(=O)N3CCC(OC)CC3)c(F)c2)c1C#Cc1ccc(N)nc1] | A-73 | 459.52 | 460 | 1.66 | 25 |
| D-108 | 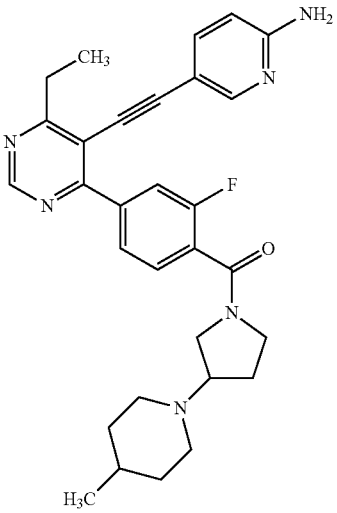 [SMILES: CCc1ncnc(-c2ccc(C(=O)N3CCC(N4CCC(C)CC4)C3)c(F)c2)c1C#Cc1ccc(N)nc1] | A-73 | 512.63 | 513 | 1.90 | 41 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-110 | 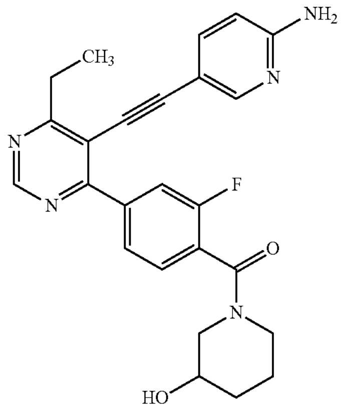 [SMILES: CCc1ncnc(-c2ccc(C(=O)N3CCCC(O)C3)c(F)c2)c1C#Cc1ccc(N)nc1] | A-73 | 445.50 | 446 | 1.51 | 30 |
| D-111 | 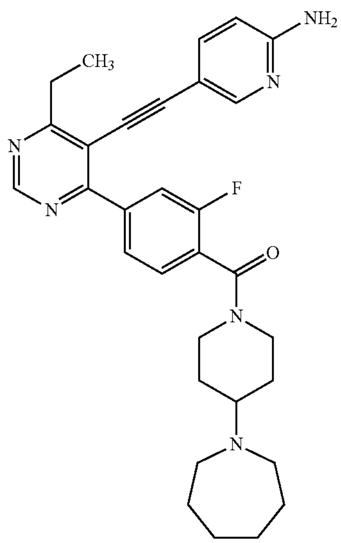 [SMILES: CCc1ncnc(-c2ccc(C(=O)N3CCC(N4CCCCCC4)CC3)c(F)c2)c1C#Cc1ccc(N)nc1] | A-73 | 526.66 | 527 | 2.05 | 87 |
| D-112 | 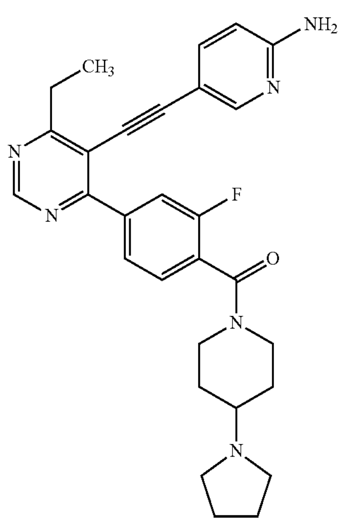 [SMILES: CCc1ncnc(-c2ccc(C(=O)N3CCC(N4CCCC4)CC3)c(F)c2)c1C#Cc1ccc(N)nc1] | A-73 | 498.60 | 499 | 1.77 | 61 |

TABLE 3-continued

Examples D-1-D240

| Nr. | Structure | Int. | MW | MW [M + H] | $t_R$ [min] | EC$_{50}$ PC3 [nM] |
|---|---|---|---|---|---|---|
| D-113 | 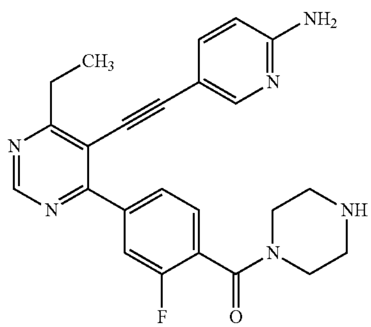 [SMILES: CCc1ncnc(-c2ccc(C(=O)N3CCNCC3)c(F)c2)c1C#Cc1ccc(N)nc1] | A-73 | 430.48 | 431 | 1.42 | 80 |
| D-114 | 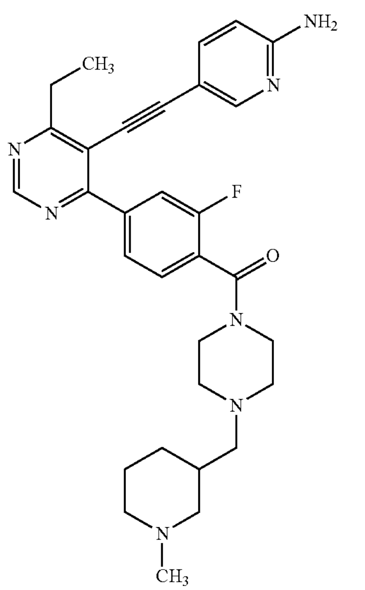 [SMILES: CCc1ncnc(-c2ccc(C(=O)N3CCN(CC4CCCN(C)C4)CC3)c(F)c2)c1C#Cc1ccc(N)nc1] | A-73 | 541.67 | 542 | 1.85 | 39 |
| D-116 | 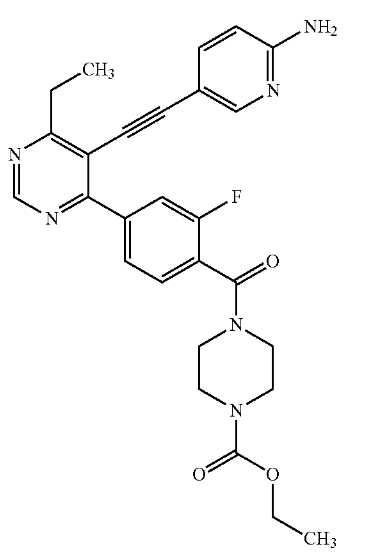 [SMILES: CCOC(=O)N1CCN(C(=O)c2ccc(-c3ncnc(CC)c3C#Cc3ccc(N)nc3)cc2F)CC1] | A-73 | 502.55 | 503 | 1.72 | 22 |

TABLE 3-continued
Examples D-1-D240
| Nr. | Structure | Int. | MW | MW [M + H] | $t_R$ [min] | EC$_{50}$ PC3 [nM] |
|---|---|---|---|---|---|---|
| D-117 | 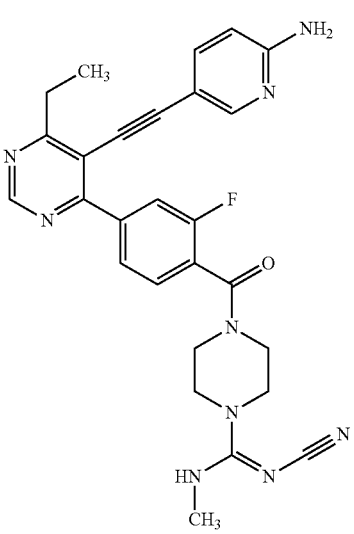 [SMILES: CCc1ncnc(-c2ccc(C(=O)N3CCN(/C(=N\C#N)NC)CC3)c(F)c2)c1C#Cc1ccc(N)nc1] | A-73 | 511.56 | 512 | 1.48 | 244 |
| D-118 | 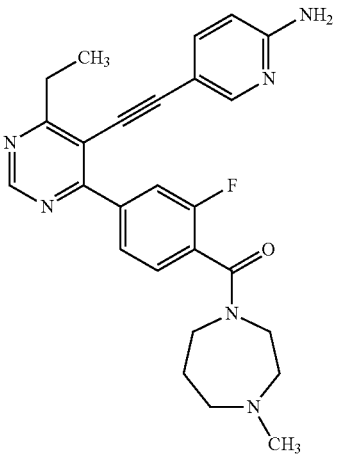 [SMILES: CCc1ncnc(-c2ccc(C(=O)N3CCCN(C)CC3)c(F)c2)c1C#Cc1ccc(N)nc1] | A-73 | 458.54 | 459 | 1.57 | 48 |
| D-119 | 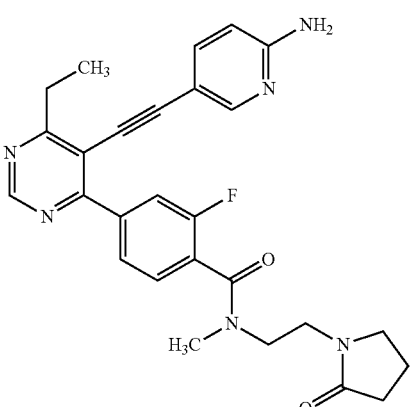 | A-73 | 486.55 | 487 | 1.49 | 114 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-120 | 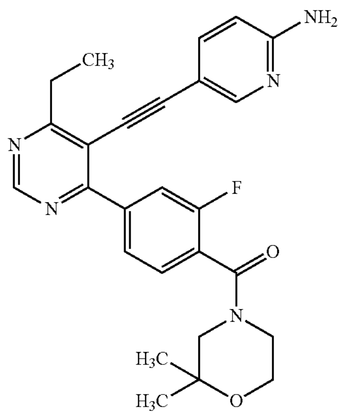 [SMILES: CCc1ncnc(-c2ccc(C(=O)N3CCOC(C)(C)C3)c(F)c2)c1C#Cc1ccc(N)nc1] | A-73 | 459.52 | 458 | 1.69 | 199 |
| D-121 | 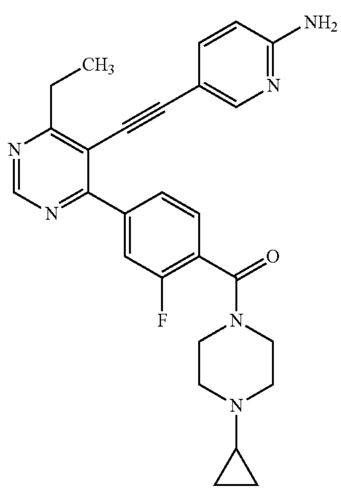 [SMILES: CCc1ncnc(-c2ccc(C(=O)N3CCN(C4CC4)CC3)c(F)c2)c1C#Cc1ccc(N)nc1] | A-73 | 470.55 | 471 | 1.59 | 17 |
| D-122 | 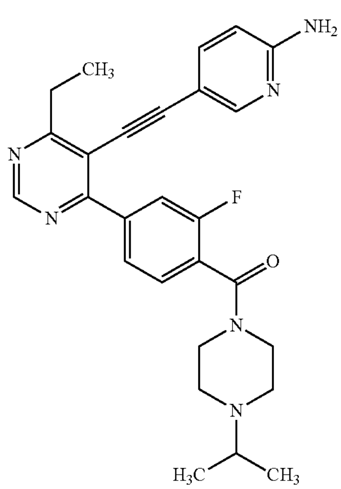 [SMILES: CCc1ncnc(-c2ccc(C(=O)N3CCN(C(C)C)CC3)c(F)c2)c1C#Cc1ccc(N)nc1] | A-73 | 472.57 | 473 | 1.58 | 15 |

TABLE 3-continued

Examples D-1-D240

| Nr. | Structure | Int. | MW | MW [M + H] | $t_R$ [min] | EC$_{50}$ PC3 [nM] |
|---|---|---|---|---|---|---|
| D-123 | 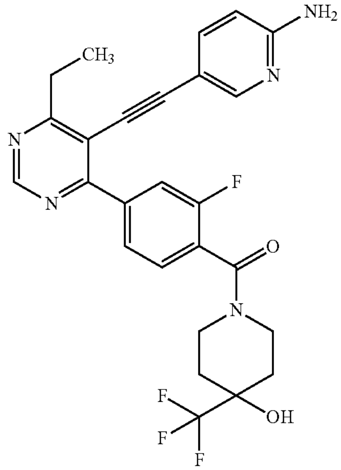 [SMILES: CCc1ncnc(-c2ccc(C(=O)N3CCC(O)(C(F)(F)F)CC3)c(F)c2)c1C#Cc1ccc(N)nc1] | A-73 | 513.49 | 514 | 1.56 | 76 |
| D-124 | 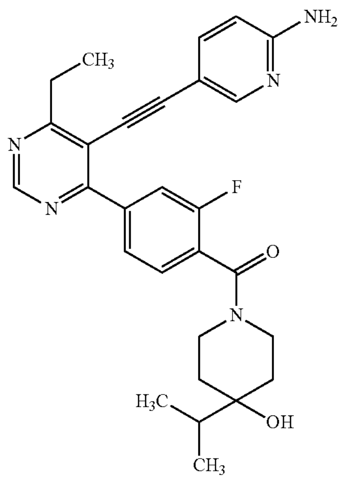 [SMILES: CCc1ncnc(-c2ccc(C(=O)N3CCC(O)(C(C)C)CC3)c(F)c2)c1C#Cc1ccc(N)nc1] | A-73 | 487.58 | 488 | 1.58 | 43 |
| D-125 | 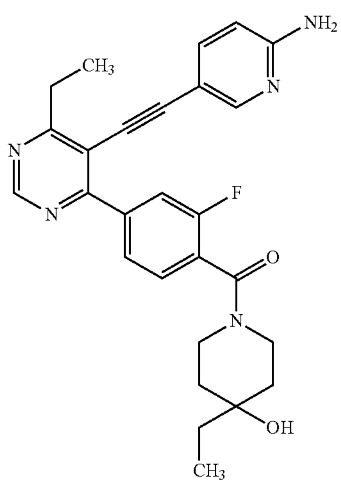 [SMILES: CCc1ncnc(-c2ccc(C(=O)N3CCC(O)(CC)CC3)c(F)c2)c1C#Cc1ccc(N)nc1] | A-73 | 473.55 | 474 | 1.48 | 93 |

TABLE 3-continued

Examples D-1-D240

| Nr. | Structure | Int. | MW | MW [M + H] | $t_R$ [min] | EC$_{50}$ PC3 [nM] |
|---|---|---|---|---|---|---|
| D-126 | 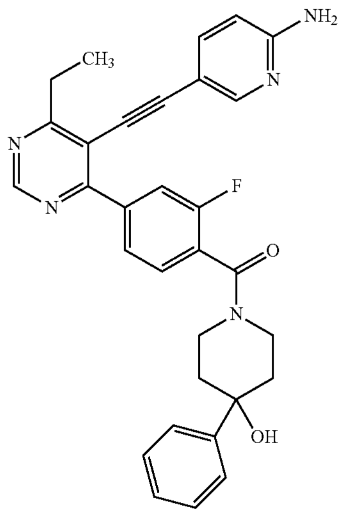 [SMILES: CCc1ncnc(-c2ccc(C(=O)N3CCC(O)(c4ccccc4)CC3)c(F)c2)c1C#Cc1ccc(N)nc1] | A-73 | 521.59 | 522 | 1.63 | 144 |
| D-127 | 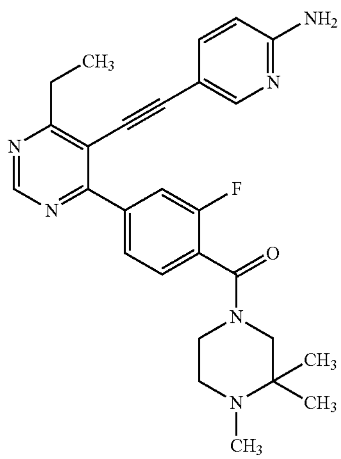 [SMILES: CCc1ncnc(-c2ccc(C(=O)N3CCN(C)C(C)(C)C3)c(F)c2)c1C#Cc1ccc(N)nc1] | A-73 | 472.57 | 473 | 1.48 | 80 |
| D-128 | 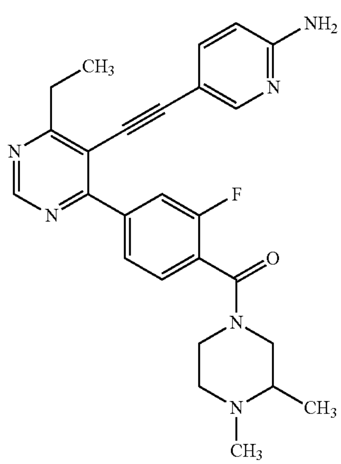 [SMILES: CCc1ncnc(-c2ccc(C(=O)N3CCN(C)C(C)C3)c(F)c2)c1C#Cc1ccc(N)nc1] | A-73 | 458.54 | 459 | 1.43 | 65 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-129 | 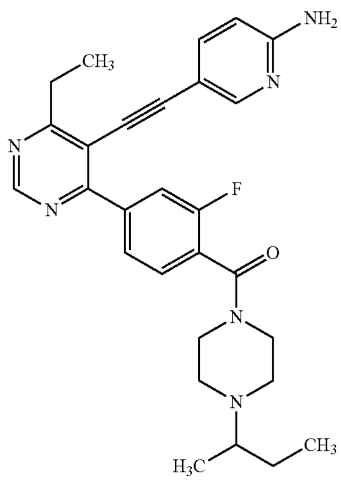 [SMILES: CCc1ncnc(-c2ccc(C(=O)N3CCN(C(C)CC)CC3)c(F)c2)c1C#Cc1ccc(N)nc1] | A-73 | 486.59 | 487 | 1.74 | 30 |
| D-130 | 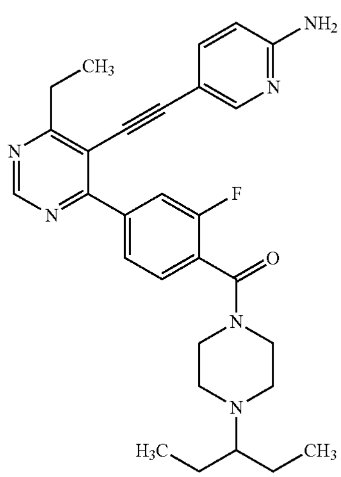 [SMILES: CCc1ncnc(-c2ccc(C(=O)N3CCN(C(CC)CC)CC3)c(F)c2)c1C#Cc1ccc(N)nc1] | A-73 | 500.62 | 501 | 1.96 | 45 |
| D-131 | 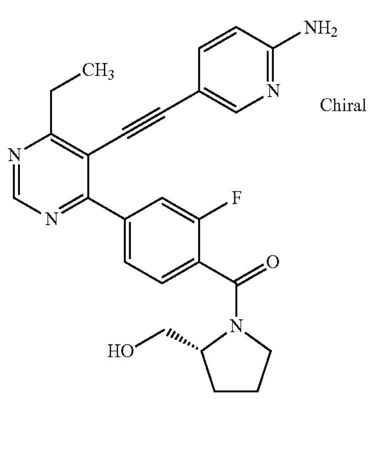 [SMILES: CCc1ncnc(-c2ccc(C(=O)N3CCC[C@@H]3CO)c(F)c2)c1C#Cc1ccc(N)nc1] | A-73 | 445.50 | 446 | 1.37 | 57 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-132 | 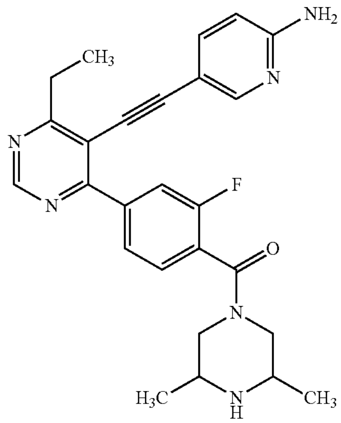 [SMILES: CCc1ncnc(-c2ccc(C(=O)N3CC(C)NC(C)C3)c(F)c2)c1C#Cc1ccc(N)nc1] | A-73 | 458.54 | 459 | 1.38 | 98 |
| D-133 | 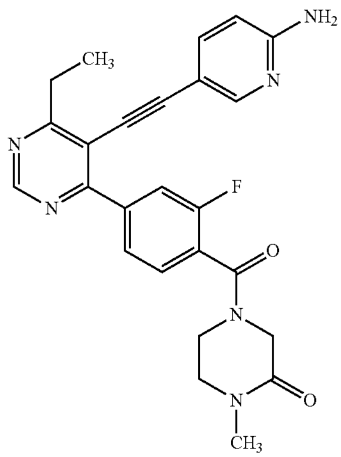 [SMILES: CCc1ncnc(-c2ccc(C(=O)N3CCN(C)C(=O)C3)c(F)c2)c1C#Cc1ccc(N)nc1] | A-73 | 458.49 | 459 | 1.29 | 27 |
| D-134 | 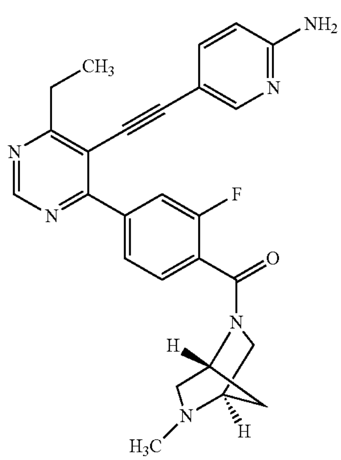 [SMILES: CCc1ncnc(-c2ccc(C(=O)N3C[C@H]4C[C@@H]3CN4C)c(F)c2)c1C#Cc1ccc(N)nc1] | A-73 | 456.52 | 455 | 1.51 | 316 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-135 | 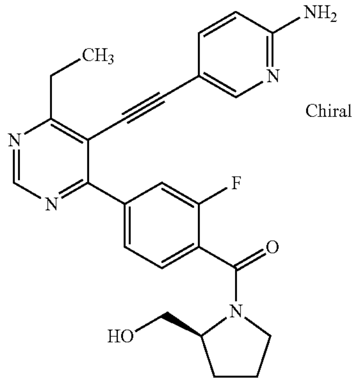 [SMILES: CCc1ncnc(-c2ccc(C(=O)N3CCC[C@H]3CO)c(F)c2)c1C#Cc1ccc(N)nc1] | A-73 | 445.50 | 446 | 1.55 | 122 |
| D-136 | 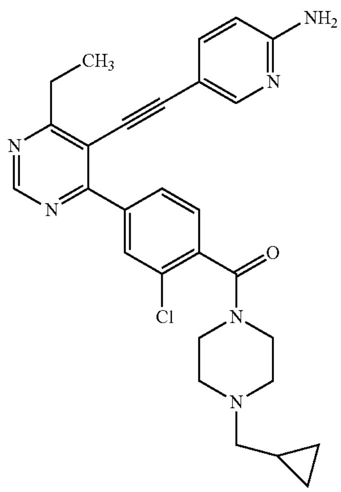 [SMILES: CCc1ncnc(-c2ccc(C(=O)N3CCN(CC4CC4)CC3)c(Cl)c2)c1C#Cc1ccc(N)nc1] | A-77 | 501.03 | 499/501 | 1.83 | 106 |
| D-138 | 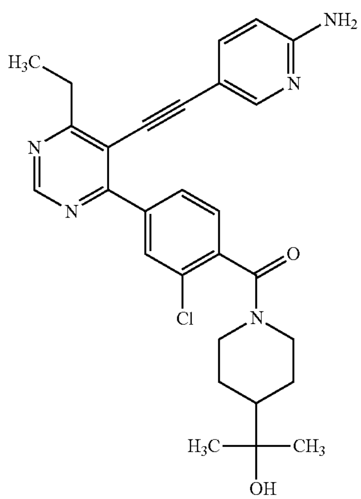 [SMILES: CCc1ncnc(-c2ccc(C(=O)N3CCC(C(C)(C)O)CC3)c(Cl)c2)c1C#Cc1ccc(N)nc1] | A-77 | 504.03 | 504 | 1.69 | 95 |

TABLE 3-continued

Examples D-1-D240

| Nr. | Structure | Int. | MW | MW [M + H] | $t_R$ [min] | EC$_{50}$ PC3 [nM] |
|---|---|---|---|---|---|---|
| D-139 | 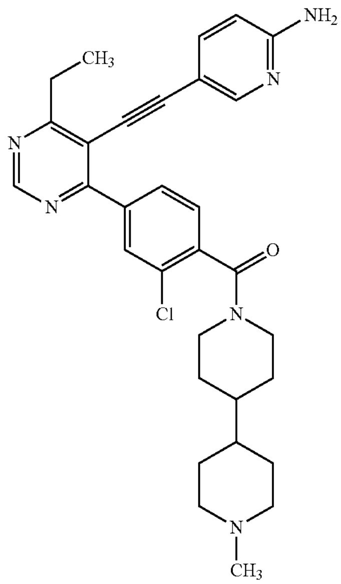 [SMILES: CCc1ncnc(-c2ccc(C(=O)N3CCC(C4CCN(C)CC4)CC3)c(Cl)c2)c1C#Cc1ccc(N)nc1] | A-77 | 543.11 | 543/545 | 1.96 | 146 |
| D-140 | 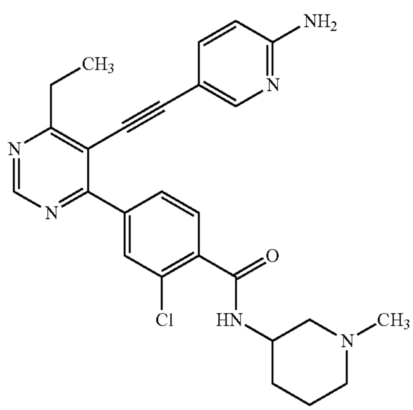 [SMILES: CCc1ncnc(-c2ccc(C(=O)NC3CCCN(C)C3)c(Cl)c2)c1C#Cc1ccc(N)nc1] | A-77 | 474.99 | 475/477 | 1.68 | 221 |
| D-141 | 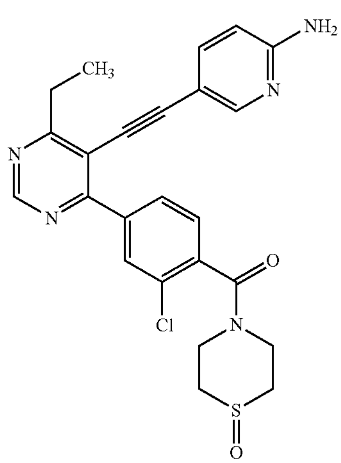 [SMILES: CCc1ncnc(-c2ccc(C(=O)N3CCS(=O)CC3)c(Cl)c2)c1C#Cc1ccc(N)nc1] | A-77 | 479.99 | 478 | 1.44 | 39 |

TABLE 3-continued
Examples D-1-D240
| Nr. | Structure | Int. | MW | MW [M + H] | $t_R$ [min] | $EC_{50}$ PC3 [nM] |
|---|---|---|---|---|---|---|
| D-142 | 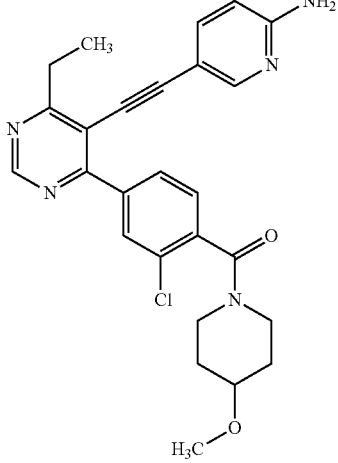 | A-77 | 475.98 | 476/478 | 1.72 | 80 |
| D-143 | 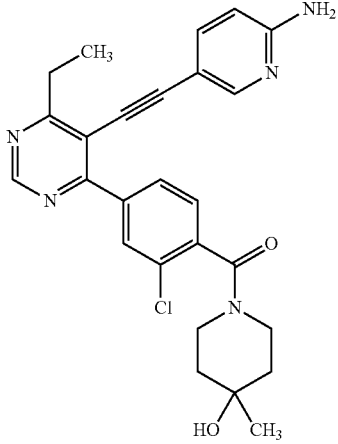 [SMILES: CCc1ncnc(-c2ccc(C(=O)N3CCC(C)(O)CC3)c(Cl)c2)c1C#Cc1ccc(N)nc1] | A-77 | 475.98 | 474/476 | 1.6 | 76 |
| D-145 | 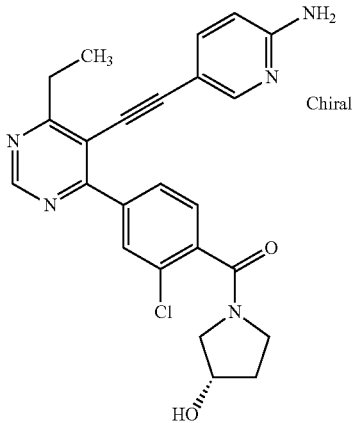 [SMILES: CCc1ncnc(-c2ccc(C(=O)N3CC[C@H](O)C3)c(Cl)c2)c1C#Cc1ccc(N)nc1] | A-77 | 447.92 | 448/450 | 1.49 | 76 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-146 | | A-77 | 447.92 | 448 | 1.49 | 79 |
| D-147 | | A-77 | 461.95 | 460/462 | 1.57 | 33 |
| D-148 | | A-77 | 543.11 | 543 | 2.08 | 115 |

TABLE 3-continued
Examples D-1-D240
| Nr. | Structure | Int. | MW | MW [M + H] | $t_R$ [min] | EC$_{50}$ PC3 [nM] |
|---|---|---|---|---|---|---|
| D-149 | 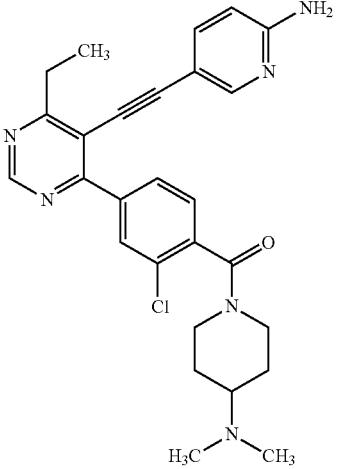 [SMILES: CCc1ncnc(-c2ccc(C(=O)N3CCC(N(C)C)CC3)c(Cl)c2)c1C#Cc1ccc(N)nc1] | A-77 | 489.02 | 487/489 | 1.69 | 105 |
| D-150 | 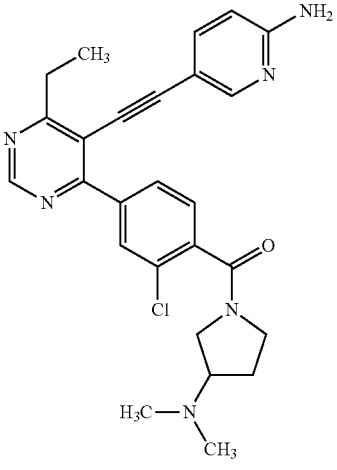 [SMILES: CCc1ncnc(-c2ccc(C(=O)N3CCC(N(C)C)C3)c(Cl)c2)c1C#Cc1ccc(N)nc1] | A-77 | 474.99 | 475/477 | 1.64 | 88 |
| D-151 | 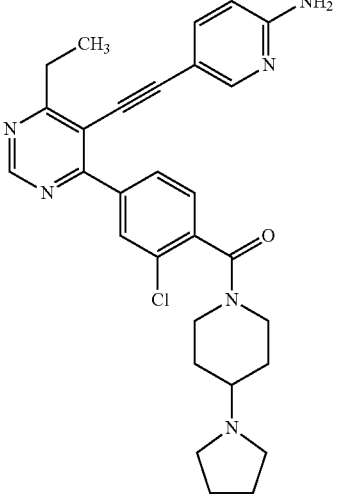 | A-77 | 515.06 | 515/517 | 1.84 | 83 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-152 | 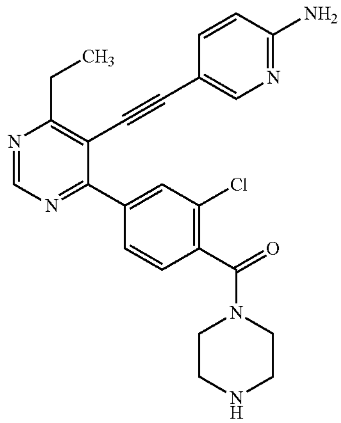 [SMILES: CCc1ncnc(-c2ccc(C(=O)N3CCNCC3)c(Cl)c2)c1C#Cc1ccc(N)nc1] | A-77 | 446.94 | 447 | 1.48 | 73 |
| D-153 | 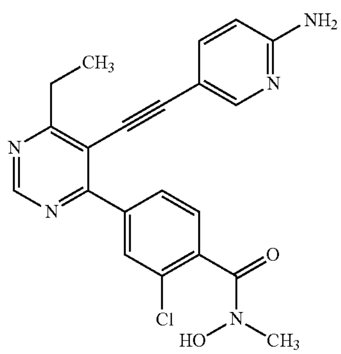 [SMILES: CCc1ncnc(-c2ccc(C(=O)N(C)O)c(Cl)c2)c1C#Cc1ccc(N)nc1] | A-77 | 407.86 | 408 | 1.11 | 55 |
| D-154 | 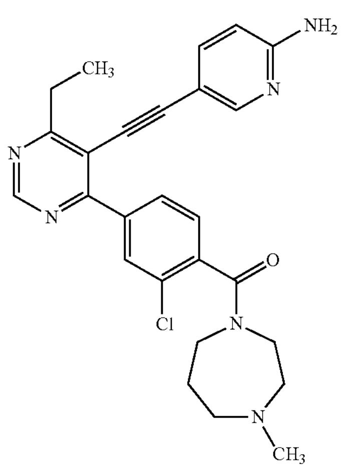 [SMILES: CCc1ncnc(-c2ccc(C(=O)N3CCCN(C)CC3)c(Cl)c2)c1C#Cc1ccc(N)nc1] | A-77 | 474.99 | 475/477 | 1.64 | 122 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-155 | 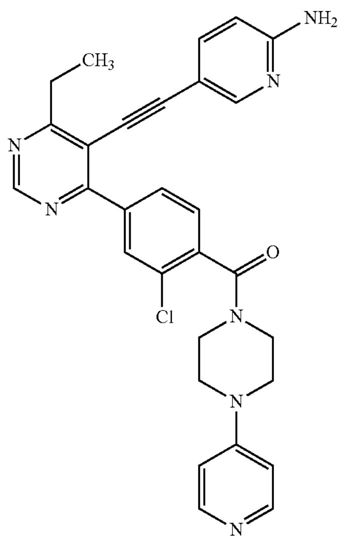 [SMILES: CCc1ncnc(-c2ccc(C(=O)N3CCN(c4ccncc4)CC3)c(Cl)c2)c1C#Cc1ccc(N)nc1] | A-77 | 524.03 | 524 | 1.68 | 64 |
| D-156 | 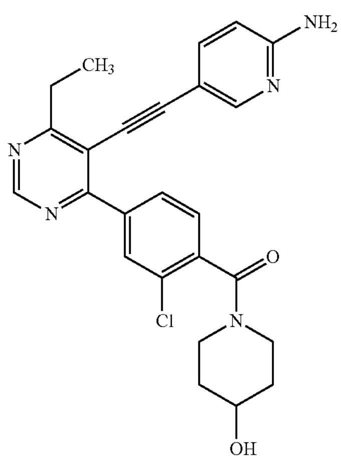 [SMILES: CCc1ncnc(-c2ccc(C(=O)N3CCC(O)CC3)c(Cl)c2)c1C#Cc1ccc(N)nc1] | A-77 | 461.95 | 462/464 | 1.52 | 40 |
| D-157 | 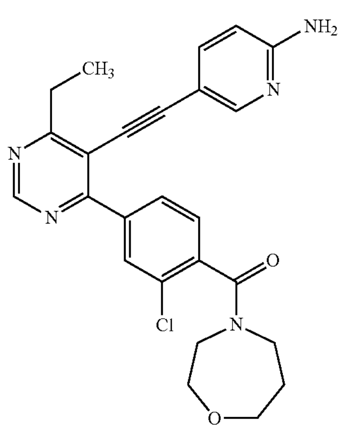 [SMILES: CCc1ncnc(-c2ccc(C(=O)N3CCCOCC3)c(Cl)c2)c1C#Cc1ccc(N)nc1] | A-77 | 461.95 | 462/464 | 1.63 | 43 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-159 | 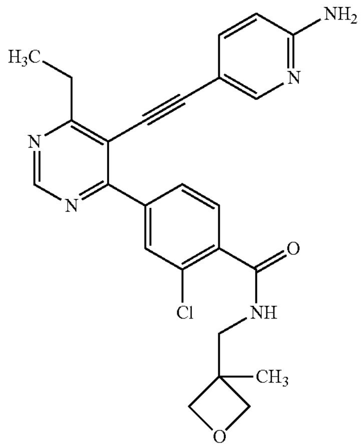 [SMILES: CCc1ncnc(-c2ccc(C(=O)NCC3(C)COC3)c(Cl)c2)c1C#Cc1ccc(N)nc1] | A-77 | 461.95 | 462 | 1.58 | 38 |
| D-160 | 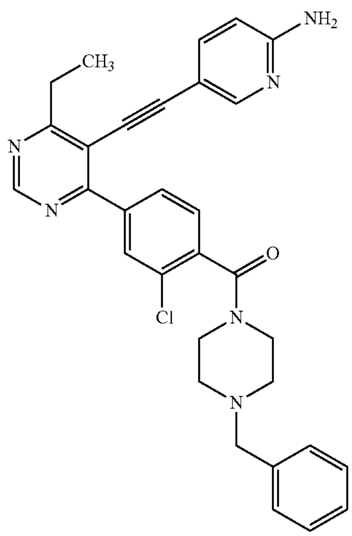 [SMILES: CCc1ncnc(-c2ccc(C(=O)N3CCN(Cc4ccccc4)CC3)c(Cl)c2)c1C#Cc1ccc(N)nc1] | A-77 | 537.06 | M + H = 537/539 | 2.10 | 133 |
| D-161 | 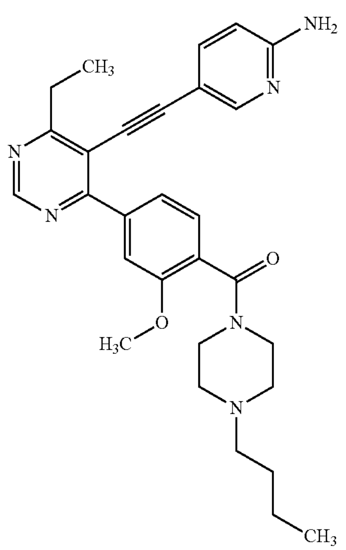 [SMILES: CCCCN1CCN(C(=O)c2ccc(-c3ncnc(CC)c3C#Cc3ccc(N)nc3)cc2OC)CC1] | A-93 | 498.63 | 499 | 1.66 | 156 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-162 | 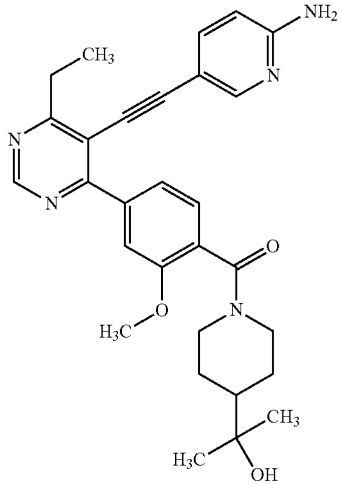 [SMILES: CCc1ncnc(-c2ccc(C(=O)N3CCC(C(C)(C)O)CC3)c(OC)c2)c1C#Cc1ccc(N)nc1] | A-93 | 499.61 | 500 | 1.41 | 124 |
| D-163 | 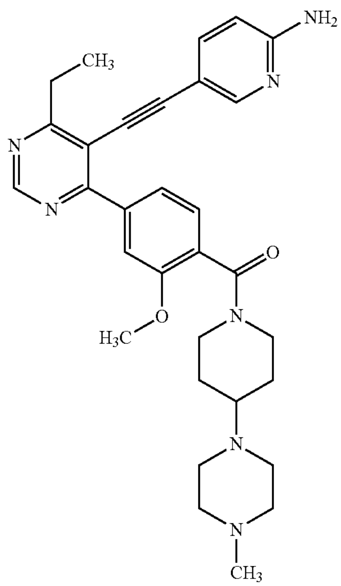 [SMILES: CCc1ncnc(-c2ccc(C(=O)N3CCC(N4CCN(C)CC4)CC3)c(OC)c2)c1C#Cc1ccc(N)nc1] | A-93 | 539.68 | 540 | 1.33 | 293 |
| D-164 | 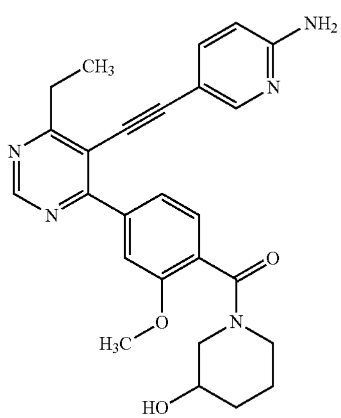 [SMILES: CCc1ncnc(-c2ccc(C(=O)N3CCCC(O)C3)c(OC)c2)c1C#Cc1ccc(N)nc1] | A-93 | 457.53 | 458 | 1.29 | 91 |

TABLE 3-continued
Examples D-1-D240
| Nr. | Structure | Int. | MW | MW [M + H] | $t_R$ [min] | $EC_{50}$ PC3 [nM] |
|---|---|---|---|---|---|---|
| D-165 | 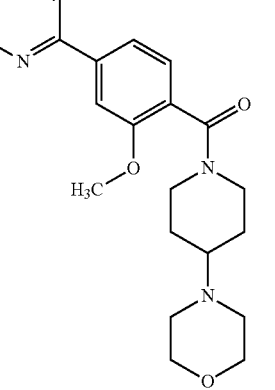 | A-93 | 526.64 | 527 | 1.35 | 167 |
| D-166 | 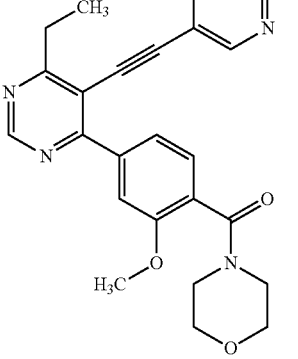 | A-93 | 443.50 | 444 | 1.32 | 116 |
| D-167 | 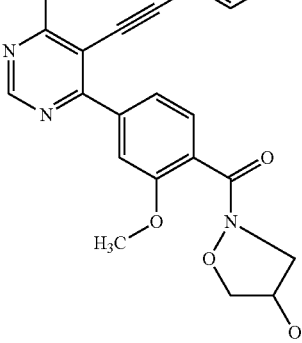 | A-93 | 445.48 | 446 | 1.21 | 383 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-168 | 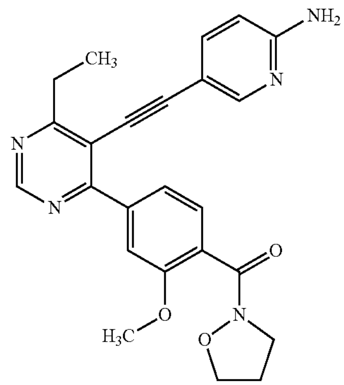 [SMILES: CCc1ncnc(-c2ccc(C(=O)N3CCCO3)c(OC)c2)c1C#Cc1ccc(N)nc1] | A-93 | 429.48 | 430 | 1.31 | 105 |
| D-169 | 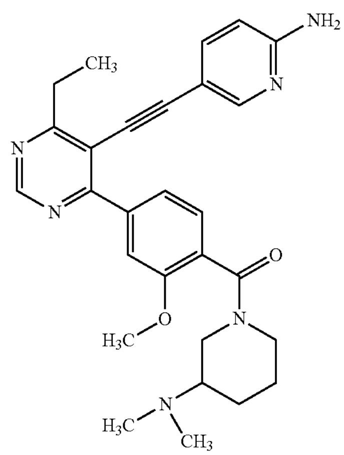 [SMILES: CCc1ncnc(-c2ccc(C(=O)N3CCCC(N(C)C)C3)c(OC)c2)c1C#Cc1ccc(N)nc1] | A-93 | 484.60 | 485 | 1.41 | Nd |
| D-170 | 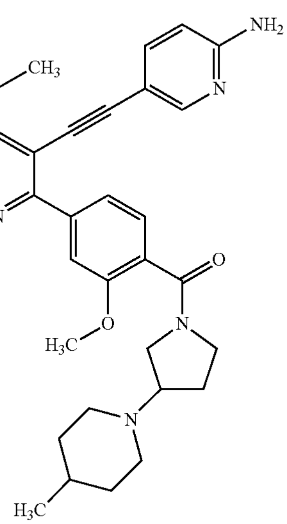 | A-93 | 524.67 | 525 | 1.84 | Nd |

TABLE 3-continued

Examples D-1-D240

| Nr. | Structure | Int. | MW | MW [M + H] | t_R [min] | EC_50 PC3 [nM] |
|---|---|---|---|---|---|---|
| D-172 | 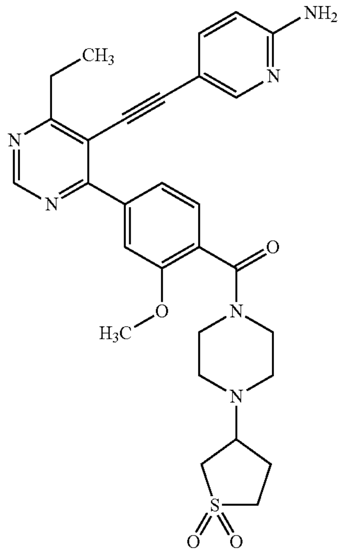 [SMILES: CCc1ncnc(-c2ccc(C(=O)N3CCN(C4CCS(=O)(=O)C4)CC3)c(OC)c2)c1C#Cc1ccc(N)nc1] | A-93 | 560.68 | 561 | 1.47 | 392 |
| D-173 | 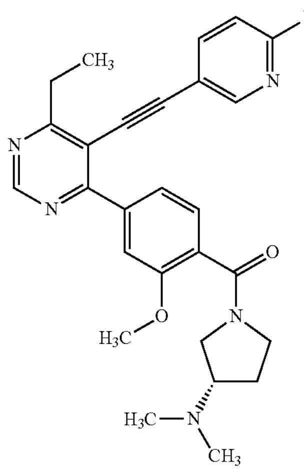 | A-93 | 470.57 | 471 | 1.53 | Nd |
| D-174 | 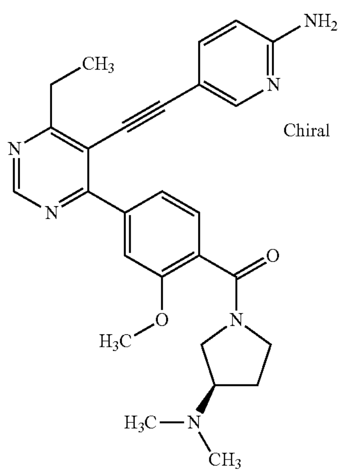 [SMILES: CCc1ncnc(-c2ccc(C(=O)N3CC[C@@H](N(C)C)C3)c(OC)c2)c1C#Cc1ccc(N)nc1] | A-93 | 470.57 | 469 | 1.53 | 282 |

TABLE 3-continued

Examples D-1-D240

| Nr. | Structure | Int. | MW | MW [M + H] | $t_R$ [min] | EC$_{50}$ PC3 [nM] |
|---|---|---|---|---|---|---|
| D-175 | 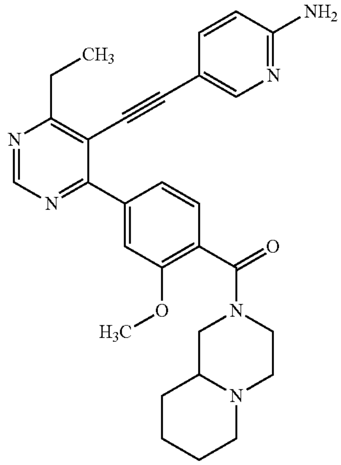 [SMILES: CCc1ncnc(-c2ccc(C(=O)N3CCN4CCCCC4C3)c(OC)c2)c1C#Cc1ccc(N)nc1] | A-93 | 496.61 | 497 | 1.66 | 95 |
| D-176 | 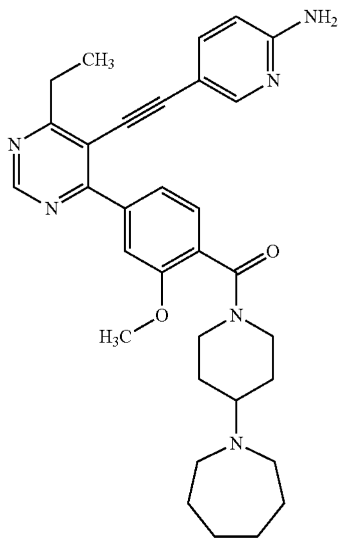 [SMILES: CCc1ncnc(-c2ccc(C(=O)N3CCC(N4CCCCCC4)CC3)c(OC)c2)c1C#Cc1ccc(N)nc1] | A-93 | 538.69 | 539 | 1.95 | 384 |
| D-177 | 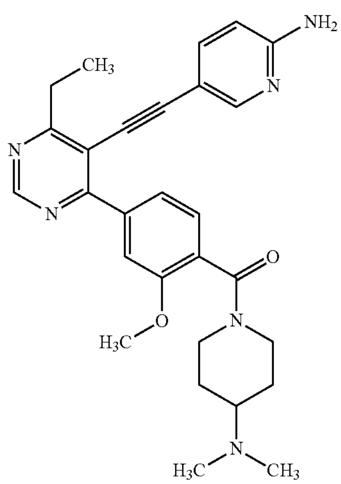 | A-93 | 484.60 | 485 | 1.58 | 280 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-178 | 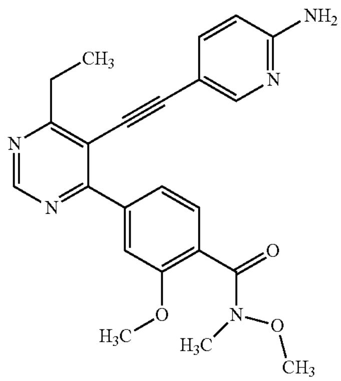 [SMILES: CCc1ncnc(-c2ccc(C(=O)N(C)OC)c(OC)c2)c1C#Cc1ccc(N)nc1] | A-93 | 417.47 | 418 | 1.36 | 85 |
| D-179 | 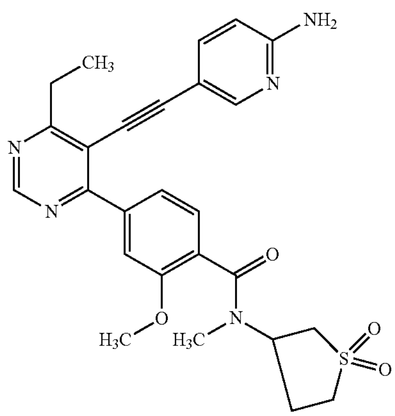 [SMILES: CCc1ncnc(-c2ccc(C(=O)N(C)C3CCS(=O)(=O)C3)c(OC)c2)c1C#Cc1ccc(N)nc1] | A-93 | 505.60 | 506 | 1.31 | 134 |
| D-180 | 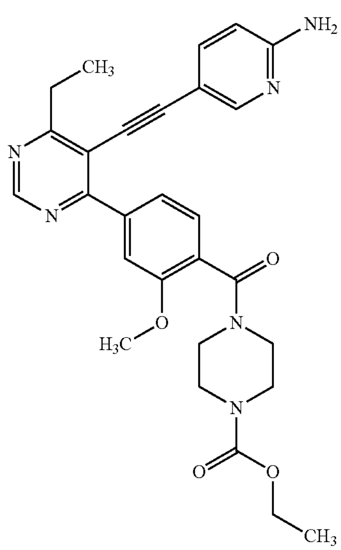 [SMILES: CCOC(=O)N1CCN(C(=O)c2ccc(-c3ncnc(CC)c3C#Cc3ccc(N)nc3)cc2OC)CC1] | A-93 | 514.58 | 515 | 1.67 | 121 |

TABLE 3-continued
Examples D-1-D240
| Nr. | Structure | Int. | MW | MW [M + H] | $t_R$ [min] | EC$_{50}$ PC3 [nM] |
|---|---|---|---|---|---|---|
| D-181 | 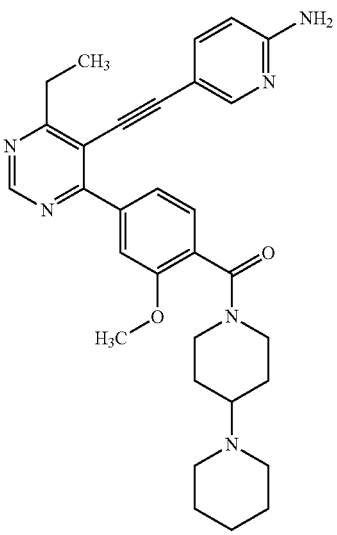 [SMILES: CCc1ncnc(-c2ccc(C(=O)N3CCC(N4CCCCC4)CC3)c(OC)c2)c1C#Cc1ccc(N)nc1] | A-93 | 524.67 | 523 | 1.81 | 205 |
| D-182 | 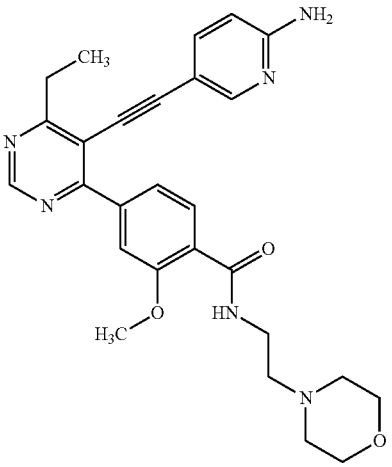 [SMILES: CCc1ncnc(-c2ccc(C(=O)NCCN3CCOCC3)c(OC)c2)c1C#Cc1ccc(N)nc1] | A-93 | 486.57 | 487 | 1.30 | 180 |
| D-183 | 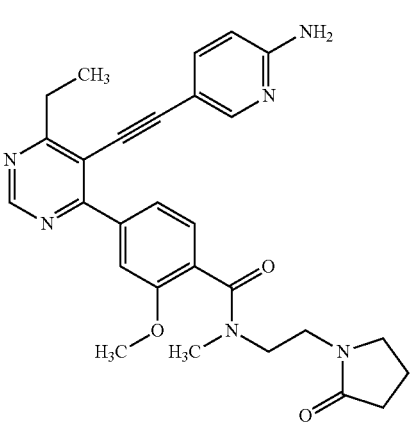 [SMILES: CCc1ncnc(-c2ccc(C(=O)N(C)CCN3CCCC3=O)c(OC)c2)c1C#Cc1ccc(N)nc1] | A-93 | 498.58 | 499 | 1.20 | 218 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-185 | 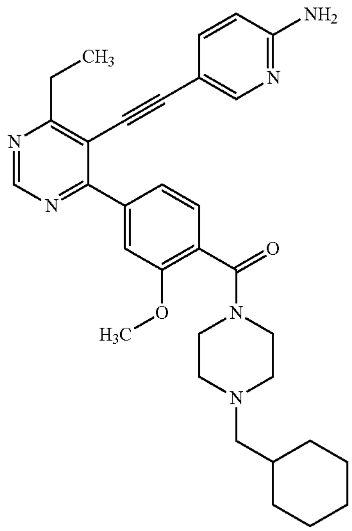 [SMILES: CCc1ncnc(-c2ccc(C(=O)N3CCN(CC4CCCCC4)CC3)c(OC)c2)c1C#Cc1ccc(N)nc1] | A-93 | 538.69 | 539 (762) | 1.94 (2.03) | 1140 |
| D-186 | 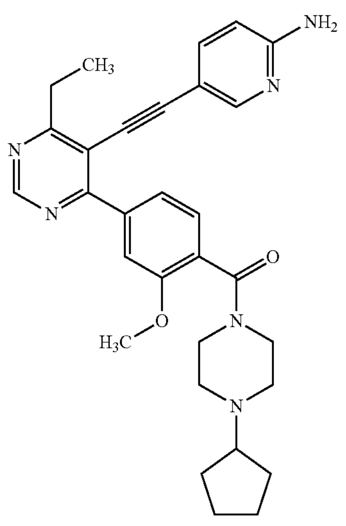 [SMILES: CCc1ncnc(-c2ccc(C(=O)N3CCN(C4CCCC4)CC3)c(OC)c2)c1C#Cc1ccc(N)nc1] | A-93 | 510.64 | 511 | 1.62 | 190 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-187 | 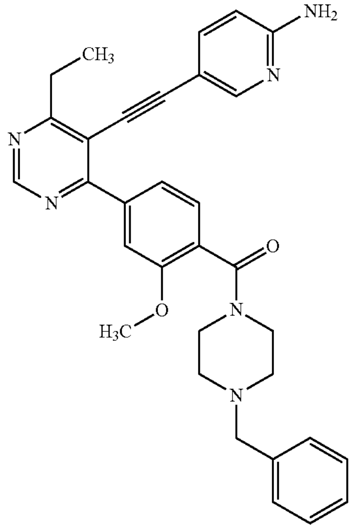 [SMILES: CCc1ncnc(-c2ccc(C(=O)N3CCN(Cc4ccccc4)CC3)c(OC)c2)c1C#Cc1ccc(N)nc1] | A-93 | 532.64 | 533 | 1.71 | 296 |
| D-188 | 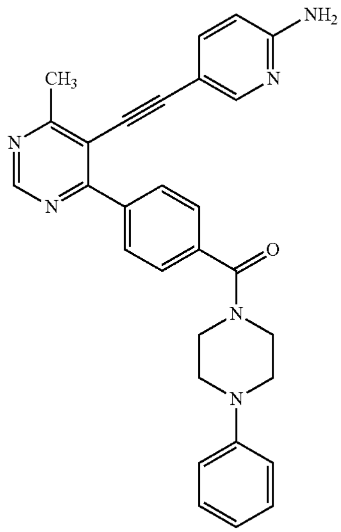 [SMILES: Cc1ncnc(-c2ccc(C(=O)N3CCN(c4ccccc4)CC3)cc2)c1C#Cc1ccc(N)nc1] | A-79 | 474.57 | 475 | 1.74 | 62 |
| D-189 | 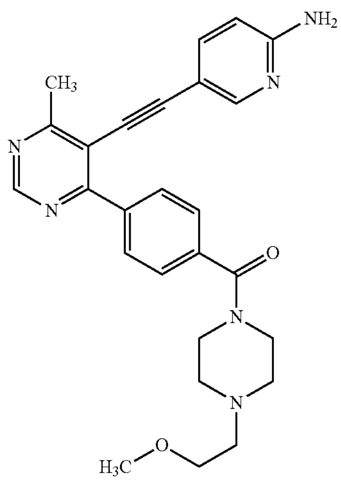 [SMILES: COCCN1CCN(C(=O)c2ccc(-c3ncnc(C)c3C#Cc3ccc(N)nc3)cc2)CC1] | A-79 | 456.55 | 457 | 1.43 | 63 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-190 | 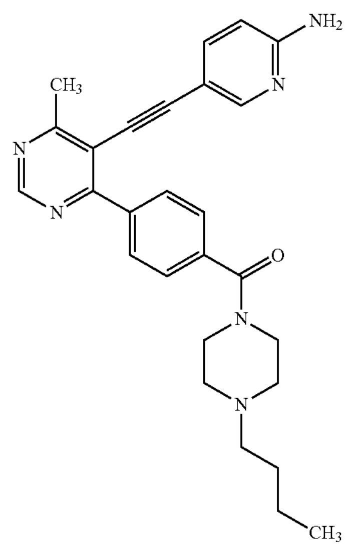 [SMILES: CCCCN1CCN(C(=O)c2ccc(-c3ncnc(C)c3C#Cc3ccc(N)nc3)cc2)CC1] | A-79 | 454.58 | 455 | 1.72 | 62 |
| D-191 | 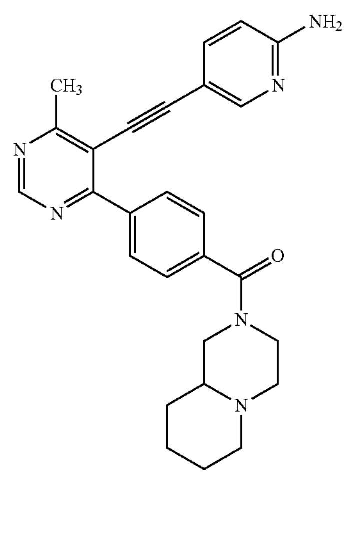 [SMILES: Cc1ncnc(-c2ccc(C(=O)N3CCN4CCCCC4C3)cc2)c1C#Cc1ccc(N)nc1] | A-79 | 452.56 | 453 | 1.54 | 55 |

TABLE 3-continued
Examples D-1-D240
| Nr. | Structure | Int. | MW | MW [M + H] | $t_R$ [min] | EC$_{50}$ PC3 [nM] |
|---|---|---|---|---|---|---|
| D-192 | 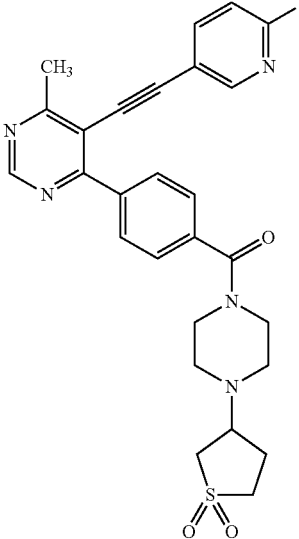 | A-79 | 516.62 | 517 | 1.34 | 140 |
| D-193 | 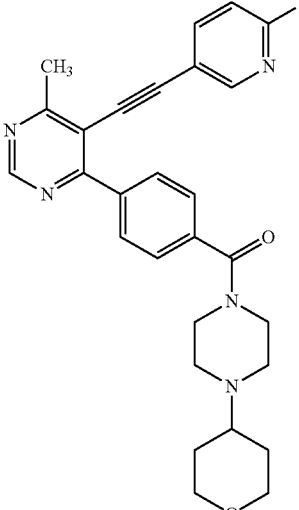 | A-79 | 482.59 | 483 | 1.42 | 69 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-194 | 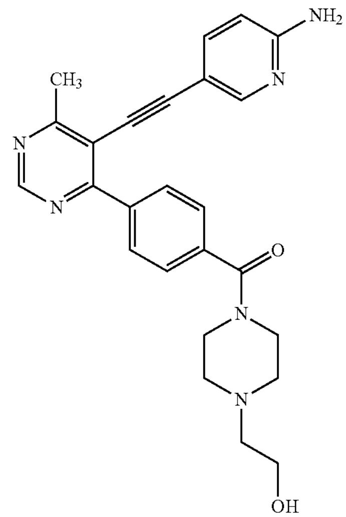 [SMILES: Cc1ncnc(-c2ccc(C(=O)N3CCN(CCO)CC3)cc2)c1C#Cc1ccc(N)nc1] | A-79 | 442.52 | 443 | 1.29 | 134 |
| D-195 | 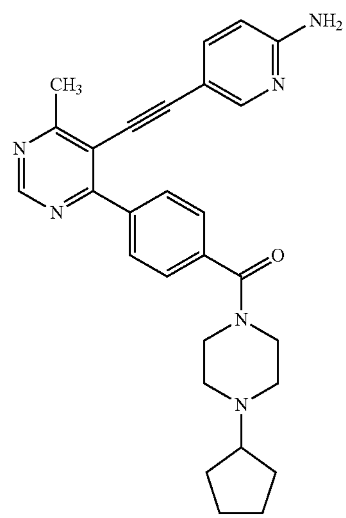 [SMILES: Cc1ncnc(-c2ccc(C(=O)N3CCN(C4CCCC4)CC3)cc2)c1C#Cc1ccc(N)nc1] | A-79 | 466.59 | 467 | 1.68 | 51 |
| D-196 | 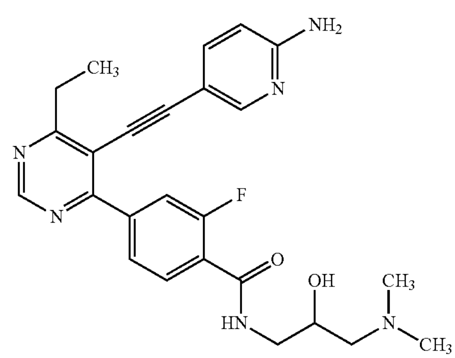 [SMILES: CCc1ncnc(-c2ccc(C(=O)NCC(O)CN(C)C)c(F)c2)c1C#Cc1ccc(N)nc1] | A-73 | 462.53 | 463 | 1.52 | 144 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-197 | 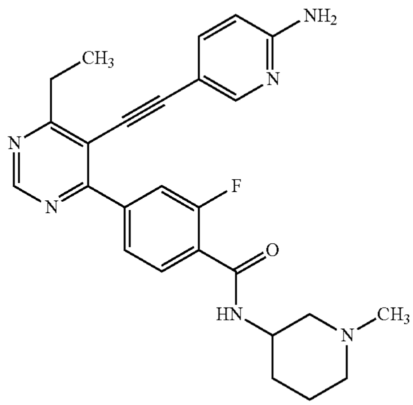 [SMILES: CCc1ncnc(-c2ccc(C(=O)NC3CCCN(C)C3)c(F)c2)c1C#Cc1ccc(N)nc1] | A-73 | 458.54 | 459; tR = 1.68 | 1.68 | 122 |
| D-198 | 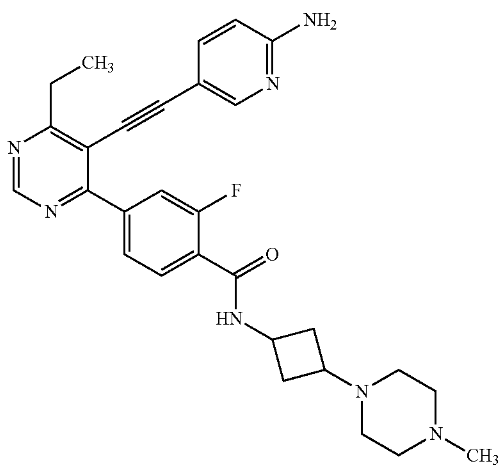 [SMILES: CCc1ncnc(-c2ccc(C(=O)NC3CC(N4CCN(C)CC4)C3)c(F)c2)c1C#Cc1ccc(N)nc1] | A-73 | 513.62 | 514 | 1.52 | 55 |
| D-199 | 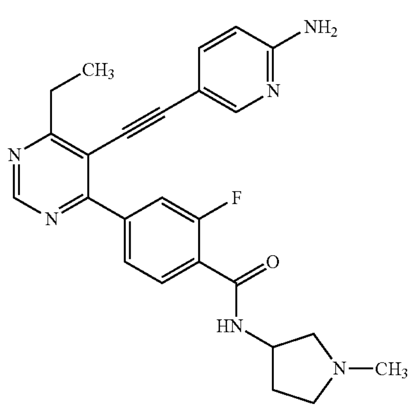 [SMILES: CCc1ncnc(-c2ccc(C(=O)NC3CCN(C)C3)c(F)c2)c1C#Cc1ccc(N)nc1] | A-73 | 444.51 | 445 | 1.57 | 127 |

TABLE 3-continued
Examples D-1-D240
| Nr. | Structure | Int. | MW | MW [M + H] | $t_R$ [min] | EC$_{50}$ PC3 [nM] |
|---|---|---|---|---|---|---|
| D-200 | 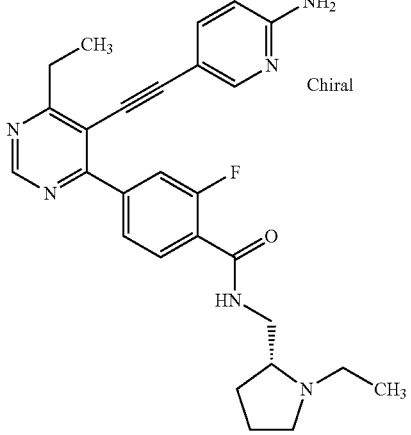 | A-73 | 472.57 | 473 | 1.81 | 451 |
| D-201 | 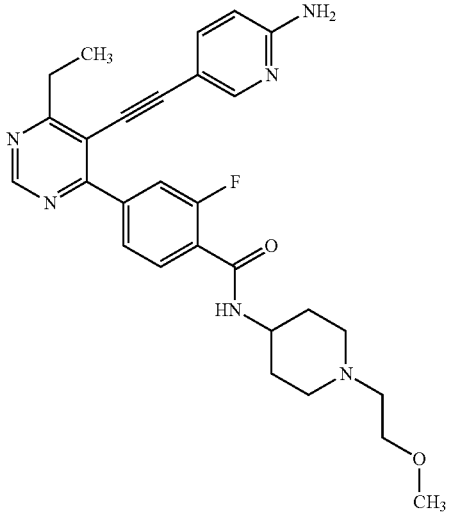 [SMILES: CCc1ncnc(-c2ccc(C(=O)NC3CCN(CCOC)CC3)c(F)c2)c1C#Cc1ccc(N)nc1] | A-73 | 502.59 | 503 | 1.60 | 90 |
| D-202 | 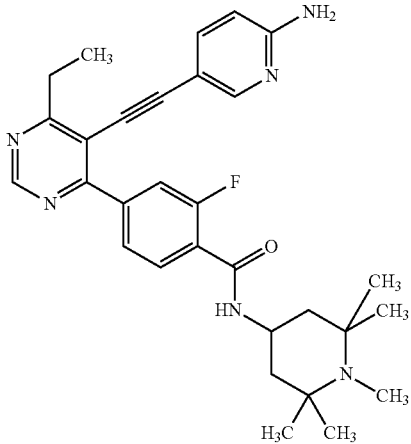 [SMILES: CCc1ncnc(-c2ccc(C(=O)NC3CC(C)(C)N(C)C(C)(C)C3)c(F)c2)c1C#Cc1ccc(N)nc1] | A-73 | 514.65 | 515 | 1.90 | 200 |

TABLE 3-continued
Examples D-1-D240
| Nr. | Structure | Int. | MW | MW [M + H] | $t_R$ [min] | $EC_{50}$ PC3 [nM] |
|---|---|---|---|---|---|---|
| D-203 | 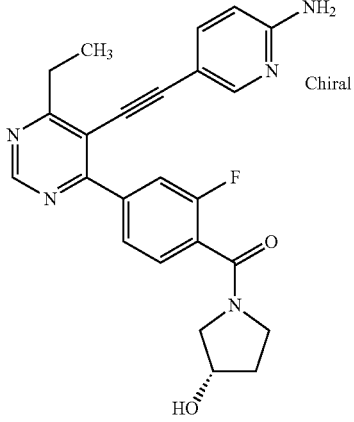 [SMILES: CCc1ncnc(-c2ccc(C(=O)N3CC[C@H](O)C3)c(F)c2)c1C#Cc1ccc(N)nc1] | A-73 | 431.47 | 432 | 1.43 | 58 |
| D-204 | 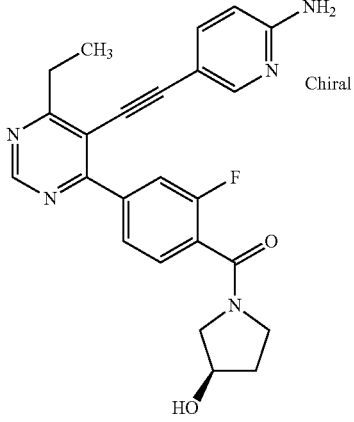 [SMILES: CCc1ncnc(-c2ccc(C(=O)N3CC[C@@H](O)C3)c(F)c2)c1C#Cc1ccc(N)nc1] | A-73 | 431.47 | 432 | 1.42 | 53 |
| D-205 | 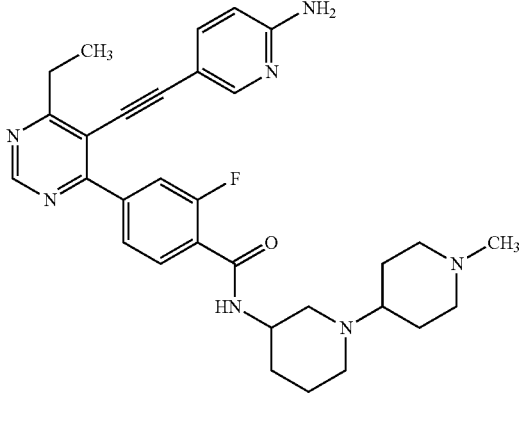 [SMILES: CCc1ncnc(-c2ccc(C(=O)NC3CCCN(C4CCN(C)CC4)C3)c(F)c2)c1C#Cc1ccc(N)nc1] | A-73 | 541.67 | 542 | 1.80 | 308 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-206 | 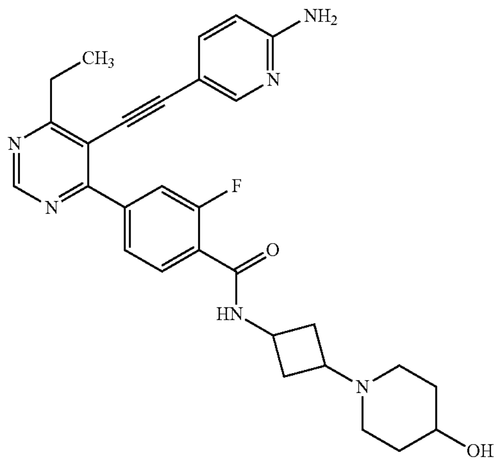 [SMILES: CCc1ncnc(-c2ccc(C(=O)NC3CC(N4CCC(O)CC4)C3)c(F)c2)c1C#Cc1ccc(N)nc1] | A-73 | 514.60 | 515 | 1.50 | 154 |
| D-207 | 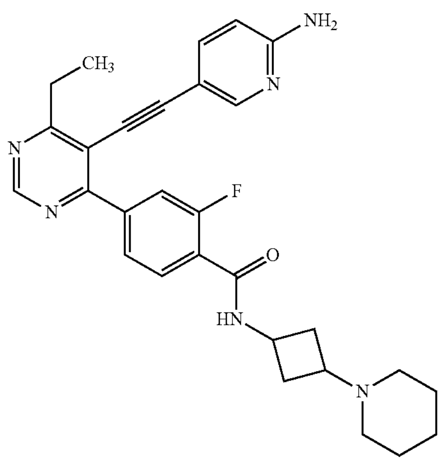 [SMILES: CCc1ncnc(-c2ccc(C(=O)NC3CC(N4CCCCC4)C3)c(F)c2)c1C#Cc1ccc(N)nc1] | A-73 | 498.60 | 499 | 1.80 | 71 |
| D-208 | 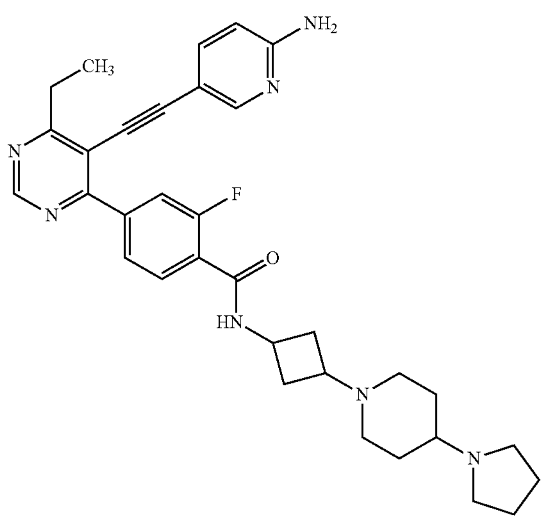 [SMILES: CCc1ncnc(-c2ccc(C(=O)NC3CC(N4CCC(N5CCCC5)CC4)C3)c(F)c2)c1C#Cc1ccc(N)nc1] | A-73 | 567.71 | 568 | 1.88 | 118 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-209 | 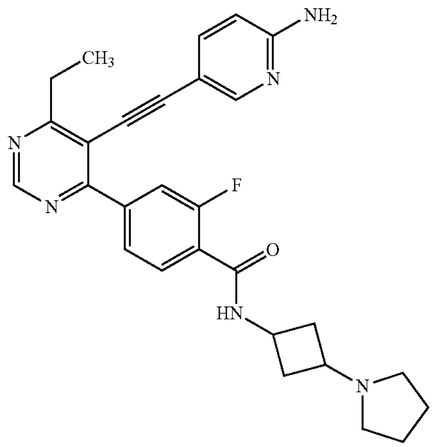 [SMILES: CCc1ncnc(-c2ccc(C(=O)NC3CC(N4CCCC4)C3)c(F)c2)c1C#Cc1ccc(N)nc1] | A-73 | 484.58 | 485 | 1.75 | 77 |
| D-210 | 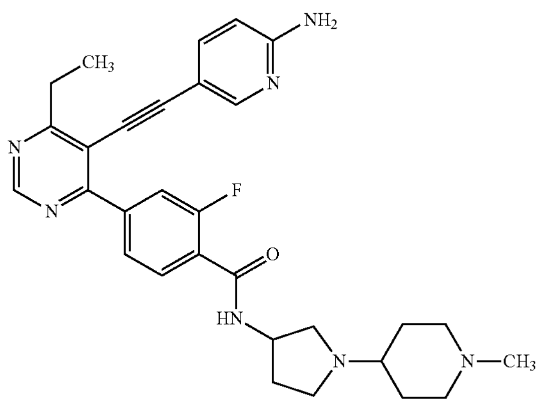 [SMILES: CCc1ncnc(-c2ccc(C(=O)NC3CCN(C4CCN(C)CC4)C3)c(F)c2)c1C#Cc1ccc(N)nc1] | A-73 | 527.64 | 528 | 1.68 | 172 |
| D-211 | 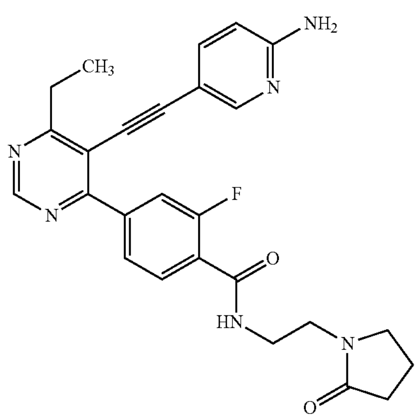 [SMILES: CCc1ncnc(-c2ccc(C(=O)NCCN3CCCC3=O)c(F)c2)c1C#Cc1ccc(N)nc1] | A-73 | 472.52 | 473 | 1.47 | 141 |

TABLE 3-continued
Examples D-1-D240
| Nr. | Structure | Int. | MW | MW [M + H] | $t_R$ [min] | $EC_{50}$ PC3 [nM] |
|---|---|---|---|---|---|---|
| D-212 | 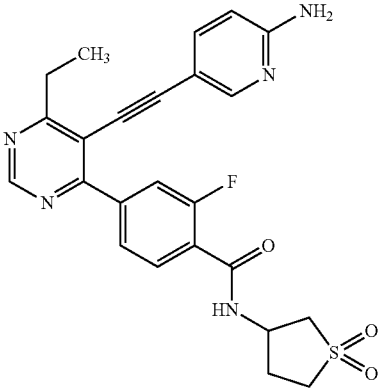 [SMILES: CCc1ncnc(-c2ccc(C(=O)NC3CCS(=O)(=O)C3)c(F)c2)c1C#Cc1ccc(N)nc1] | A-73 | 479.53 | 480 | 1.49 | 75 |
| D-213 | 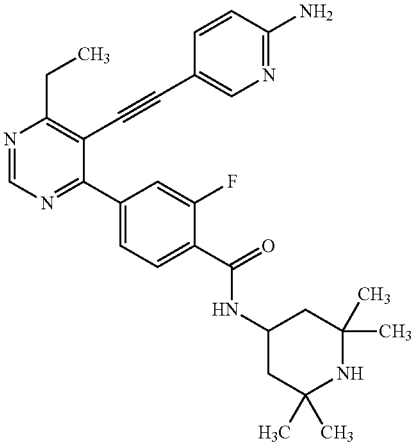 [SMILES: CCc1ncnc(-c2ccc(C(=O)NC3CC(C)(C)NC(C)(C)C3)c(F)c2)c1C#Cc1ccc(N)nc1] | A-73 | 500.62 | 501 | 1.76 | 132 |
| D-214 | 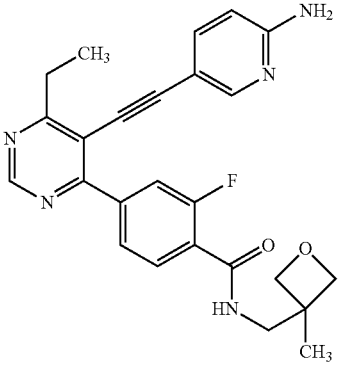 [SMILES: CCc1ncnc(-c2ccc(C(=O)NCC3(C)COC3)c(F)c2)c1C#Cc1ccc(N)nc1] | A-73 | 445.50 | 446 | 1.55 | 45 |

TABLE 3-continued
Examples D-1-D240
| Nr. | Structure | Int. | MW | MW [M + H] | $t_R$ [min] | $EC_{50}$ PC3 [nM] |
|---|---|---|---|---|---|---|
| D-215 | 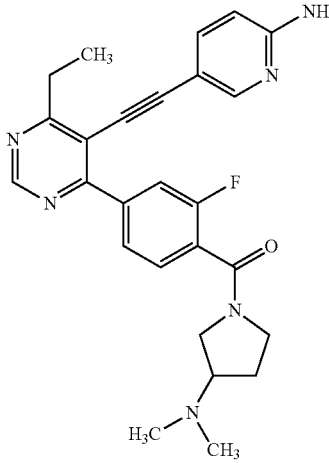 | A-73 | 458.54 | 459 | 1.57 | 64 |
| D-216 | 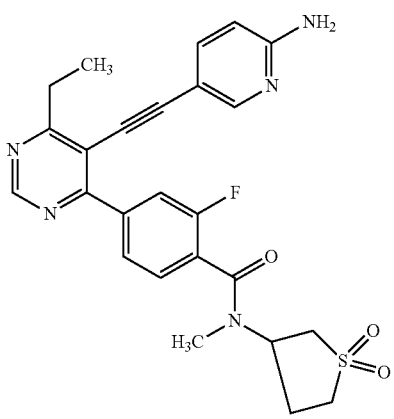 [SMILES: CCc1ncnc(-c2ccc(C(=O)N(C)C3CCS(=O)(=O)C3)c(F)c2)c1C#Cc1ccc(N)nc1] | A-73 | 493.56 | 494 | 1.52 | 42 |
| D-217 | 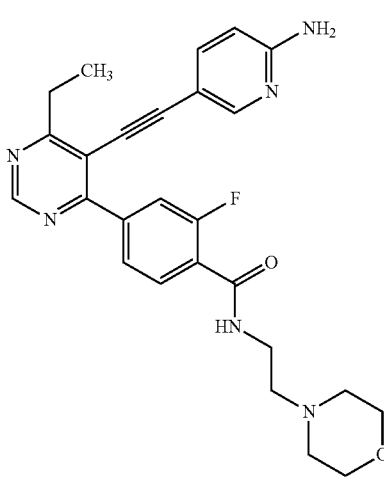 | A-73 | 474.54 | 475 | 1.55 | 97 |

TABLE 3-continued

Examples D-1-D240

| Nr. | Structure | Int. | MW | MW [M + H] | $t_R$ [min] | EC$_{50}$ PC3 [nM] |
|---|---|---|---|---|---|---|
| D-218 | 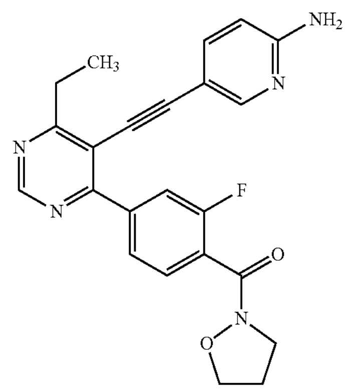 [SMILES: CCc1ncnc(-c2ccc(C(=O)N3CCCO3)c(F)c2)c1C#Cc1ccc(N)nc1] | A-73 | 417.44 | 418 | 1.56 | 57 |
| D-219 | 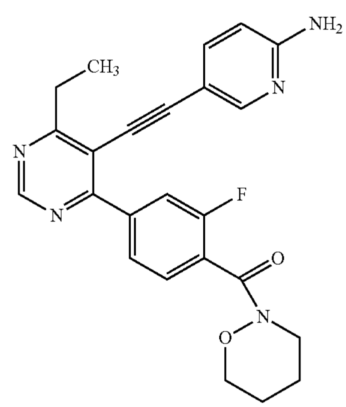 [SMILES: CCc1ncnc(-c2ccc(C(=O)N3CCCCO3)c(F)c2)c1C#Cc1ccc(N)nc1] | A-73 | 431.47 | 432 | 1.68 | 58 |
| D-220 | 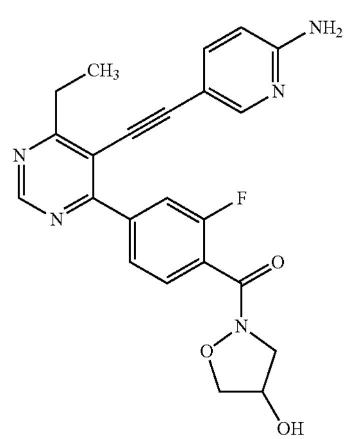 [SMILES: CCc1ncnc(-c2ccc(C(=O)N3CC(O)CO3)c(F)c2)c1C#Cc1ccc(N)nc1] | A-73 | 433.44 | 433 | 1.41 | 65 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-221 | 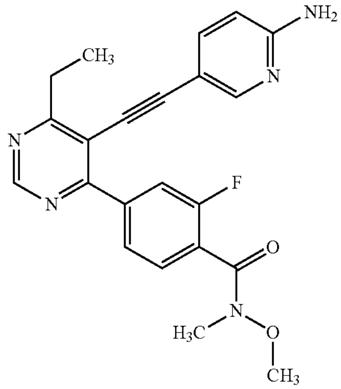 [SMILES: CCc1ncnc(-c2ccc(C(=O)N(C)OC)c(F)c2)c1C#Cc1ccc(N)nc1] | A-73 | 405.43 | 406 | 1.60 | 35 |
| D-222 | 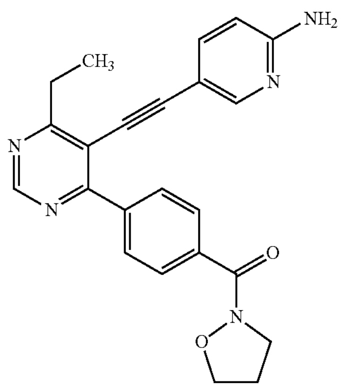 [SMILES: CCc1ncnc(-c2ccc(C(=O)N3CCCO3)cc2)c1C#Cc1ccc(N)nc1] | A-75 | 399.45 | 400 | 1.52 | 63 |
| D-223 | 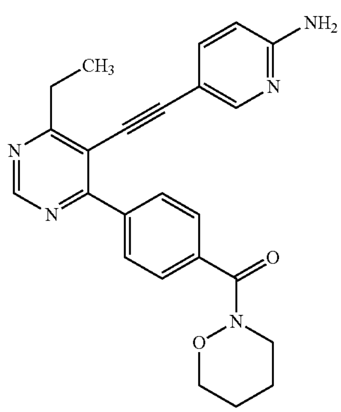 [SMILES: CCc1ncnc(-c2ccc(C(=O)N3CCCCO3)cc2)c1C#Cc1ccc(N)nc1] | A-75 | 413.48 | 414 | 1.62 | 85 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-224 | 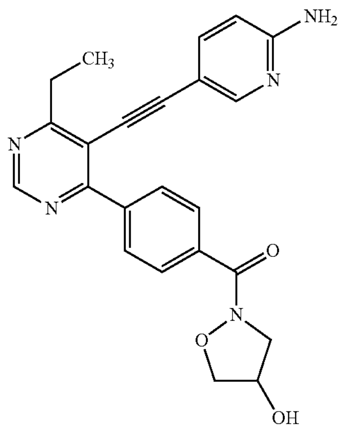 [SMILES: CCc1ncnc(-c2ccc(C(=O)N3CC(O)CO3)cc2)c1C#Cc1ccc(N)nc1] | A-75 | 415.45 | 416 | 1.39 | 106 |
| D-225 | 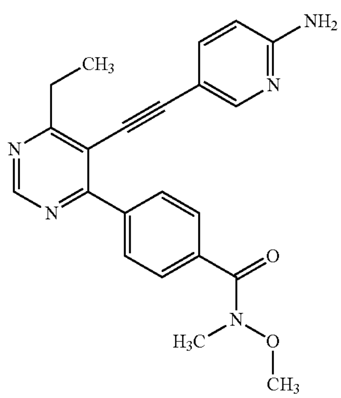 [SMILES: CCc1ncnc(-c2ccc(C(=O)N(C)OC)cc2)c1C#Cc1ccc(N)nc1] | A-75 | 387.44 | 388 | 1.54 | 66 |
| D-226 | 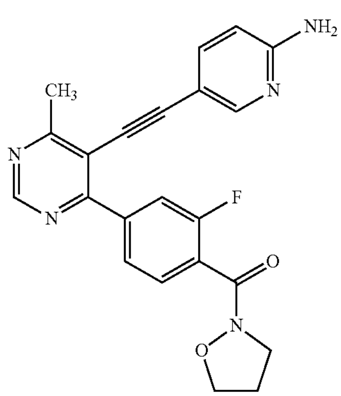 [SMILES: Cc1ncnc(-c2ccc(C(=O)N3CCCO3)c(F)c2)c1C#Cc1ccc(N)nc1] | A-83 | 403.42 | 404 | 1.44 | 49 |

TABLE 3-continued

Examples D-1-D240

| Nr. | Structure | Int. | MW | MW [M + H] | $t_R$ [min] | EC$_{50}$ PC3 [nM] |
|---|---|---|---|---|---|---|
| D-227 | 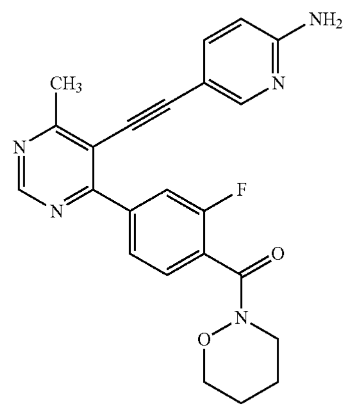 [SMILES: Cc1ncnc(-c2ccc(C(=O)N3CCCCO3)c(F)c2)c1C#Cc1ccc(N)nc1] | A-83 | 417.44 | 418 (363) | 1.55 (1.63) | 100 |
| D-228 | 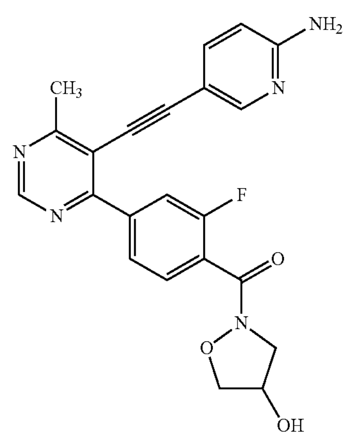 [SMILES: Cc1ncnc(-c2ccc(C(=O)N3CC(O)CO3)c(F)c2)c1C#Cc1ccc(N)nc1] | A-83 | 419.41 | 420 | 1.30 | 82 |
| D-229 | 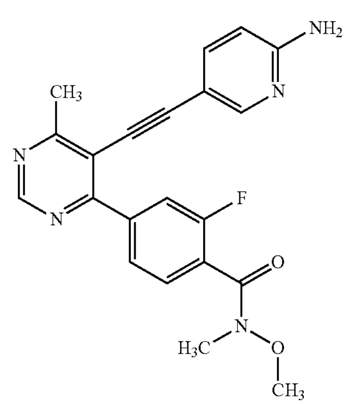 [SMILES: CON(C)C(=O)c1ccc(-c2ncnc(C)c2C#Cc2ccc(N)nc2)cc1F] | A-83 | 391.40 | 392 | 1.47 | 64 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-230 | 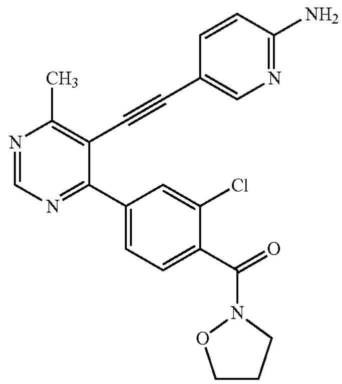 [SMILES: Cc1ncnc(-c2ccc(C(=O)N3CCCO3)c(Cl)c2)c1C#Cc1ccc(N)nc1] | A-81 | 419.87 | 420/422 | 1.47 | 62 |
| D-231 | 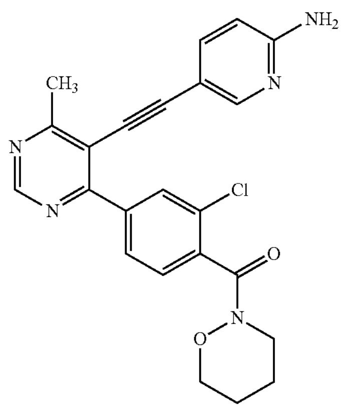 | A-81 | 433.90 | 434/436 | 1.59 | 78 |
| D-232 | 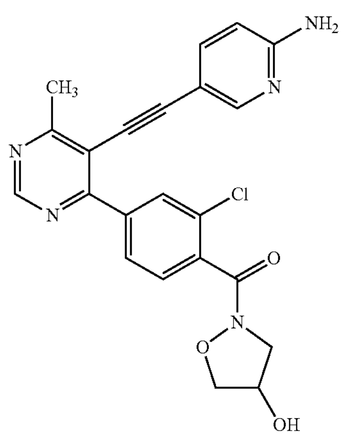 [SMILES: Cc1ncnc(-c2ccc(C(=O)N3CC(O)CO3)c(Cl)c2)c1C#Cc1ccc(N)nc1] | A-81 | 435.87 | 436/438 | 1.34 | 101 |

TABLE 3-continued

Examples D-1-D240

| Nr. | Structure | Int. | MW | MW [M + H] | $t_R$ [min] | $EC_{50}$ PC3 [nM] |
|---|---|---|---|---|---|---|
| D-233 | 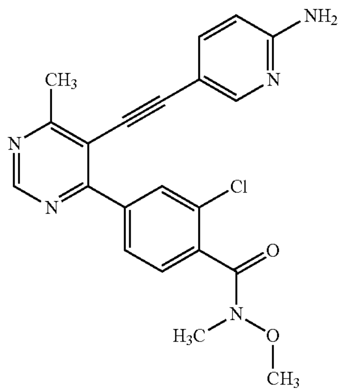 [SMILES: CON(C)C(=O)c1ccc(-c2ncnc(C)c2C#Cc2ccc(N)nc2)cc1Cl] | A-81 | 407.86 | 408/410 | 1.52 | 61 |
| D-234 | 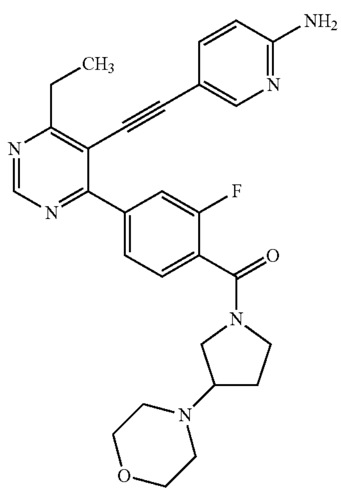 [SMILES: CCc1ncnc(-c2ccc(C(=O)N3CCC(N4CCOCC4)C3)c(F)c2)c1C#Cc1ccc(N)nc1] | A-73 | 500.58 | 501 | 1.36 | 73 |
| D-235 | 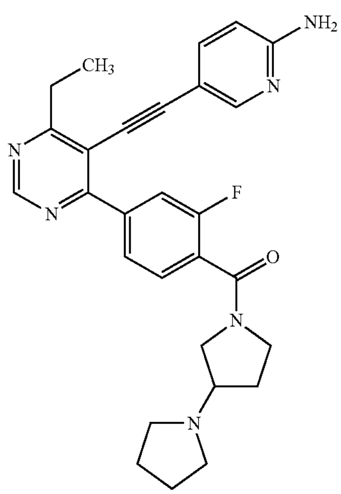 [SMILES: CCc1ncnc(-c2ccc(C(=O)N3CCC(N4CCCC4)C3)c(F)c2)c1C#Cc1ccc(N)nc1] | A-73 | 484.58 | 485 | 1.52 | 78 |

TABLE 3-continued

Examples D-1-D240

| Nr. | Structure | Int. | MW | MW [M + H] | $t_R$ [min] | EC$_{50}$ PC3 [nM] |
|---|---|---|---|---|---|---|
| D-236 | 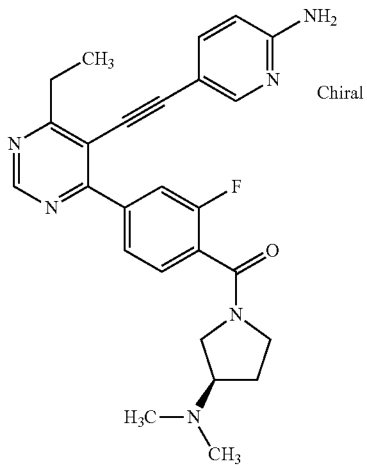 [SMILES: CCc1ncnc(-c2ccc(C(=O)N3CC[C@@H](N(C)C)C3)c(F)c2)c1C#Cc1ccc(N)nc1] | A-73 | 458.54 | 459 | 1.40 | 49 |
| D-237 | 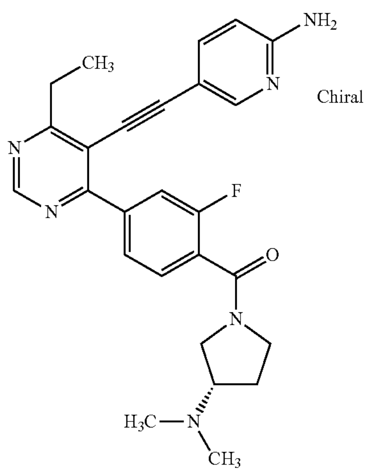 [SMILES: CCc1ncnc(-c2ccc(C(=O)N3CC[C@H](N(C)C)C3)c(F)c2)c1C#Cc1ccc(N)nc1] | A-73 | 458.54 | 459 | 1.40 | 77 |
| D-238 | 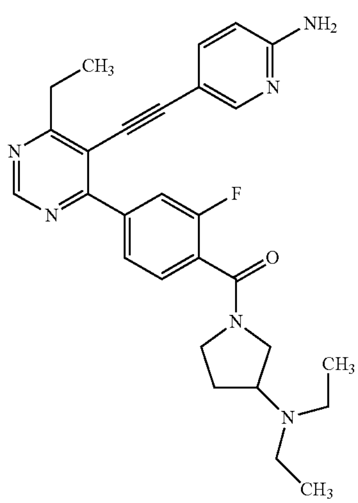 [SMILES: CCc1ncnc(-c2ccc(C(=O)N3CCC(N(CC)CC)C3)c(F)c2)c1C#Cc1ccc(N)nc1] | A-73 | 486.59 | 487 | 1.58 | 71 |

TABLE 3-continued
Examples D-1-D240
| Nr. | Structure | Int. | MW | MW [M + H] | $t_R$ [min] | $EC_{50}$ PC3 [nM] |
|---|---|---|---|---|---|---|
| D-239 | 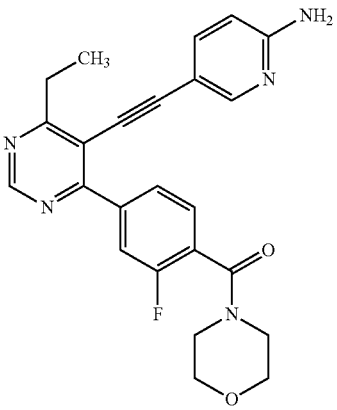 [SMILES: CCc1ncnc(-c2ccc(C(=O)N3CCOCC3)c(F)c2)c1C#Cc1ccc(N)nc1] | A-73 | 431.47 | 432 | 1.38 | 53 |
| D-240 | 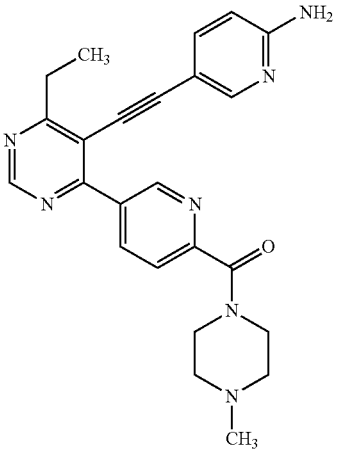 [SMILES: CCc1ncnc(-c2ccc(C(=O)N3CCN(C)CC3)nc2)c1C#Cc1ccc(N)nc1] | A-52 | 427.51 | 428 | 1.41 | 248 |

Examples E

Examples E-1 to E-349 can be synthesized according to the general procedure GP9 (Amide formation) outlined above. The appropriate intermediates for synthesis can be deduced from the table of the examples.

TABLE 4

Examples E-1-E-349

| Nr. | Structure | Int. | MW | MW [M + H] | tR [min] |
|---|---|---|---|---|---|
| E-1 | 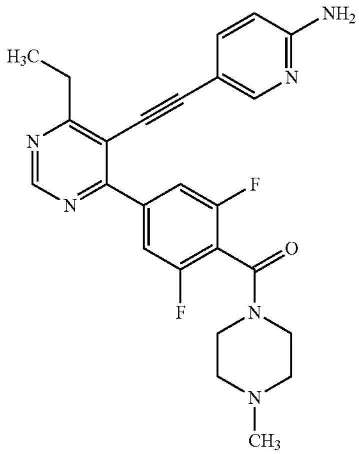 [SMILES: CCc1ncnc(-c2cc(F)c(C(=O)N3CCN(C)CC3)c(F)c2)c1C#Cc1ccc(N)nc1] | A-100 | 462.5 | 463 | 1.63 |
| E-2 | 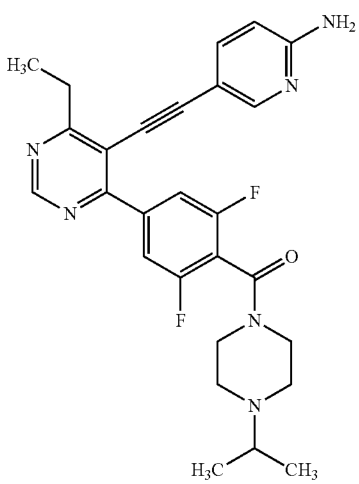 [SMILES: CCc1ncnc(-c2cc(F)c(C(=O)N3CCN(C(C)C)CC3)c(F)c2)c1C#Cc1ccc(N)nc1] | A-100 | 490.56 | 491 | 1.82 |

TABLE 4-continued
Examples E-1-E-349
| Nr. | Structure | Int. | MW | MW [M + H] | tR [min] |
|---|---|---|---|---|---|
| E-3 | 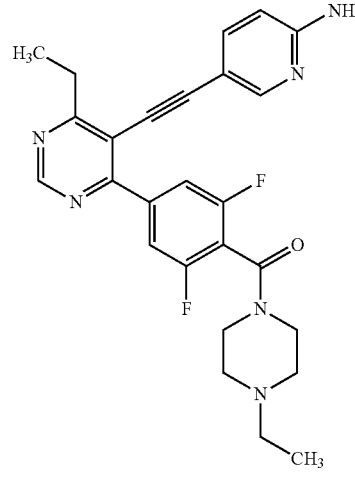 | A-100 | 476.53 | 477 | 1.72 |
| E-4 | 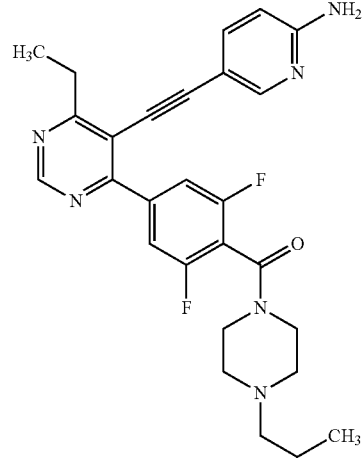 [SMILES: CCCN1CCN(C(=O)c2c(F)cc(-c3ncnc(CC)c3C#Cc3ccc(N)nc3)cc2F)CC1] | A-100 | 490.56 | 491 | 1.86 |
| E-5 | 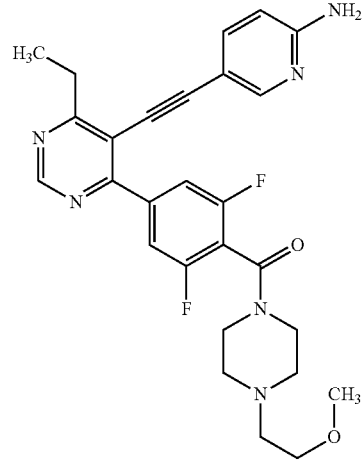 [SMILES: CCc1ncnc(-c2cc(F)c(C(=O)N3CCN(CCOC)CC3)c(F)c2)c1C#Cc1ccc(N)nc1] | A-100 | 506.55 | 507 | 1.68 |

TABLE 4-continued

Examples E-1-E-349

| Nr. | Structure | Int. | MW | MW [M + H] | tR [min] |
|---|---|---|---|---|---|
| E-6 | 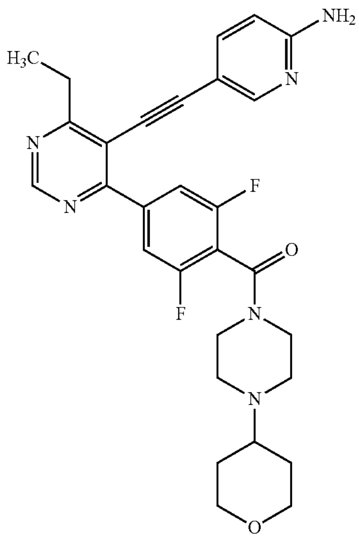 [SMILES: CCc1ncnc(-c2cc(F)c(C(=O)N3CCN(C4CCOCC4)CC3)c(F)c2)c1C#Cc1ccc(N)nc1] | A-100 | 532.59 | 533 | 1.68 |
| E-7 | 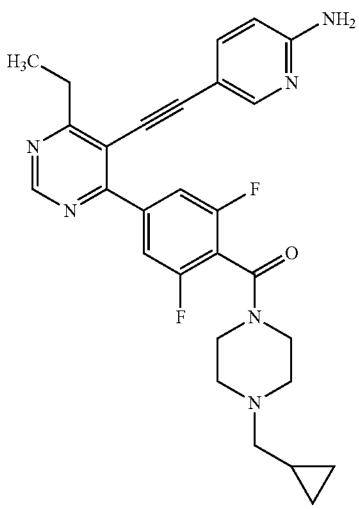 [SMILES: CCc1ncnc(-c2cc(F)c(C(=O)N3CCN(CC4CC4)CC3)c(F)c2)c1C#Cc1ccc(N)nc1] | A-100 | 502.57 | 503 | 1.86 |
| E-8 | 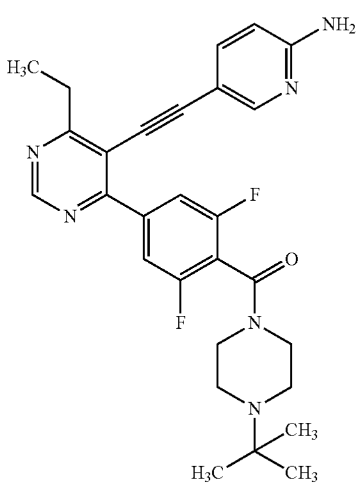 [SMILES: CCc1ncnc(-c2cc(F)c(C(=O)N3CCN(C(C)(C)C)CC3)c(F)c2)c1C#Cc1ccc(N)nc1] | A-100 | 504.58 | 505 | 1.94 |

TABLE 4-continued

Examples E-1-E-349

| Nr. | Structure | Int. | MW | MW [M + H] | tR [min] |
|---|---|---|---|---|---|
| E-9 | 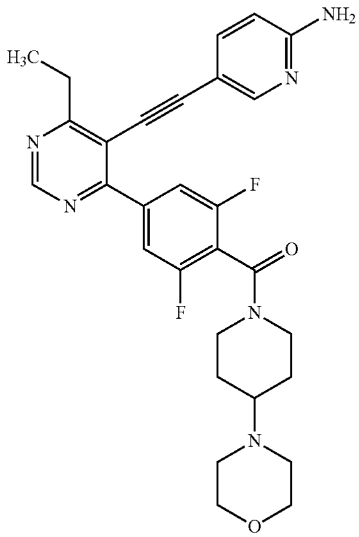 [SMILES: CCc1ncnc(-c2cc(F)c(C(=O)N3CCC(N4CCOCC4)CC3)c(F)c2)c1C#Cc1ccc(N)nc1] | A-100 | 532.59 | 533 | 1.65 |
| E-10 | 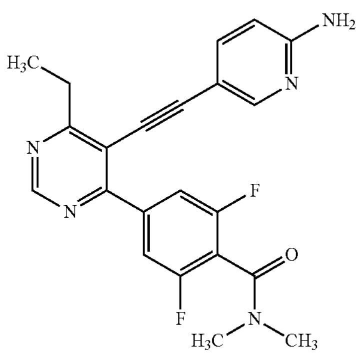 [SMILES: CCc1ncnc(-c2cc(F)c(C(=O)N(C)C)c(F)c2)c1C#Cc1ccc(N)nc1] | A-100 | 407.42 | 408 | 1.63 |
| E-11 | 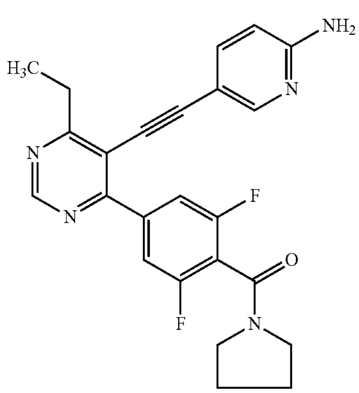 [SMILES: CCc1ncnc(-c2cc(F)c(C(=O)N3CCCC3)c(F)c2)c1C#Cc1ccc(N)nc1] | A-100 | 433.46 | 434 | 1.73 |

TABLE 4-continued

Examples E-1-E-349

| Nr. | Structure | Int. | MW | MW [M + H] | tR [min] |
|---|---|---|---|---|---|
| E-12 | 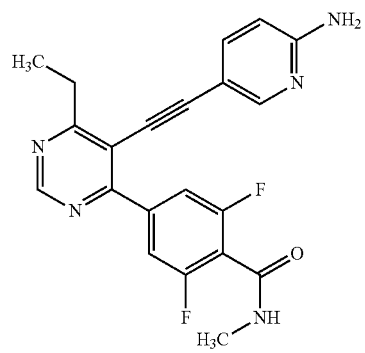 [SMILES: CCc1ncnc(-c2cc(F)c(C(=O)NC)c(F)c2)c1C#Cc1ccc(N)nc1] | A-100 | 393.4 | 394 | 1.5 |
| E-13 | 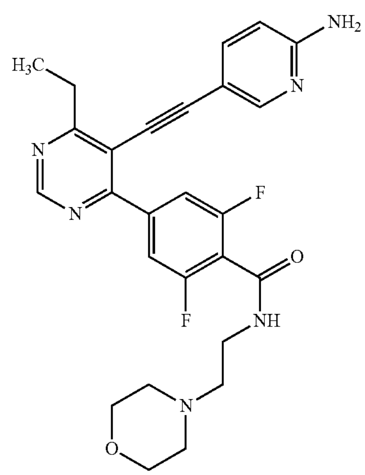 [SMILES: CCc1ncnc(-c2cc(F)c(C(=O)NCCN3CCOCC3)c(F)c2)c1C#Cc1ccc(N)nc1] | A-100 | 492.53 | 493 | 1.55 |
| E-14 | 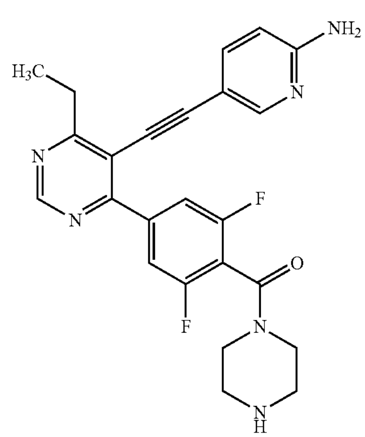 [SMILES: CCc1ncnc(-c2cc(F)c(C(=O)N3CCNCC3)c(F)c2)c1C#Cc1ccc(N)nc1] | A-100 | 448.47 | 449 | 1.50 |

TABLE 4-continued
Examples E-1-E-349
| Nr. | Structure | Int. | MW | MW [M + H] | tR [min] |
|---|---|---|---|---|---|
| E-15 | 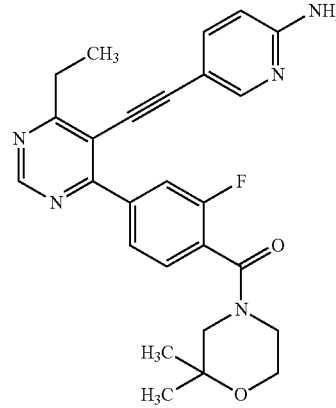 | A-73 | 459.52 | 458 | 1.69 |
| E-16 | 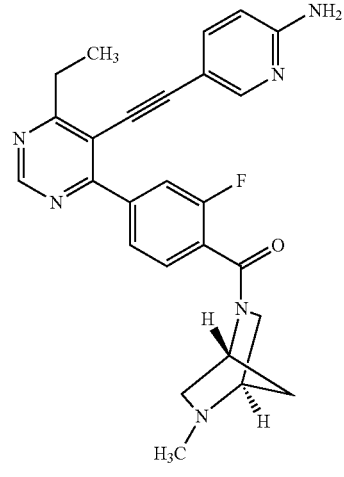 [SMILES: CCc1ncnc(-c2ccc(C(=O)N3C[C@H]4C[C@@H]3CN4C)c(F)c2)c1C#Cc1ccc(N)nc1] | A-73 | 456.52 | 455 | 1.51 |
| E-17 | 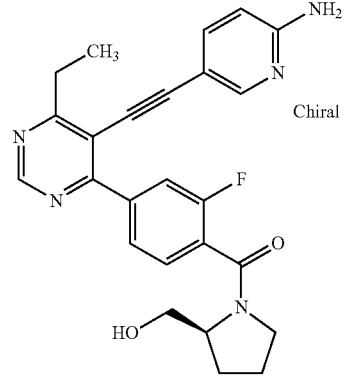 [SMILES: CCc1ncnc(-c2ccc(C(=O)N3CCC[C@H]3CO)c(F)c2)c1C#Cc1ccc(N)nc1] | A-73 | 445.5 | 446 | 1.55 |

TABLE 4-continued

Examples E-1-E-349

| Nr. | Structure | Int. | MW | MW [M + H] | tR [min] |
|---|---|---|---|---|---|
| E-18 | 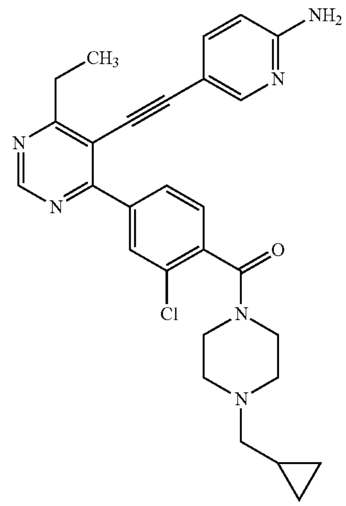 [SMILES: CCc1ncnc(-c2ccc(C(=O)N3CCN(CC4CC4)CC3)c(Cl)c2)c1C#Cc1ccc(N)nc1] | A-77 | 501.03 | 499/501 | 1.83 |
| E-19 | 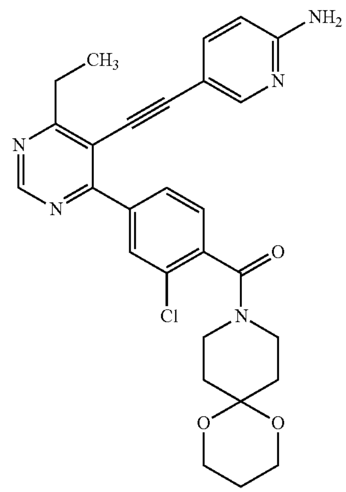 [SMILES: CCc1ncnc(-c2ccc(C(=O)N3CCC4(CC3)OCCCO4)c(Cl)c2)c1C#Cc1ccc(N)nc1] | A-77 | 518.01 | 518/520 | 1.74 |
| E-20 | 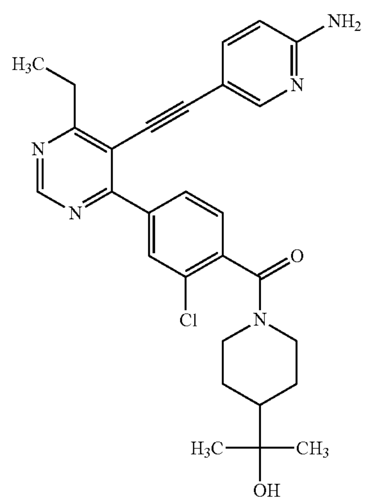 [SMILES: CCc1ncnc(-c2ccc(C(=O)N3CCC(C(C)(C)O)CC3)c(Cl)c2)c1C#Cc1ccc(N)nc1] | A-77 | 504.03 | 504 | 1.69 |

TABLE 4-continued

Examples E-1-E-349

| Nr. | Structure | Int. | MW | MW [M + H] | tR [min] |
|---|---|---|---|---|---|
| E-21 | 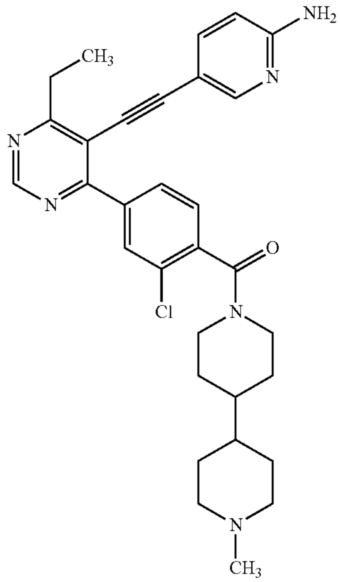 [SMILES: CCc1ncnc(-c2ccc(C(=O)N3CCC(C4CCN(C)CC4)CC3)c(Cl)c2)c1C#Cc1ccc(N)nc1] | A-77 | 543.11 | 543/545 | 1.96 |
| E-22 | 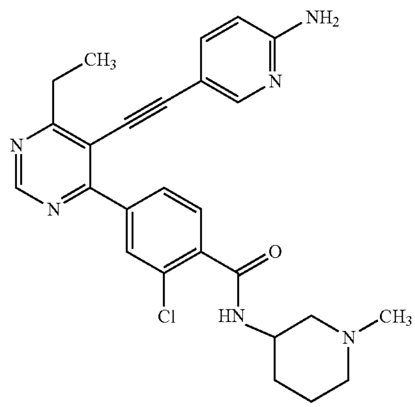 [SMILES: CCc1ncnc(-c2ccc(C(=O)NC3CCCN(C)C3)c(Cl)c2)c1C#Cc1ccc(N)nc1] | A-77 | 474.99 | 475/477 | 1.68 |
| E-23 | 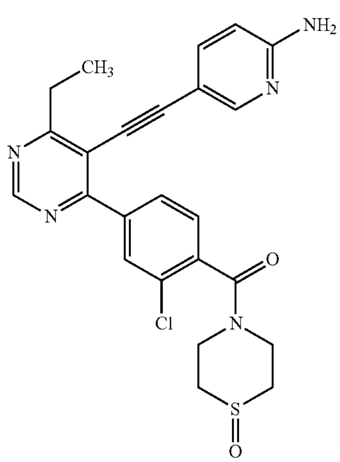 [SMILES: CCc1ncnc(-c2ccc(C(=O)N3CCS(=O)CC3)c(Cl)c2)c1C#Cc1ccc(N)nc1] | A-77 | 479.99 | 478 | 1.44 |

TABLE 4-continued

Examples E-1-E-349

| Nr. | Structure | Int. | MW | MW [M + H] | tR [min] |
|---|---|---|---|---|---|
| E-24 | 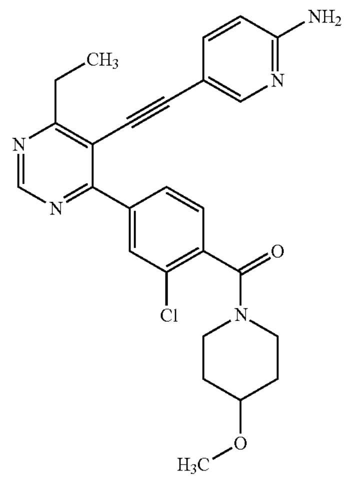 [SMILES: CCc1ncnc(-c2ccc(C(=O)N3CCC(OC)CC3)c(Cl)c2)c1C#Cc1ccc(N)nc1] | A-77 | 475.98 | 476/478 | 1.75 |
| E-25 | 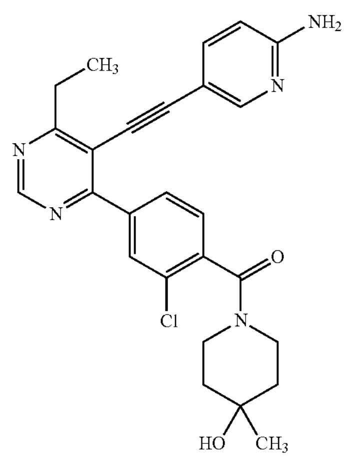 [SMILES: CCc1ncnc(-c2ccc(C(=O)N3CCC(C)(O)CC3)c(Cl)c2)c1C#Cc1ccc(N)nc1] | A-77 | 475.98 | 474/476 | 1.6 |
| E-26 | 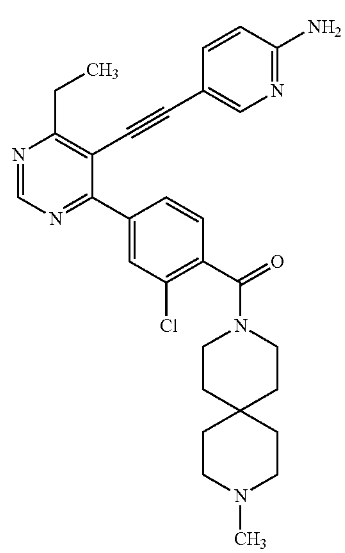 [SMILES: CCc1ncnc(-c2ccc(C(=O)N3CCC4(CCN(C)CC4)CC3)c(Cl)c2)c1C#Cc1ccc(N)nc1] | A-77 | 529.08 | 529/531 | 1.81 |

TABLE 4-continued

Examples E-1-E-349

| Nr. | Structure | Int. | MW | MW [M + H] | tR [min] |
|---|---|---|---|---|---|
| E-27 | 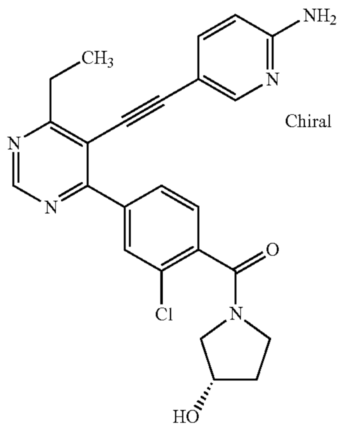 [SMILES: CCc1ncnc(-c2ccc(C(=O)N3CC[C@H](O)C3)c(Cl)c2)c1C#Cc1ccc(N)nc1] | A-77 | 447.92 | 448/450 | 1.49 |
| E-28 | 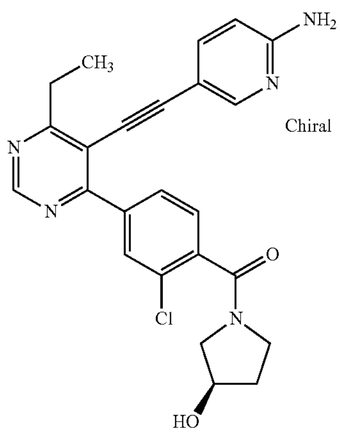 [SMILES: CCc1ncnc(-c2ccc(C(=O)N3CC[C@@H](O)C3)c(Cl)c2)c1C#Cc1ccc(N)nc1] | A-77 | 447.92 | 448 | 1.49 |
| E-29 | 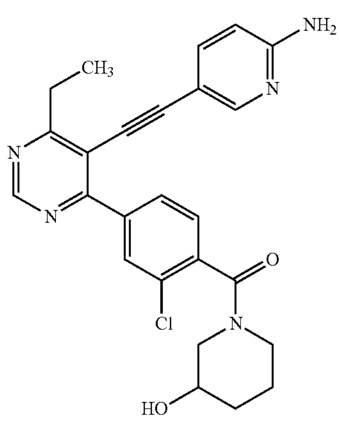 [SMILES: CCc1ncnc(-c2ccc(C(=O)N3CCCC(O)C3)c(Cl)c2)c1C#Cc1ccc(N)nc1] | A-77 | 461.95 | 460/462 | 1.57 |

TABLE 4-continued

Examples E-1-E-349

| Nr. | Structure | Int. | MW | MW [M + H] | tR [min] |
|---|---|---|---|---|---|
| E-30 | 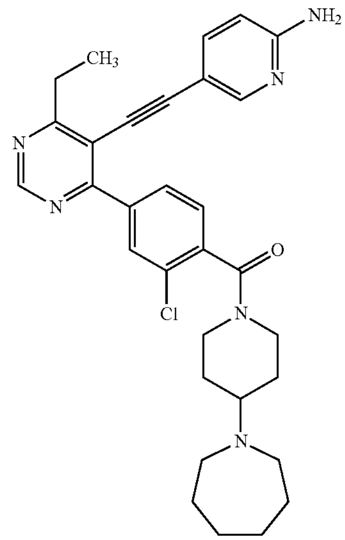 [SMILES: CCc1ncnc(-c2ccc(C(=O)N3CCC(N4CCCCCC4)CC3)c(Cl)c2)c1C#Cc1ccc(N)nc1] | A-77 | 543.11 | 543 | 2.08 |
| E-31 | 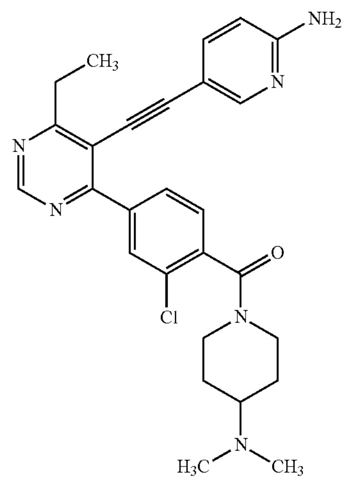 | A-77 | 489.02 | 487/489 | 1.69 |
| E-32 | 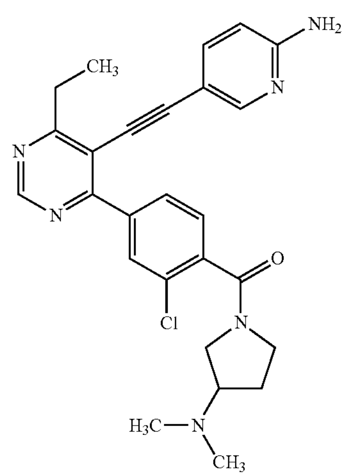 [SMILES: CCc1ncnc(-c2ccc(C(=O)N3CCC(N(C)C)C3)c(Cl)c2)c1C#Cc1ccc(N)nc1] | A-77 | 474.99 | 475/477 | 1.64 |

TABLE 4-continued

Examples E-1-E-349

| Nr. | Structure | Int. | MW | MW [M + H] | tR [min] |
|---|---|---|---|---|---|
| E-33 | 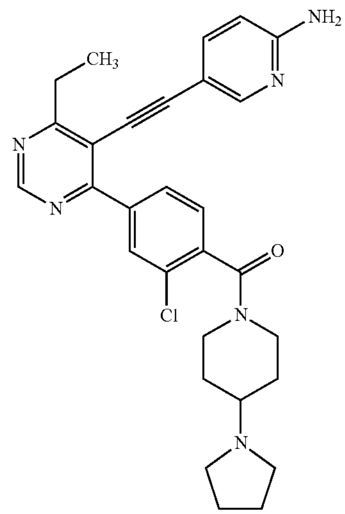 [SMILES: CCc1ncnc(-c2ccc(C(=O)N3CCC(N4CCCC4)CC3)c(Cl)c2)c1C#Cc1ccc(N)nc1] | A-77 | 515.06 | 515/517 | 1.84 |
| E-34 | 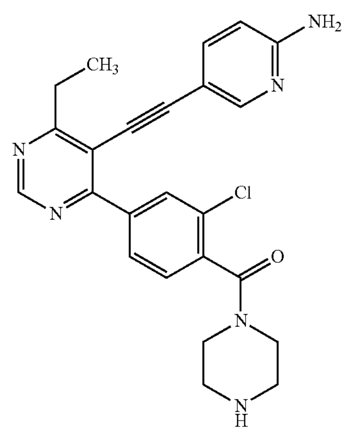 [SMILES: CCc1ncnc(-c2ccc(C(=O)N3CCNCC3)c(Cl)c2)c1C#Cc1ccc(N)nc1] | A-77 | 446.94 | 447 | 1.48 |
| E-35 | 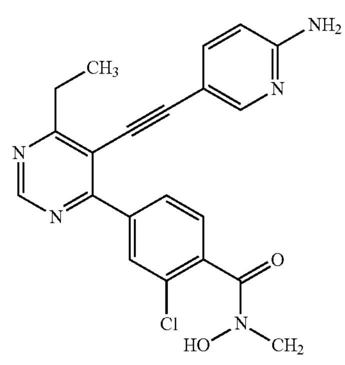 [SMILES: CCc1ncnc(-c2ccc(C(=O)N(C)O)c(Cl)c2)c1C#Cc1ccc(N)nc1] | A-77 | 407.86 | 408 | 1.11 |

TABLE 4-continued

Examples E-1-E-349

| Nr. | Structure | Int. | MW | MW [M + H] | tR [min] |
|---|---|---|---|---|---|
| E-36 | 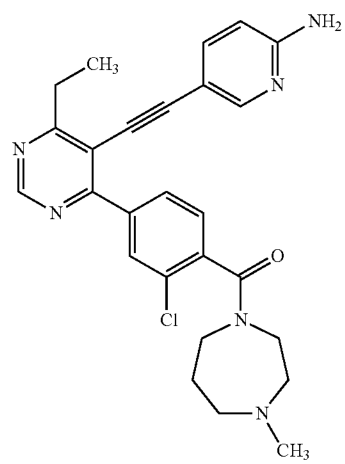 [SMILES: CCc1ncnc(-c2ccc(C(=O)N3CCCN(C)CC3)c(Cl)c2)c1C#Cc1ccc(N)nc1] | A-77 | 474.99 | 475/477 | 1.64 |
| E-37 | 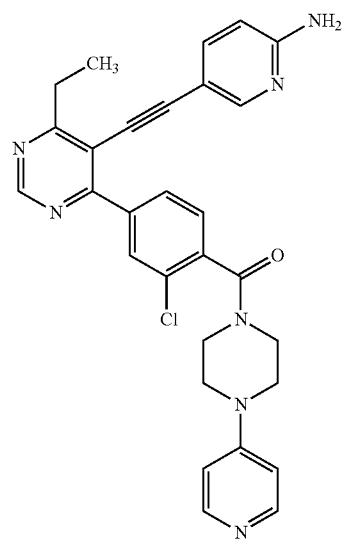 [SMILES: CCc1ncnc(-c2ccc(C(=O)N3CCN(c4ccncc4)CC3)c(Cl)c2)c1C#Cc1ccc(N)nc1] | A-77 | 524.03 | 524 | 1.68 |
| E-38 | 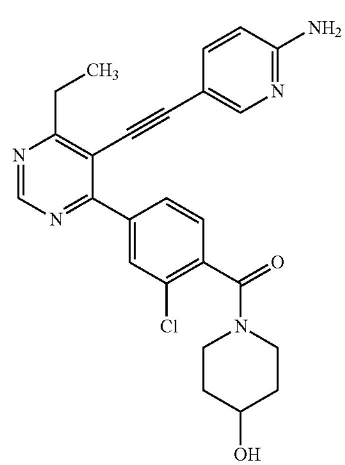 [SMILES: CCc1ncnc(-c2ccc(C(=O)N3CCC(O)CC3)c(Cl)c2)c1C#Cc1ccc(N)nc1] | A-77 | 461.95 | 462/464 | 1.52 |

TABLE 4-continued

Examples E-1-E-349

| Nr. | Structure | Int. | MW | MW [M + H] | tR [min] |
|---|---|---|---|---|---|
| E-39 | 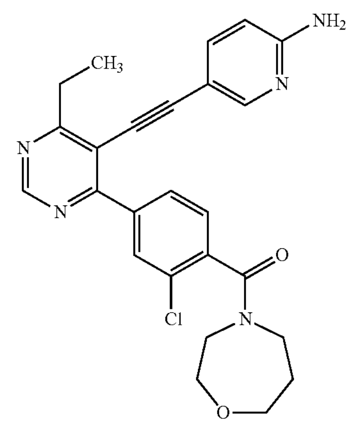 [SMILES: CCc1ncnc(-c2ccc(C(=O)N3CCCOCC3)c(Cl)c2)c1C#Cc1ccc(N)nc1] | A-77 | 461.95 | 462/464 | 1.63 |
| E-40 | 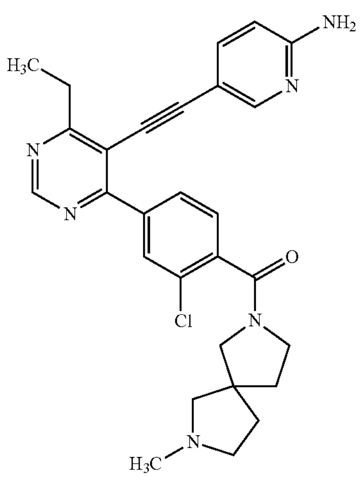 [SMILES: CCc1ncnc(-c2ccc(C(=O)N3CCC4(CCN(C)C4)C3)c(Cl)c2)c1C#Cc1ccc(N)nc1] | A-77 | 501.03 | 501 | 1.72 |
| E-41 | 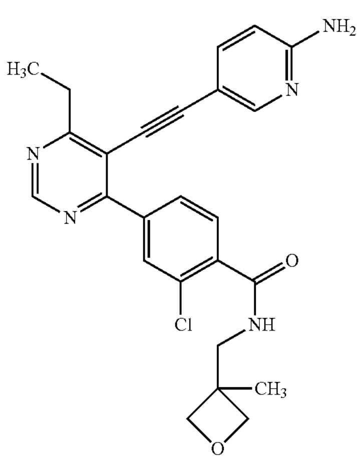 [SMILES: CCc1ncnc(-c2ccc(C(=O)NCC3(C)COC3)c(Cl)c2)c1C#Cc1ccc(N)nc1] | A-77 | 461.95 | 462 | 1.58 |

TABLE 4-continued

Examples E-1-E-349

| Nr. | Structure | Int. | MW | MW [M + H] | tR [min] |
|---|---|---|---|---|---|
| E-42 | 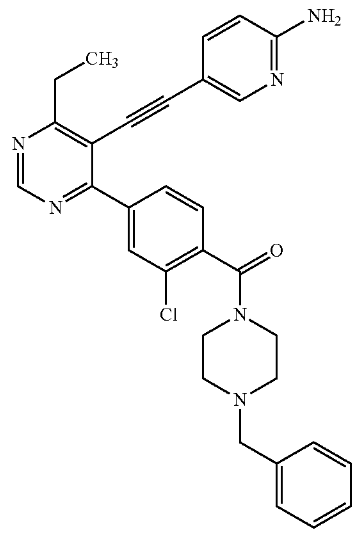 [SMILES: CCc1ncnc(-c2ccc(C(=O)N3CCN(Cc4ccccc4)CC3)c(Cl)c2)c1C#Cc1ccc(N)nc1] | A-77 | 537.06 | 537/539 | 2.1 |
| E-43 | 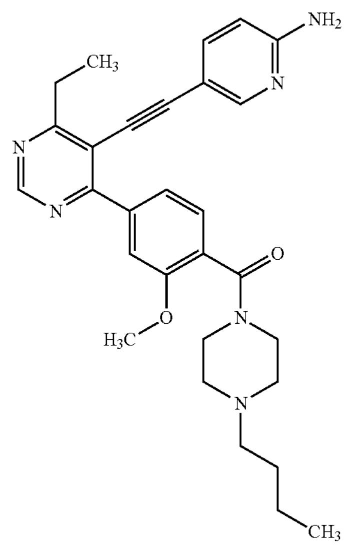 [SMILES: CCCCN1CCN(C(=O)c2ccc(-c3ncnc(CC)c3C#Cc3ccc(N)nc3)cc2OC)CC1] | A-93 | 498.63 | 499 | 1.66 |
| E-44 | 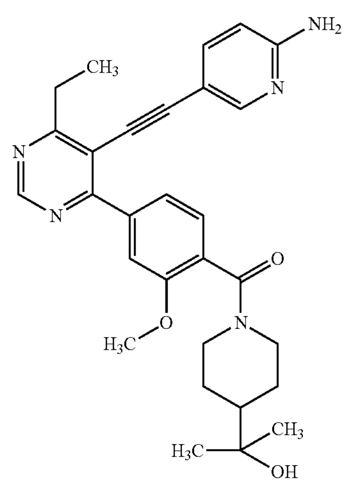 [SMILES: CCc1ncnc(-c2ccc(C(=O)N3CCC(C(C)(C)O)CC3)c(OC)c2)c1C#Cc1ccc(N)nc1] | A-93 | 499.61 | 500 | 1.41 |

TABLE 4-continued

Examples E-1-E-349

| Nr. | Structure | Int. | MW | MW [M + H] | tR [min] |
|---|---|---|---|---|---|
| E-45 | 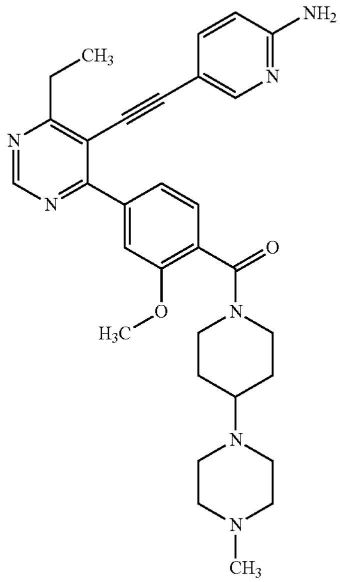 [SMILES: CCc1ncnc(-c2ccc(C(=O)N3CCC(N4CCN(C)CC4)CC3)c(OC)c2)c1C#Cc1ccc(N)nc1] | A-93 | 539.68 | 540 | 1.33 |
| E-46 | 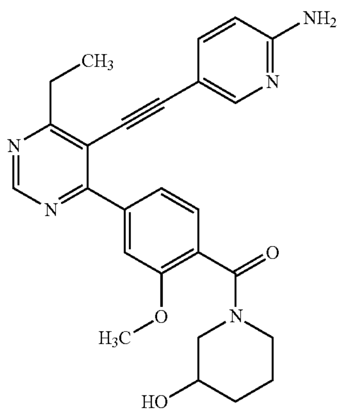 [SMILES: CCc1ncnc(-c2ccc(C(=O)N3CCCC(O)C3)c(OC)c2)c1C#Cc1ccc(N)nc1] | A-93 | 457.53 | 458 | 1.29 |
| E-47 | 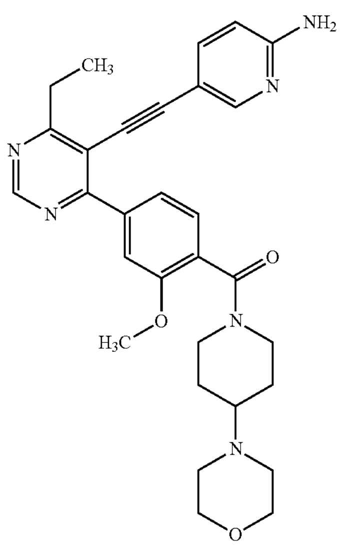 [SMILES: CCc1ncnc(-c2ccc(C(=O)N3CCC(N4CCOCC4)CC3)c(OC)c2)c1C#Cc1ccc(N)nc1] | A-93 | 526.64 | 527 | 1.35 |

TABLE 4-continued

Examples E-1-E-349

| Nr. | Structure | Int. | MW | MW [M + H] | tR [min] |
|---|---|---|---|---|---|
| E-48 | 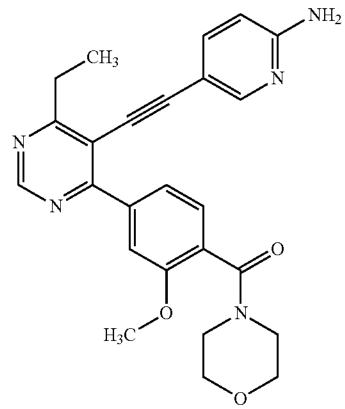 [SMILES: CCc1ncnc(-c2ccc(C(=O)N3CCOCC3)c(OC)c2)c1C#Cc1ccc(N)nc1] | A-93 | 443.5 | 444 | 1.32 |
| E-49 | 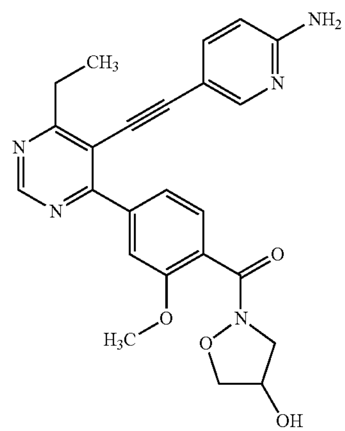 [SMILES: CCc1ncnc(-c2ccc(C(=O)N3CC(O)CO3)c(OC)c2)c1C#Cc1ccc(N)nc1] | A-93 | 445.48 | 446 | 1.21 |
| E-50 | 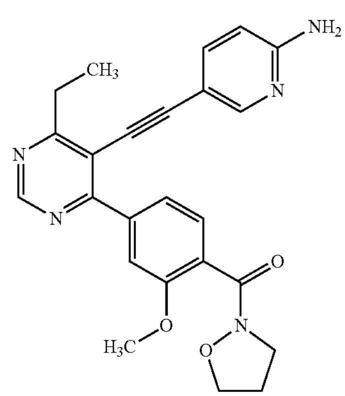 [SMILES: CCc1ncnc(-c2ccc(C(=O)N3CCCO3)c(OC)c2)c1C#Cc1ccc(N)nc1] | A-93 | 429.48 | 430 | 1.31 |

TABLE 4-continued

Examples E-1-E-349

| Nr. | Structure | Int. | MW | MW [M + H] | tR [min] |
|---|---|---|---|---|---|
| E-51 | 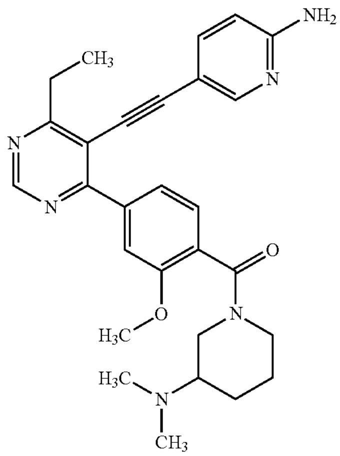 [SMILES: CCc1ncnc(-c2ccc(C(=O)N3CCCC(N(C)C)C3)c(OC)c2)c1C#Cc1ccc(N)nc1] | A-93 | 484.6 | 485 | 1.41 |
| E-52 | 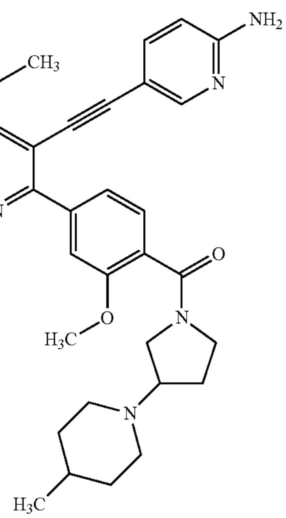 | A-93 | 524.67 | 525 | 1.84 |
| E-53 | 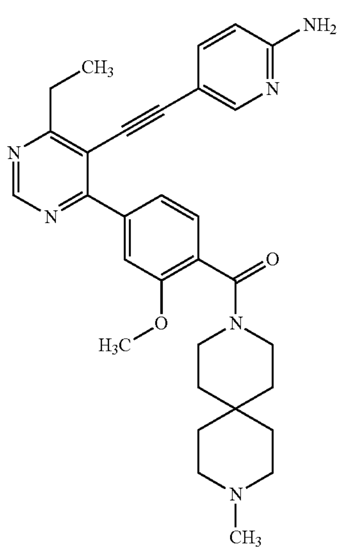 [SMILES: CCc1ncnc(-c2ccc(C(=O)N3CCC4(CCN(C)CC4)CC3)c(OC)c2)c1C#Cc1ccc(N)nc1] | A-93 | 524.67 | 525 | 1.56 |

TABLE 4-continued

Examples E-1-E-349

| Nr. | Structure | Int. | MW | MW [M + H] | tR [min] |
|---|---|---|---|---|---|
| E-54 | 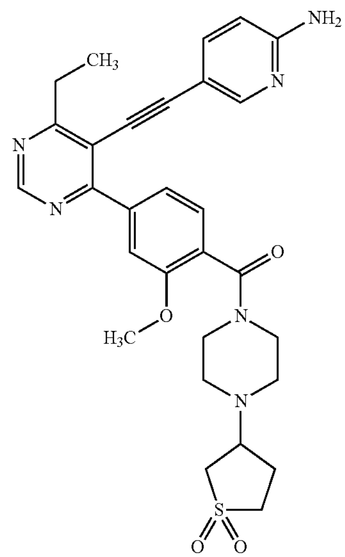 [SMILES: CCc1ncnc(-c2ccc(C(=O)N3CCN(C4CCS(=O)(=O)C4)CC3)c(OC)c2)c1C#Cc1ccc(N)nc1] | A-93 | 560.68 | 561 | 1.47 |
| E-55 | 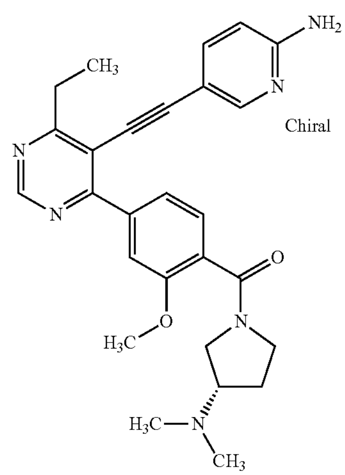 [SMILES: CCc1ncnc(-c2ccc(C(=O)N3CC[C@H](N(C)C)C3)c(OC)c2)c1C#Cc1ccc(N)nc1] | A-93 | 470.57 | 471 | 1.53 |
| E-56 | 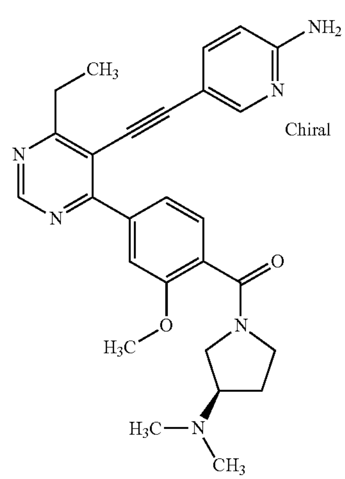 [SMILES: CCc1ncnc(-c2ccc(C(=O)N3CC[C@@H](N(C)C)C3)c(OC)c2)c1C#Cc1ccc(N)nc1] | A-93 | 470.57 | 469 | 1.53 |

TABLE 4-continued

Examples E-1-E-349

| Nr. | Structure | Int. | MW | MW [M + H] | tR [min] |
|---|---|---|---|---|---|
| E-57 | 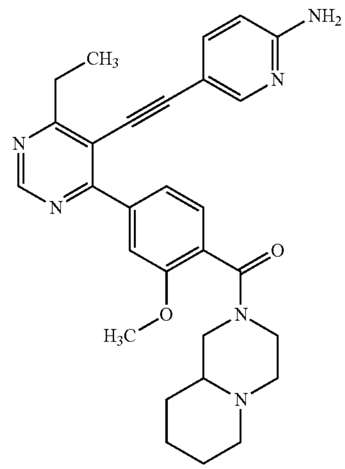 [SMILES: CCc1ncnc(-c2ccc(C(=O)N3CCN4CCCCC4C3)c(OC)c2)c1C#Cc1ccc(N)nc1] | A-93 | 496.61 | 497 | 1.66 |
| E-58 | 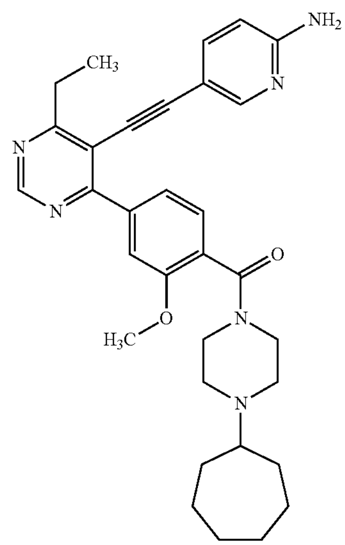 | A-93 | 538.69 | 539 | 1.95 |
| E-59 | 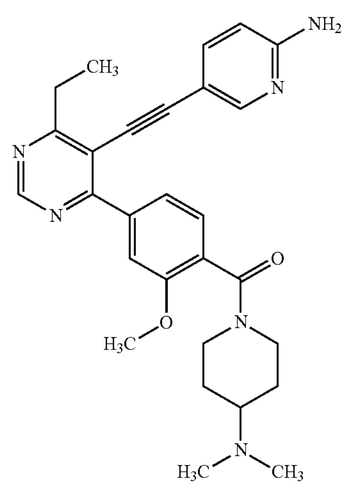 [SMILES: CCc1ncnc(-c2ccc(C(=O)N3CCC(N(C)C)CC3)c(OC)c2)c1C#Cc1ccc(N)nc1] | A-93 | 484.6 | 485 | 1.58 |

TABLE 4-continued

Examples E-1-E-349

| Nr. | Structure | Int. | MW | MW [M + H] | tR [min] |
|---|---|---|---|---|---|
| E-60 | 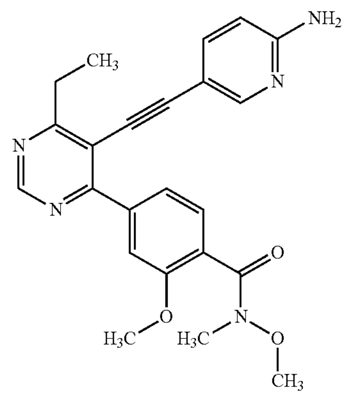 [SMILES: CCc1ncnc(-c2ccc(C(=O)N(C)OC)c(OC)c2)c1C#Cc1ccc(N)nc1] | A-93 | 417.47 | 418 | 1.36 |
| E-61 | 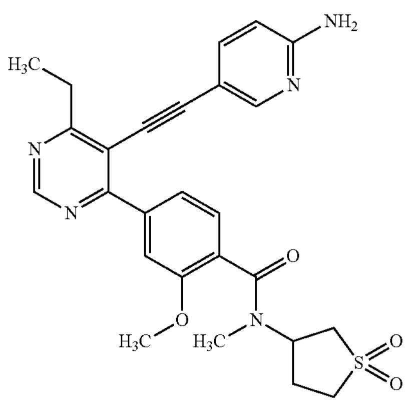 [SMILES: CCc1ncnc(-c2ccc(C(=O)N(C)C3CCS(=O)(=O)C3)c(OC)c2)c1C#Cc1ccc(N)nc1] | A-93 | 505.6 | 506 | 1.3 |
| E-62 | 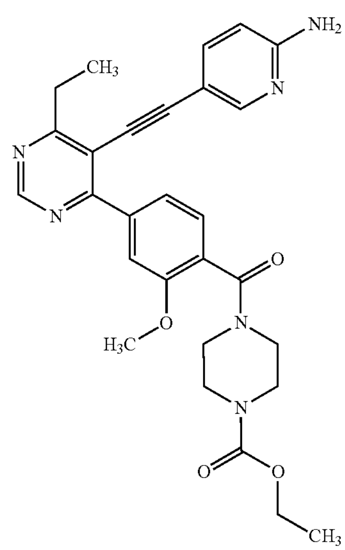 [SMILES: CCOC(=O)N1CCN(C(=O)c2ccc(-c3ncnc(CC)c3C#Cc3ccc(N)nc3)cc2OC)CC1] | A-93 | 515.58 | 515 | 1.67 |

TABLE 4-continued

Examples E-1-E-349

| Nr. | Structure | Int. | MW | MW [M + H] | tR [min] |
|---|---|---|---|---|---|
| E-63 | 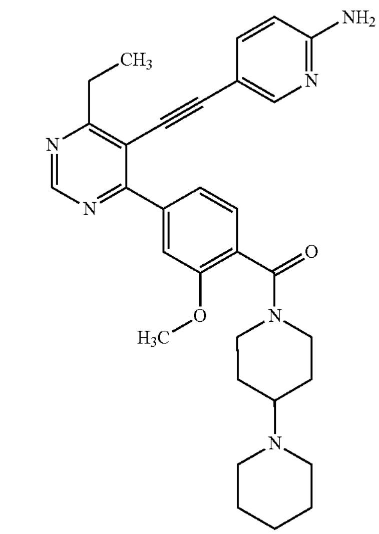 [SMILES: CCc1ncnc(-c2ccc(C(=O)N3CCC(N4CCCCC4)CC3)c(OC)c2)c1C#Cc1ccc(N)nc1] | A-93 | 524.67 | 523 | 1.81 |
| E-64 | 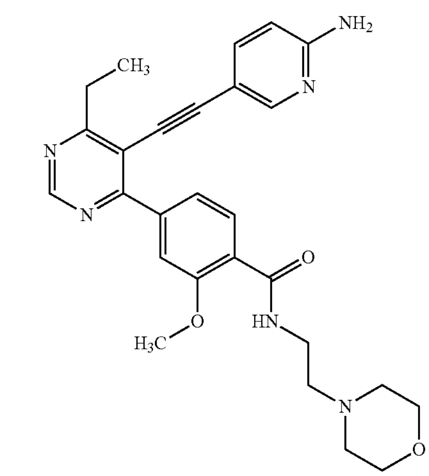 [SMILES: CCc1ncnc(-c2ccc(C(=O)NCCN3CCOCC3)c(OC)c2)c1C#Cc1ccc(N)nc1] | A-93 | 486.57 | 487 | 1.3 |
| E-65 | 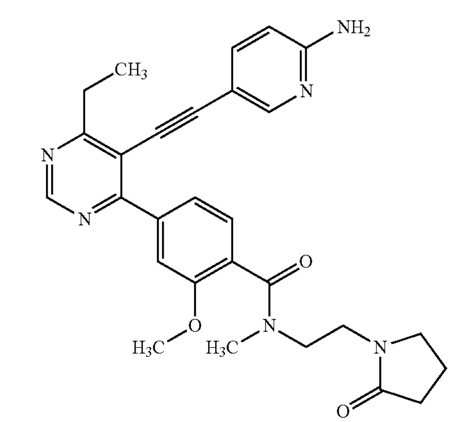 [SMILES: CCc1ncnc(-c2ccc(C(=O)N(C)CCN3CCCC3=O)c(OC)c2)c1C#Cc1ccc(N)nc1] | A-93 | 498.58 | 499 | 1.2 |

TABLE 4-continued

Examples E-1-E-349

| Nr. | Structure | Int. | MW | MW [M + H] | tR [min] |
|---|---|---|---|---|---|
| E-66 | 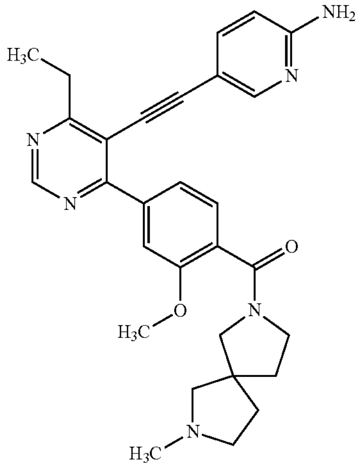 [SMILES: CCc1ncnc(-c2ccc(C(=O)N3CCC4(CCN(C)C4)C3)c(OC)c2)c1C#Cc1ccc(N)nc1] | A-93 | 496.61 | 497 | 1.45 |
| E-67 | 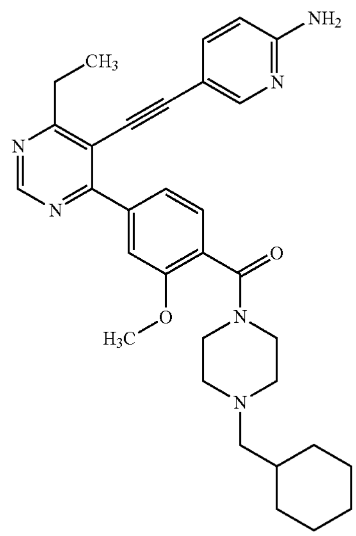 [SMILES: CCc1ncnc(-c2ccc(C(=O)N3CCN(CC4CCCCC4)CC3)c(OC)c2)c1C#Cc1ccc(N)nc1] | A-93 | 538.69 | 539 | 1.94 |
| E-68 | 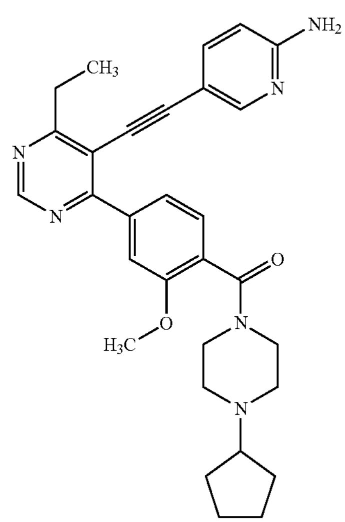 [SMILES: CCc1ncnc(-c2ccc(C(=O)N3CCN(C4CCCC4)CC3)c(OC)c2)c1C#Cc1ccc(N)nc1] | A-93 | 510.64 | 511 | 1.62 |

TABLE 4-continued

Examples E-1-E-349

| Nr. | Structure | Int. | MW | MW [M + H] | tR [min] |
|---|---|---|---|---|---|
| E-69 | 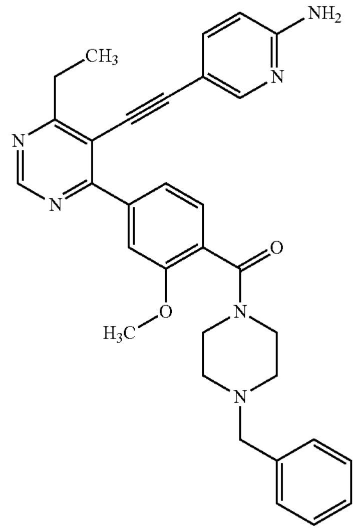 [SMILES: CCc1ncnc(-c2ccc(C(=O)N3CCN(Cc4ccccc4)CC3)c(OC)c2)c1C#Cc1ccc(N)nc1] | A-93 | 532.64 | 533 | 1.71 |
| E-70 | 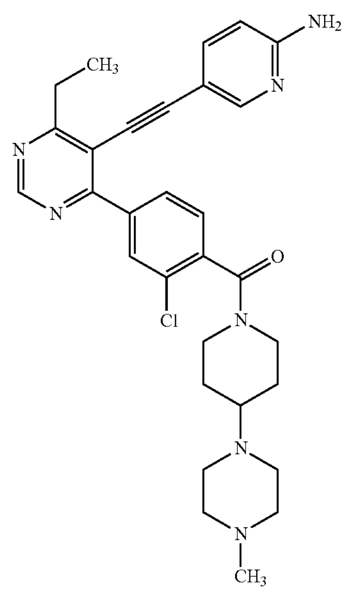 | A-77 | 544.1 | 542/544 | 1.59 |

TABLE 4-continued

Examples E-1-E-349

| Nr. | Structure | Int. | MW | MW [M + H] | tR [min] |
|---|---|---|---|---|---|
| E-71 | 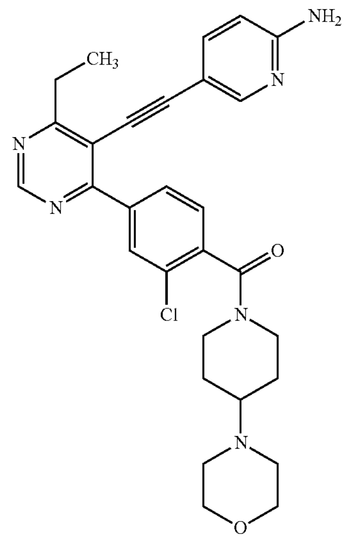 | A-77 | 531.06 | 531 | 1.62 |
| E-72 | 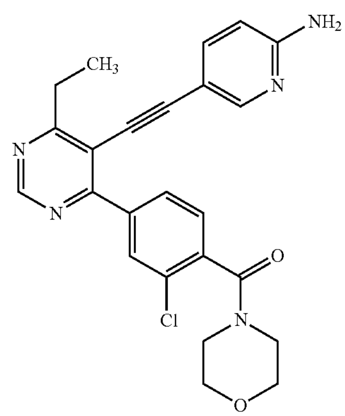 [SMILES: CCc1ncnc(-c2ccc(C(=O)N3CCOCC3)c(Cl)c2)c1C#Cc1ccc(N)nc1] | A-77 | 447.92 | 446/448 | 1.59 |
| E-73 | 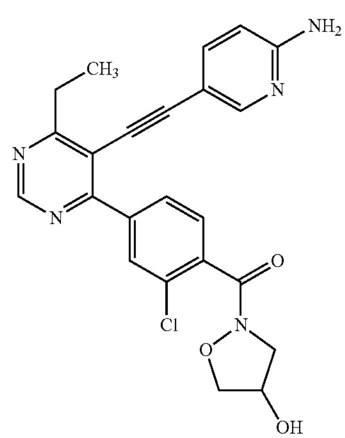 [SMILES: CCc1ncnc(-c2ccc(C(=O)N3CC(O)CO3)c(Cl)c2)c1C#Cc1ccc(N)nc1] | A-77 | 449.9 | 448/450 | 1.46 |

TABLE 4-continued

Examples E-1-E-349

| Nr. | Structure | Int. | MW | MW [M + H] | tR [min] |
|---|---|---|---|---|---|
| E-74 | 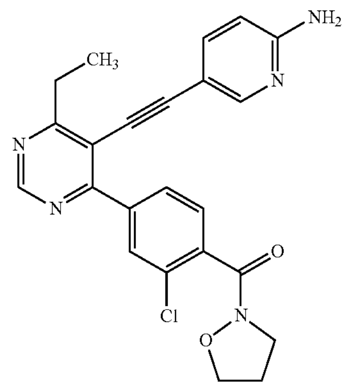 [SMILES: CCc1ncnc(-c2ccc(C(=O)N3CCCO3)c(Cl)c2)c1C#Cc1ccc(N)nc1] | A-77 | 433.9 | 432/434 | 1.59 |
| E-75 | 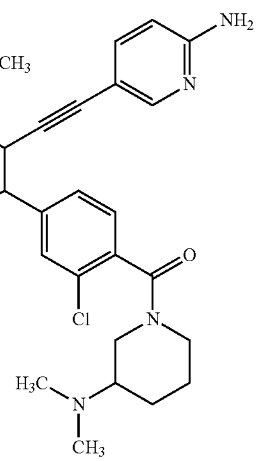 | A-77 | 489.02 | 487/489 | 1.68 |
| E-76 | 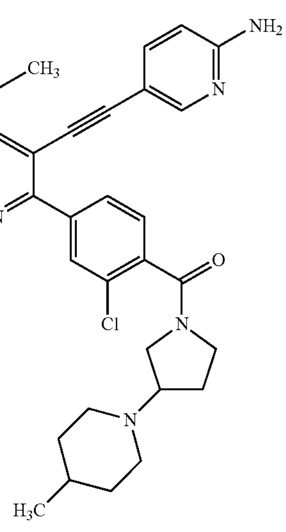 | A-77 | 529.08 | 527/529 | 1.95 |

TABLE 4-continued

Examples E-1-E-349

| Nr. | Structure | Int. | MW | MW [M + H] | tR [min] |
|---|---|---|---|---|---|
| E-77 | 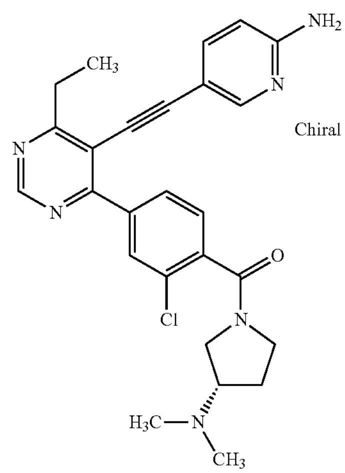 [SMILES: CCc1ncnc(-c2ccc(C(=O)N3CC[C@H](N(C)C)C3)c(Cl)c2)c1C#Cc1ccc(N)nc1] | A-77 | 474.99 | 473/475 | 1.62 |
| E-78 | 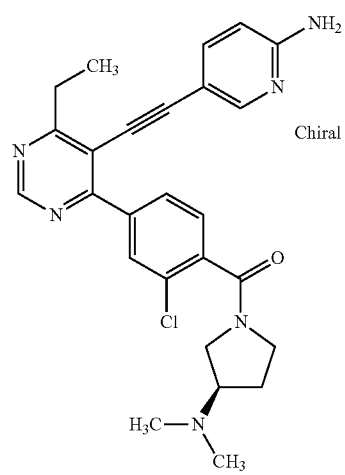 [SMILES: CCc1ncnc(-c2ccc(C(=O)N3CC[C@@H](N(C)C)C3)c(Cl)c2)c1C#Cc1ccc(N)nc1] | A-77 | 474.99 | 473/475 | 1.61 |
| E-79 | 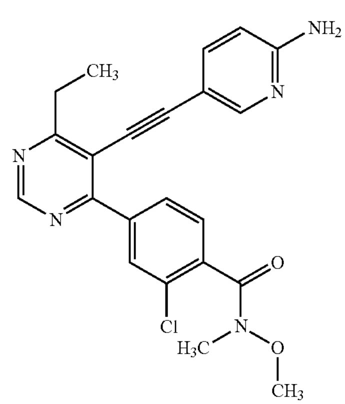 [SMILES: CCc1ncnc(-c2ccc(C(=O)N(C)OC)c(Cl)c2)c1C#Cc1ccc(N)nc1] | A-77 | 421.89 | 422 | 1.64 |

TABLE 4-continued

Examples E-1-E-349

| Nr. | Structure | Int. | MW | MW [M + H] | tR [min] |
|---|---|---|---|---|---|
| E-80 | 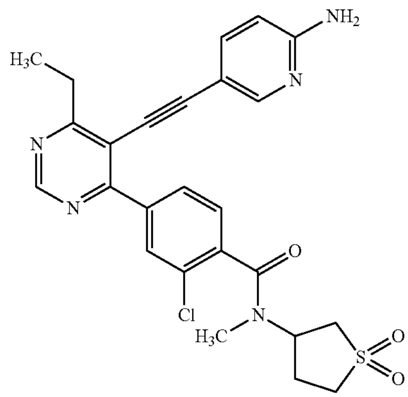 [SMILES: CCc1ncnc(-c2ccc(C(=O)N(C)C3CCS(=O)(=O)C3)c(Cl)c2)c1C#Cc1ccc(N)nc1] | A-77 | 510.02 | 510/512 | 1.57 |
| E-81 | 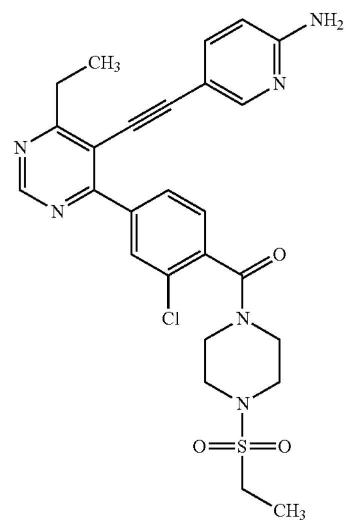 [SMILES: CCc1ncnc(-c2ccc(C(=O)N3CCN(S(=O)(=O)CC)CC3)c(Cl)c2)c1C#Cc1ccc(N)nc1] | A-77 | 539.06 | 539 | 1.66 |
| E-82 | 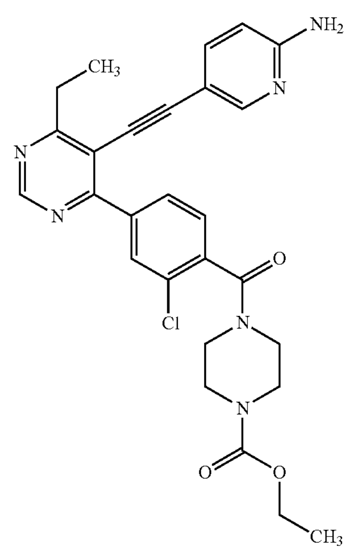 [SMILES: CCOC(=O)N1CCN(C(=O)c2ccc(-c3ncnc(CC)c3C#Cc3ccc(N)nc3)cc2Cl)CC1] | A-77 | 519 | 517/519 | 1.76 |

TABLE 4-continued

Examples E-1-E-349

| Nr. | Structure | Int. | MW | MW [M + H] | tR [min] |
|---|---|---|---|---|---|
| E-83 | 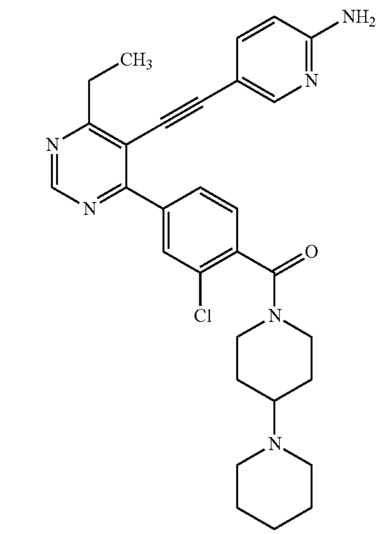 [SMILES: CCc1ncnc(-c2ccc(C(=O)N3CCC(N4CCCCC4)CC3)c(Cl)c2)c1C#Cc1ccc(N)nc1] | A-77 | 529.08 | 529 | 1.91 |
| E-84 | 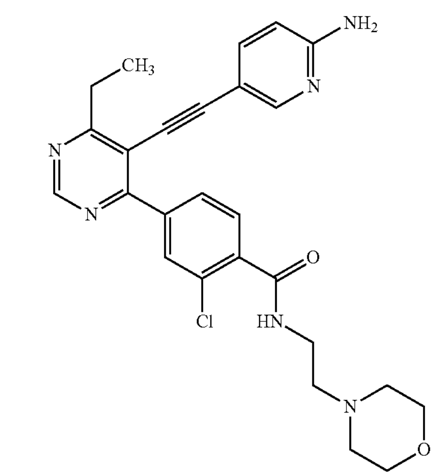 [SMILES: CCc1ncnc(-c2ccc(C(=O)NCCN3CCOCC3)c(Cl)c2)c1C#Cc1ccc(N)nc1] | A-77 | 490.99 | 491 | 1.54 |
| E-85 | 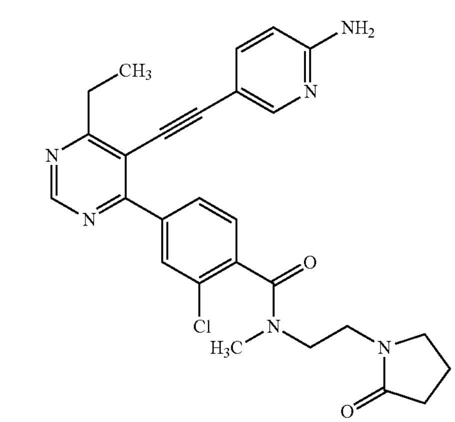 [SMILES: CCc1ncnc(-c2ccc(C(=O)N(C)CCN3CCCC3=O)c(Cl)c2)c1C#Cc1ccc(N)nc1] | A-77 | 503 | 503 | 1.54 |

TABLE 4-continued

Examples E-1-E-349

| Nr. | Structure | Int. | MW | MW [M + H] | tR [min] |
|---|---|---|---|---|---|
| E-86 | 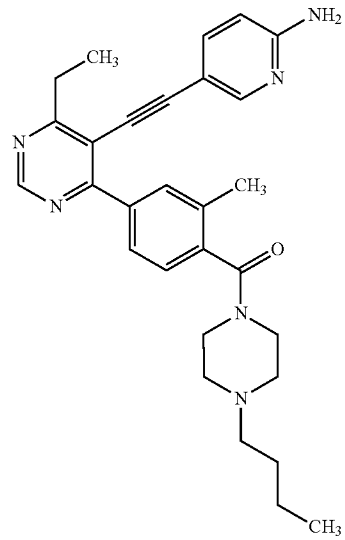 [SMILES: CCCCN1CCN(C(=O)c2ccc(-c3ncnc(CC)c3C#Cc3ccc(N)nc3)cc2C)CC1] | A-106 | 482.63 | 483 | 1.87 |
| E-87 | 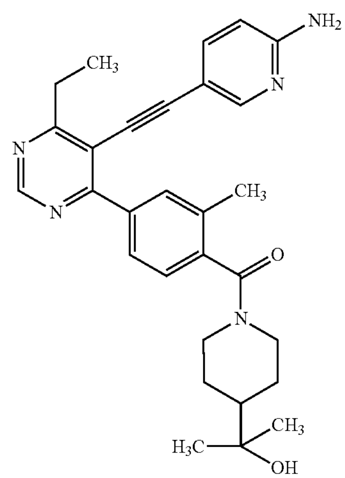 [SMILES: CCc1ncnc(-c2ccc(C(=O)N3CCC(C(C)(C)O)CC3)c(C)c2)c1C#Cc1ccc(N)nc1] | A-106 | 483.61 | 484 | 1.62 |
| E-88 | 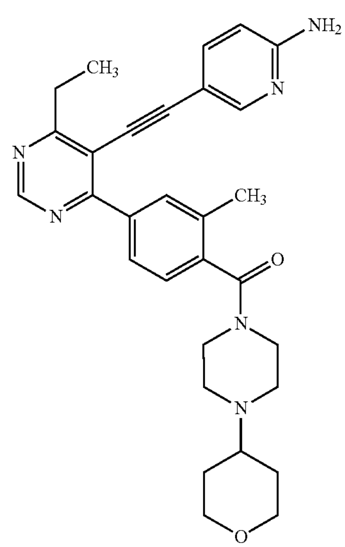 [SMILES: CCc1ncnc(-c2ccc(C(=O)N3CCN(C4CCOCC4)CC3)c(C)c2)c1C#Cc1ccc(N)nc1] | A-106 | 510.64 | 511 | 1.57 |

TABLE 4-continued

Examples E-1-E-349

| Nr. | Structure | Int. | MW | MW [M + H] | tR [min] |
|---|---|---|---|---|---|
| E-89 | 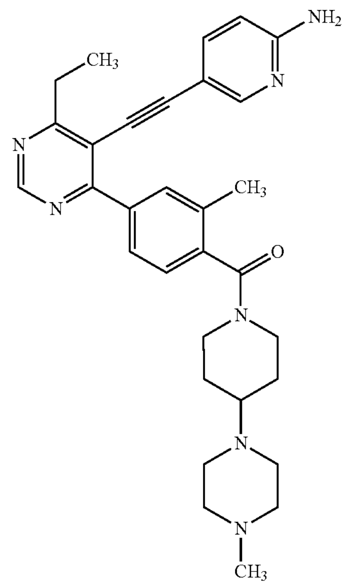 [SMILES: CCc1ncnc(-c2ccc(C(=O)N3CCC(N4CCN(C)CC4)CC3)c(C)c2)c1C#Cc1ccc(N)nc1] | A-106 | 523.68 | 522 | 1.54 |
| E-90 | 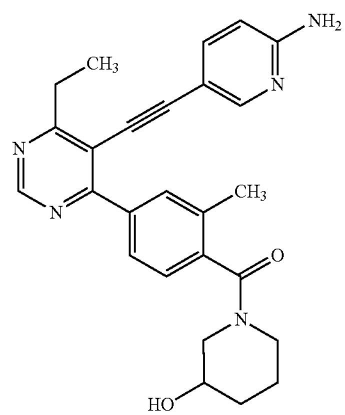 [SMILES: CCc1ncnc(-c2ccc(C(=O)N3CCCC(O)C3)c(C)c2)c1C#Cc1ccc(N)nc1] | A-106 | 441.53 | 440 | 1.5 |
| E-91 | 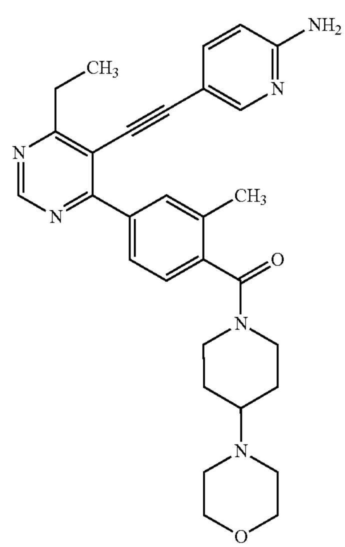 [SMILES: CCc1ncnc(-c2ccc(C(=O)N3CCC(N4CCOCC4)CC3)c(C)c2)c1C#Cc1ccc(N)nc1] | A-106 | 510.64 | 511 | 1.56 |

TABLE 4-continued

Examples E-1-E-349

| Nr. | Structure | Int. | MW | MW [M + H] | tR [min] |
|---|---|---|---|---|---|
| E-92 | 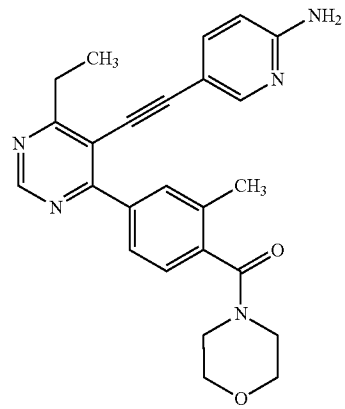 [SMILES: CCc1ncnc(-c2ccc(C(=O)N3CCOCC3)c(C)c2)c1C#Cc1ccc(N)nc1] | A-106 | 427.51 | 428 | 4.52 |
| E-93 | 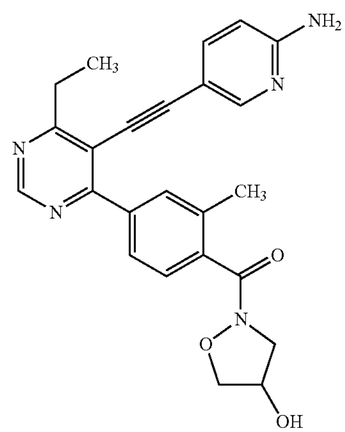 [SMILES: CCc1ncnc(-c2ccc(C(=O)N3CC(O)CO3)c(C)c2)c1C#Cc1ccc(N)nc1] | A-106 | 429.48 | 430 | 1.41 |
| E-94 | 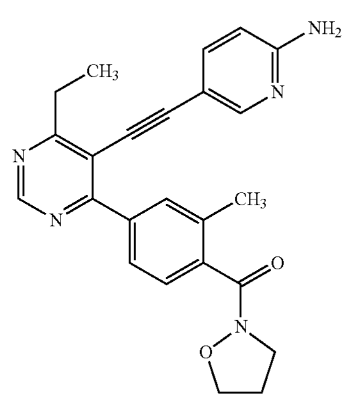 [SMILES: CCc1ncnc(-c2ccc(C(=O)N3CCCO3)c(C)c2)c1C#Cc1ccc(N)nc1] | A-106 | 413.48 | 414 | 1.53 |

TABLE 4-continued

Examples E-1-E-349

| Nr. | Structure | Int. | MW | MW [M + H] | tR [min] |
|---|---|---|---|---|---|
| E-95 | 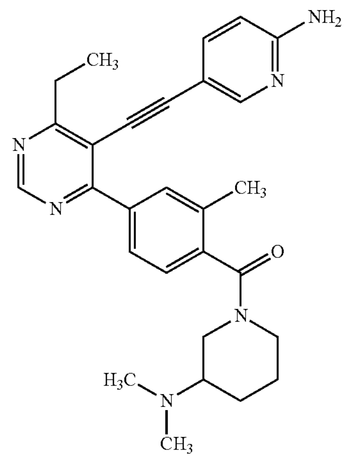 [SMILES: CCc1ncnc(-c2ccc(C(=O)N3CCCC(N(C)C)C3)c(C)c2)c1C#Cc1ccc(N)nc1] | A-106 | 468.6 | 467 | 1.62 |
| E-96 | 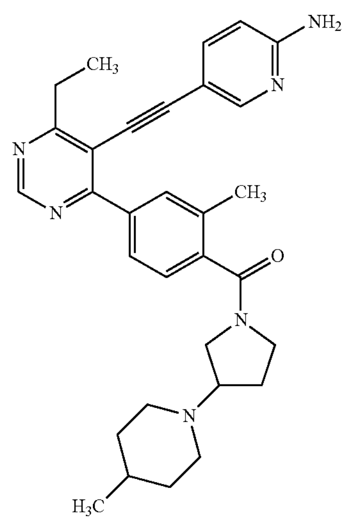 [SMILES: CCc1ncnc(-c2ccc(C(=O)N3CCC(N4CCC(C)CC4)C3)c(C)c2)c1C#Cc1ccc(N)nc1] | A-106 | 508.67 | 507 | 1.88 |
| E-97 | 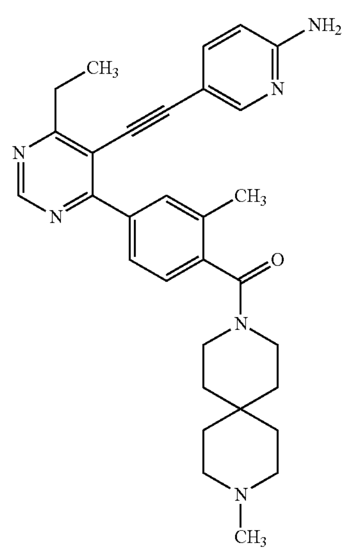 [SMILES: CCc1ncnc(-c2ccc(C(=O)N3CCC4(CCN(C)CC4)CC3)c(C)c2)c1C#Cc1ccc(N)nc1] | A-106 | 508.67 | 509 | 1.74 |

TABLE 4-continued

Examples E-1-E-349

| Nr. | Structure | Int. | MW | MW [M + H] | tR [min] |
|---|---|---|---|---|---|
| E-98 | 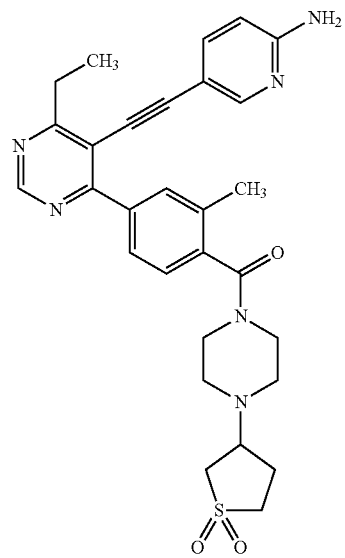 [SMILES: CCc1ncnc(-c2ccc(C(=O)N3CCN(C4CCS(=O)(=O)C4)CC3)c(C)c2)c1C#Cc1ccc(N)nc1] | A-106 | 544.68 | 545 | 1.49 |
| E-99 | 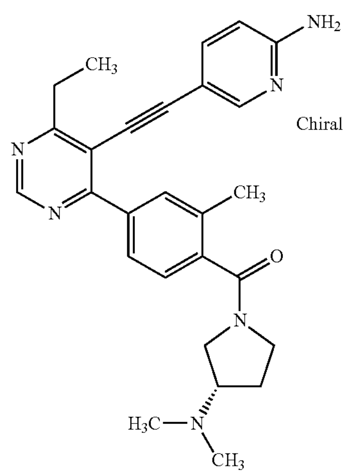 [SMILES: CCc1ncnc(-c2ccc(C(=O)N3CC[C@H](N(C)C)C3)c(C)c2)c1C#Cc1ccc(N)nc1] | A-106 | 454.58 | 453 | 1.56 |
| E-100 | 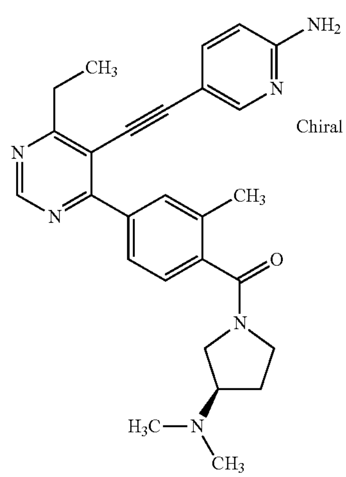 [SMILES: CCc1ncnc(-c2ccc(C(=O)N3CC[C@@H](N(C)C)C3)c(C)c2)c1C#Cc1ccc(N)nc1] | A-106 | 454.58 | 453 | 1.55 |

TABLE 4-continued

Examples E-1-E-349

| Nr. | Structure | Int. | MW | MW [M + H] | tR [min] |
|---|---|---|---|---|---|
| E-101 | 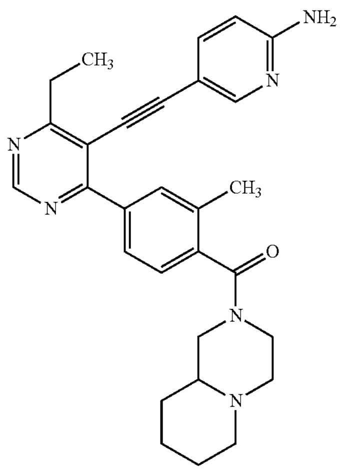 [SMILES: CCc1ncnc(-c2ccc(C(=O)N3CCN4CCCCC4C3)c(C)c2)c1C#Cc1ccc(N)nc1] | A-106 | 480.61 | 479 | 1.7 |
| E-102 | 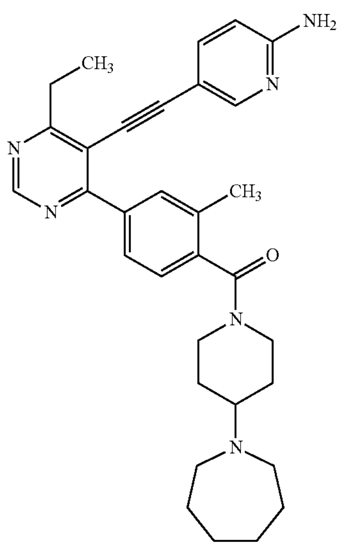 [SMILES: CCc1ncnc(-c2ccc(C(=O)N3CCC(N4CCCCCC4)CC3)c(C)c2)c1C#Cc1ccc(N)nc1] | A-106 | 522.69 | 523 | 1.99 |
| E-103 | 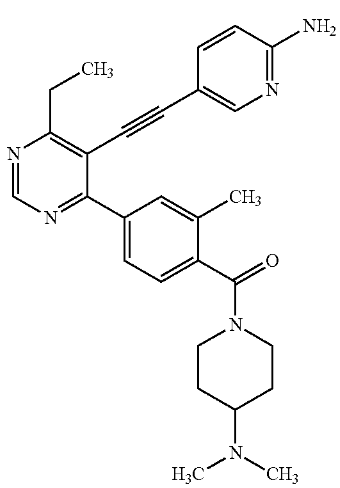 [SMILES: CCc1ncnc(-c2ccc(C(=O)N3CCC(N(C)C)CC3)c(C)c2)c1C#Cc1ccc(N)nc1] | A-106 | 468.6 | 467 | 1.61 |

TABLE 4-continued

Examples E-1-E-349

| Nr. | Structure | Int. | MW | MW [M + H] | tR [min] |
|---|---|---|---|---|---|
| E-104 | 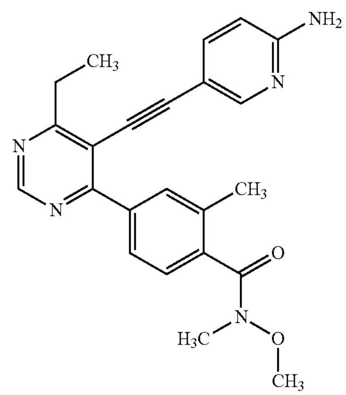 [SMILES: CCc1ncnc(-c2ccc(C(=O)N(C)OC)c(C)c2)c1C#Cc1ccc(N)nc1] | A-106 | 401.47 | 402 | 1.57 |
| E-105 | 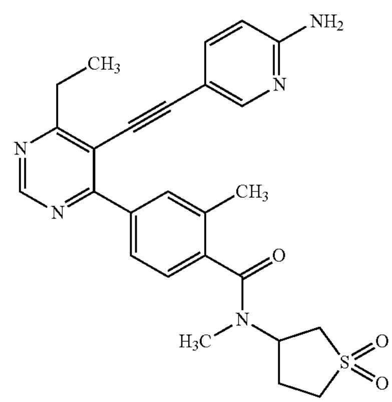 [SMILES: CCc1ncnc(-c2ccc(C(=O)N(C)C3CCS(=O)(=O)C3)c(C)c2)c1C#Cc1ccc(N)nc1] | A-106 | 489.6 | 490 | 1.51 |
| E-106 | 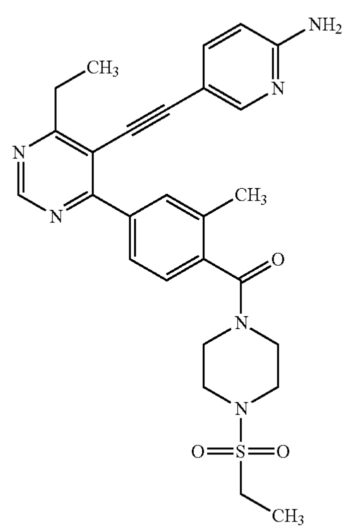 [SMILES: CCc1ncnc(-c2ccc(C(=O)N3CCN(S(=O)(=O)CC)CC3)c(C)c2)c1C#Cc1ccc(N)nc1] | A-106 | 518.64 | 517 | 1.61 |

TABLE 4-continued

Examples E-1-E-349

| Nr. | Structure | Int. | MW | MW [M + H] | tR [min] |
|---|---|---|---|---|---|
| E-107 | 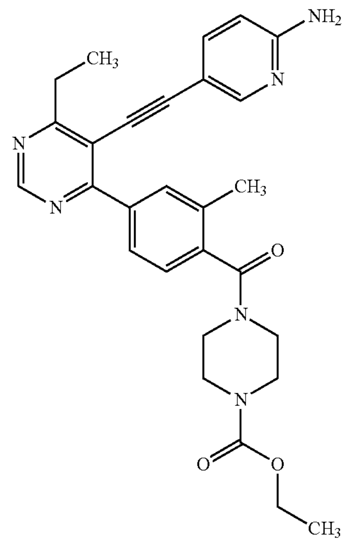 [SMILES: CCOC(=O)N1CCN(C(=O)c2ccc(-c3ncnc(CC)c3C#Cc3ccc(N)nc3)cc2C)CC1] | A-106 | 498.58 | 499 | 1.69 |
| E-108 | 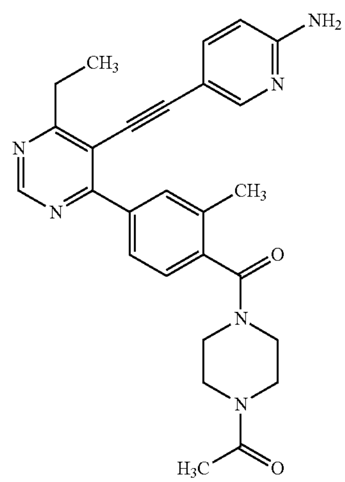 [SMILES: CCc1ncnc(-c2ccc(C(=O)N3CCN(C(C)=O)CC3)c(C)c2)c1C#Cc1ccc(N)nc1] | A-106 | 468.56 | 469 | 1.46 |
| E-109 | 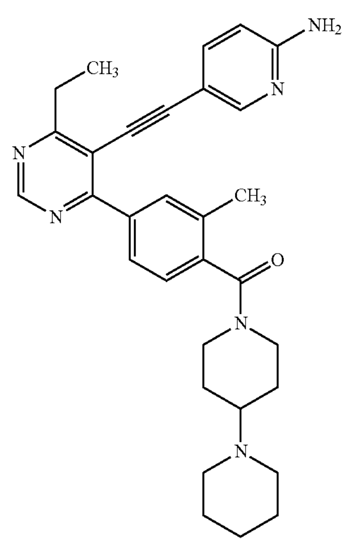 [SMILES: CCc1ncnc(-c2ccc(C(=O)N3CCC(N4CCCCC4)CC3)c(C)c2)c1C#Cc1ccc(N)nc1] | A-106 | 508.67 | 509 | 1.84 |

TABLE 4-continued

Examples E-1-E-349

| Nr. | Structure | Int. | MW | MW [M + H] | tR [min] |
|---|---|---|---|---|---|
| E-110 | 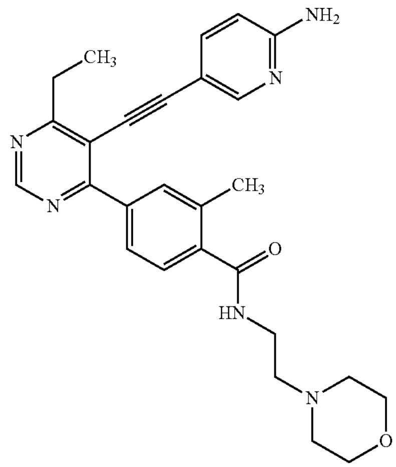 [SMILES: CCc1ncnc(-c2ccc(C(=O)NCCN3CCOCC3)c(C)c2)c1C#Cc1ccc(N)nc1] | A-106 | 470.57 | 469 | 1.5 |
| E-111 | 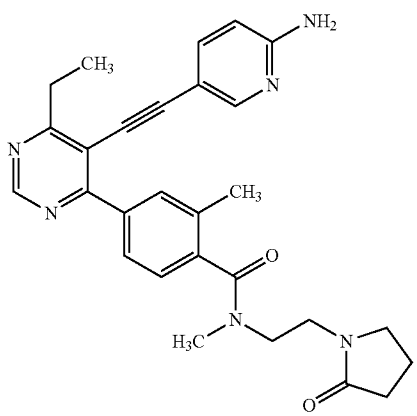 | A-106 | 482.58 | 481 | 1.48 |
| E-112 | 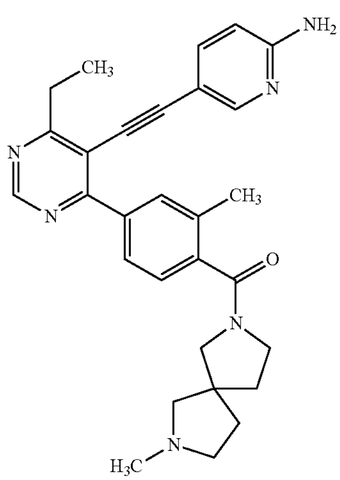 [SMILES: CCc1ncnc(-c2ccc(C(=O)N3CCC4(CCN(C)C4)C3)c(C)c2)c1C#Cc1ccc(N)nc1] | A-106 | 480.61 | 481 | 1.64 |

TABLE 4-continued
Examples E-1-E-349
| Nr. | Structure | Int. | MW | MW [M + H] | tR [min] |
|---|---|---|---|---|---|
| E-113 | 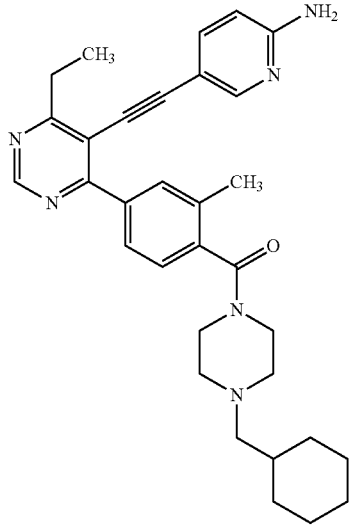 [SMILES: CCc1ncnc(-c2ccc(C(=O)N3CCN(CC4CCCCC4)CC3)c(C)c2)c1C#Cc1ccc(N)nc1] | A-106 | 522.69 | 523 | 2.19 |
| E-114 | 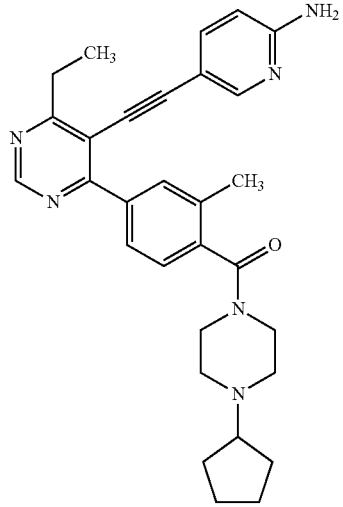 [SMILES: CCc1ncnc(-c2ccc(C(=O)N3CCN(C4CCCC4)CC3)c(C)c2)c1C#Cc1ccc(N)nc1] | A-106 | 494.64 | 493 | 1.84 |

TABLE 4-continued

Examples E-1-E-349

| Nr. | Structure | Int. | MW | MW [M + H] | tR [min] |
|---|---|---|---|---|---|
| E-115 | 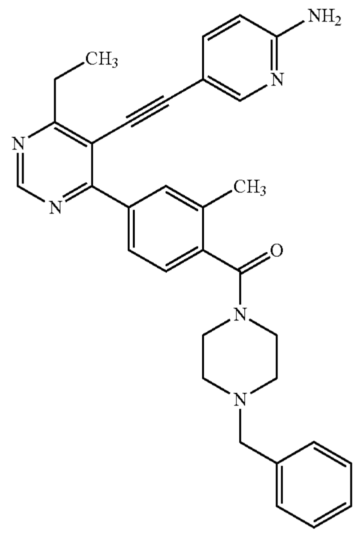 [SMILES: CCc1ncnc(-c2ccc(C(=O)N3CCN(Cc4ccccc4)CC3)c(C)c2)c1C#Cc1ccc(N)nc1] | A-106 | 516.65 | 517 | 1.92 |
| E-116 | 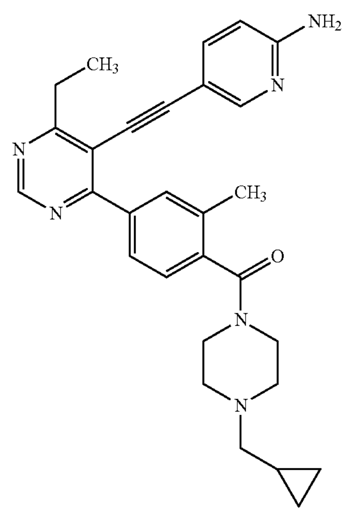 [SMILES: CCc1ncnc(-c2ccc(C(=O)N3CCN(CC4CC4)CC3)c(C)c2)c1C#Cc1ccc(N)nc1] | A-106 | 480.61 | 481 | 1.82 |
| E-117 | 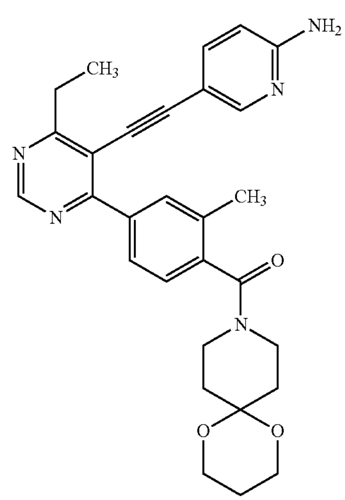 [SMILES: CCc1ncnc(-c2ccc(C(=O)N3CCC4(CC3)OCCCO4)c(C)c2)c1C#Cc1ccc(N)nc1] | A-106 | 497.6 | 498 | 1.71 |

TABLE 4-continued

Examples E-1-E-349

| Nr. | Structure | Int. | MW | MW [M + H] | tR [min] |
|---|---|---|---|---|---|
| E-118 | 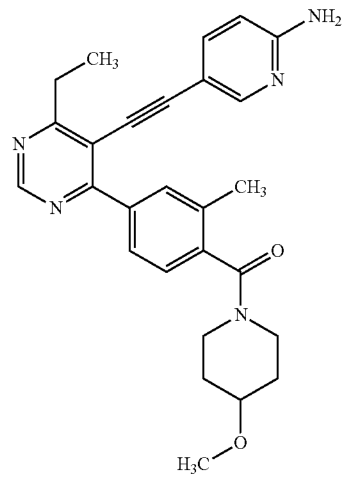 [SMILES: CCc1ncnc(-c2ccc(C(=O)N3CCC(OC)CC3)c(C)c2)c1C#Cc1ccc(N)nc1] | A-106 | 455.56 | 454 | 1.68 |
| E-119 | 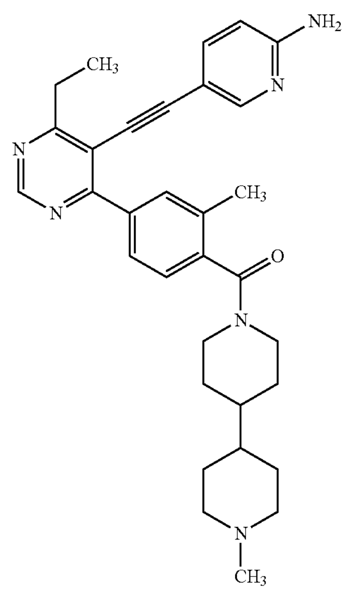 | A-106 | 522.69 | 523 | 2.03 |
| E-120 | 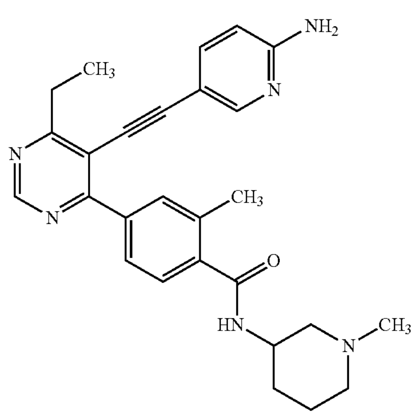 [SMILES: CCc1ncnc(-c2ccc(C(=O)NC3CCCN(C)C3)c(C)c2)c1C#Cc1ccc(N)nc1] | A-106 | 454.58 | 455 | 1.65 |

TABLE 4-continued

Examples E-1-E-349

| Nr. | Structure | Int. | MW | MW [M + H] | tR [min] |
|---|---|---|---|---|---|
| E-121 | 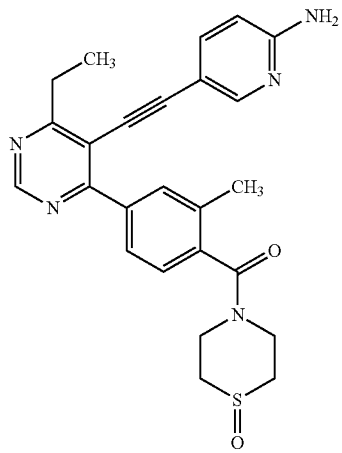 [SMILES: CCc1ncnc(-c2ccc(C(=O)N3CCS(=O)CC3)c(C)c2)c1C#Cc1ccc(N)nc1] | A-106 | 459.57 | 460 | 1.41 |
| E-122 | 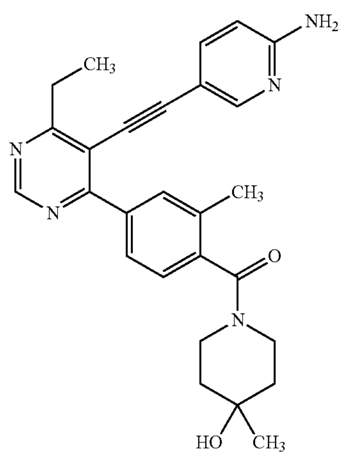 [SMILES: CCc1ncnc(-c2ccc(C(=O)N3CCC(C)(O)CC3)c(C)c2)c1C#Cc1ccc(N)nc1] | A-106 | 455.56 | 456 | 1.56 |
| E-123 | 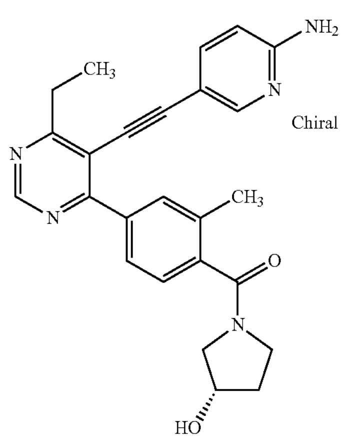 [SMILES: CCc1ncnc(-c2ccc(C(=O)N3CC[C@H](O)C3)c(C)c2)c1C#Cc1ccc(N)nc1] | A-106 | 427.51 | 428 | 1.45 |

TABLE 4-continued
Examples E-1-E-349
| Nr. | Structure | Int. | MW | MW [M + H] | tR [min] |
|---|---|---|---|---|---|
| E-124 | 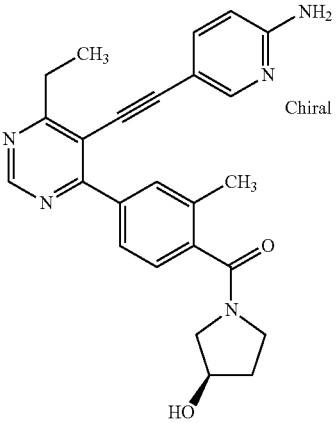 [SMILES: CCc1ncnc(-c2ccc(C(=O)N3CC[C@@H](O)C3)c(C)c2)c1C#Cc1ccc(N)nc1] | A-106 | 427.51 | 428 | 1.45 |
| E-125 | 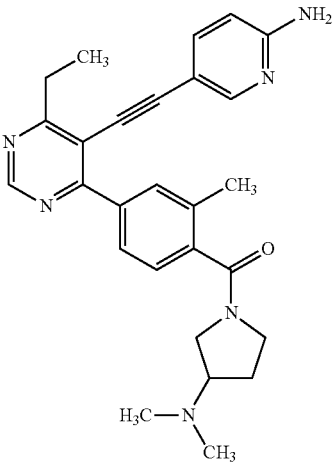 [SMILES: CCc1ncnc(-c2ccc(C(=O)N3CCC(N(C)C)C3)c(C)c2)c1C#Cc1ccc(N)nc1] | A-106 | 454.58 | 455 | 1.60 |
| E-126 | 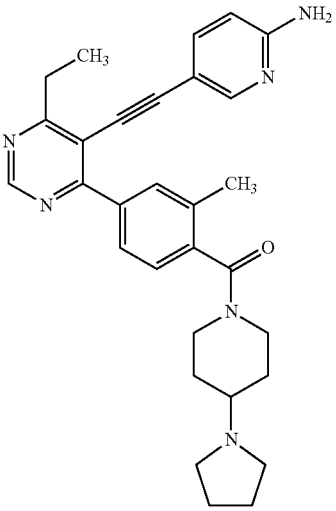 [SMILES: CCc1ncnc(-c2ccc(C(=O)N3CCC(N4CCCC4)CC3)c(C)c2)c1C#Cc1ccc(N)nc1] | A-106 | 494.64 | 495 | 1.83 |

TABLE 4-continued

Examples E-1-E-349

| Nr. | Structure | Int. | MW | MW [M + H] | tR [min] |
|---|---|---|---|---|---|
| E-127 | 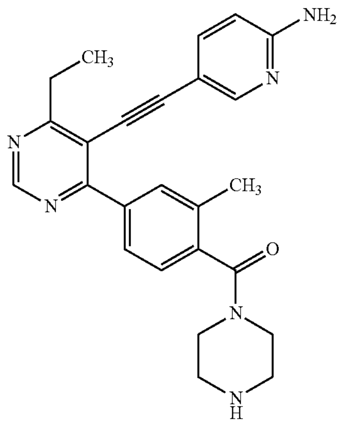 [SMILES: CCc1ncnc(-c2ccc(C(=O)N3CCNCC3)c(C)c2)c1C#Cc1ccc(N)nc1] | A-106 | 426.52 | 427 | 1.46 |
| E-128 | 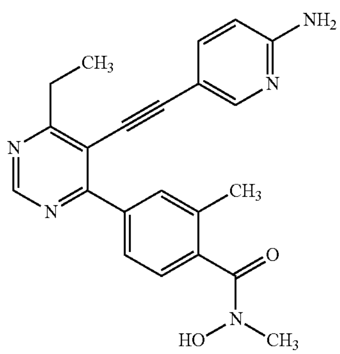 | A-106 | 387.44 | 388 | 1.25 |
| E-129 | 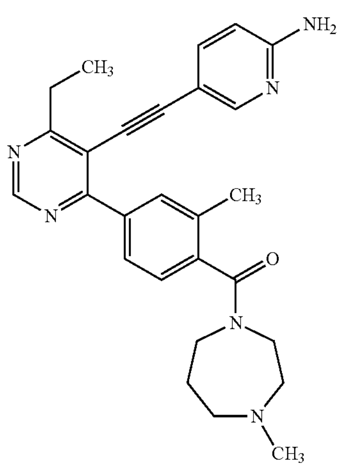 [SMILES: CCc1ncnc(-c2ccc(C(=O)N3CCCN(C)CC3)c(C)c2)c1C#Cc1ccc(N)nc1] | A-106 | 454.58 | 455 | 1.61 |

TABLE 4-continued

Examples E-1-E-349

| Nr. | Structure | Int. | MW | MW [M + H] | tR [min] |
|---|---|---|---|---|---|
| E-130 | 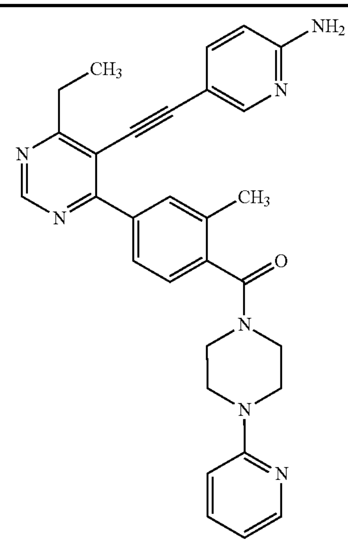 | A-106 | 503.61 | 504 | 1.81 |
| E-131 | 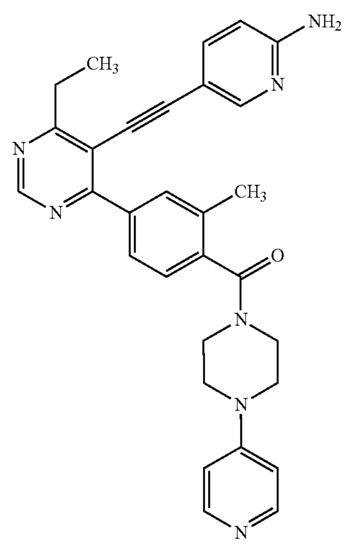 [SMILES: CCc1ncnc(-c2ccc(C(=O)N3CCN(c4ccncc4)CC3)c(C)c2)c1C#Cc1ccc(N)nc1] | A-106 | 503.61 | 504 | 1.64 |
| E-132 | 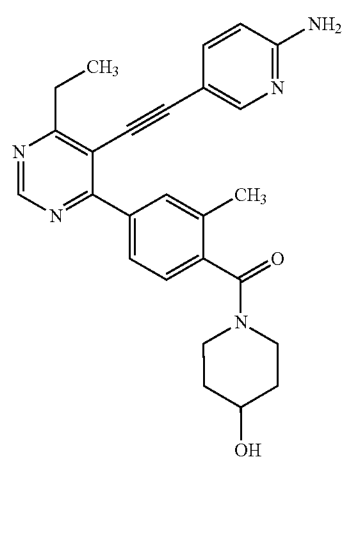 [SMILES: CCc1ncnc(-c2ccc(C(=O)N3CCC(O)CC3)c(C)c2)c1C#Cc1ccc(N)nc1] | A-106 | 441.53 | 442 | 1.47 |

TABLE 4-continued
Examples E-1-E-349
| Nr. | Structure | Int. | MW | MW [M + H] | tR [min] |
|---|---|---|---|---|---|
| E-133 | 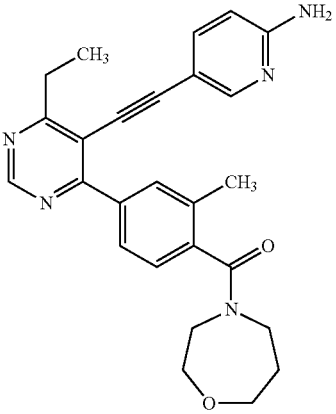 [SMILES: CCc1ncnc(-c2ccc(C(=O)N3CCCOCC3)c(C)c2)c1C#Cc1ccc(N)nc1] | A-106 | 441.53 | 442 | 1.58 |
| E-134 | 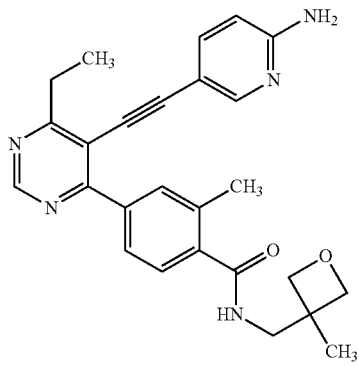 [SMILES: CCc1ncnc(-c2ccc(C(=O)NCC3(C)COC3)c(C)c2)c1C#Cc1ccc(N)nc1] | A-106 | 441.53 | 442 | 1.54 |
| E-135 | 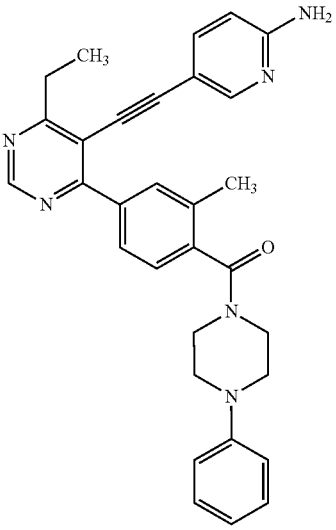 [SMILES: CCc1ncnc(-c2ccc(C(=O)N3CCN(c4ccccc4)CC3)c(C)c2)c1C#Cc1ccc(N)nc1] | A-106 | 502.62 | 503 | 1.95 |

TABLE 4-continued
Examples E-1-E-349
| Nr. | Structure | Int. | MW | MW [M + H] | tR [min] |
|---|---|---|---|---|---|
| E-139 | 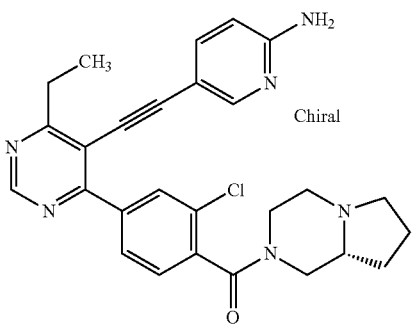 [SMILES: CCc1ncnc(-c2ccc(C(=O)N3CCN4CCC[C@@H]4C3)c(Cl)c2)c1C#Cc1ccc(N)nc1] | A-77 | 487 | 487/489 | 1.71 |
| E-140 | 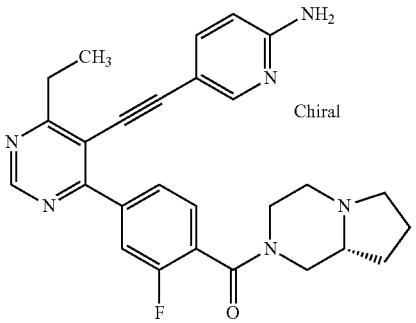 [SMILES: CCc1ncnc(-c2ccc(C(=O)N3CCN4CCC[C@@H]4C3)c(F)c2)c1C#Cc1ccc(N)nc1] | A-73 | 470.55 | 471 | 1.67 |
| E-141 | 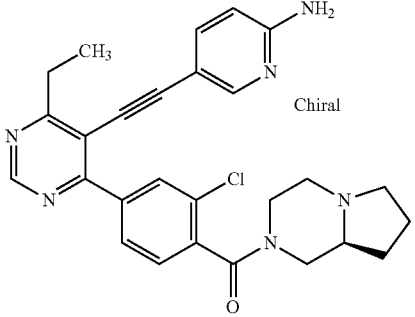 [SMILES: CCc1ncnc(-c2ccc(C(=O)N3CCN4CCC[C@H]4C3)c(Cl)c2)c1C#Cc1ccc(N)nc1] | A-77 | 487 | 487/488 | 1.71 |
| E-142 | 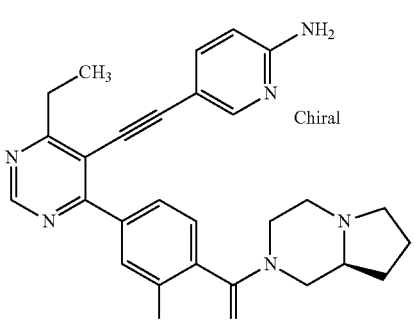 | A-73 | 470.55 | 471 | 1.67 |

TABLE 4-continued
Examples E-1-E-349
| Nr. | Structure | Int. | MW | MW [M + H] | tR [min] |
|---|---|---|---|---|---|
| E-143 | 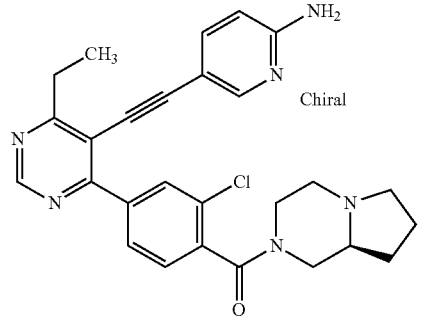 [SMILES: CCc1ncnc(-c2ccc(C(=O)N3CCN4CCC[C@H]4C3)c(Cl)c2)c1C#Cc1ccc(N)nc1] | A-77 | 501.03 | 501/503 | 1.74 |
| E-144 | 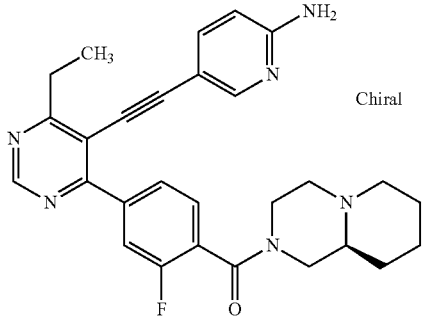 [SMILES: CCc1ncnc(-c2ccc(C(=O)N3CCN4CCCC[C@H]4C3)c(F)c2)c1C#Cc1ccc(N)nc1] | A-73 | 484.58 | 485 | 1.7 |
| E-145 | 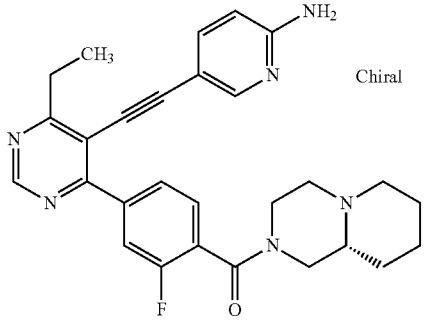 [SMILES: CCc1ncnc(-c2ccc(C(=O)N3CCN4CCCC[C@@H]4C3)c(F)c2)c1C#Cc1ccc(N)nc1] | A-73 | 484.58 | 485 | 1.56 |
| E-146 | 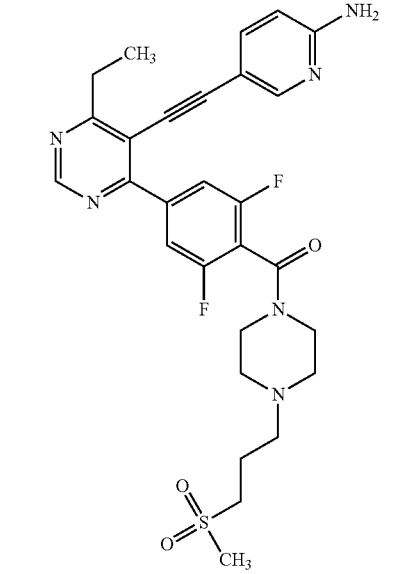 [SMILES: CCc1ncnc(-c2cc(F)c(C(=O)N3CCN(CCCS(C)(=O)=O)CC3)c(F)c2)c1C#Cc1ccc(N)nc1] | A-100 | 568.65 | 569 | 1.28 |

TABLE 4-continued

Examples E-1-E-349

| Nr. | Structure | Int. | MW | MW [M + H] | tR [min] |
|---|---|---|---|---|---|
| E-147 | 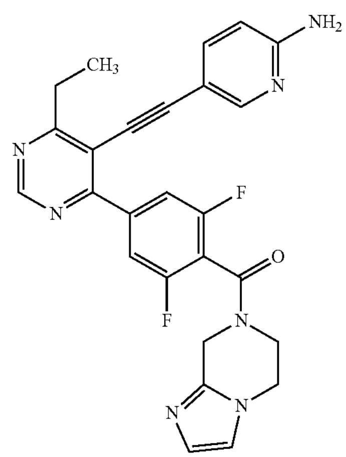 [SMILES: CCc1ncnc(-c2cc(F)c(C(=O)N3CCn4ccnc4C3)c(F)c2)c1C#Cc1ccc(N)nc1] | A-100 | 485.5 | 486 | 1.25 |
| E-148 | 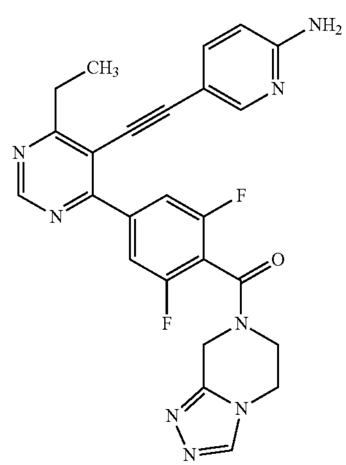 [SMILES: CCc1ncnc(-c2cc(F)c(C(=O)N3CCn4cnnc4C3)c(F)c2)c1C#Cc1ccc(N)nc1] | A-100 | 486.48 | 487 | 1.17 |
| E-149 | 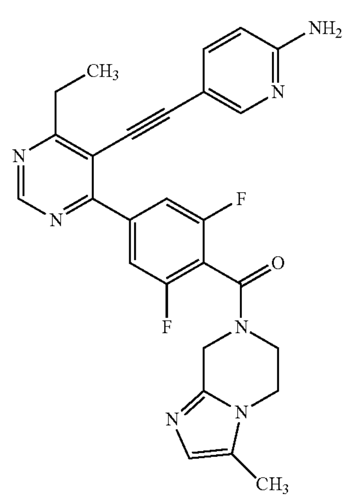 [SMILES: CCc1ncnc(-c2cc(F)c(C(=O)N3CCn4c(C)cnc4C3)c(F)c2)c1C#Cc1ccc(N)nc1] | A-100 | 499.52 | 500 | 1.30 |

TABLE 4-continued

Examples E-1-E-349

| Nr. | Structure | Int. | MW | MW [M + H] | tR [min] |
|---|---|---|---|---|---|
| E-150 | 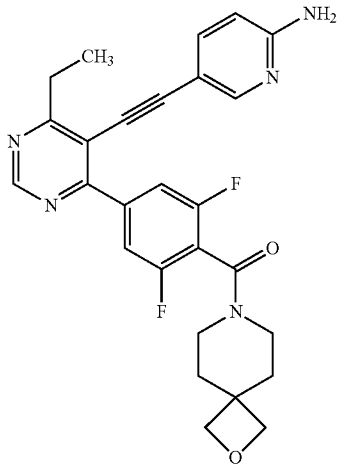 [SMILES: CCc1ncnc(-c2cc(F)c(C(=O)N3CCC4(CC3)COC4)c(F)c2)c1C#Cc1ccc(N)nc1] | A-100 | 489.52 | 490 | 1.33 |
| E-152 | 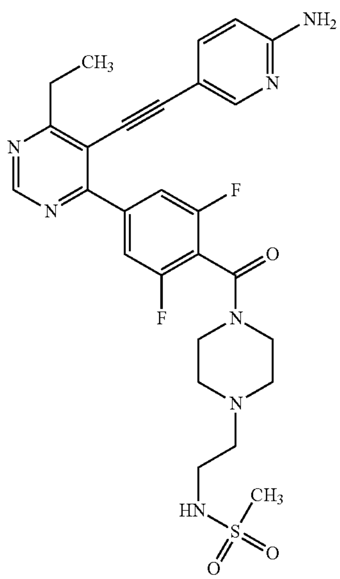 [SMILES: CCc1ncnc(-c2cc(F)c(C(=O)N3CCN(CCNS(C)(=O)=O)CC3)c(F)c2)c1C#Cc1ccc(N)nc1] | A-100 | 569.63 | 570 | 1.28 |
| E-153 | 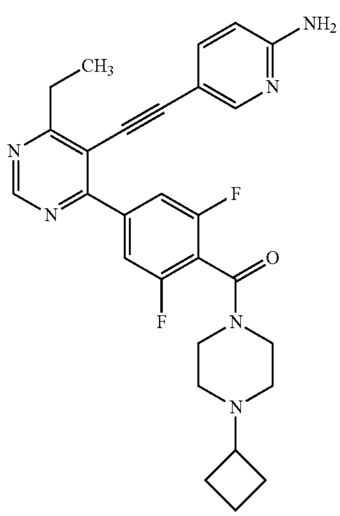 [SMILES: CCc1ncnc(-c2cc(F)c(C(=O)N3CCN(C4CCC4)CC3)c(F)c2)c1C#Cc1ccc(N)nc1] | A-100 | 502.57 | 503 | 1.50 |

TABLE 4-continued

Examples E-1-E-349

| Nr. | Structure | Int. | MW | MW [M + H] | tR [min] |
|---|---|---|---|---|---|
| E-154 | 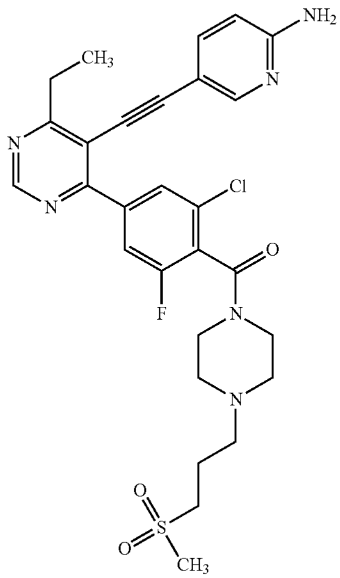 [SMILES: CCc1ncnc(-c2cc(F)c(C(=O)N3CCN(CCCS(C)(=O)=O)CC3)c(Cl)c2)c1C#Cc1ccc(N)nc1] | A-101 | 585.1 | 585/587 | 1.31 |
| E-155 | 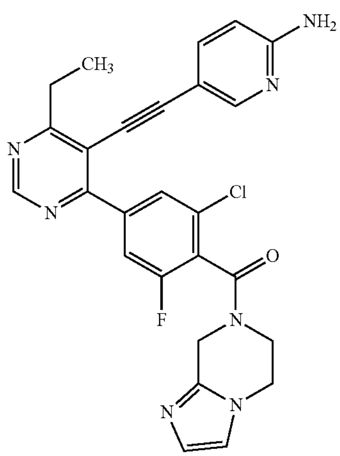 [SMILES: CCc1ncnc(-c2cc(F)c(C(=O)N3CCn4ccnc4C3)c(Cl)c2)c1C#Cc1ccc(N)nc1] | A-101 | 501.95 | 502/504 | 1.29 |
| E-156 | 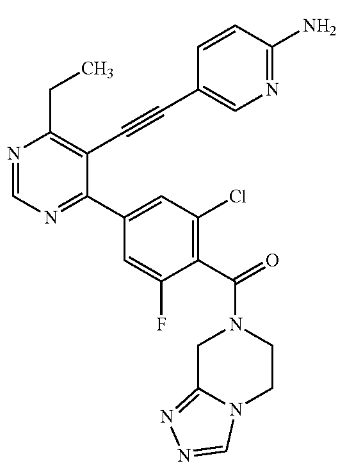 [SMILES: CCc1ncnc(-c2cc(F)c(C(=O)N3CCn4cnnc4C3)c(Cl)c2)c1C#Cc1ccc(N)nc1] | A-101 | 502.94 | 503/505 | 1.2 |

TABLE 4-continued

Examples E-1-E-349

| Nr. | Structure | Int. | MW | MW [M + H] | tR [min] |
|---|---|---|---|---|---|
| E-157 | 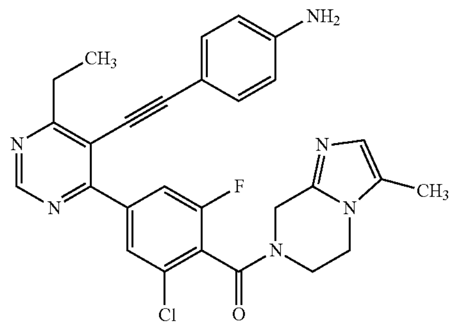 [SMILES: CCc1ncnc(-c2cc(F)c(C(=O)N3CCn4c(C)cnc4C3)c(Cl)c2)c1C#Cc1ccc(N)cc1] | A-100 | 515.98 | 516 | 1.34 |
| E-158 | 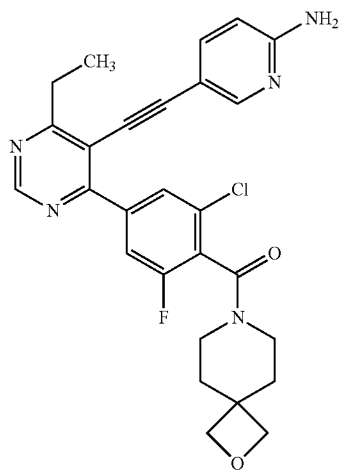 [SMILES: CCc1ncnc(-c2cc(F)c(C(=O)N3CCC4(CC3)COC4)c(Cl)c2)c1C#Cc1ccc(N)nc1] | A-100 | 505.98 | 506 | 1.37 |
| E-159 | 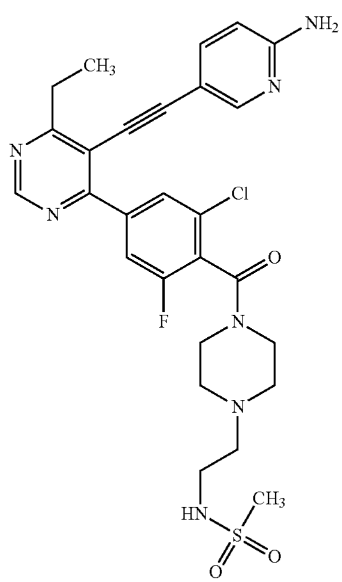 [SMILES: CCc1ncnc(-c2cc(F)c(C(=O)N3CCN(CCNS(C)(=O)=O)CC3)c(Cl)c2)c1C#Cc1ccc(N)nc1] | A-100 | 586.09 | 586 | 1.31 |

TABLE 4-continued
Examples E-1-E-349
| Nr. | Structure | Int. | MW | MW [M + H] | tR [min] |
|---|---|---|---|---|---|
| E-160 | 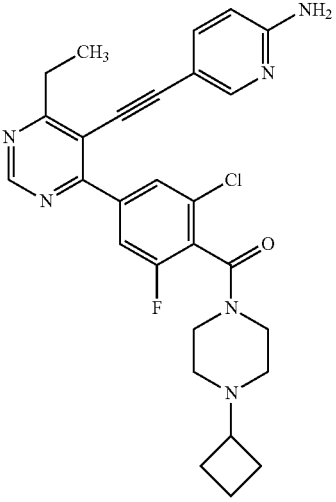 [SMILES: CCc1ncnc(-c2cc(F)c(C(=O)N3CCN(C4CCC4)CC3)c(Cl)c2)c1C#Cc1ccc(N)nc1] | A-101 | 519.02 | 519 | 1.54 |
| E-161 | 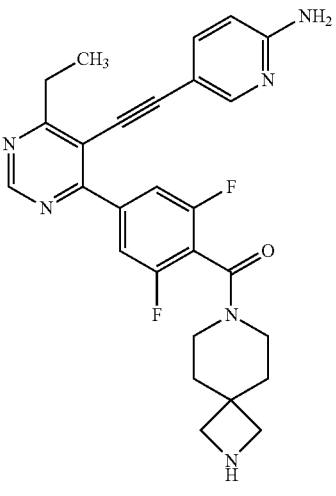 [SMILES: CCc1ncnc(-c2cc(F)c(C(=O)N3CCC4(CC3)CNC4)c(F)c2)c1C#Cc1ccc(N)nc1] | A-101 | 488.54 | 489 | 1.23 |
| E-162 | 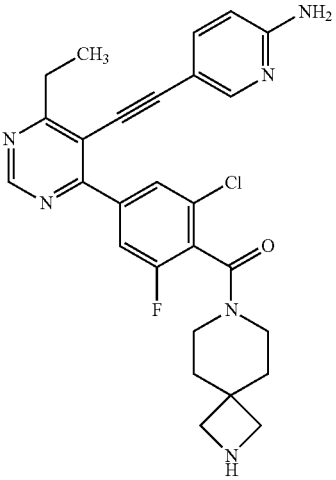 [SMILES: CCc1ncnc(-c2cc(F)c(C(=O)N3CCC4(CC3)CNC4)c(Cl)c2)c1C#Cc1ccc(N)nc1] | A-101 | 504.99 | 505/507 | 1.26 |

TABLE 4-continued

Examples E-1-E-349

| Nr. | Structure | Int. | MW | MW [M + H] | tR [min] |
|---|---|---|---|---|---|
| E-163 | 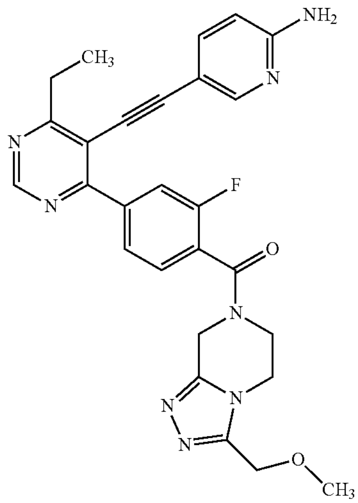 [SMILES: CCc1ncnc(-c2ccc(C(=O)N3CCn4c(COC)nnc4C3)c(F)c2)c1C#Cc1ccc(N)nc1] | A-73 | 512.55 | 513 | 1.25 |
| E-164 | 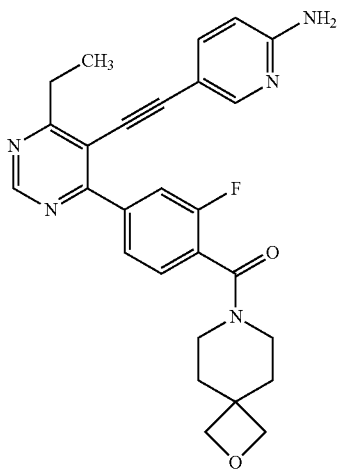 [SMILES: CCc1ncnc(-c2ccc(C(=O)N3CCC4(CC3)COC4)c(F)c2)c1C#Cc1ccc(N)nc1] | A-73 | 471.53 | 472 | 1.42 |
| E-165 | 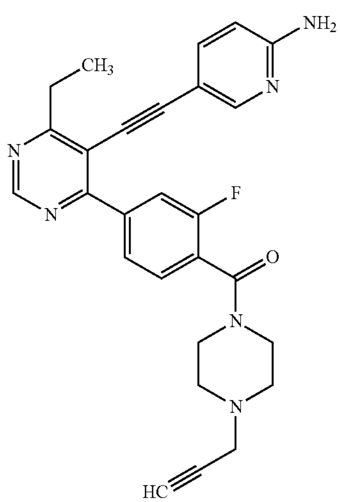 [SMILES: C#CCN1CCN(C(=O)c2ccc(-c3ncnc(CC)c3C#Cc3ccc(N)nc3)cc2F)CC1] | A-73 | 468.53 | 469 | 1.48 |

TABLE 4-continued

Examples E-1-E-349

| Nr. | Structure | Int. | MW | MW [M + H] | tR [min] |
|---|---|---|---|---|---|
| E-166 | 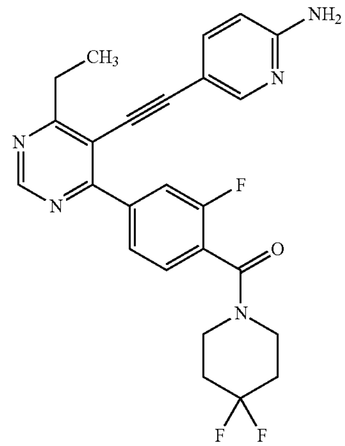 [SMILES: CCc1ncnc(-c2ccc(C(=O)N3CCC(F)(F)CC3)c(F)c2)c1C#Cc1ccc(N)nc1] | A-73 | 465.48 | 466 | 1.62 |
| E-167 | 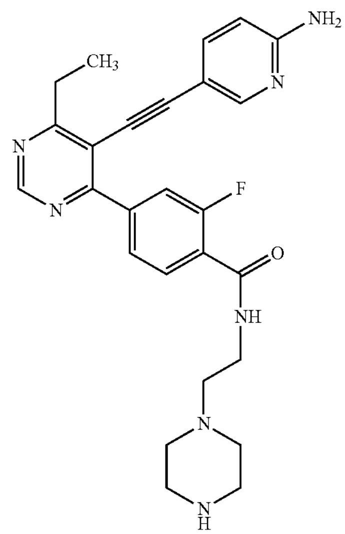 [SMILES: CCc1ncnc(-c2ccc(C(=O)NCCN3CCNCC3)c(F)c2)c1C#Cc1ccc(N)nc1] | A-73 | 473.55 | 474 | 1.49 |
| E-168 | 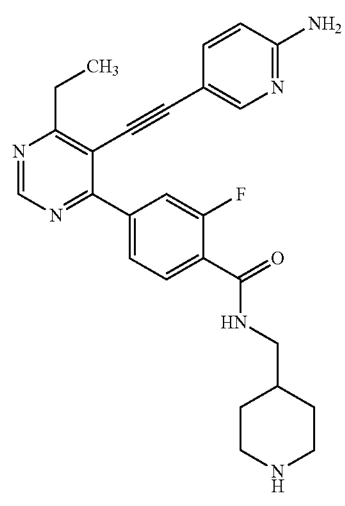 [SMILES: CCc1ncnc(-c2ccc(C(=O)NCC3CCNCC3)c(F)c2)c1C#Cc1ccc(N)nc1] | A-73 | 458.54 | 459 | 1.32 |

TABLE 4-continued
Examples E-1-E-349
| Nr. | Structure | Int. | MW | MW [M + H] | tR [min] |
|---|---|---|---|---|---|
| E-169 | 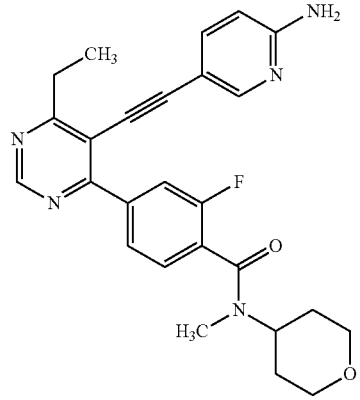 [SMILES: CCc1ncnc(-c2ccc(C(=O)N(C)C3CCOCC3)c(F)c2)c1C#Cc1ccc(N)nc1] | A-73 | 459.52 | 460 | 1.24 |
| E-170 | 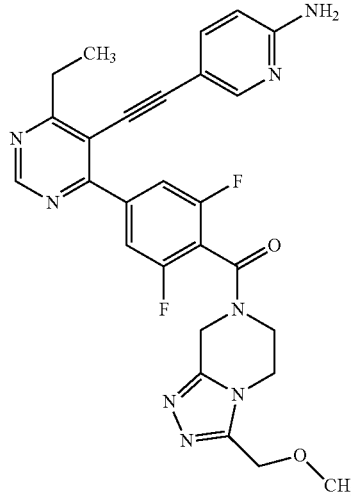 | A-100 | 530.54 | 531 | 1.16 |
| E-171 | 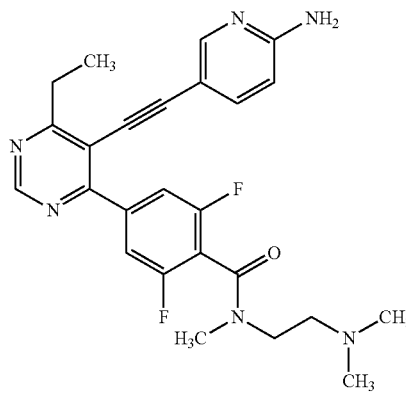 | A-100 | 464.52 | 465 | 1.28 |

TABLE 4-continued

Examples E-1-E-349

| Nr. | Structure | Int. | MW | MW [M + H] | tR [min] |
|---|---|---|---|---|---|
| E-172 | 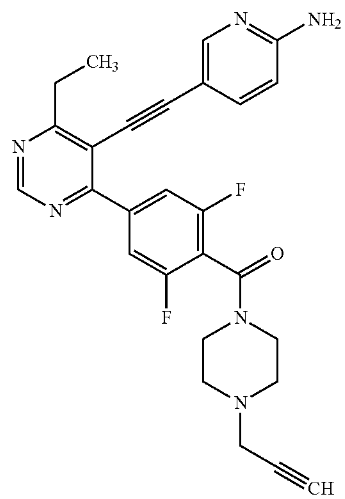 [SMILES: C#CCN1CCN(C(=O)c2c(F)cc(-c3ncnc(CC)c3C#Cc3ccc(N)nc3)cc2F)CC1] | A-100 | 486.52 | 487 | 1.31 |
| E-173 | 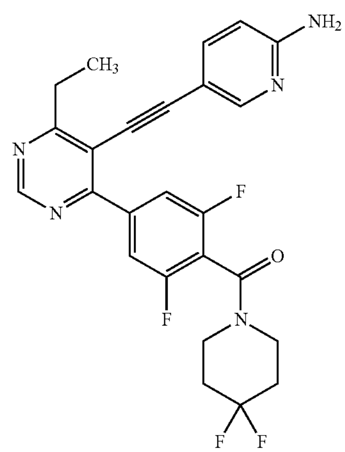 [SMILES: CCc1ncnc(-c2cc(F)c(C(=O)N3CCC(F)(F)CC3)c(F)c2)c1C#Cc1ccc(N)nc1] | A-100 | 483.47 | 484 | 1.41 |
| E-174 | 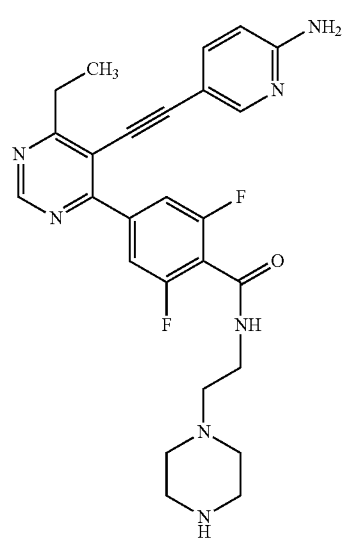 [SMILES: CCc1ncnc(-c2cc(F)c(C(=O)NCCN3CCNCC3)c(F)c2)c1C#Cc1ccc(N)nc1] | A-100 | 491.54 | 492 | 1.14 |

TABLE 4-continued
Examples E-1-E-349
| Nr. | Structure | Int. | MW | MW [M + H] | tR [min] |
|---|---|---|---|---|---|
| E-175 | 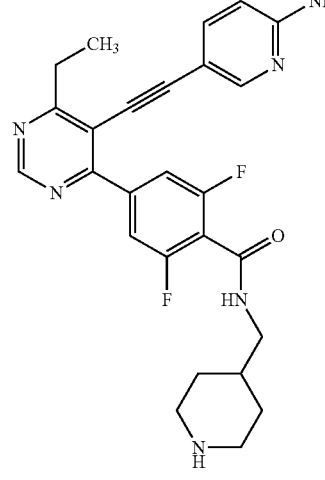 | A-100 | 476.53 | 477 | 1.3 |
| E-176 | 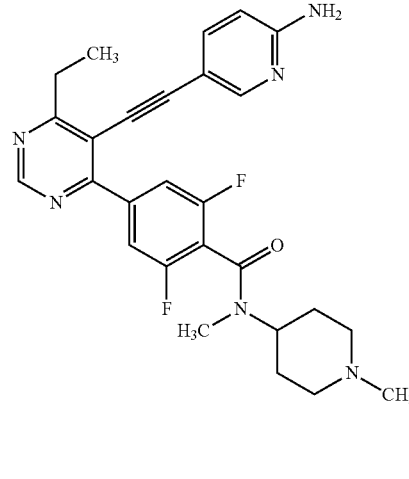 | A-100 | 490.56 | 491 | 1.28 |
| E-177 | 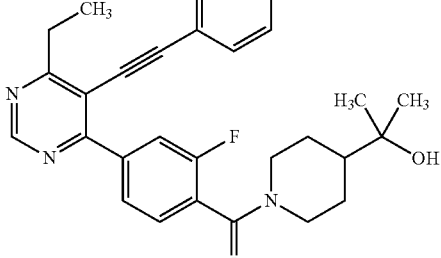 | A-103 | 501.6 | 502 | 1.75 |

TABLE 4-continued

Examples E-1-E-349

| Nr. | Structure | Int. | MW | MW [M + H] | tR [min] |
|---|---|---|---|---|---|
| E-178 | 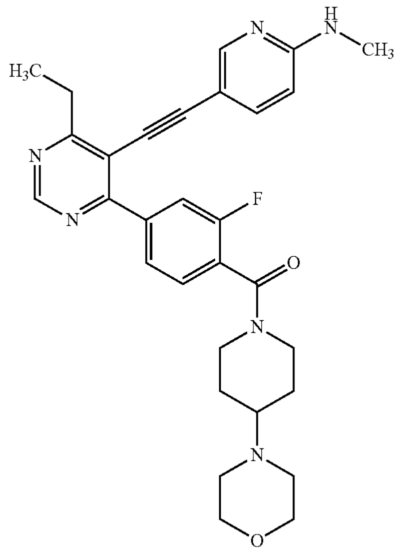 [SMILES: CCc1ncnc(-c2ccc(C(=O)N3CCC(N4CCOCC4)CC3)c(F)c2)c1C#Cc1ccc(NC)nc1] | A-103 | 528.63 | 529 | 1.69 |
| E-179 | 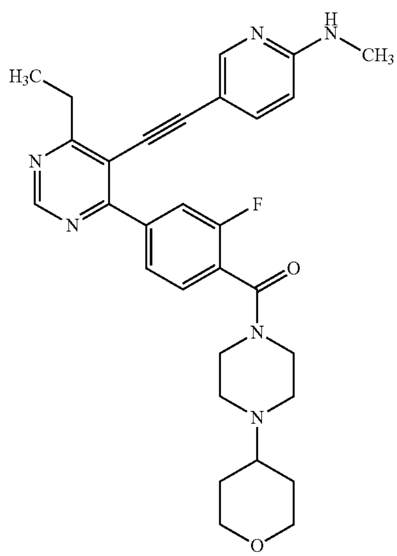 [SMILES: CCc1ncnc(-c2ccc(C(=O)N3CCN(C4CCOCC4)CC3)c(F)c2)c1C#Cc1ccc(NC)nc1] | A-103 | 528.63 | 529 | 1.71 |
| E-180 | 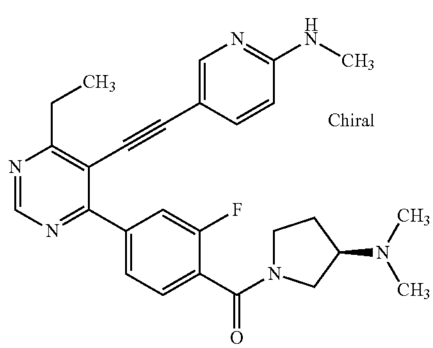 [SMILES: CCc1ncnc(-c2ccc(C(=O)N3CC[C@@H](N(C)C)C3)c(F)c2)c1C#Cc1ccc(NC)nc1] | A-103 | 472.57 | 473 | 1.68 |

TABLE 4-continued
Examples E-1-E-349
| Nr. | Structure | Int. | MW | MW [M + H] | tR [min] |
|---|---|---|---|---|---|
| E-181 | 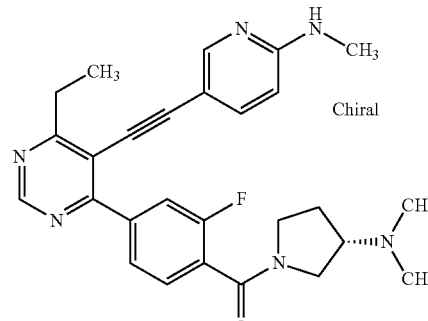 | A-103 | 472.57 | 473 | 1.68 |
| E-182 | 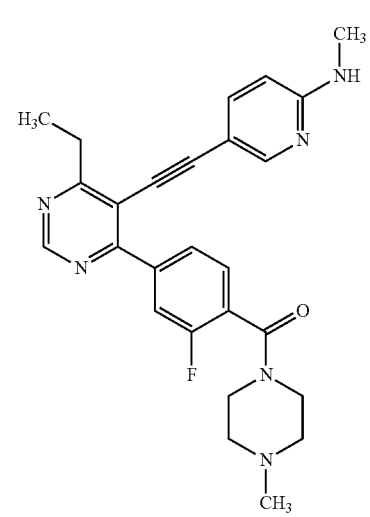 [SMILES: CCc1ncnc(-c2ccc(C(=O)N3CCN(C)CC3)c(F)c2)c1C#Cc1ccc(NC)nc1] | A-103 | 458.54 | 459 | 1.66 |
| E-183 | 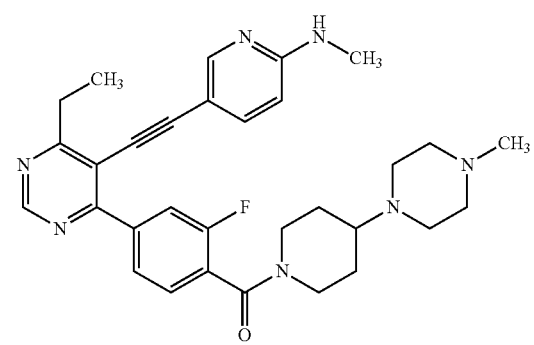 [SMILES: CCc1ncnc(-c2ccc(C(=O)N3CCC(N4CCN(C)CC4)CC3)c(F)c2)c1C#Cc1ccc(NC)nc1] | A-103 | 541.67 | 542 | 1.65 |
| E-184 | 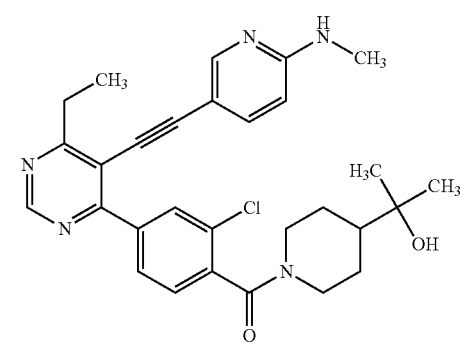 [SMILES: CCc1ncnc(-c2ccc(C(=O)N3CCC(C(C)(C)O)CC3)c(Cl)c2)c1C#Cc1ccc(NC)nc1] | A-105 | 518.06 | 518 | 1.80 |

TABLE 4-continued

Examples E-1-E-349

| Nr. | Structure | Int. | MW | MW [M + H] | tR [min] |
|---|---|---|---|---|---|
| E-185 | 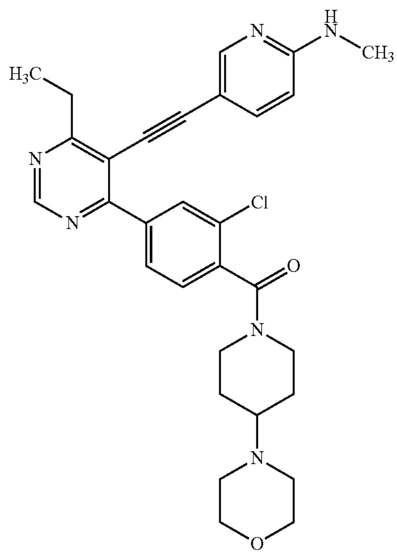 [SMILES: CCc1ncnc(-c2ccc(C(=O)N3CCC(N4CCOCC4)CC3)c(Cl)c2)c1C#Cc1ccc(NC)nc1] | A-105 | 545.08 | 545 | 1.73 |
| E-186 | 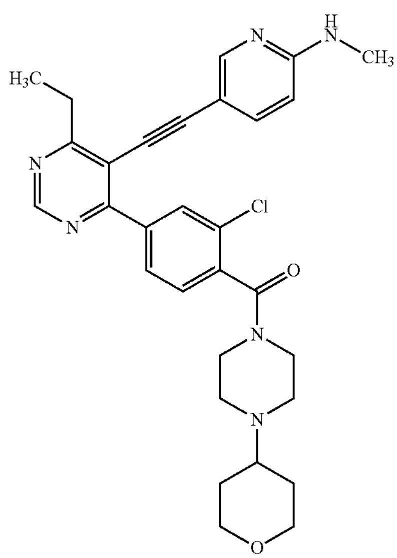 [SMILES: CCc1ncnc(-c2ccc(C(=O)N3CCN(C4CCOCC4)CC3)c(Cl)c2)c1C#Cc1ccc(NC)nc1] | A-105 | 545.08 | 545 | 1.75 |
| E-187 | 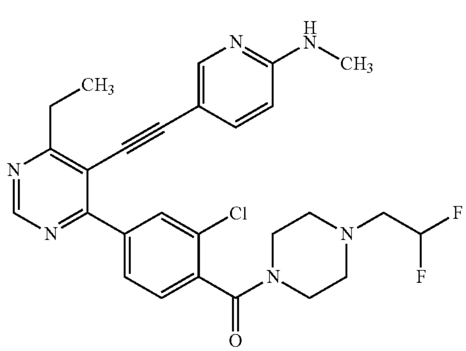 [SMILES: CCc1ncnc(-c2ccc(C(=O)N3CCN(CC(F)F)CC3)c(Cl)c2)c1C#Cc1ccc(NC)nc1] | A-105 | 525 | 525 | 1.88 |

TABLE 4-continued

Examples E-1-E-349

| Nr. | Structure | Int. | MW | MW [M + H] | tR [min] |
|---|---|---|---|---|---|
| E-188 | 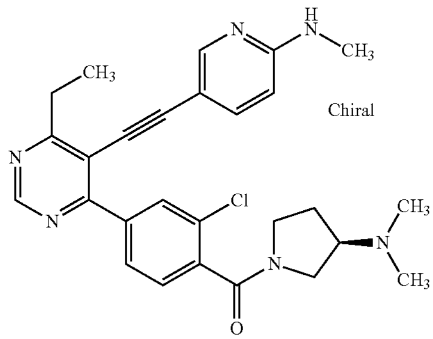 [SMILES: CCc1ncnc(-c2ccc(C(=O)N3CC[C@@H](N(C)C)C3)c(Cl)c2)c1C#Cc1ccc(NC)nc1] | A-105 | 489.02 | 489 | 1.73 |
| E-189 | 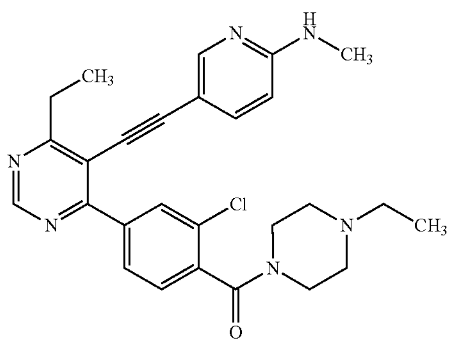 [SMILES: CCc1ncnc(-c2ccc(C(=O)N3CCN(CC)CC3)c(Cl)c2)c1C#Cc1ccc(NC)nc1] | A-105 | 489.02 | 489 | 1.80 |
| E-190 | 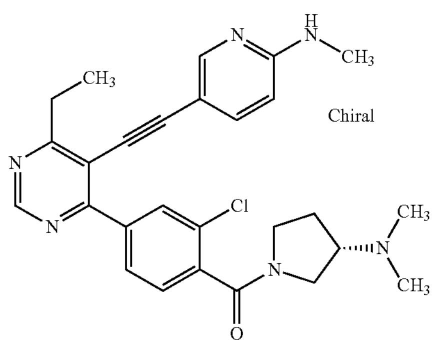 [SMILES: CCc1ncnc(-c2ccc(C(=O)N3CC[C@H](N(C)C)C3)c(Cl)c2)c1C#Cc1ccc(NC)nc1] | A-105 | 489.02 | 489 | 1.73 |
| E-191 | 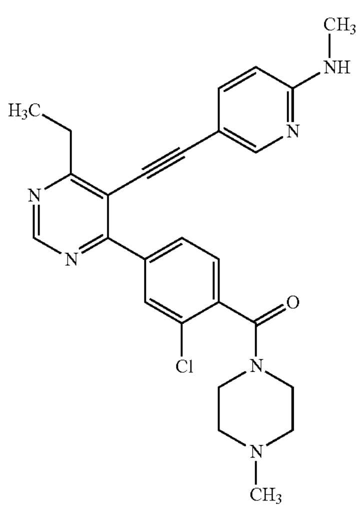 | A-105 | 474.99 | 475 | 1.70 |

TABLE 4-continued

Examples E-1-E-349

| Nr. | Structure | Int. | MW | MW [M + H] | tR [min] |
|---|---|---|---|---|---|
| E-192 | 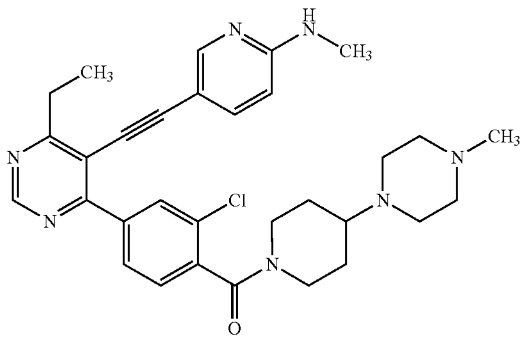 [SMILES: CCc1ncnc(-c2ccc(C(=O)N3CCC(N4CCN(C)CC4)CC3)c(Cl)c2)c1C#Cc1ccc(NC)nc1] | A-105 | 558.13 | 558 | 1.69 |
| E-194 | 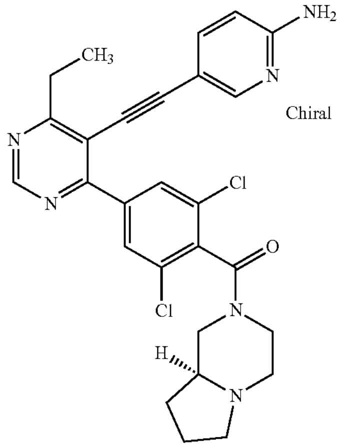 [SMILES: CCc1ncnc(-c2cc(Cl)c(C(=O)N3CCN4CCC[C@H]4C3)c(Cl)c2)c1C#Cc1ccc(N)nc1] | A-102 | 521.45 | 521/525/525 | 1.82 |
| E-195 | 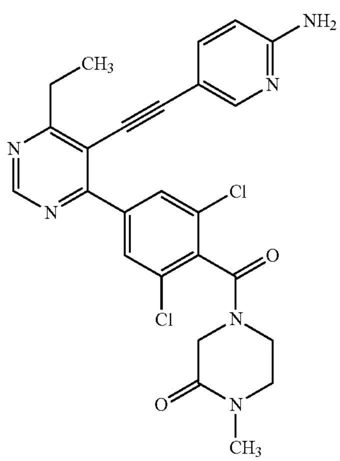 [SMILES: CCc1ncnc(-c2cc(Cl)c(C(=O)N3CCN(C)C(=O)C3)c(Cl)c2)c1C#Cc1ccc(N)nc1] | A-102 | 509.39 | 509 | 1.58 |

TABLE 4-continued

Examples E-1-E-349

| Nr. | Structure | Int. | MW | MW [M + H] | tR [min] |
|---|---|---|---|---|---|
| E-196 | 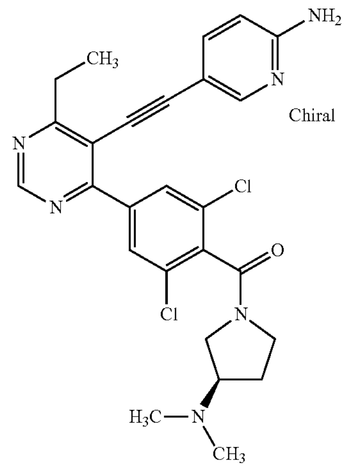 [SMILES: CCc1ncnc(-c2cc(Cl)c(C(=O)N3CC[C@@H](N(C)C)C3)c(Cl)c2)c1C#Cc1ccc(N)nc1] | A-102 | 509.44 | 509/511/513 | 1.73 |
| E-197 | 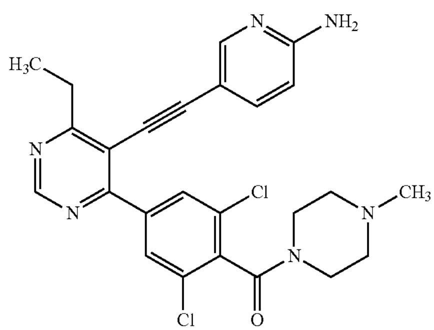 [SMILES: CCc1ncnc(-c2cc(Cl)c(C(=O)N3CCN(C)CC3)c(Cl)c2)c1C#Cc1ccc(N)nc1] | A-102 | 495.41 | 495 | 1.69 |
| E-198 | 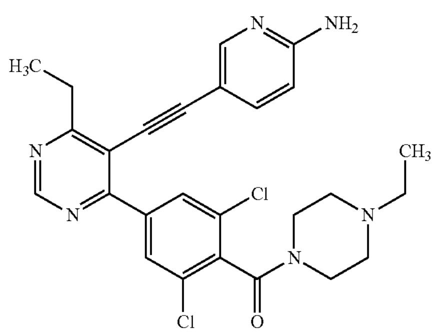 [SMILES: CCc1ncnc(-c2cc(Cl)c(C(=O)N3CCN(CC)CC3)c(Cl)c2)c1C#Cc1ccc(N)nc1] | A-102 | 509.44 | 509/511/513 | 1.61 |
| E-199 | 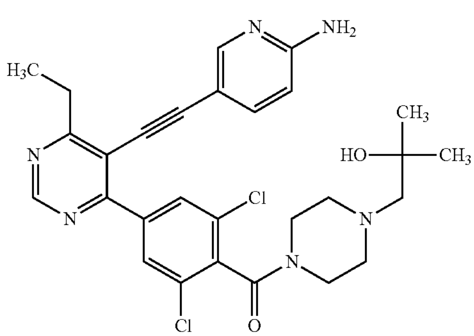 [SMILES: CCc1ncnc(-c2cc(Cl)c(C(=O)N3CCN(CC(C)(C)O)CC3)c(Cl)c2)c1C#Cc1ccc(N)nc1] | A-102 | 553.49 | 553/55/557 | 1.64 |

TABLE 4-continued

Examples E-1-E-349

| Nr. | Structure | Int. | MW | MW [M + H] | tR [min] |
|---|---|---|---|---|---|
| E-200 | 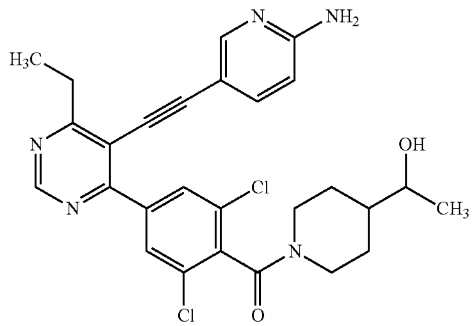 [SMILES: CCc1ncnc(-c2cc(Cl)c(C(=O)N3CCC(C(C)O)CC3)c(Cl)c2)c1C#Cc1ccc(N)nc1] | A-102 | 524.45 | 524 | 1.55 |
| E-201 | 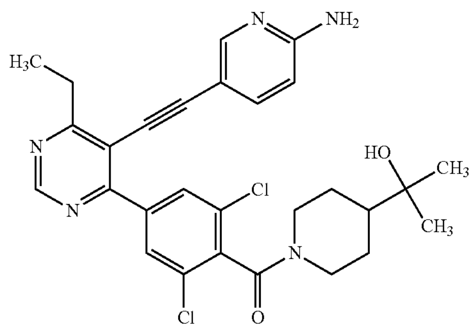 [SMILES: CCc1ncnc(-c2cc(Cl)c(C(=O)N3CCC(C(C)(C)O)CC3)c(Cl)c2)c1C#Cc1ccc(N)nc1] | A-102 | 538.48 | 538 | 1.60 |
| E-202 | 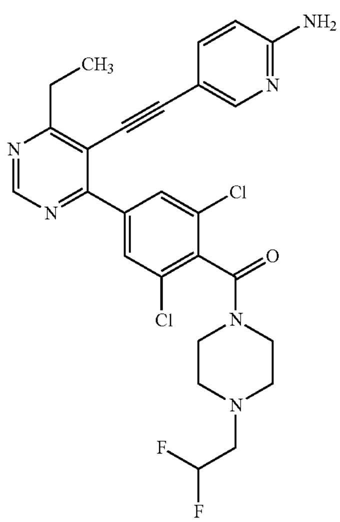 [SMILES: CCc1ncnc(-c2cc(Cl)c(C(=O)N3CCN(CC(F)F)CC3)c(Cl)c2)c1C#Cc1ccc(N)nc1] | A-102 | 545.42 | 545/547/549 | 1.69 |
| E-203 | 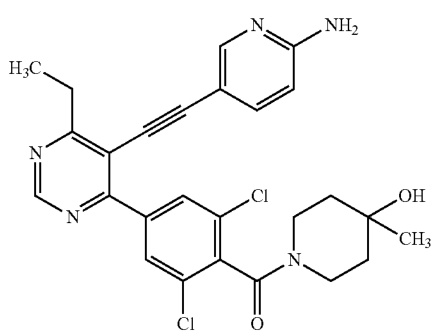 [SMILES: CCc1ncnc(-c2cc(Cl)c(C(=O)N3CCC(C)(O)CC3)c(Cl)c2)c1C#Cc1ccc(N)nc1] | A-102 | 510.42 | 510 | 1.50 |

TABLE 4-continued

Examples E-1-E-349

| Nr. | Structure | Int. | MW | MW [M + H] | tR [min] |
|---|---|---|---|---|---|
| E-204 | 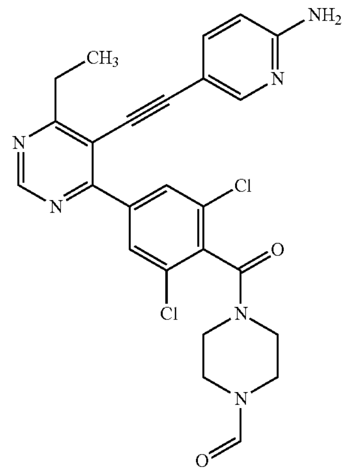 [SMILES: CCc1ncnc(-c2cc(Cl)c(C(=O)N3CCN(C=O)CC3)c(Cl)c2)c1C#Cc1ccc(N)nc1] | A-102 | 509.39 | 509 | 1.45 |
| E-205 | 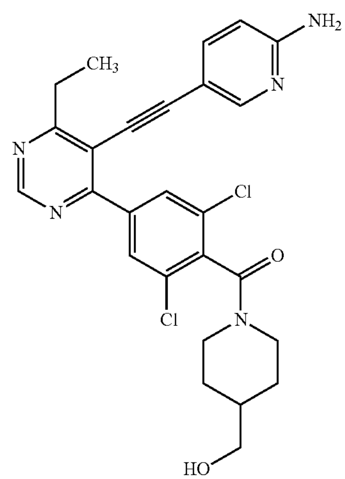 [SMILES: CCc1ncnc(-c2cc(Cl)c(C(=O)N3CCC(CO)CC3)c(Cl)c2)c1C#Cc1ccc(N)nc1] | A-102 | 510.42 | 510/512/514 | 1.47 |
| E-206 | 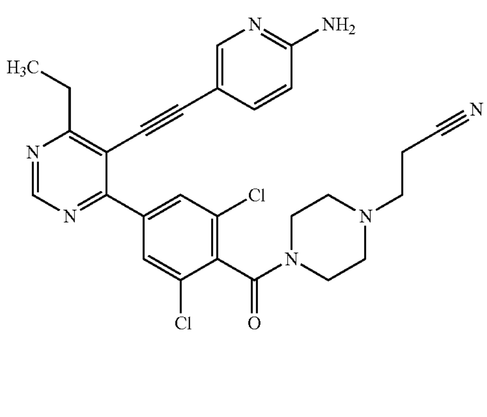 [SMILES: CCc1ncnc(-c2cc(Cl)c(C(=O)N3CCN(CCC#N)CC3)c(Cl)c2)c1C#Cc1ccc(N)nc1] | A-102 | 534.45 | 534 | 1.54 |

TABLE 4-continued
Examples E-1-E-349
| Nr. | Structure | Int. | MW | MW [M + H] | tR [min] |
|---|---|---|---|---|---|
| E-207 | 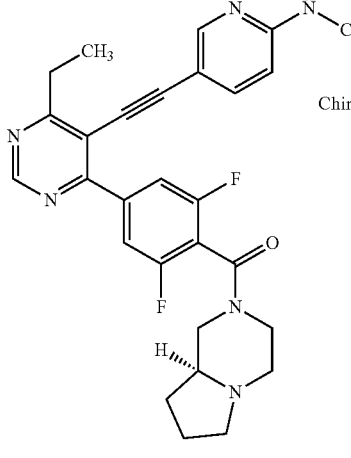 | A-104 | 502.57 | 503 | 1.69 |
| E-208 | 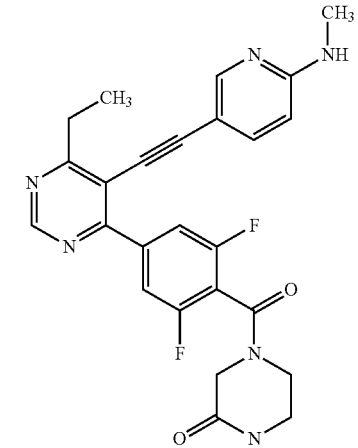 | A-104 | 490.51 | 491 | 1.45 |
| E-209 | 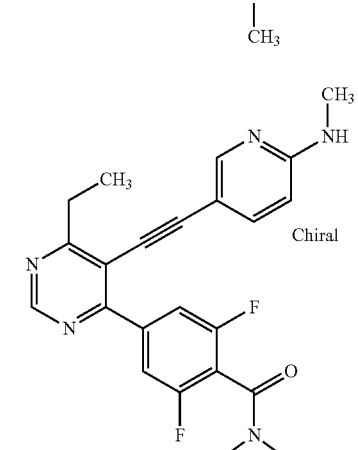 | A-104 | 490.56 | 491 | 1.58 |

TABLE 4-continued

Examples E-1-E-349

| Nr. | Structure | Int. | MW | MW [M + H] | tR [min] |
|---|---|---|---|---|---|
| E-210 | 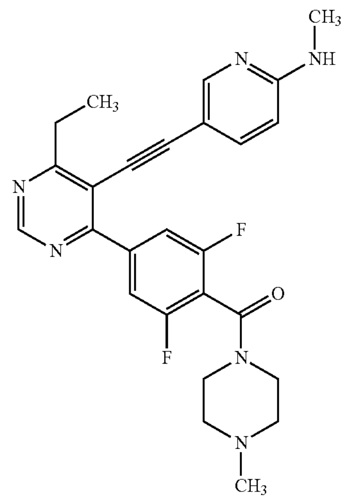 [SMILES: CCc1ncnc(-c2cc(F)c(C(=O)N3CCN(C)CC3)c(F)c2)c1C#Cc1ccc(NC)nc1] | A-104 | 476.53 | 477 | 1.56 |
| E-211 | 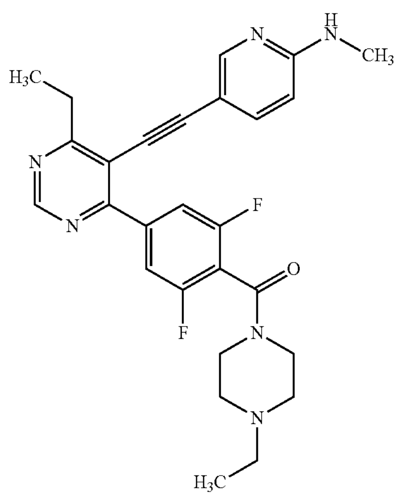 [SMILES: CCc1ncnc(-c2cc(F)c(C(=O)N3CCN(CC)CC3)c(F)c2)c1C#Cc1ccc(NC)nc1] | A-104 | 490.56 | 491 | 1.65 |
| E-212 | 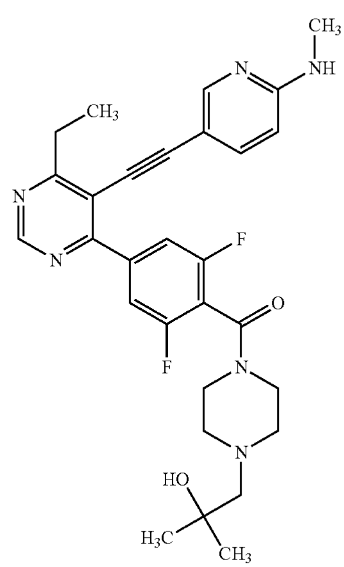 [SMILES: CCc1ncnc(-c2cc(F)c(C(=O)N3CCN(CC(C)(C)O)CC3)c(F)c2)c1C#Cc1ccc(NC)nc1] | A-104 | 534.61 | 535 | 1.86 |

TABLE 4-continued

Examples E-1-E-349

| Nr. | Structure | Int. | MW | MW [M + H] | tR [min] |
|---|---|---|---|---|---|
| E-213 | 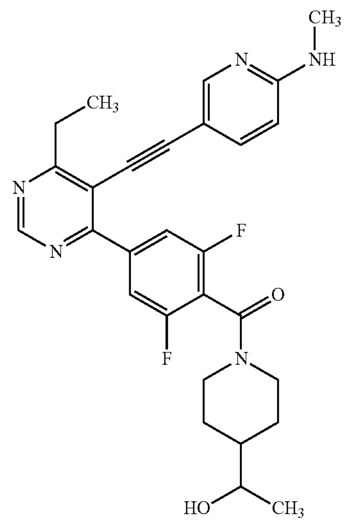 [SMILES: CCc1ncnc(-c2cc(F)c(C(=O)N3CCC(C(C)O)CC3)c(F)c2)c1C#Cc1ccc(NC)nc1] | A-104 | 505.57 | 506 | 1.76 |
| E-214 | 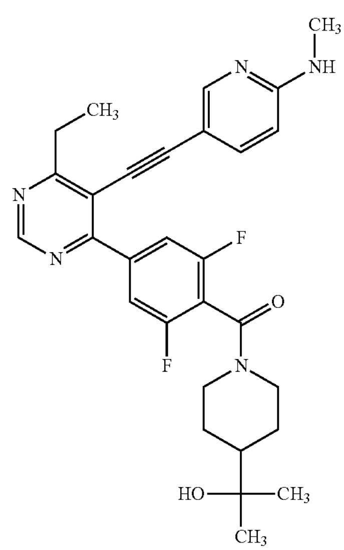 [SMILES: CCc1ncnc(-c2cc(F)c(C(=O)N3CCC(C(C)(C)O)CC3)c(F)c2)c1C#Cc1ccc(NC)nc1] | A-104 | 519.59 | 520 | 1.82 |

TABLE 4-continued

Examples E-1-E-349

| Nr. | Structure | Int. | MW | MW [M + H] | tR [min] |
|---|---|---|---|---|---|
| E-215 | 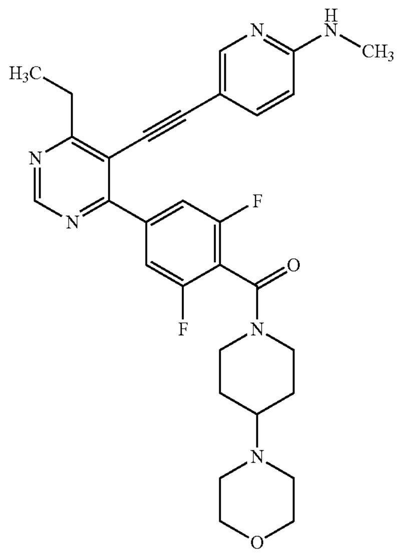 [SMILES: CCc1ncnc(-c2cc(F)c(C(=O)N3CCC(N4CCOCC4)CC3)c(F)c2)c1C#Cc1ccc(NC)nc1] | A-104 | 546.62 | 547 | 1.58 |
| E-216 | 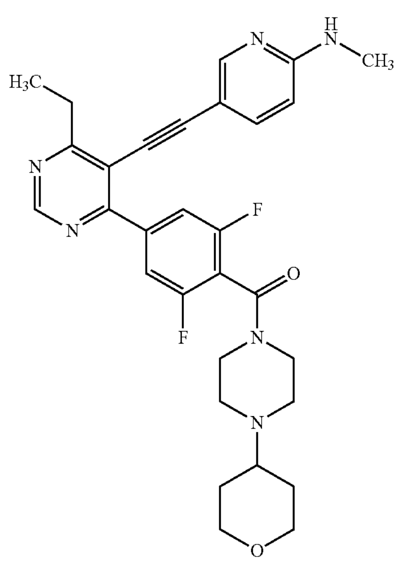 [SMILES: CCc1ncnc(-c2cc(F)c(C(=O)N3CCN(C4CCOCC4)CC3)c(F)c2)c1C#Cc1ccc(NC)nc1] | A-104 | 546.62 | 547 | 1.60 |

TABLE 4-continued

Examples E-1-E-349

| Nr. | Structure | Int. | MW | MW [M + H] | tR [min] |
|---|---|---|---|---|---|
| E-217 | 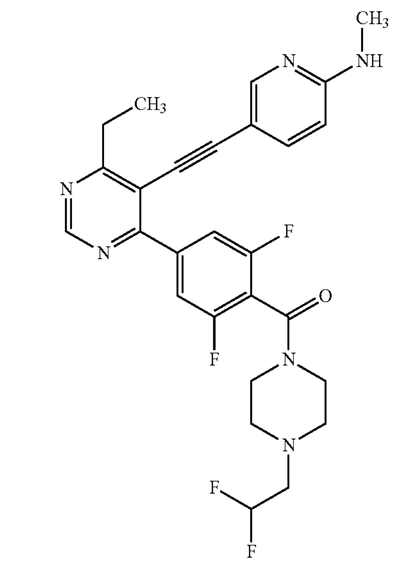 [SMILES: CCc1ncnc(-c2cc(F)c(C(=O)N3CCN(CC(F)F)CC3)c(F)c2)c1C#Cc1ccc(NC)nc1] | A-104 | 526.54 | 527 | 1.74 |
| E-218 | 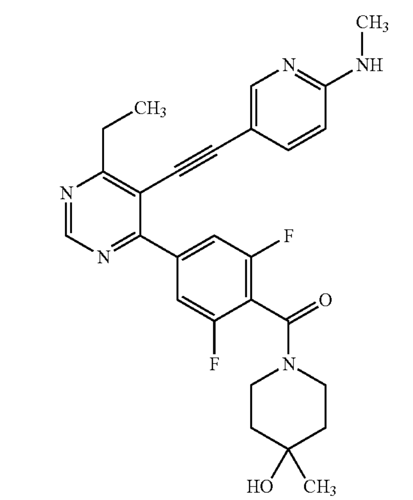 [SMILES: CCc1ncnc(-c2cc(F)c(C(=O)N3CCC(C)(O)CC3)c(F)c2)c1C#Cc1ccc(NC)nc1] | A-104 | 491.54 | 492 | 1.55 |
| E-219 | 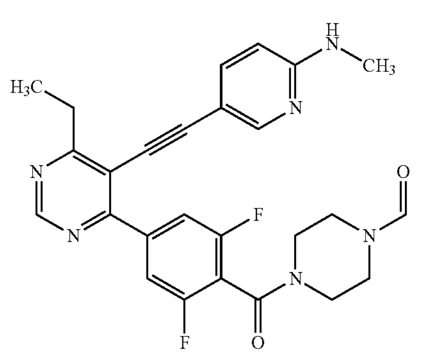 [SMILES: CCc1ncnc(-c2cc(F)c(C(=O)N3CCN(C=O)CC3)c(F)c2)c1C#Cc1ccc(NC)nc1] | A-104 | 490.51 | 491 | 1.45 |

TABLE 4-continued

Examples E-1-E-349

| Nr. | Structure | Int. | MW | MW [M + H] | tR [min] |
|---|---|---|---|---|---|
| E-220 | 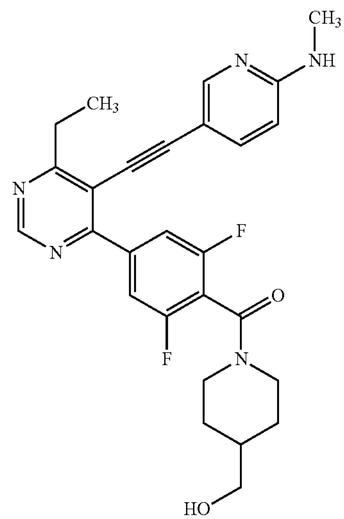 [SMILES: CCc1ncnc(-c2cc(F)c(C(=O)N3CCC(CO)CC3)c(F)c2)c1C#Cc1ccc(NC)nc1] | A-104 | 491.54 | 492 | 1.69 |
| E-221 | 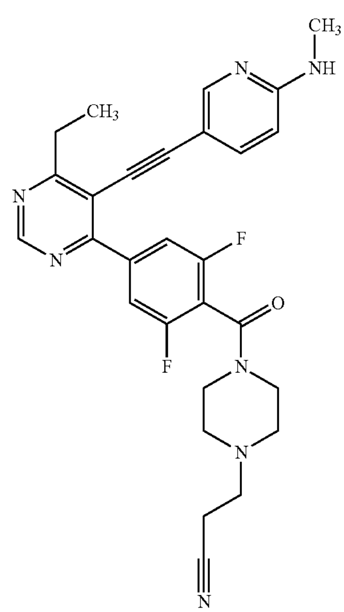 [SMILES: CCc1ncnc(-c2cc(F)c(C(=O)N3CCN(CCC#N)CC3)c(F)c2)c1C#Cc1ccc(NC)nc1] | A-104 | 515.57 | 516 | 1.76 |

TABLE 4-continued

Examples E-1-E-349

| Nr. | Structure | Int. | MW | MW [M + H] | tR [min] |
|---|---|---|---|---|---|
| E-222 | 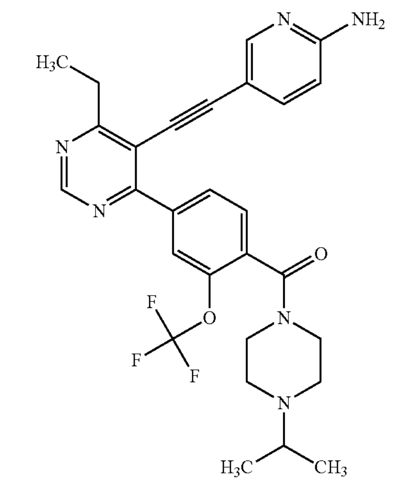 [SMILES: CCc1ncnc(-c2ccc(C(=O)N3CCN(C(C)C)CC3)c(OC(F)(F)F)c2)c1C#Cc1ccc(N)nc1] | A-108 | 538.57 | 539 | 1.86 |
| E-223 | 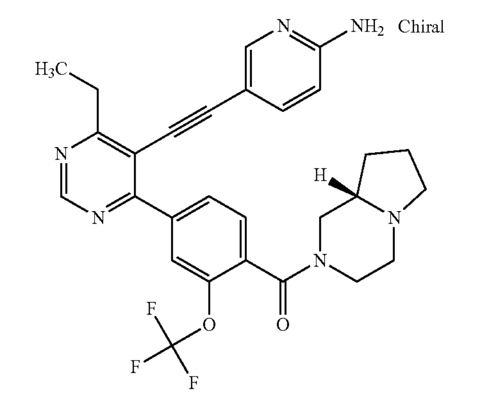 [SMILES: CCc1ncnc(-c2ccc(C(=O)N3CCN4CCC[C@H]4C3)c(OC(F)(F)F)c2)c1C#Cc1ccc(N)nc1] | A-108 | 536.56 | 537 | 1.86 |
| E-224 | 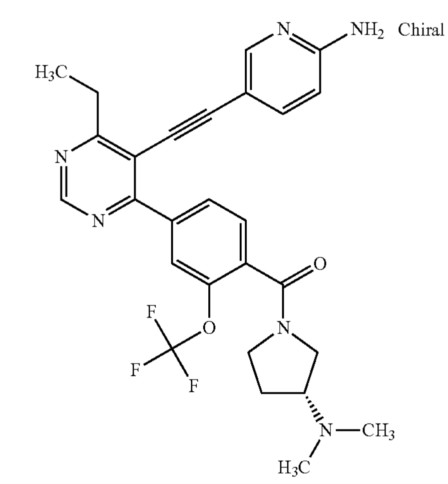 [SMILES: CCc1ncnc(-c2ccc(C(=O)N3CC[C@@H](N(C)C)C3)c(OC(F)(F)F)c2)c1C#Cc1ccc(N)nc1] | A-108 | 524.54 | 525 | 1.69 |

TABLE 4-continued

Examples E-1-E-349

| Nr. | Structure | Int. | MW | MW [M + H] | tR [min] |
|---|---|---|---|---|---|
| E-225 | 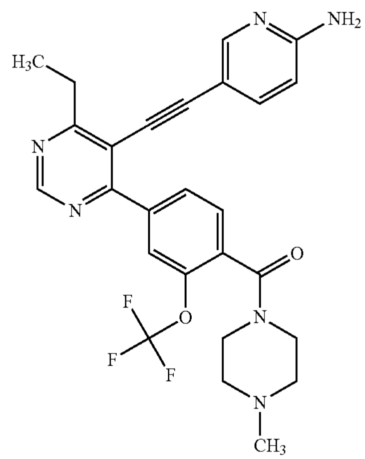 [SMILES: CCc1ncnc(-c2ccc(C(=O)N3CCN(C)CC3)c(OC(F)(F)F)c2)c1C#Cc1ccc(N)nc1] | A-108 | 510.52 | 511 | 1.67 |
| E-226 | 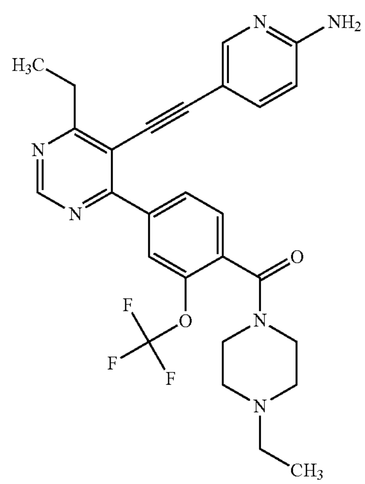 [SMILES: CCc1ncnc(-c2ccc(C(=O)N3CCN(CC)CC3)c(OC(F)(F)F)c2)c1C#Cc1ccc(N)nc1] | A-108 | 524.54 | 525 | 1.76 |
| E-227 | 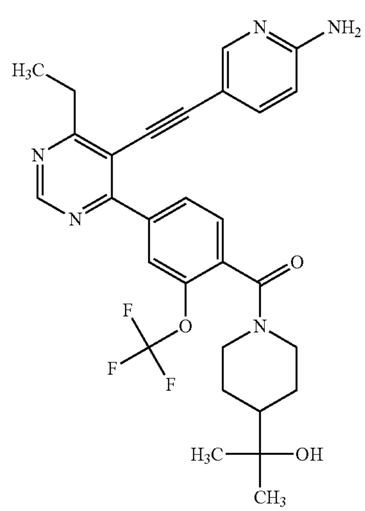 [SMILES: CCc1ncnc(-c2ccc(C(=O)N3CCC(C(C)(C)O)CC3)c(OC(F)(F)F)c2)c1C#Cc1ccc(N)nc1] | A-108 | 553.58 | 554 | 1.76 |

TABLE 4-continued

Examples E-1-E-349

| Nr. | Structure | Int. | MW | MW [M + H] | tR [min] |
|---|---|---|---|---|---|
| E-228 | 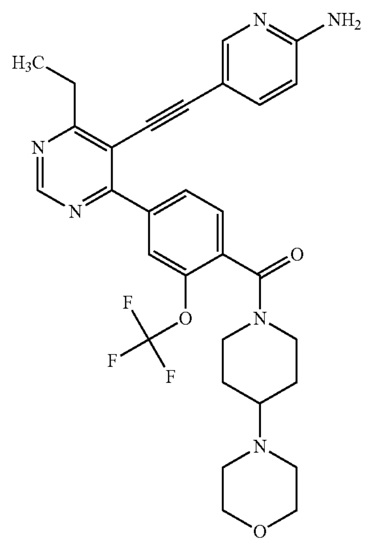 [SMILES: CCc1ncnc(-c2ccc(C(=O)N3CCC(N4CCOCC4)CC3)c(OC(F)(F)F)c2)c1C#Cc1ccc(N)nc1] | A-108 | 580.61 | 581 | 1.70 |
| E-229 | 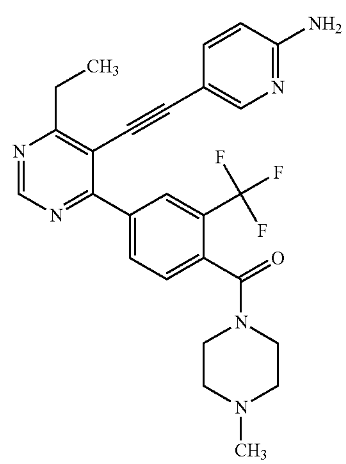 [SMILES: CCc1ncnc(-c2ccc(C(=O)N3CCN(C)CC3)c(C(F)(F)F)c2)c1C#Cc1ccc(N)nc1] | A-107 | 494.52 | 495 | 1.47 |
| E-230 | 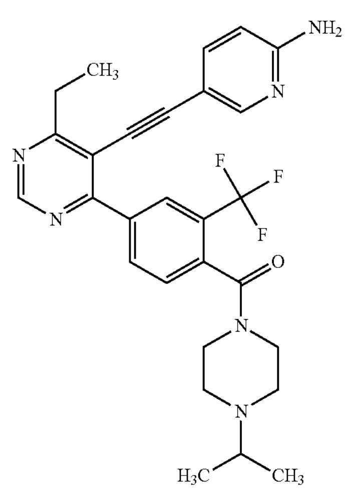 [SMILES: CCc1ncnc(-c2ccc(C(=O)N3CCN(C(C)C)CC3)c(C(F)(F)F)c2)c1C#Cc1ccc(N)nc1] | A-107 | 522.57 | 523 | 1.66 |

TABLE 4-continued

Examples E-1-E-349

| Nr. | Structure | Int. | MW | MW [M + H] | tR [min] |
|---|---|---|---|---|---|
| E-231 | 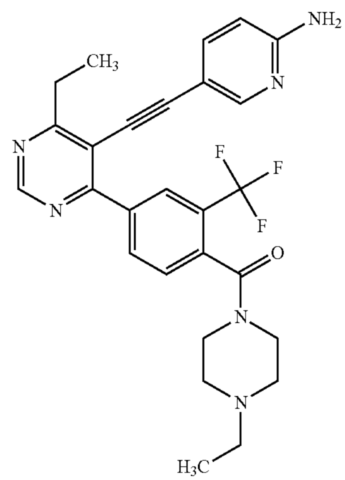 [SMILES: CCc1ncnc(-c2ccc(C(=O)N3CCN(CC)CC3)c(C(F)(F)F)c2)c1C#Cc1ccc(N)nc1] | A-107 | 508.55 | 509 | 1.74 |
| E-232 | 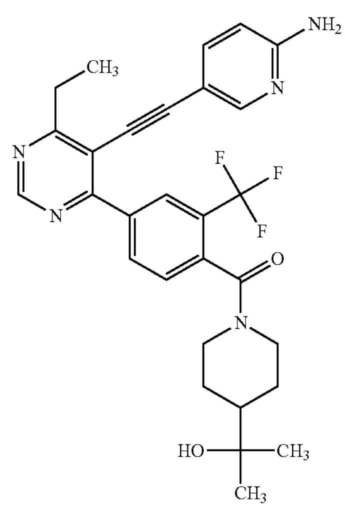 [SMILES: CCc1ncnc(-c2ccc(C(=O)N3CCC(C(C)(C)O)CC3)c(C(F)(F)F)c2)c1C#Cc1ccc(N)nc1] | A-107 | 537.58 | 538 | 1.73 |
| E-233 | 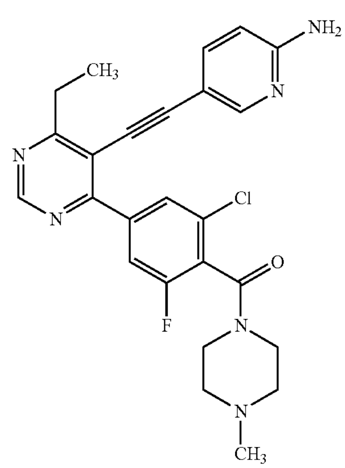 [SMILES: CCc1ncnc(-c2cc(F)c(C(=O)N3CCN(C)CC3)c(Cl)c2)c1C#Cc1ccc(N)nc1] | A-101 | 478.96 | 479 | 1.47 |

TABLE 4-continued

Examples E-1-E-349

| Nr. | Structure | Int. | MW | MW [M + H] | tR [min] |
|---|---|---|---|---|---|
| E-234 | 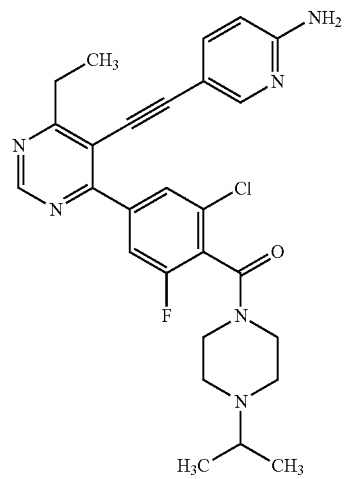 [SMILES: CCc1ncnc(-c2cc(F)c(C(=O)N3CCN(C(C)C)CC3)c(Cl)c2)c1C#Cc1ccc(N)nc1] | A-101 | 507.01 | 507 | 1.67 |
| E-235 | 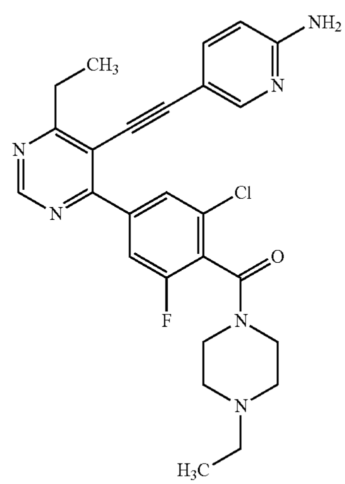 [SMILES: CCc1ncnc(-c2cc(F)c(C(=O)N3CCN(CC)CC3)c(Cl)c2)c1C#Cc1ccc(N)nc1] | A-101 | 492.98 | 493 | 1.56 |
| E-236 | 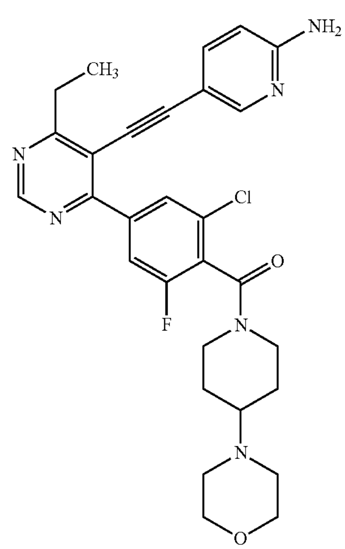 [SMILES: CCc1ncnc(-c2cc(F)c(C(=O)N3CCC(N4CCOCC4)CC3)c(Cl)c2)c1C#Cc1ccc(N)nc1] | A-101 | 549.05 | 549 | 1.49 |

TABLE 4-continued

Examples E-1-E-349

| Nr. | Structure | Int. | MW | MW [M + H] | tR [min] |
|---|---|---|---|---|---|
| E-237 | 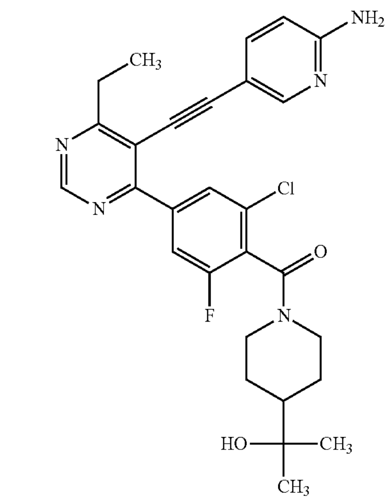 [SMILES: CCc1ncnc(-c2cc(F)c(C(=O)N3CCC(C(C)(C)O)CC3)c(Cl)c2)c1C#Cc1ccc(N)nc1] | A-101 | 522.02 | 522 | 1.55 |
| E-238 | 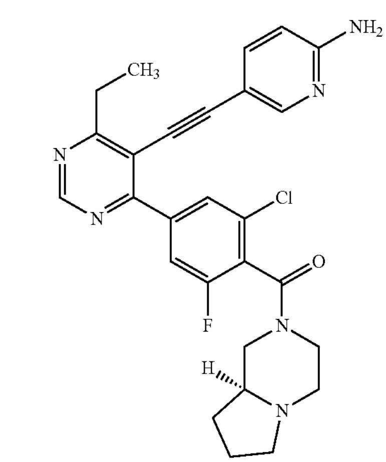 | A-101 | 504.99 | 505/507 | 1.59 |
| E-239 | 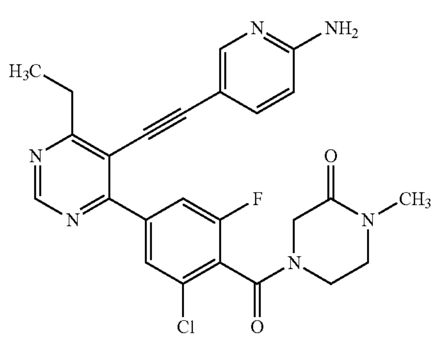 [SMILES: CCc1ncnc(-c2cc(F)c(C(=O)N3CCN(C)C(=O)C3)c(Cl)c2)c1C#Cc1ccc(N)nc1] | A-101 | 492.94 | 493 | 1.37 |

E-238: Chiral

TABLE 4-continued

Examples E-1-E-349

| Nr. | Structure | Int. | MW | MW [M + H] | tR [min] |
|---|---|---|---|---|---|
| E-240 | 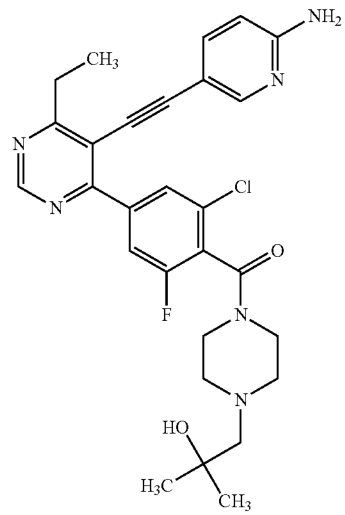 [SMILES: CCc1ncnc(-c2cc(F)c(C(=O)N3CCN(CC(C)(C)O)CC3)c(Cl)c2)c1C#Cc1ccc(N)nc1] | A-101 | 537.04 | 537/539 | 1.59 |
| E-241 | 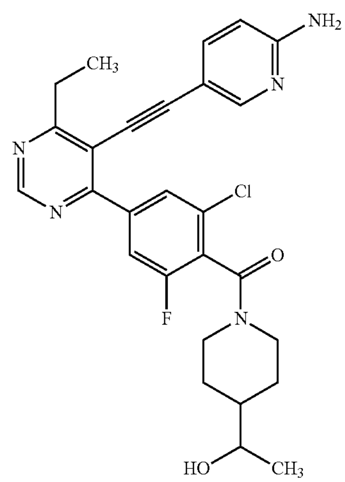 [SMILES: CCc1ncnc(-c2cc(F)c(C(=O)N3CCC(C(C)O)CC3)c(Cl)c2)c1C#Cc1ccc(N)nc1] | A-101 | 507.99 | 508/510 | 1.5 |
| E-242 | 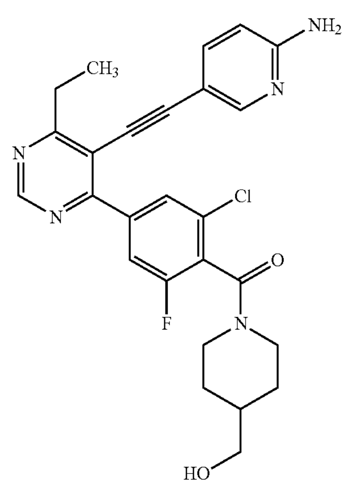 [SMILES: CCc1ncnc(-c2cc(F)c(C(=O)N3CCC(CO)CC3)c(Cl)c2)c1C#Cc1ccc(N)nc1] | A-101 | 493.97 | 494 | 1.43 |

TABLE 4-continued

Examples E-1-E-349

| Nr. | Structure | Int. | MW | MW [M + H] | tR [min] |
|---|---|---|---|---|---|
| E-243 | 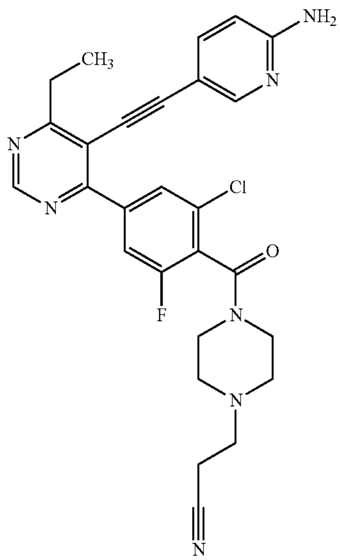 [SMILES: CCc1ncnc(-c2cc(F)c(C(=O)N3CCN(CCC#N)CC3)c(Cl)c2)c1C#Cc1ccc(N)nc1] | A-101 | 517.99 | 518 | 1.49 |
| E-245 | 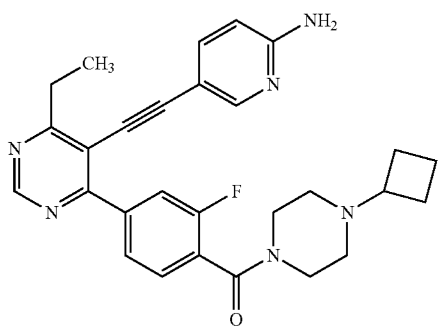 [SMILES: CCc1ncnc(-c2ccc(C(=O)N3CCN(C4CCC4)CC3)c(F)c2)c1C#Cc1ccc(N)nc1] | A-73 | 484.58 | 485 | 1.83 |
| E-246 | 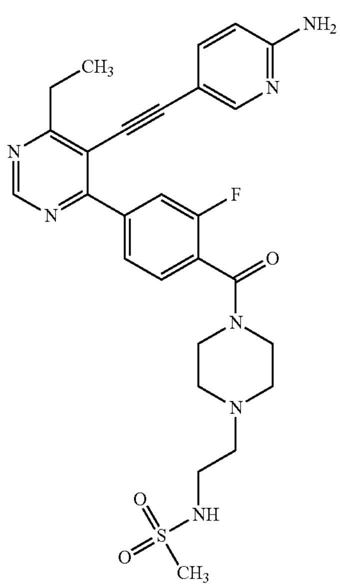 [SMILES: CCc1ncnc(-c2ccc(C(=O)N3CCN(CCNS(C)(=O)=O)CC3)c(F)c2)c1C#Cc1ccc(N)nc1] | A-73 | 551.64 | 552 | 1.55 |

TABLE 4-continued

Examples E-1-E-349

| Nr. | Structure | Int. | MW | MW [M + H] | tR [min] |
|---|---|---|---|---|---|
| E-247 | 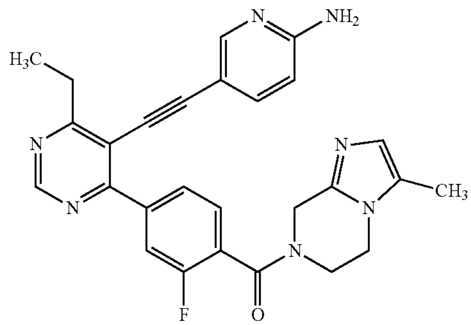 [SMILES: CCc1ncnc(-c2ccc(C(=O)N3CCn4c(C)cnc4C3)c(F)c2)c1C#Cc1ccc(N)nc1] | A-73 | 481.53 | 482 | 1.61 |
| E-248 | 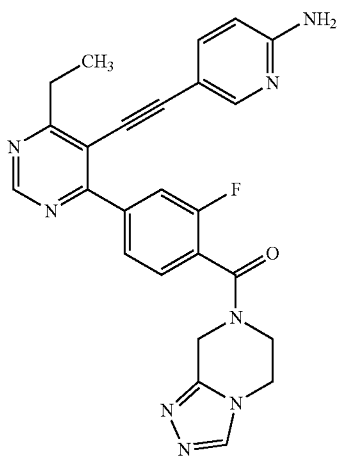 [SMILES: CCc1ncnc(-c2ccc(C(=O)N3CCn4cnnc4C3)c(F)c2)c1C#Cc1ccc(N)nc1] | A-73 | 468.49 | 469 | 1.42 |
| E-249 | 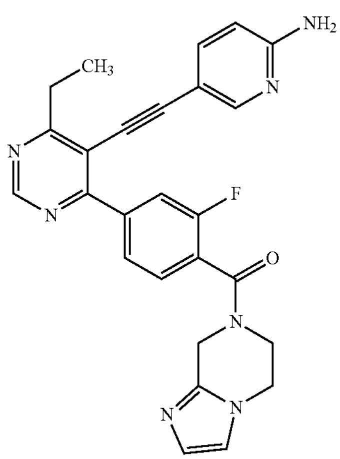 [SMILES: CCc1ncnc(-c2ccc(C(=O)N3CCn4ccnc4C3)c(F)c2)c1C#Cc1ccc(N)nc1] | A-73 | 467.51 | 468 | 1.53 |
| E-250 | 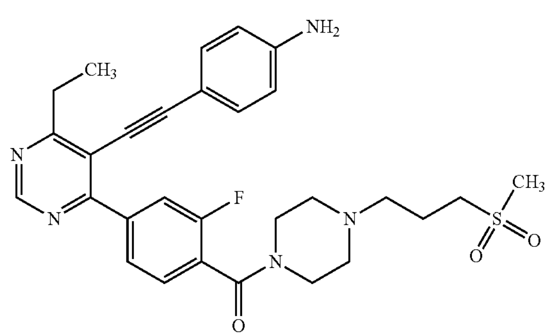 [SMILES: CCc1ncnc(-c2ccc(C(=O)N3CCN(CCCS(C)(=O)=O)CC3)c(F)c2)c1C#Cc1ccc(N)cc1] | A-73 | 550.66 | 551 | 1.55 |

TABLE 4-continued
Examples E-1-E-349
| Nr. | Structure | Int. | MW | MW [M + H] | tR [min] |
|---|---|---|---|---|---|
| E-251 | 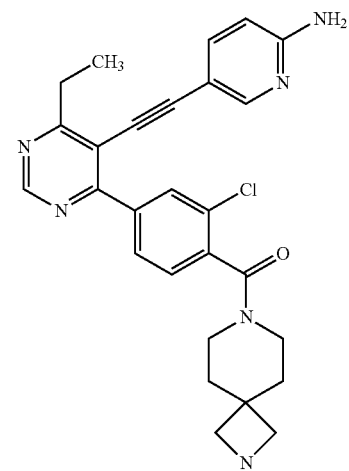 | A-77 | 487 | 487 | 1.74 |
| E-252 | 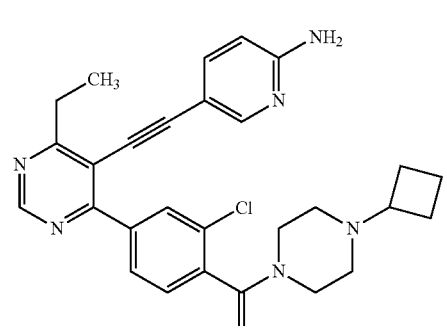 | A-77 | 501.03 | 501 | 1.89 |
| E-253 | 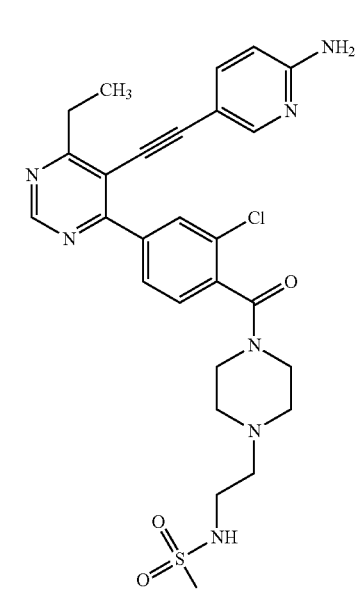 | A-77 | 568.1 | 568 | 1.59 |

TABLE 4-continued

Examples E-1-E-349

| Nr. | Structure | Int. | MW | MW [M + H] | tR [min] |
|---|---|---|---|---|---|
| E-254 | 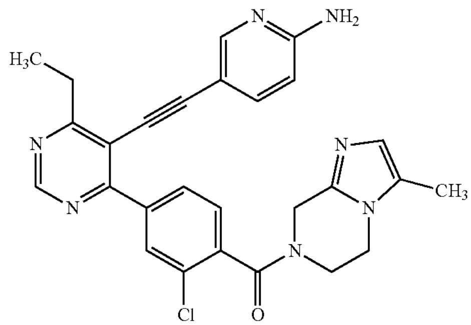 [SMILES: CCc1ncnc(-c2ccc(C(=O)N3CCn4c(C)cnc4C3)c(Cl)c2)c1C#Cc1ccc(N)nc1] | A-77 | 497.99 | 498 | 1.64 |
| E-255 | 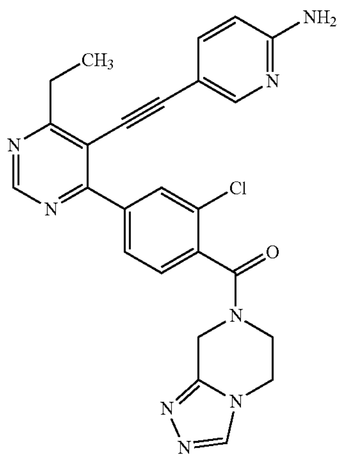 [SMILES: CCc1ncnc(-c2ccc(C(=O)N3CCn4cnnc4C3)c(Cl)c2)c1C#Cc1ccc(N)nc1] | A-77 | 484.95 | 485 | 1.46 |
| E-256 | 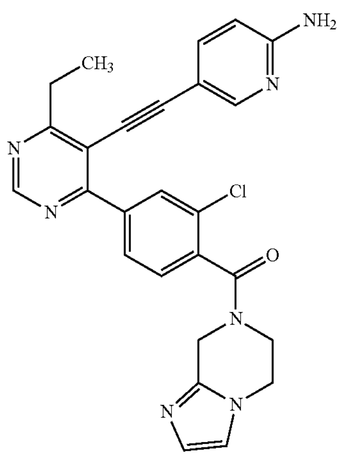 [SMILES: CCc1ncnc(-c2ccc(C(=O)N3CCn4ccnc4C3)c(Cl)c2)c1C#Cc1ccc(N)nc1] | A-77 | 483.96 | 484 | 1.57 |
| E-257 | 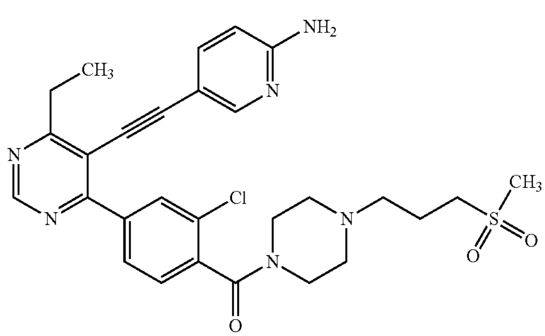 [SMILES: CCc1ncnc(-c2ccc(C(=O)N3CCN(CCCS(C)(=O)=O)CC3)c(Cl)c2)c1C#Cc1ccc(N)nc1] | A-77 | 567.11 | 567 | 1.59 |

TABLE 4-continued

Examples E-1-E-349

| Nr. | Structure | Int. | MW | MW [M + H] | tR [min] |
|---|---|---|---|---|---|
| E-258 | 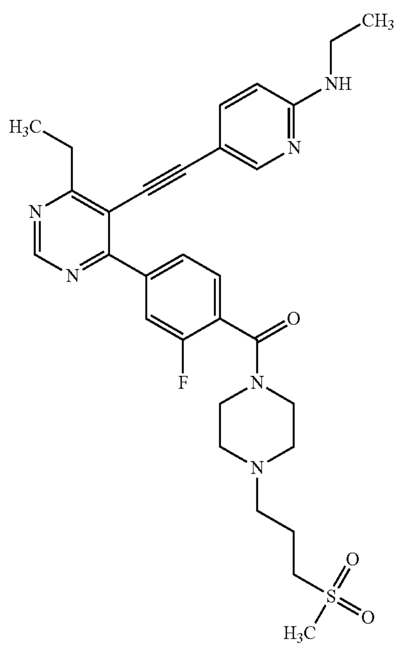 [SMILES: CCNc1ccc(C#Cc2c(CC)ncnc2-c2ccc(C(=O)N3CCN(CCCS(C)(=O)=O)CC3)c(F)c2)cn1] | A-109 | 578.71 | 579 | 1.61 |
| E-259 | 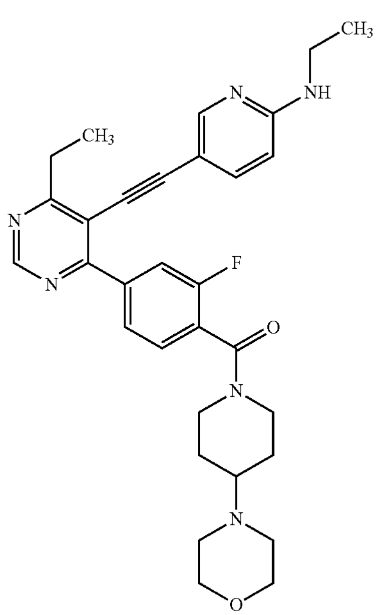 [SMILES: CCNc1ccc(C#Cc2c(CC)ncnc2-c2ccc(C(=O)N3CCC(N4CCOCC4)CC3)c(F)c2)cn1] | A-109 | 542.66 | 543 | 1.68 |

TABLE 4-continued

Examples E-1-E-349

| Nr. | Structure | Int. | MW | MW [M + H] | tR [min] |
|---|---|---|---|---|---|
| E-260 | 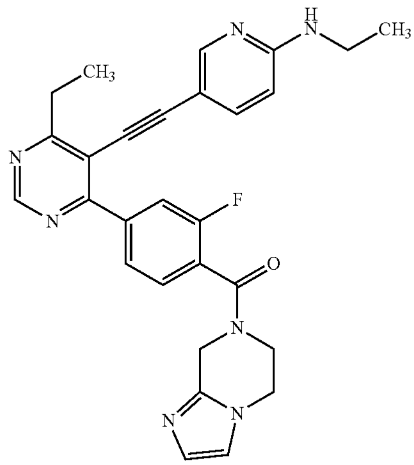 [SMILES: CCNc1ccc(C#Cc2c(CC)ncnc2-c2ccc(C(=O)N3CCn4ccnc4C3)c(F)c2)cn1] | A-109 | 495.56 | 496 | 1.6 |
| E-261 | 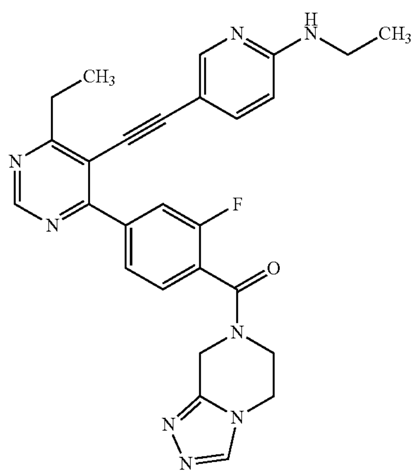 [SMILES: CCNc1ccc(C#Cc2c(CC)ncnc2-c2ccc(C(=O)N3CCn4cnnc4C3)c(F)c2)cn1] | A-109 | 496.55 | 497 | 1.48 |
| E-262 | 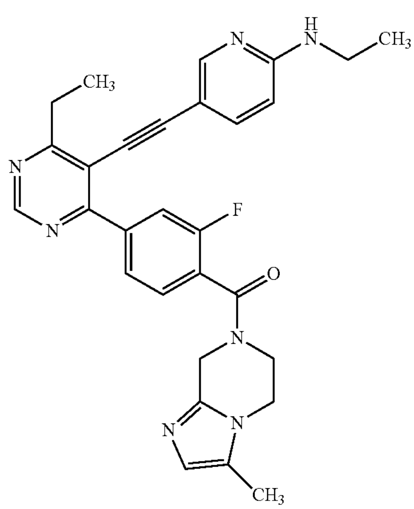 [SMILES: CCNc1ccc(C#Cc2c(CC)ncnc2-c2ccc(C(=O)N3CCn4c(C)cnc4C3)c(F)c2)cn1] | A-109 | 509.59 | 510 | 1.66 |

TABLE 4-continued
Examples E-1-E-349
| Nr. | Structure | Int. | MW | MW [M + H] | tR [min] |
|---|---|---|---|---|---|
| E-263 | 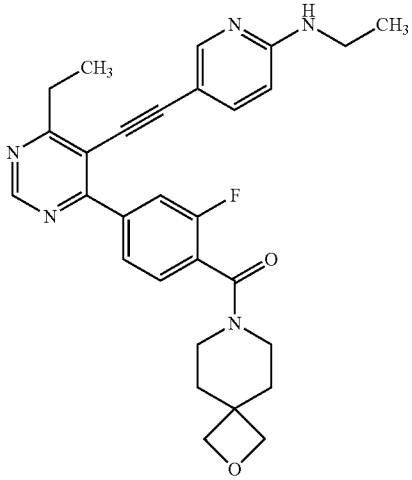 [SMILES: CCNc1ccc(C#Cc2c(CC)ncnc2-c2ccc(C(=O)N3CCC4(CC3)COC4)c(F)c2)cn1] | A-109 | 499.59 | 500 | 1.69 |
| E-264 | 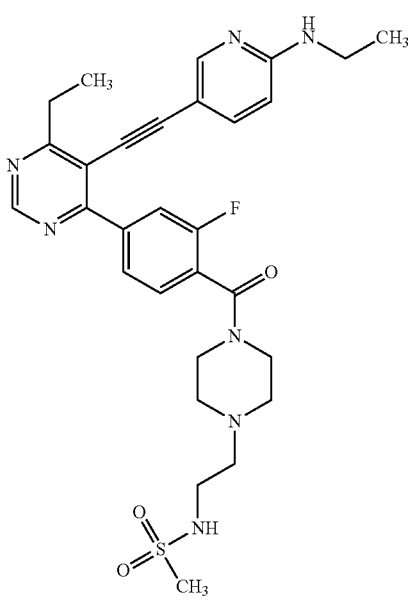 [SMILES: CCNc1ccc(C#Cc2c(CC)ncnc2-c2ccc(C(=O)N3CCN(CCNS(C)(=O)=O)CC3)c(F)c2)cn1] | A-109 | 579.7 | 580 | 1.60 |
| E-265 | 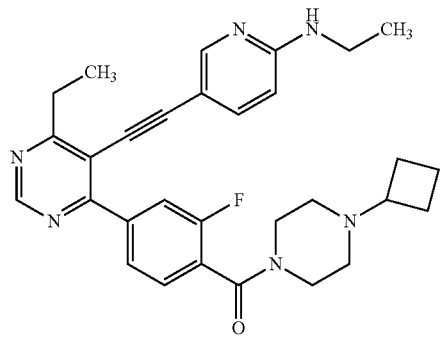 [SMILES: CCNc1ccc(C#Cc2c(CC)ncnc2-c2ccc(C(=O)N3CCN(C4CCC4)CC3)c(F)c2)cn1] | A-109 | 512.63 | 512 | 1.91 |

TABLE 4-continued
Examples E-1-E-349
| Nr. | Structure | Int. | MW | MW [M + H] | tR [min] |
|---|---|---|---|---|---|
| E-266 | 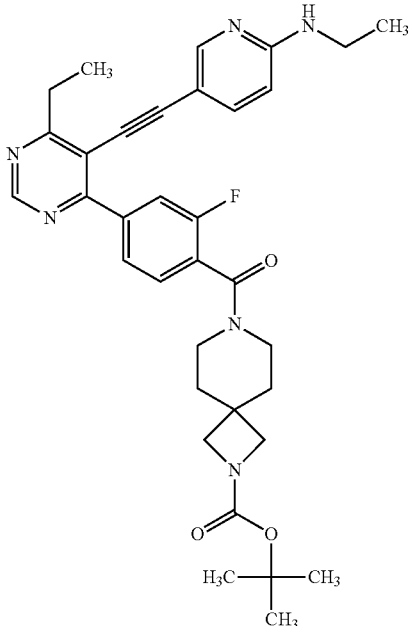 [SMILES: CCNc1ccc(C#Cc2c(CC)ncnc2-c2ccc(C(=O)N3CCC4(CC3)CN(C(=O)OC(C)(C)C)C4)c(F)c2)cn1] | A-109 | 598.72 | 599 | 2.05 |
| E-267 | 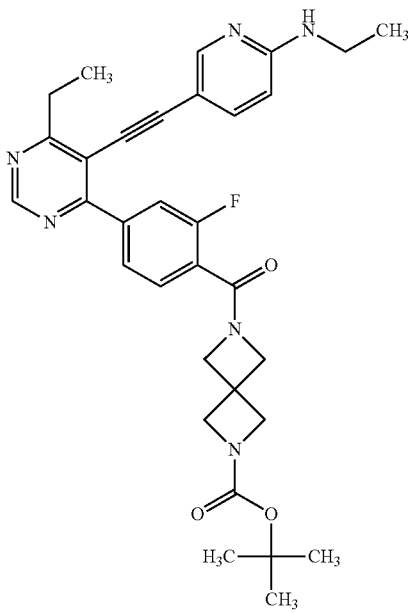 [SMILES: CCNc1ccc(C#Cc2c(CC)ncnc2-c2ccc(C(=O)N3CC4(CN(C(=O)OC(C)(C)C)C4)C3)c(F)c2)cn1] | A-109 | 570.67 | 571 | 1.95 |

TABLE 4-continued

Examples E-1-E-349

| Nr. | Structure | Int. | MW | MW [M + H] | tR [min] |
|---|---|---|---|---|---|
| E-268 | 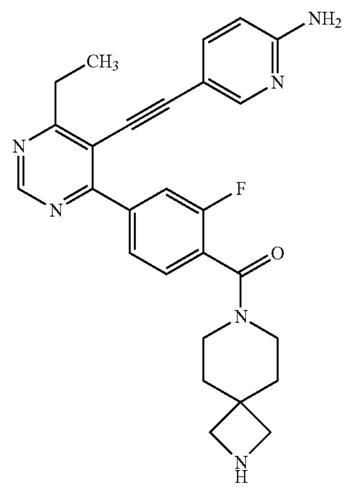 [SMILES: CCc1ncnc(-c2ccc(C(=O)N3CCC4(CC3)CNC4)c(F)c2)c1C#Cc1ccc(N)nc1] | A-73 | 470.55 | 471 | 1.18 |
| E-269 | 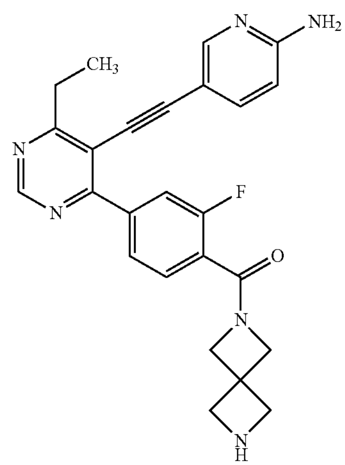 [SMILES: CCc1ncnc(-c2ccc(C(=O)N3CC4(CNC4)C3)c(F)c2)c1C#Cc1ccc(N)nc1] | A-73 | 442.5 | 443 | 1.11 |
| E-270 | 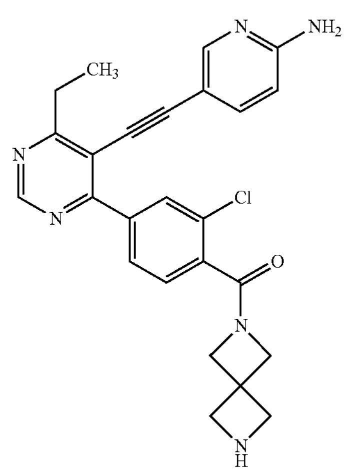 [SMILES: CCc1ncnc(-c2ccc(C(=O)N3CC4(CNC4)C3)c(Cl)c2)c1C#Cc1ccc(N)nc1] | A-77 | 458.95 | 459 | 1.13 |

TABLE 4-continued
Examples E-1-E-349
| Nr. | Structure | Int. | MW | MW [M + H] | tR [min] |
|---|---|---|---|---|---|
| E-271 | 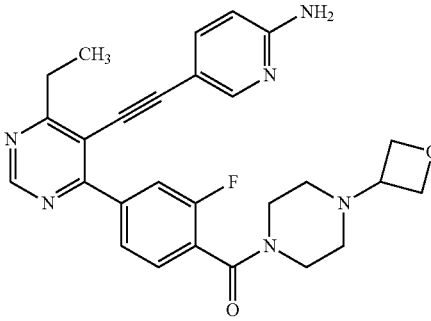 | A-73 | 486.55 | 487 | 1.13 |
| E-272 | 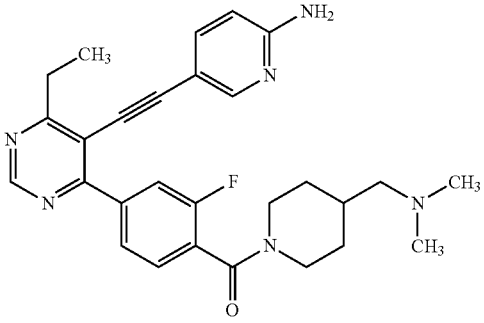 [SMILES: CCc1ncnc(-c2ccc(C(=O)N3CCC(CN(C)C)CC3)c(F)c2)c1C#Cc1ccc(N)nc1] | A-73 | 486.59 | 487 | 1.3 |
| E-273 | 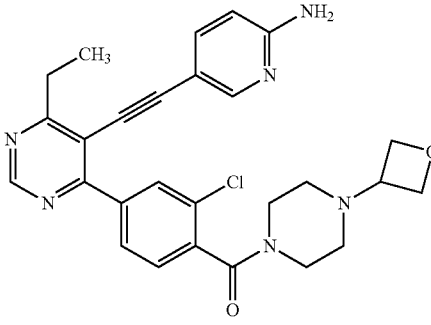 | A-77 | 503 | 503 | 1.15 |
| E-274 | 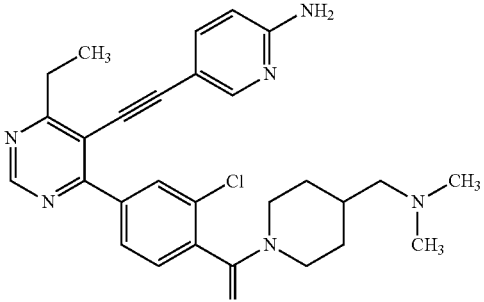 | A-77 | 503.05 | 503 | 1.33 |

TABLE 4-continued

Examples E-1-E-349

| Nr. | Structure | Int. | MW | MW [M + H] | tR [min] |
|---|---|---|---|---|---|
| E-275 | 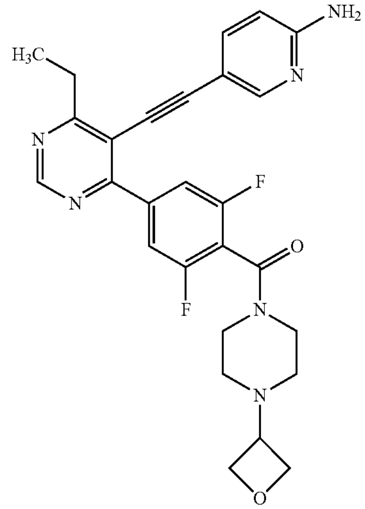 [SMILES: CCc1ncnc(-c2cc(F)c(C(=O)N3CCN(C4COC4)CC3)c(F)c2)c1C#Cc1ccc(N)nc1] | A-100 | 504.54 | 505 | 1.17 |
| E-280 | 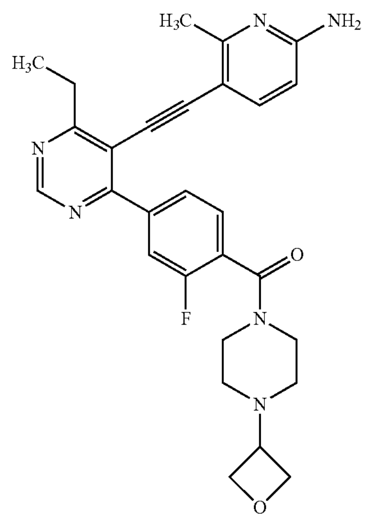 [SMILES: CCc1ncnc(-c2ccc(C(=O)N3CCN(C4COC4)CC3)c(F)c2)c1C#Cc1ccc(N)nc1C] | A-87 | 500.58 | 501 | 1.16 |
| E-281 | 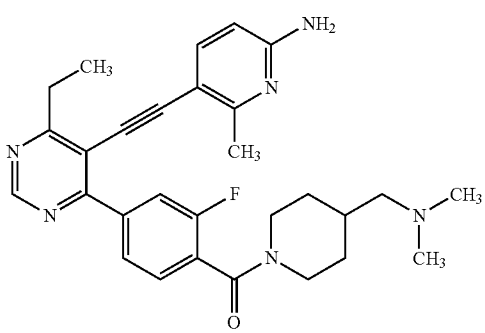 [SMILES: CCc1ncnc(-c2ccc(C(=O)N3CCC(CN(C)C)CC3)c(F)c2)c1C#Cc1ccc(N)nc1C] | A-87 | 500.62 | 501 | 1.33 |

TABLE 4-continued

Examples E-1-E-349

| Nr. | Structure | Int. | MW | MW [M + H] | tR [min] |
|---|---|---|---|---|---|
| E-282 | 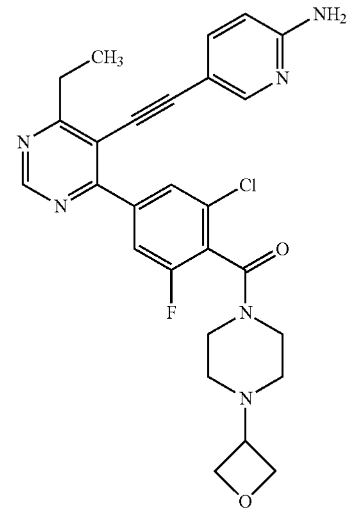 [SMILES: CCc1ncnc(-c2cc(F)c(C(=O)N3CCN(C4COC4)CC3)c(Cl)c2)c1C#Cc1ccc(N)nc1] | A-101 | 520.99 | 521 | 1.20 |
| E-283 | 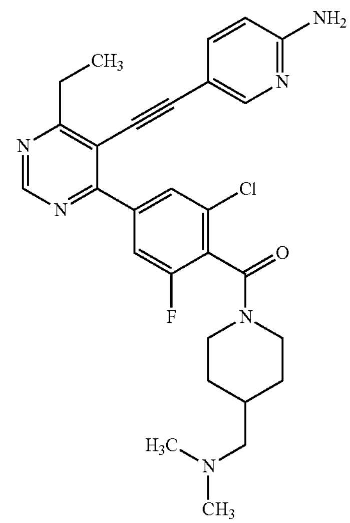 [SMILES: CCc1ncnc(-c2cc(F)c(C(=O)N3CCC(CN(C)C)CC3)c(Cl)c2)c1C#Cc1ccc(N)nc1] | A-101 | 521.04 | 521 | 1.38 |
| E-284 | 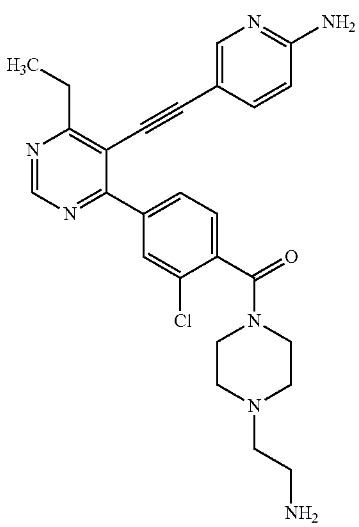 [SMILES: CCc1ncnc(-c2ccc(C(=O)N3CCN(CCN)CC3)c(Cl)c2)c1C#Cc1ccc(N)nc1] | A-77 | 490.01 | 490/492 | 1.12 |

TABLE 4-continued

Examples E-1-E-349

| Nr. | Structure | Int. | MW | MW [M + H] | tR [min] |
|---|---|---|---|---|---|
| E-285 | 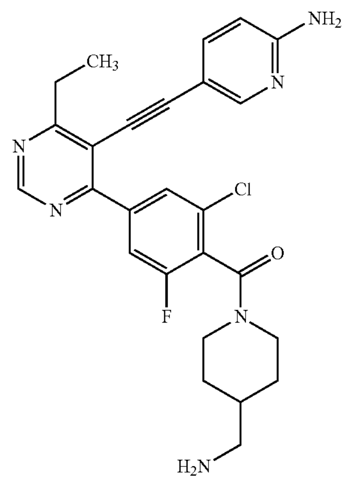 [SMILES: CCc1ncnc(-c2cc(F)c(C(=O)N3CCC(CN)CC3)c(Cl)c2)c1C#Cc1ccc(N)nc1] | A-101 | 492.98 | 493 | 1.22 |
| E-286 | 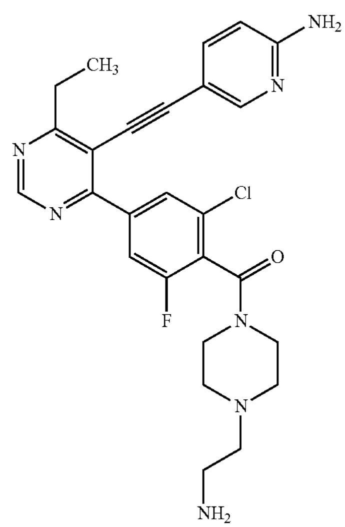 [SMILES: CCc1ncnc(-c2cc(F)c(C(=O)N3CCN(CCN)CC3)c(Cl)c2)c1C#Cc1ccc(N)nc1] | A-101 | 508 | 508 | 1.19 |
| E-287 | 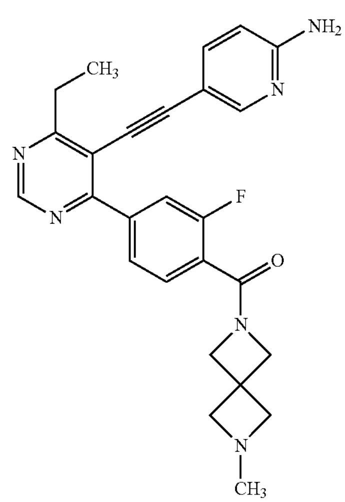 [SMILES: CCc1ncnc(-c2ccc(C(=O)N3CC4(CN(C)C4)C3)c(F)c2)c1C#Cc1ccc(N)nc1] | A-73 | 456.52 | 457 | 1.15 |

TABLE 4-continued
Examples E-1-E-349
| Nr. | Structure | Int. | MW | MW [M + H] | tR [min] |
|---|---|---|---|---|---|
| E-288 | 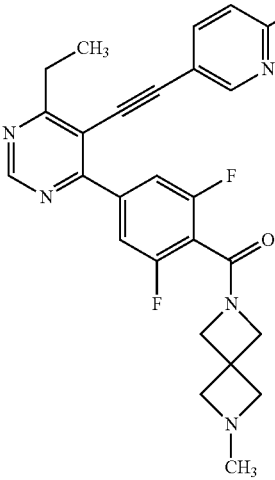 | A-100 | 474.51 | 475 | 1.19 |
| E-289 | 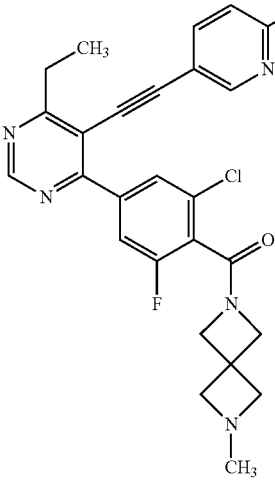 | A-101 | 490.97 | 491 | 1.22 |
| E-290 | 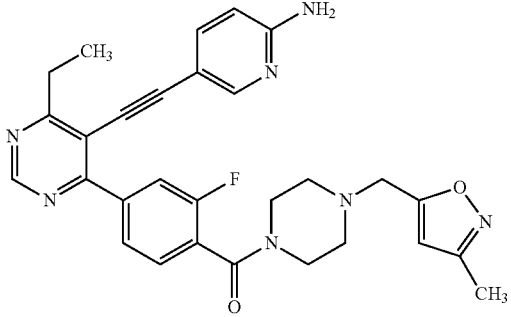 [SMILES: CCc1ncnc(-c2ccc(C(=O)N3CCN(Cc4cc(C)no4)CC3)c(F)c2)c1C#Cc1ccc(N)nc1] | A-73 | 525.59 | 526 | 1.25 |

TABLE 4-continued
Examples E-1-E-349
| Nr. | Structure | Int. | MW | MW [M + H] | tR [min] |
|---|---|---|---|---|---|
| E-291 | 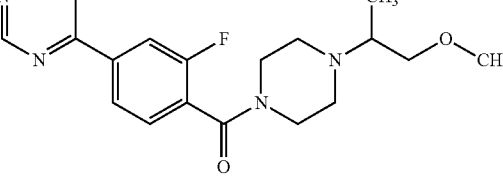 | A-73 | 502.59 | 503 | 1.28 |
| E-292 | 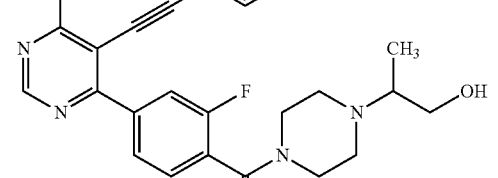 | A-73 | 488.56 | 489 | 1.16 |
| E-293 | 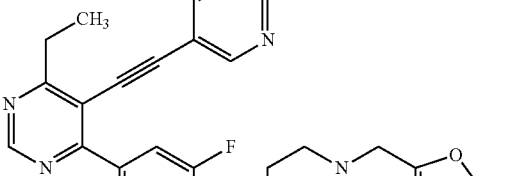 | A-73 | 539.61 | 540 | 1.29 |
| E-294 | 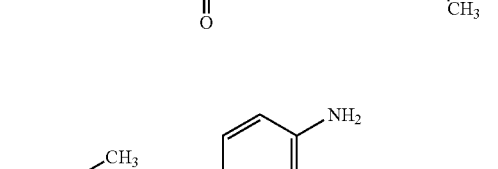 | A-73 | 514.6 | 515 | 1.20 |

TABLE 4-continued

Examples E-1-E-349

| Nr. | Structure | Int. | MW | MW [M + H] | tR [min] |
|---|---|---|---|---|---|
| E-295 | 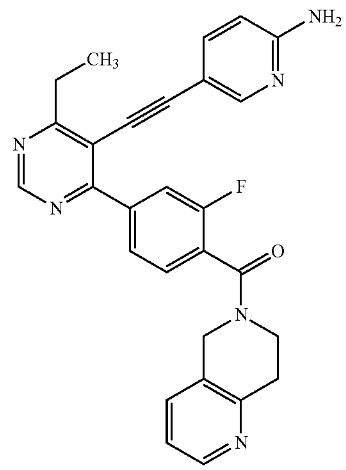 [SMILES: CCc1ncnc(-c2ccc(C(=O)N3CCc4ncccc4C3)c(F)c2)c1C#Cc1ccc(N)nc1] | A-73 | 478.53 | 479 | 1.27 |
| E-296 | 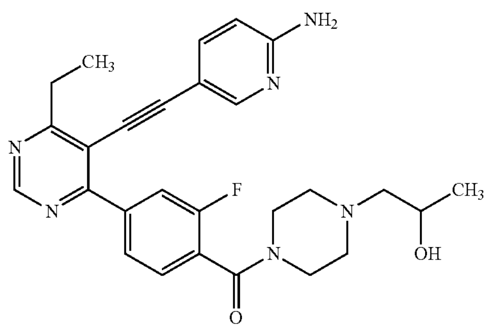 [SMILES: CCc1ncnc(-c2ccc(C(=O)N3CCN(CC(C)O)CC3)c(F)c2)c1C#Cc1ccc(N)nc1] | A-73 | 488.56 | 489 | 1.18 |
| E-297 | 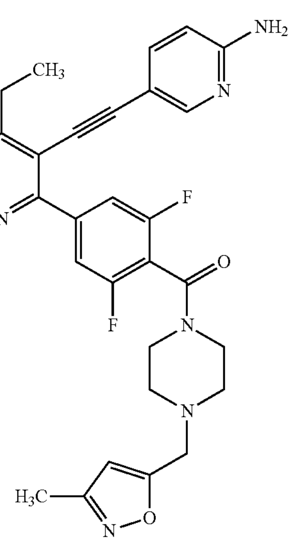 | A-100 | 543.58 | 544 | 1.29 |

TABLE 4-continued

Examples E-1-E-349

| Nr. | Structure | Int. | MW | MW [M + H] | tR [min] |
|---|---|---|---|---|---|
| E-298 | 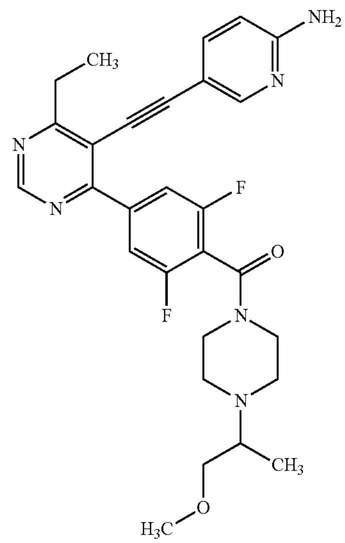 [SMILES: CCc1ncnc(-c2cc(F)c(C(=O)N3CCN(C(C)COC)CC3)c(F)c2)c1C#Cc1ccc(N)nc1] | A-100 | 520.58 | 521 | 1.33 |
| E-299 | 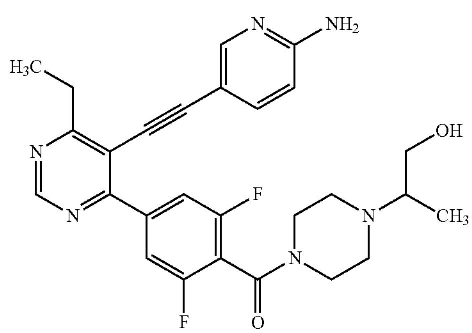 [SMILES: CCc1ncnc(-c2cc(F)c(C(=O)N3CCN(C(C)CO)CC3)c(F)c2)c1C#Cc1ccc(N)nc1] | A-100 | 506.55 | 507 | 1.21 |
| E-300 | 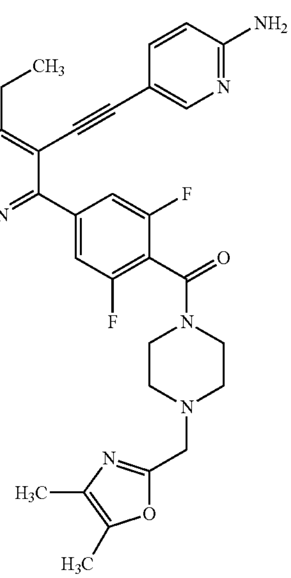 | A-100 | 557.6 | 558 | 1.33 |

TABLE 4-continued

Examples E-1-E-349

| Nr. | Structure | Int. | MW | MW [M + H] | tR [min] |
|---|---|---|---|---|---|
| E-301 | 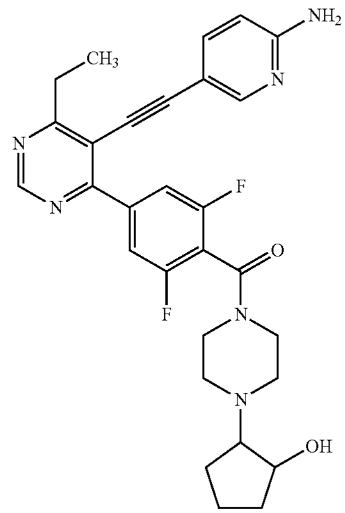 [SMILES: CCc1ncnc(-c2cc(F)c(C(=O)N3CCN(C4CCCC4O)CC3)c(F)c2)c1C#Cc1ccc(N)nc1] | A-100 | 532.59 | 533 | 1.22 |
| E-302 | 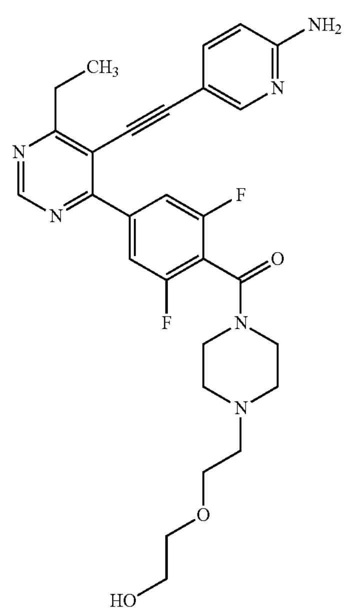 [SMILES: CCc1ncnc(-c2cc(F)c(C(=O)N3CCN(CCOCCO)CC3)c(F)c2)c1C#Cc1ccc(N)nc1] | A-100 | 536.58 | 537 | 1.17 |

TABLE 4-continued
Examples E-1-E-349
| Nr. | Structure | Int. | MW | MW [M + H] | tR [min] |
|---|---|---|---|---|---|
| E-303 | 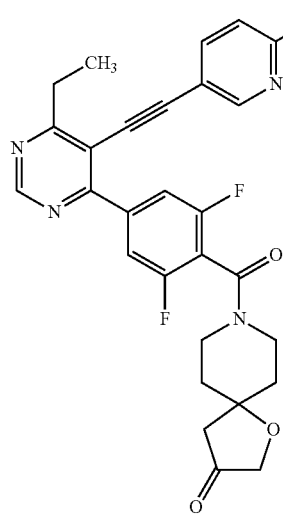 | A-100 | 517.53 | 516 | 1.26 |
| E-304 | 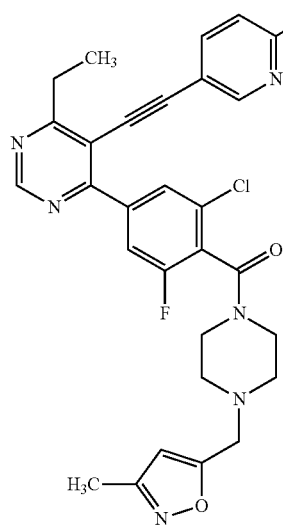 | A-101 | 560.03 | 560 | 1.32 |

TABLE 4-continued

Examples E-1-E-349

| Nr. | Structure | Int. | MW | MW [M + H] | tR [min] |
|---|---|---|---|---|---|
| E-305 | 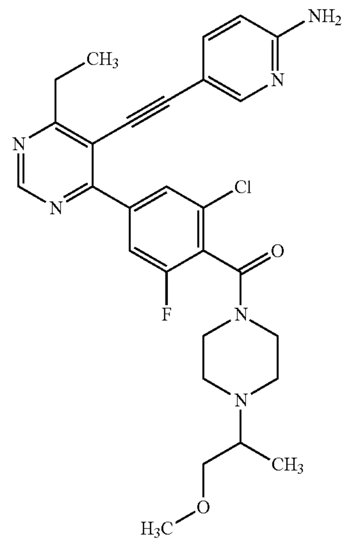 [SMILES: CCc1ncnc(-c2cc(F)c(C(=O)N3CCN(C(C)COC)CC3)c(Cl)c2)c1C#Cc1ccc(N)nc1] | A-101 | 537.04 | 537 | 1.36 |
| E-306 | 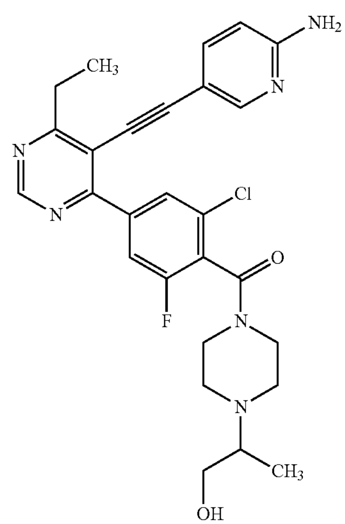 [SMILES: CCc1ncnc(-c2cc(F)c(C(=O)N3CCN(C(C)CO)CC3)c(Cl)c2)c1C#Cc1ccc(N)nc1] | A-101 | 523.01 | 523 | 1.24 |

TABLE 4-continued
Examples E-1-E-349
| Nr. | Structure | Int. | MW | MW [M + H] | tR [min] |
|---|---|---|---|---|---|
| E-307 | 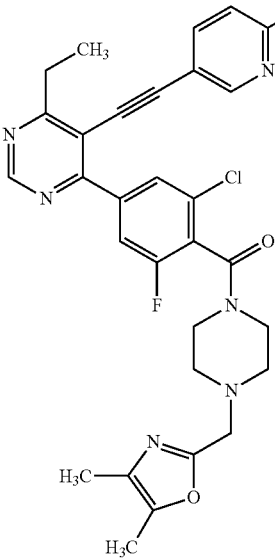 | A-101 | 574.06 | 574 | 1.36 |
| E-308 | 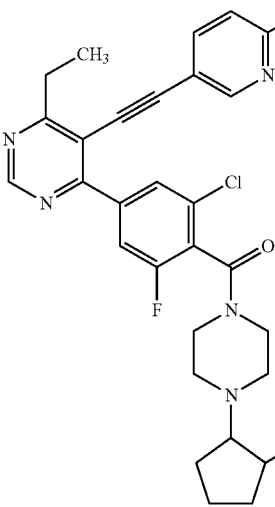 | A-101 | 549.05 | 549 | 1.25 |

TABLE 4-continued
Examples E-1-E-349
| Nr. | Structure | Int. | MW | MW [M + H] | tR [min] |
|---|---|---|---|---|---|
| E-309 | 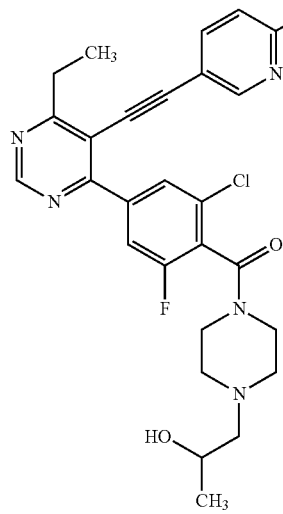 | A-101 | 523.01 | 523 | 1.25 |
| E-310 | 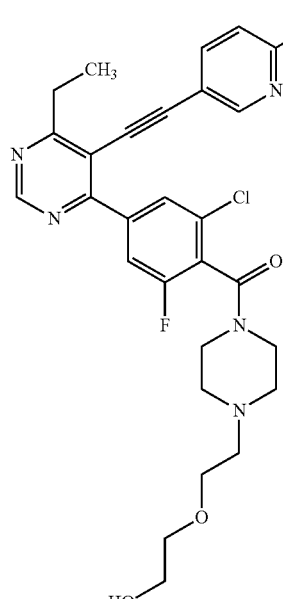 | A-101 | 553.04 | 553 | 1.2 |

TABLE 4-continued

Examples E-1-E-349

| Nr. | Structure | Int. | MW | MW [M + H] | tR [min] |
|---|---|---|---|---|---|
| E-311 | 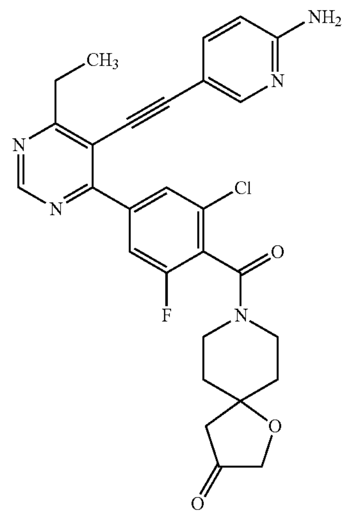 [SMILES: CCc1ncnc(-c2cc(F)c(C(=O)N3CCC4(CC3)CC(=O)CO4)c(Cl)c2)c1C#Cc1ccc(N)nc1] | A-101 | 533.99 | 534/536 | 1.3 |
| E-312 | 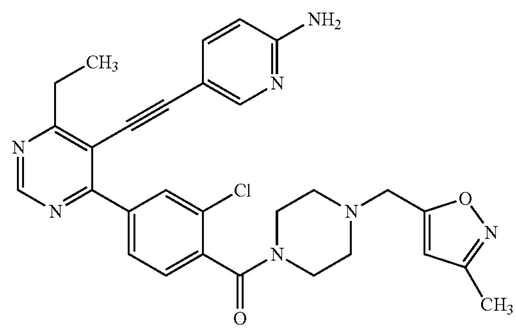 | A-77 | 542.04 | 542/544 | 1.28 |
| E-313 | 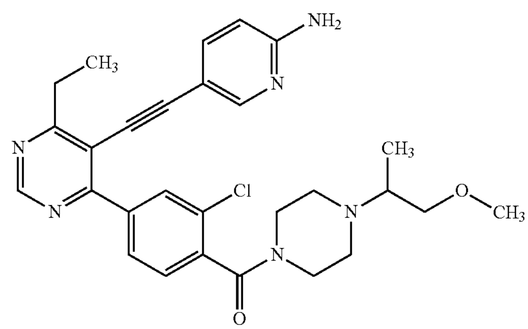 | A-77 | 519.05 | 519 | 1.3 |
| E-314 | 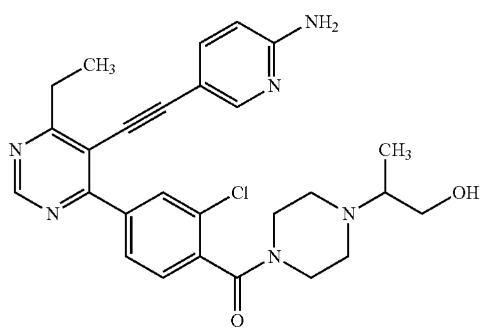 [SMILES: CCc1ncnc(-c2ccc(C(=O)N3CCN(C(C)CO)CC3)c(Cl)c2)c1C#Cc1ccc(N)nc1] | A-77 | 505.02 | 505 | 1.19 |

TABLE 4-continued
Examples E-1-E-349
| Nr. | Structure | Int. | MW | MW [M + H] | tR [min] |
|---|---|---|---|---|---|
| E-315 | 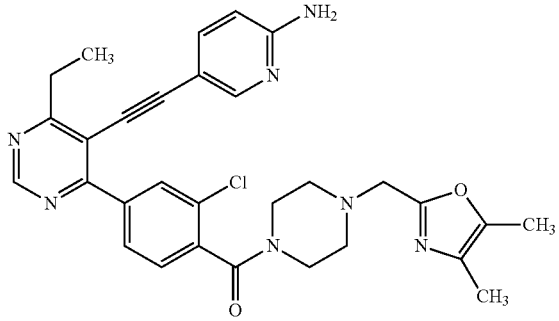 | A-77 | 556.07 | 556/558 | 1.31 |
| E-316 | 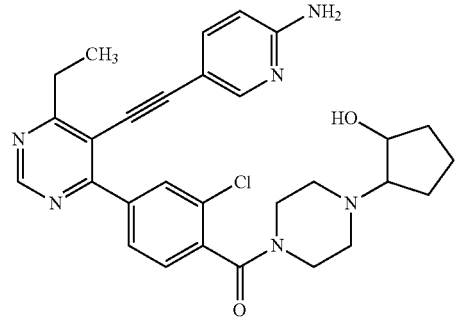 [SMILES: CCc1ncnc(-c2ccc(C(=O)N3CCN(C4CCCC4O)CC3)c(Cl)c2)c1C#Cc1ccc(N)nc1] | A-77 | 531.06 | 531/533 | 1.21 |
| E-317 | 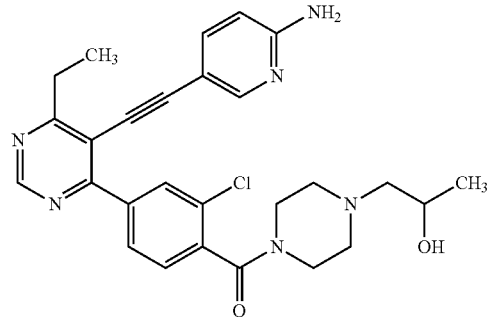 [SMILES: CCc1ncnc(-c2ccc(C(=O)N3CCN(CC(C)O)CC3)c(Cl)c2)c1C#Cc1ccc(N)nc1] | A-77 | 505.02 | 505 | 1.21 |
| E-318 | 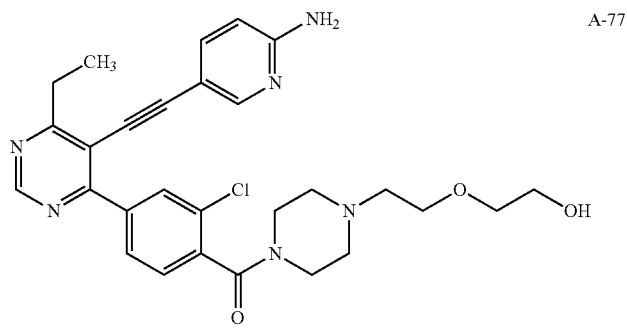 | A-77 | 535.04 | 535/537 | 1.16 |

TABLE 4-continued
Examples E-1-E-349
| Nr. | Structure | Int. | MW | MW [M + H] | tR [min] |
|---|---|---|---|---|---|
| E-319 | 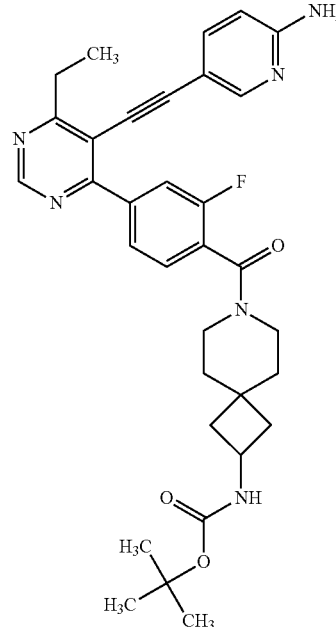 | A-73 | 584.69 | 585 | 1.46 |
| E-320 | 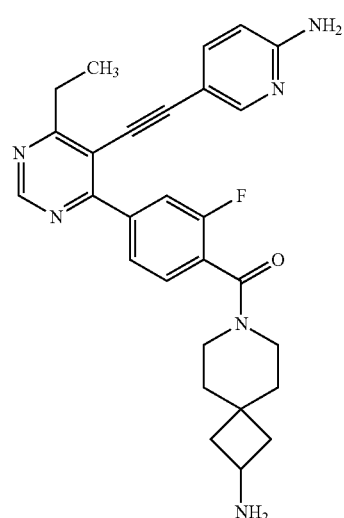 | A-73 | 484.58 | 485 | 1.19 |
| E-321 | 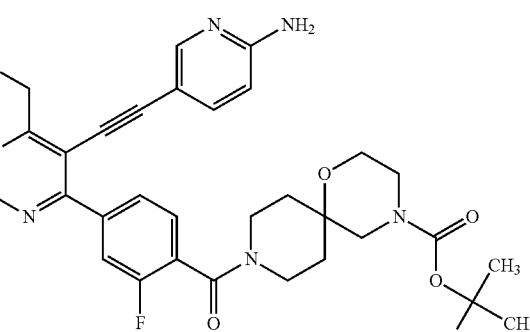 | A-73 | 600.69 | 601 | 1.43 |

TABLE 4-continued

Examples E-1-E-349

| Nr. | Structure | Int. | MW | MW [M + H] | tR [min] |
|---|---|---|---|---|---|
| E-322 | 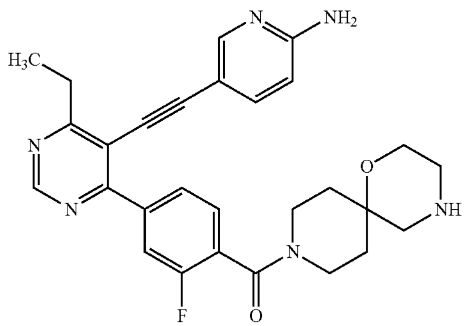 [SMILES: CCc1ncnc(-c2ccc(C(=O)N3CCC4(CC3)CNCCO4)c(F)c2)c1C#Cc1ccc(N)nc1] | A-73 | 500.58 | 501 | 1.15 |
| E-323 | 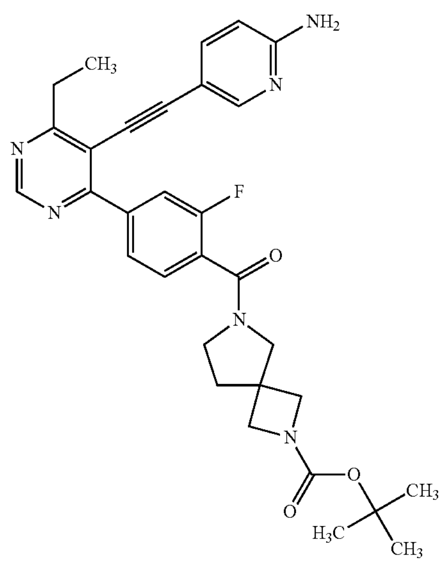 [SMILES: CCc1ncnc(-c2ccc(C(=O)N3CCC4(CN(C(=O)OC(C)(C)C)C4)C3)c(F)c2)c1C#Cc1ccc(N)nc1] | A-73 | 556.64 | 557 | 1.40 |
| E-324 | 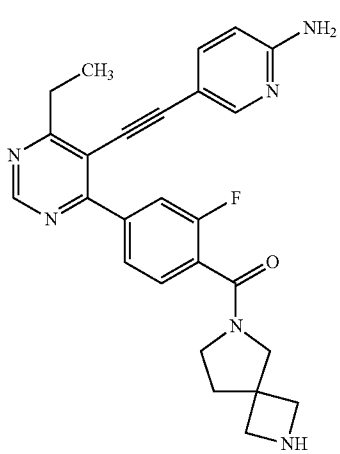 [SMILES: CCc1ncnc(-c2ccc(C(=O)N3CCC4(CNC4)C3)c(F)c2)c1C#Cc1ccc(N)nc1] | A-73 | 456.52 | 457 | 1.12 |

TABLE 4-continued
Examples E-1-E-349
| Nr. | Structure | Int. | MW | MW [M + H] | tR [min] |
|---|---|---|---|---|---|
| E-325 | 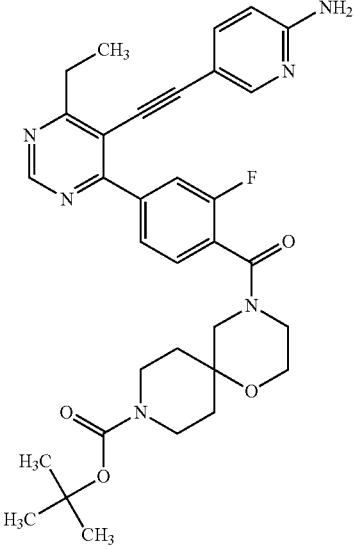 [SMILES: CCc1ncnc(-c2ccc(C(=O)N3CCOC4(CCN(C(=O)OC(C)(C)C)CC4)C3)c(F)c2)c1C#Cc1ccc(N)nc1] | A-73 | 600.69 | 601 | 1.45 |
| E-326 | 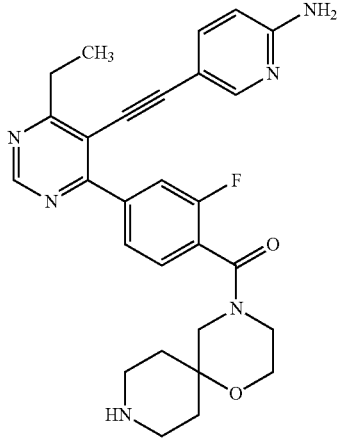 [SMILES: CCc1ncnc(-c2ccc(C(=O)N3CCOC4(CCNCC4)C3)c(F)c2)c1C#Cc1ccc(N)nc1] | A-73 | 500.58 | 501 | 1.15 |

TABLE 4-continued
Examples E-1-E-349
| Nr. | Structure | Int. | MW | MW [M + H] | tR [min] |
|---|---|---|---|---|---|
| E-327 | 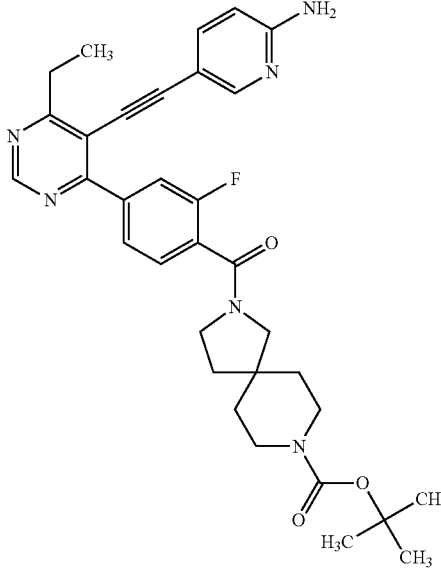 | A-73 | 584.69 | 585 | 1.46 |
| E-328 | 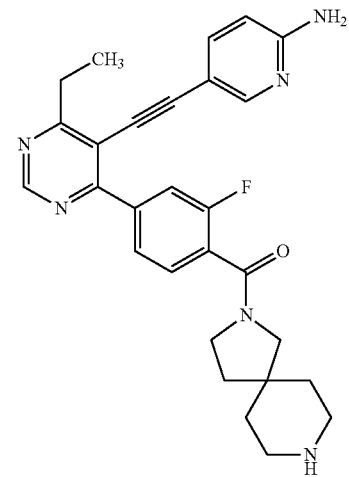 [SMILES: CCc1ncnc(-c2ccc(C(=O)N3CCC4(CCNCC4)C3)c(F)c2)c1C#Cc1ccc(N)nc1] | A-73 | 484.58 | 485 | 1.18 |

TABLE 4-continued
Examples E-1-E-349
| Nr. | Structure | Int. | MW | MW [M + H] | tR [min] |
|---|---|---|---|---|---|
| E-329 | 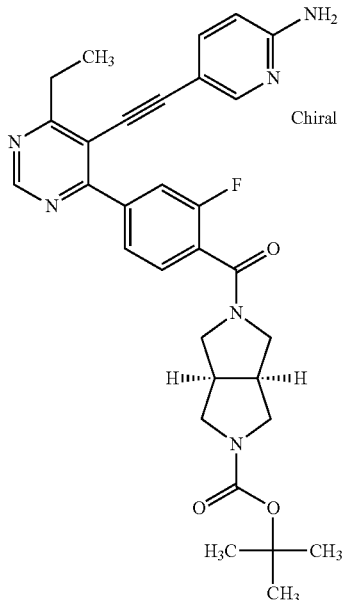 [SMILES: CCc1ncnc(-c2ccc(C(=O)N3C[C@H]4CN(C(=O)OC(C)(C)C)C[C@H]4C3)c(F)c2)c1C#Cc1ccc(N)nc1] | A-73 | 556.64 | 557 | 1.38 |
| E-330 | 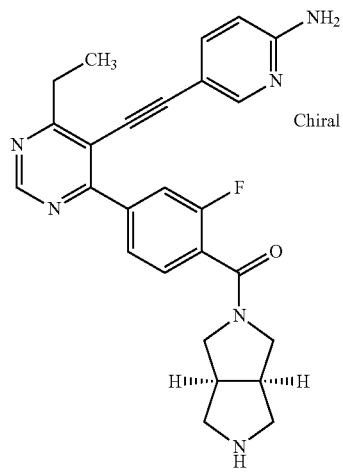 [SMILES: CCc1ncnc(-c2ccc(C(=O)N3C[C@H]4CNC[C@H]4C3)c(F)c2)c1C#Cc1ccc(N)nc1] | A-73 | 456.52 | 457 | 1.12 |

TABLE 4-continued
Examples E-1-E-349
| Nr. | Structure | Int. | MW | MW [M + H] | tR [min] |
|---|---|---|---|---|---|
| E-331 | 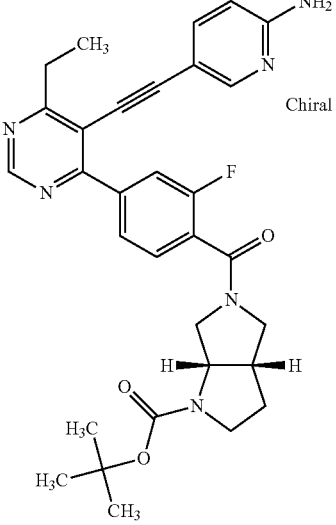 [SMILES: CCc1ncnc(-c2ccc(C(=O)N3C[C@@H]4CCN(C(=O)OC(C)(C)C)[C@@H]4C3)c(F)c2)c1C#Cc1ccc(N)nc1] | A-73 | 556.64 | 557 | 1.38 |
| E-332 | 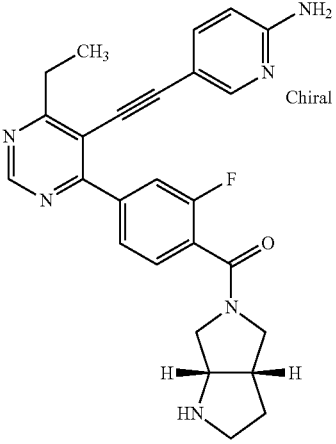 [SMILES: CCc1ncnc(-c2ccc(C(=O)N3C[C@@H]4CCN[C@@H]4C3)c(F)c2)c1C#Cc1ccc(N)nc1] | A-73 | 456.52 | 457 | 1.14 |
| E-333 | 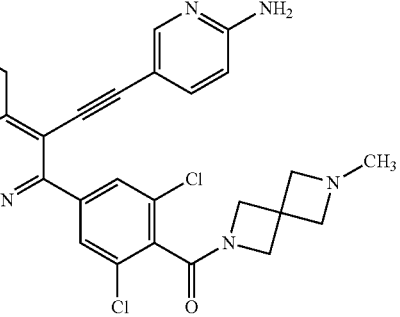 | A-102 | 507.42 | 507/509/511 | 1.26 |

TABLE 4-continued

Examples E-1-E-349

| Nr. | Structure | Int. | MW | MW [M + H] | tR [min] |
|---|---|---|---|---|---|
| E-334 | 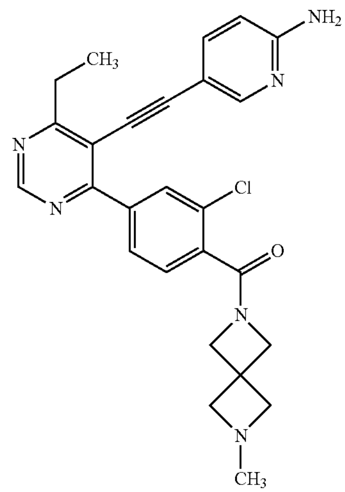 [SMILES: CCc1ncnc(-c2ccc(C(=O)N3CC4(CN(C)C4)C3)c(Cl)c2)c1C#Cc1ccc(N)nc1] | A-77 | 472.98 | 473/475 | 1.19 |
| E-335 | 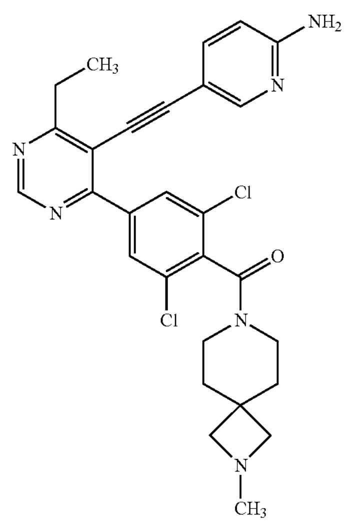 [SMILES: CCc1ncnc(-c2cc(Cl)c(C(=O)N3CCC4(CC3)CN(C)C4)c(Cl)c2)c1C#Cc1ccc(N)nc1] | A-102 | 535.48 | 535 | 1.35 |
| E-336 | 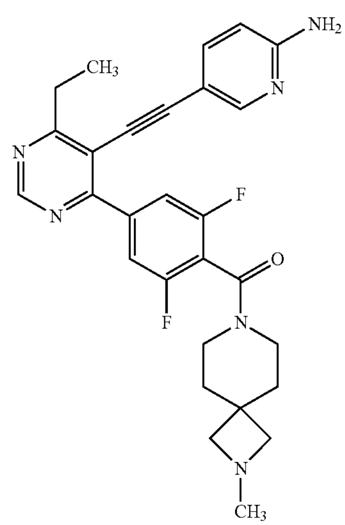 [SMILES: CCc1ncnc(-c2cc(F)c(C(=O)N3CCC4(CC3)CN(C)C4)c(F)c2)c1C#Cc1ccc(N)nc1] | A-100 | 502.57 | 503 | 1.28 |

TABLE 4-continued
Examples E-1-E-349
| Nr. | Structure | Int. | MW | MW [M + H] | tR [min] |
|---|---|---|---|---|---|
| E-337 | 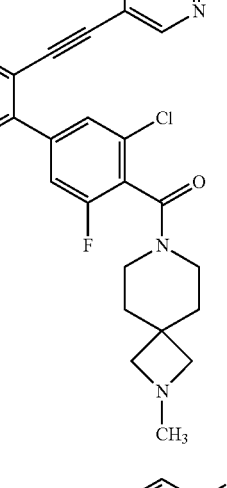 | A-101 | 519.02 | 519 | 1.32 |
| E-338 | 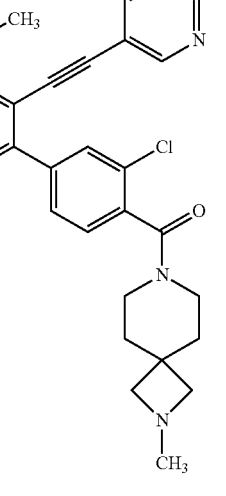 | A-77 | 501.03 | 501/503 | 1.28 |
| E-339 | 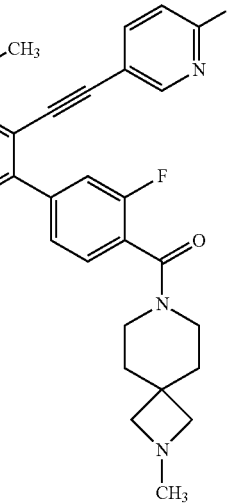 | A-73 | 484.58 | 485 | 1.25 |

TABLE 4-continued
Examples E-1-E-349
| Nr. | Structure | Int. | MW | MW [M + H] | tR [min] |
|---|---|---|---|---|---|
| E-340 | 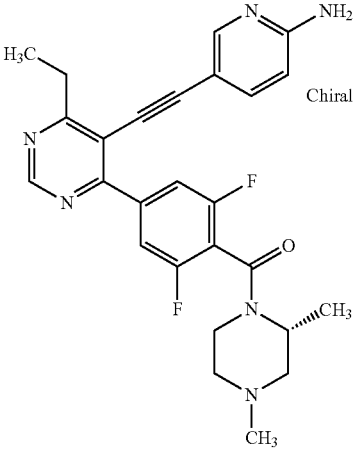 [SMILES: CCc1ncnc(-c2cc(F)c(C(=O)N3CCN(C)C[C@H]3C)c(F)c2)c1C#Cc1ccc(N)nc1] | A-100 | 476.53 | 477 | 1.36 |
| E-341 | 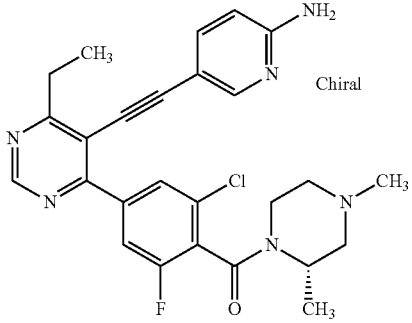 [SMILES: CCc1ncnc(-c2cc(F)c(C(=O)N3CCN(C)C[C@@H]3C)c(Cl)c2)c1C#Cc1ccc(N)nc1] | A-101 | 492.98 | 493/495 | 1.35 |
| E-342 | 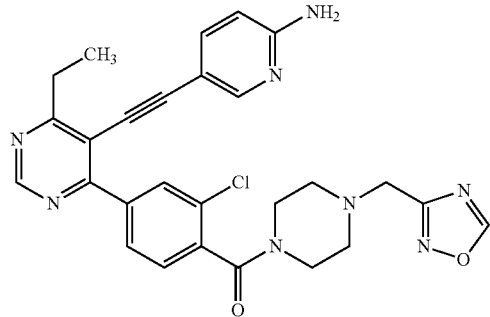 [SMILES: CCc1ncnc(-c2ccc(C(=O)N3CCN(Cc4ncon4)CC3)c(Cl)c2)c1C#Cc1ccc(N)nc1] | A-77 | 529 | 529/531 | 1.24 |
| E-343 | 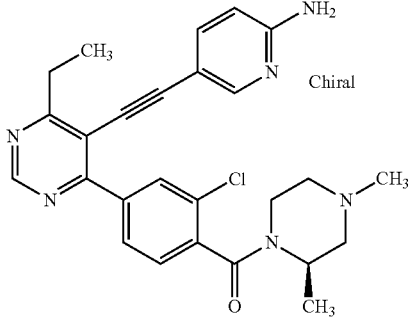 [SMILES: CCc1ncnc(-c2ccc(C(=O)N3CCN(C)C[C@H]3C)c(Cl)c2)c1C#Cc1ccc(N)nc1] | A-77 | 474.99 | 475 | 1.28 |

TABLE 4-continued
Examples E-1-E-349
| Nr. | Structure | Int. | MW | MW [M + H] | tR [min] |
|---|---|---|---|---|---|
| E-344 | 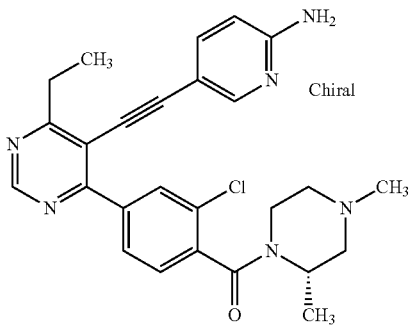 [SMILES: CCc1ncnc(-c2ccc(C(=O)N3CCN(C)C[C@@H]3C)c(Cl)c2)c1C#Cc1ccc(N)nc1] | A-77 | 474.99 | 475 | 1.28 |
| E-345 | 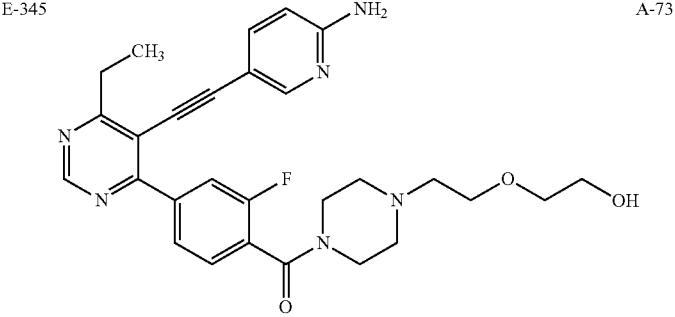 | A-73 | 518.59 | 519 | 1.15 |
| E-346 | 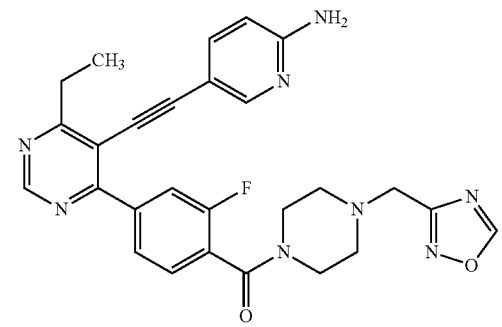 [SMILES: CCc1ncnc(-c2ccc(C(=O)N3CCN(Cc4ncon4)CC3)c(F)c2)c1C#Cc1ccc(N)nc1] | A-73 | 512.55 | 513 | 1.20 |
| E-347 | 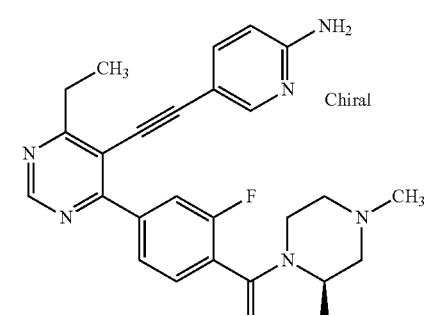 | A-73 | 458.54 | 459 | 1.25 |

TABLE 4-continued
Examples E-1-E-349
| Nr. | Structure | Int. | MW | MW [M + H] | tR [min] |
|---|---|---|---|---|---|
| E-348 | 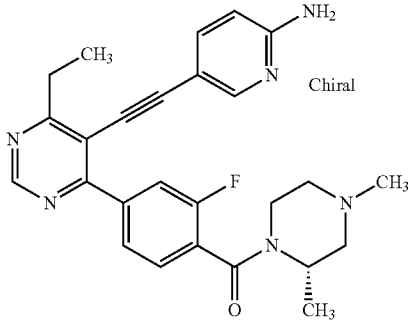 [SMILES: CCc1ncnc(-c2ccc(C(=O)N3CCN(C)C[C@@H]3C)c(F)c2)c1C#Cc1ccc(N)nc1] | A-73 | 458.54 | 459 | 1.25 |
| E-349 | 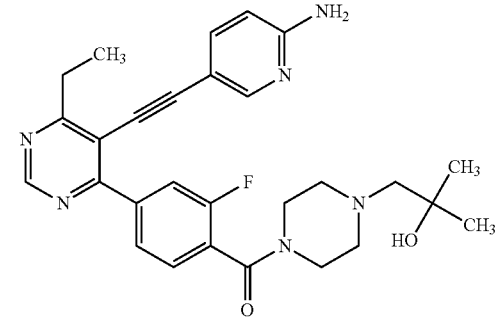 [SMILES: CCc1ncnc(-c2ccc(C(=O)N3CCN(CC(C)(C)O)CC3)c(F)c2)c1C#Cc1ccc(N)nc1] | A-73 | 502.59 | 503 | 1.27 |
TABLE 5
Biological Data of Examples C-1 to C-50
| Nr. | IC$_{50}$ mTOR [nM] | IC$_{50}$ PI3K [nM] |
|---|---|---|
| C-01 | 24 | 26 |
| C-02 | 24 | 24 |
| C-03 | 11 | 40 |
| C-04 | 8 | 29 |
| C-05 | 3 | 50 |
| C-06 | 5 | 86 |
| C-07 | 30 | 39 |
| C-08 | 8 | 65 |
| C-09 | 6 | 254 |
| C-10 | 17 | 401 |
| C-11 | 2 | 47 |
| C-12 | 5 | 71 |
| C-13 | 64 | 99 |
| C-14 | 18 | 66 |
| C-15 | 20 | 189 |
| C-15A | 2 | 57 |
| C-16 | 18 | 236 |
| C-17 | 69 | 99 |
| C-18 | 29 | 137 |
| C-19 | 19 | 222 |
| C-20 | 40 | 58 |
| C-21 | 44 | 99 |
| C-22 | 76 | 30 |
| C-23 | 63 | 78 |
| C-24 | 34 | 59 |
| C-25 | 163 | 64 |
| C-26 | 57 | 43 |
| C-27 | 20 | 57 |
| C-28 | 50 | 58 |
| C-29 | 34 | 24 |
| C-30 | 51 | 40 |
| C-31 | 22 | 30 |
| C-32 | 41 | 32 |
| C-33 | 34 | 61 |
| C-34 | 79 | 37 |
| C-35 | 32 | 29 |
| C-36 | 82 | 308 |
| C-37 | 90 | 224 |
| C-38 | 24 | 68 |
| C-39 | 13 | 380 |
| C-40 | 4 | 459 |
| C-41 | 14 | 539 |
| C-42 | 13 | 309 |
| C-43 | 32 | 184 |
| C-44 | 109 | 188 |
| C-45 | 4 | 194 |
| C-46 | 31 | 226 |
| C-47 | 17 | 541 |
| C-48 | 28 | 596 |
| C-49 | 31 | 67 |
| C-50 | 44 | 72 |
TABLE 6
Biological Data for Examples D1-D240
| Nr. | IC$_{50}$ mTOR [nM] | IC$_{50}$ PI3K [nM] |
|---|---|---|
| D-1 | 3 | 78 |
| D-2 | 30 | 402 |
| D-3 | 33 | 574 |
| D-4 | 1 | 58 |
| D-5 | 8 | 225 |
| D-6 | 2 | 135 |
| D-7 | 2 | 103 |
| D-8 | 2 | 215 |

TABLE 6-continued

Biological Data for Examples D1-D240

| Nr. | IC₅₀ mTOR [nM] | IC₅₀ PI3K [nM] |
|---|---|---|
| D-9 | 33 | 591 |
| D-10 | 4 | 206 |
| D-11 | 2 | 109 |
| D-12 | 3 | 163 |
| D-13 | 4 | 312 |
| D-14 | 27 | 647 |
| D-15 | 3 | 215 |
| D-16 | 5 | 192 |
| D-17 | 7 | 178 |
| D-18 | 8 | 481 |
| D-19 | 9 | 92 |
| D-20 | 8 | 116 |
| D-21 | 8 | 270 |
| D-22 | 68 | 1269 |
| D-23 | 2 | 123 |
| D-24 | 9 | 1017 |
| D-25 | 26 | 498 |
| D-26 | 7 | 552 |
| D-27 | 5 | 370 |
| D-28 | 0.99 | 65 |
| D-29 | 1 | 162 |
| D-30 | 3 | 68 |
| D-31 | 0.88 | 97 |
| D-32 | 0.74 | 121 |
| D-33 | 3 | 181 |
| D-34 | 1 | 36 |
| D-35 | 2 | 63 |
| D-36 | 0.6 | 84 |
| D-37 | 3 | 118 |
| D-38 | 4 | 366 |
| D-39 | 5 | 89 |
| D-40 | 18 | 499 |
| D-41 | 2 | 177 |
| D-42 | 0.84 | 246 |
| D-43 | 2 | 436 |
| D-44 | 0.82 | 27 |
| D-45 | 2 | 186 |
| D-46 | 2 | 97 |
| D-47 | 2 | 63 |
| D-48 | 3 | 251 |
| D-49 | 2 | 60 |
| D-50 | 2 | 211 |
| D-51 | 1 | 121 |
| D-52 | 1 | 134 |
| D-53 | 3 | 213 |
| D-54 | 4 | 81 |
| D-55 | 2 | 36 |
| D-56 | 2 | 73 |
| D-57 | 3 | 152 |
| D-58 | 2 | 217 |
| D-59 | 1 | 19 |
| D-60 | 8 | 546 |
| D-61 | 1 | 86 |
| D-62 | 3 | 205 |
| D-63 | 2 | 234 |
| D-64 | 2 | 198 |
| D-65 | 30 | 436 |
| D-66 | 2 | 110 |
| D-67 | 2 | 244 |
| D-68 | 4 | 42 |
| D-69 | 3 | 133 |
| D-70 | 5 | 490 |
| D-71 | 1 | 85 |
| D-73 | 24 | 324 |
| D-74 | 33 | 630 |
| D-75 | 33 | 335 |
| D-76 | 13 | 339 |
| D-77 | 28 | 303 |
| D-78 | 5 | 305 |
| D-79 | 1 | 170 |
| D-80 | 5 | 68 |
| D-81 | 4 | 84 |
| D-82 | 4 | 146 |
| D-83 | 4 | 219 |
| D-84 | 3 | 127 |
| D-85 | 7 | 115 |
| D-86 | 4 | 95 |
| D-87 | 7 | 233 |
| D-88 | 4 | 118 |
| D-89 | 5 | 52 |
| D-90 | 6 | 62 |
| D-91 | 4 | 109 |
| D-92 | 7 | 124 |
| D-93 | 7 | 266 |
| D-94 | 39 | 1825 |
| D-95 | 6 | 145 |
| D-96 | 6 | 151 |
| D-97 | 12 | 476 |
| D-98 | 10 | 199 |
| D-99 | 16 | 452 |
| D-100 | 16 | 347 |
| D-101 | 2 | 49 |
| D-103 | 28 | 470 |
| D-104 | 6 | 125 |
| D-105 | 3 | 46 |
| D-106 | 5 | 249 |
| D-107 | 9 | 82 |
| D-108 | 13 | 313 |
| D-110 | 6 | 64 |
| D-111 | 24 | 359 |
| D-112 | 17 | 323 |
| D-113 | 13 | 57 |
| D-114 | 12 | 188 |
| D-116 | 16 | 129 |
| D-117 | 8 | 27 |
| D-118 | 17 | 404 |
| D-119 | 14 | 55 |
| D-120 | 9 | 108 |
| D-121 | 3 | 127 |
| D-122 | 6 | 198 |
| D-123 | 17 | 324 |
| D-124 | 7 | 228 |
| D-125 | 4 | 269 |
| D-126 | 8 | 142 |
| D-127 | 13 | 344 |
| D-128 | 8 | 157 |
| D-129 | 10 | 392 |
| D-130 | 16 | 384 |
| D-131 | 5 | 119 |
| D-132 | 26 | 184 |
| D-133 | 2 | 115 |
| D-134 | 21 | 333 |
| D-135 | 3 | 136 |
| D-136 | 5 | 228 |
| D-138 | 5 | 101 |
| D-139 | 7 | 374 |
| D-140 | 57 | 510 |
| D-141 | 3 | 64 |
| D-142 | 6 | 94 |
| D-143 | 6 | 77 |
| D-145 | 2 | 58 |
| D-146 | 4 | 66 |
| D-147 | 3 | 65 |
| D-148 | 43 | 420 |
| D-149 | 30 | 433 |
| D-150 | 20 | 177 |
| D-151 | 10 | 467 |
| D-152 | 8 | 164 |
| D-153 | 17 | 67 |
| D-154 | 22 | 405 |
| D-155 | 10 | 209 |
| D-156 | 3 | 53 |
| D-157 | 5 | 65 |
| D-159 | 7 | 66 |
| D-160 | 29 | 658 |
| D-161 | 7 | |
| D-162 | 7 | |
| D-163 | 12 | |
| D-164 | 12 | |
| D-165 | 12 | |
| D-166 | 6 | |
| D-167 | 7 | |

TABLE 6-continued

Biological Data for Examples D1-D240

| Nr. | IC$_{50}$ mTOR [nM] | IC$_{50}$ PI3K [nM] |
|---|---|---|
| D-168 | 9 | |
| D-169 | 88 | |
| D-170 | 75 | |
| D-172 | 7 | |
| D-173 | 62 | |
| D-174 | 34 | |
| D-175 | 21 | |
| D-176 | 50 | |
| D-177 | 33 | |
| D-178 | 6 | |
| D-179 | 5 | |
| D-180 | 20 | |
| D-181 | 32 | |
| D-182 | 22 | |
| D-183 | 16 | |
| D-185 | 16 | |
| D-186 | 7 | |
| D-187 | 7 | |
| D-188 | 4 | 67 |
| D-189 | 3 | 118 |
| D-190 | 8 | 153 |
| D-191 | 17 | 81 |
| D-192 | 4 | 134 |
| D-193 | 3 | 65 |
| D-194 | 3 | 106 |
| D-195 | 4 | 125 |
| D-196 | 19 | 292 |
| D-197 | 31 | 280 |
| D-198 | 3 | 203 |
| D-199 | 15 | 347 |
| D-200 | 46 | 566 |
| D-201 | 11 | 134 |
| D-202 | 16 | 413 |
| D-203 | 1 | 57 |
| D-204 | 2 | 69 |
| D-205 | 28 | 335 |
| D-206 | 13 | 351 |
| D-207 | 10 | 436 |
| D-208 | 8 | 308 |
| D-209 | 11 | 158 |
| D-210 | 7 | 370 |
| D-211 | 5 | 46 |
| D-212 | 5 | 79 |
| D-213 | 18 | 272 |
| D-214 | 1 | 72 |
| D-215 | 2 | 227 |
| D-216 | 1 | 59 |
| D-217 | 4 | 44 |
| D-218 | 5 | 80 |
| D-219 | 11 | 105 |
| D-220 | 7 | 64 |
| D-221 | 7 | 63 |
| D-222 | 10 | 42 |
| D-223 | 13 | 77 |
| D-224 | 12 | 39 |
| D-225 | 16 | 66 |
| D-226 | 10 | 48 |
| D-227 | 17 | 47 |
| D-228 | 8 | 52 |
| D-229 | 12 | 65 |
| D-230 | 15 | 37 |
| D-231 | 22 | 46 |
| D-232 | 9 | 38 |
| D-233 | 17 | 45 |
| D-234 | 8 | 156 |
| D-235 | 17 | 226 |
| D-236 | 8 | 269 |
| D-237 | 18 | 161 |
| D-238 | 25 | 382 |
| D-239 | 3 | 55 |
| D-240 | 24 | 214 |

TABLE 7

Biological Data for Examples E-1-E-349

| Nr. | IC$_{50}$ mTOR [nM] | IC$_{50}$ PI3K [nM] | EC$_{50}$ BT474 [nM] | EC$_{50}$ U87MG [nM] |
|---|---|---|---|---|
| E-1 | 1.29 | 132.4 | 18.19 | 46.87 |
| E-2 | 2.18 | 237.3 | | 45.25 |
| E-3 | 2.24 | 275.8 | 14.67 | 47.13 |
| E-4 | 2.14 | 133.4 | 27.34 | 75.29 |
| E-5 | 2.15 | 78.8 | 27.46 | 49.43 |
| E-6 | 0.35 | 123.8 | | 24.89 |
| E-7 | 0.94 | 189.1 | 16.41 | 131.1 |
| E-8 | 7.52 | 1325 | | 84.01 |
| E-9 | 0.4 | 199.4 | 9.76 | 13.03 |
| E-10 | 2.49 | 49.06 | | 48.69 |
| E-11 | 0.94 | 124.8 | | 79.82 |
| E-12 | 3.42 | 65 | | 89.94 |
| E-13 | 3.79 | 154.1 | | 85.29 |
| E-14 | 1.02 | 352.7 | 16.58 | 58.69 |
| E-15 | 8.89 | 108.2 | | 64.15 |
| E-16 | 20.91 | 333.2 | | 124.9 |
| E-17 | 3.4 | 135.9 | | 96.53 |
| E-18 | 5.41 | 228.2 | | 42.04 |
| E-19 | 8.74 | 90.45 | 30.32 | 30.31 |
| E-20 | 4.5 | 100.6 | | 55.29 |
| E-21 | 6.99 | 374.3 | | 77.58 |
| E-22 | 56.51 | 509.7 | | 224.9 |
| E-23 | 2.5 | 63.59 | | 42.97 |
| E-24 | 6.2 | 93.52 | | 57.8 |
| E-25 | 5.9 | 76.79 | | 57.33 |
| E-26 | 32.11 | 497.6 | | 338.1 |
| E-27 | 1.99 | 58.28 | | 148.9 |
| E-28 | 3.94 | 65.6 | | 229.1 |
| E-29 | 3.14 | 65.05 | | 69.6 |
| E-30 | 42.96 | 420.1 | | 186.1 |
| E-31 | 29.7 | 432.9 | | 243.6 |
| E-32 | 19.76 | 176.5 | | 231.5 |
| E-33 | 18.68 | 467.3 | | 202.3 |
| E-34 | 7.85 | 163.5 | | 174 |
| E-35 | 16.87 | 67.44 | | 134.5 |
| E-36 | 22.18 | 405.2 | | 254.8 |
| E-37 | 9.65 | 208.8 | | 117.2 |
| E-38 | 2.8 | 52.89 | | 137.2 |
| E-39 | 4.57 | 65.32 | | 75.62 |
| E-40 | 40.09 | 513.8 | | 373 |
| E-41 | 6.99 | 66 | | 77.98 |
| E-42 | 29.33 | 658 | | 247.8 |
| E-43 | 4.52 | 501.7 | | 206.6 |
| E-44 | 11.35 | 232.2 | | 199.7 |
| E-45 | 10.2 | 96.86 | | 448 |
| E-46 | 11.86 | 104.2 | | 186.1 |
| E-47 | 12.48 | 146.4 | | 192.2 |
| E-48 | 6.34 | 100.3 | | 159.6 |
| E-49 | 6.64 | 74.54 | | 1063 |
| E-50 | 8.86 | 156.9 | | 148.6 |
| E-51 | 88.48 | 205.4 | | |
| E-52 | 75.07 | 578.1 | | |
| E-53 | 51.12 | 460.3 | | 794.7 |
| E-54 | 7.24 | 165 | | 514.6 |
| E-55 | 61.95 | 148.4 | | |
| E-56 | 33.76 | 357 | | 451.6 |
| E-57 | 20.94 | 279.5 | | 201.5 |
| E-58 | 50.49 | 253.2 | | 449.6 |
| E-59 | 33.19 | 294.4 | | 481 |
| E-60 | 6.43 | 69.38 | | 124.3 |
| E-61 | 4.84 | 102.7 | | 243.5 |
| E-62 | 19.5 | 246.1 | | 268.7 |
| E-63 | 32.4 | 342.9 | | 352.9 |
| E-64 | 21.85 | 118.4 | | 225.6 |
| E-65 | 15.76 | 88 | | 444.4 |
| E-66 | 53.75 | 661.6 | | 715.5 |
| E-67 | 15.89 | 3052 | | 3296 |
| E-68 | 6.82 | 411.5 | | 151 |
| E-69 | 4.95 | 415.3 | | 531.5 |
| E-70 | 1.18 | 136.6 | 28.55 | 74.86 |
| E-71 | 1.09 | 99.86 | | 35.36 |
| E-72 | 0.46 | 66.47 | | 102.1 |
| E-73 | 0.8 | 88.29 | | 242.9 |
| E-74 | 0.27 | 53.88 | | 102 |
| E-75 | 12.36 | 274.8 | | 299.4 |

TABLE 7-continued

Biological Data for Examples E-1-E-349

| Nr. | IC$_{50}$ mTOR [nM] | IC$_{50}$ PI3K [nM] | EC$_{50}$ BT474 [nM] | EC$_{50}$ U87MG [nM] |
|---|---|---|---|---|
| E-76 | 1.78 | 232.8 | | 100.2 |
| E-77 | 2.87 | 129.2 | | 115.6 |
| E-78 | 3.38 | 232 | | 167.2 |
| E-79 | 1.37 | 49.97 | | 77.94 |
| E-80 | 2.64 | 48.19 | | 112.8 |
| E-81 | 0.36 | 39.47 | | 34.32 |
| E-82 | 3.59 | 81.71 | | 107.8 |
| E-83 | 6 | 465.5 | | 64.41 |
| E-84 | 3.8 | 113.4 | | 68.43 |
| E-85 | 4.4 | 56.4 | | 280.3 |
| E-86 | 1.52 | 147 | | 90.18 |
| E-87 | 3.64 | 78.85 | | 146.9 |
| E-88 | 1.57 | 84.39 | | 47.65 |
| E-89 | 4.84 | 307 | | 222 |
| E-90 | 2.69 | 52.47 | | 164.9 |
| E-91 | 3.43 | 178.6 | | 132.4 |
| E-92 | 2.79 | 59.45 | | 122.6 |
| E-93 | 1.82 | 106.9 | | 152 |
| E-94 | 2.42 | 145.6 | | 119.3 |
| E-95 | 12.84 | 173.1 | | 267.4 |
| E-96 | 10.41 | 199.8 | | 124.8 |
| E-97 | 14.54 | 366.8 | | 289.8 |
| E-98 | 1.41 | 160.2 | | 121.1 |
| E-99 | 11.05 | 190.5 | | 270.3 |
| E-101 | 1.78 | 114.6 | | 81.85 |
| E-102 | 7.8 | 289.2 | | 108.8 |
| E-103 | 11.54 | 232.1 | | 209.8 |
| E-104 | 3.23 | 71.94 | | 104.3 |
| E-105 | 2.87 | 51.68 | | 144.6 |
| E-106 | 0.92 | 36.82 | | 44.26 |
| E-107 | 2.48 | 62.89 | | 117 |
| E-108 | 2.68 | 71.52 | | 143.1 |
| E-109 | 9.66 | 259 | | 82.8 |
| E-110 | 3.5 | 82.31 | | 140.6 |
| E-111 | 5.98 | 31.84 | | 266.8 |
| E-112 | 15.32 | 248.6 | | 336.2 |
| E-113 | 4.51 | 413.5 | | 356.4 |
| E-114 | 1.23 | 90.69 | | 47.43 |
| E-115 | 1.83 | 153.6 | | 152.9 |
| E-116 | 6.82 | 110 | | 18.58 |
| E-117 | 11.03 | 73.48 | | 26.69 |
| E-118 | 5.09 | 67.85 | | 30.89 |
| E-119 | 10.94 | 281.1 | | 44.96 |
| E-120 | 73.02 | 349.3 | | |
| E-121 | 3.43 | 63.89 | | 53.62 |
| E-122 | 5.86 | 62.81 | | 55.69 |
| E-123 | 6.62 | 46.61 | | 114.5 |
| E-124 | 8.91 | 53.3 | | 141 |
| E-125 | 28.7 | 160.8 | | 101.2 |
| E-126 | 24.16 | 194.7 | | 88.96 |
| E-127 | 11.91 | 158.3 | | 67.76 |
| E-128 | 13.88 | 37.16 | | 55.15 |
| E-129 | 27.44 | 237.1 | | 86.45 |
| E-130 | 14.3 | 69.07 | | 33.32 |
| E-131 | 17.09 | 158.3 | | 82.7 |
| E-132 | 9.55 | 45.55 | | 69.67 |
| E-133 | 6.85 | 77.85 | | 43.11 |
| E-134 | 4.16 | 44.88 | | 34.75 |
| E-135 | 16.74 | 149.1 | | 59.12 |
| E-139 | 3.15 | 160.2 | | 74.2 |
| E-140 | 0.99 | 198.5 | 13.72 | 39.16 |
| E-141 | 1.69 | 259.8 | | 33.14 |
| E-142 | 1.5 | 107.4 | 16.14 | 18.79 |
| E-143 | 1.15 | 126.7 | 22.39 | |
| E-144 | 2.98 | 169.2 | 17.58 | |
| E-145 | 5.45 | 358.3 | 48.31 | |
| E-146 | 0.73 | 45.78 | 11.91 | |
| E-147 | 0.54 | 55.7 | 13.79 | |
| E-148 | 1.36 | 70.64 | 33.5 | |
| E-149 | 0.89 | 85.79 | 32.81 | |
| E-150 | 1.75 | 120.1 | 20.22 | |
| E-152 | 0.88 | 67.85 | 17.75 | |
| E-153 | 0.89 | 212.7 | 14.25 | |
| E-154 | 0.7 | 30.2 | 18.68 | |
| E-155 | 0.71 | 15.47 | 23.72 | |
| E-156 | 0.51 | 18.28 | 12.09 | |
| E-157 | 0.59 | 37.51 | 18.28 | |
| E-158 | 2.22 | 122.3 | 22.58 | |
| E-159 | 0.53 | 25.82 | 19.68 | |
| E-160 | 1.88 | 114.7 | 114 | |
| E-161 | 13.63 | 924.7 | 236.6 | |
| E-162 | 10.4 | 539.9 | 208.4 | |
| E-163 | 1.71 | 50.82 | | |
| E-164 | 2.22 | 154.2 | 22.17 | |
| E-165 | 1.47 | 178.3 | 18.59 | |
| E-166 | 2.49 | 153.8 | 28.84 | |
| E-167 | 21.06 | 156.8 | | |
| E-168 | 66.44 | 373.2 | | |
| E-169 | 6.8 | 69.98 | | |
| E-170 | 1.56 | 96.52 | 25.69 | |
| E-171 | 23.12 | 358.1 | | |
| E-172 | 2.11 | 268.3 | 32.11 | |
| E-173 | 8.6 | 163.9 | 39.71 | |
| E-174 | 18.75 | 164.7 | 141.5 | |
| E-175 | 17.16 | 163.3 | 575.9 | |
| E-176 | 39.16 | 490.6 | | |
| E-177 | 4.63 | 337.4 | 57.04 | |
| E-178 | 5.19 | 335 | 47.1 | |
| E-179 | 3.11 | 275.9 | 28.72 | |
| E-180 | 5.43 | 357.4 | 67.05 | |
| E-181 | 8.83 | 275.3 | 93.82 | |
| E-182 | 2.44 | 246.7 | 54.51 | |
| E-183 | 4.7 | 308.1 | 104.2 | |
| E-184 | 2.81 | 399.4 | 39.78 | |
| E-185 | 3.43 | 201.5 | 25.91 | |
| E-186 | 0.68 | 325.3 | 22.36 | |
| E-187 | 1.93 | 161.5 | 29.84 | |
| E-188 | 4.69 | 355.6 | 77.53 | |
| E-189 | 1.6 | 186.4 | 44.78 | |
| E-190 | 19.97 | 175.4 | 82.41 | |
| E-191 | 5.16 | 141.5 | 45.04 | |
| E-192 | 2.86 | 333.7 | 52.68 | |
| E-193 | 276.6 | 183.8 | | |
| E-194 | 0.87 | 129.3 | 25.06 | |
| E-195 | 1.99 | 20.33 | | |
| E-196 | 5.28 | 234.7 | 45.59 | |
| E-197 | 3.78 | 122.8 | 16.37 | |
| E-198 | 1.4 | 90.89 | 9.84 | |
| E-199 | 1.34 | 74.6 | 9.81 | |
| E-200 | 1.11 | 58.79 | 9.82 | |
| E-201 | 1.62 | 98.1 | 9.77 | |
| E-202 | 2.27 | 85.82 | 14.19 | |
| E-203 | 3.29 | 95.16 | 14.93 | |
| E-204 | 3.92 | 138.2 | 54.62 | |
| E-205 | 0.59 | 48.89 | 20.15 | |
| E-206 | 1.38 | 71.77 | 12.14 | |
| E-207 | 2.51 | 581.2 | 58.69 | |
| E-208 | 2.87 | 175.6 | 40.36 | |
| E-209 | 5.71 | 545.6 | 80.73 | |
| E-210 | 2.84 | 388.1 | 59.39 | |
| E-211 | 3.58 | 472.3 | 96.74 | |
| E-212 | 2.3 | 645 | 72.36 | |
| E-213 | 1.51 | 465.1 | 55.13 | |
| E-214 | 3.49 | 599.9 | 84.08 | |
| E-215 | 1.96 | 423.3 | 48 | |
| E-216 | 2.14 | 465.9 | 38.33 | |
| E-217 | 7.56 | 326.6 | 47.96 | |
| E-218 | 4.69 | 361.8 | 57.39 | |
| E-219 | 3.2 | 163 | 37.33 | |
| E-220 | 4.33 | 292.6 | 33.86 | |
| E-221 | 2.21 | 212.8 | 33.7 | |
| E-222 | 21.17 | 530.1 | | |
| E-223 | 9.33 | 157 | 66.44 | |
| E-224 | 55.47 | 401.8 | | |
| E-225 | 14.07 | 223.7 | | |
| E-226 | 14.41 | 195.6 | | |
| E-227 | 13.28 | 267.2 | | |
| E-228 | 27.93 | 356.5 | | |
| E-229 | 8.85 | 173.8 | 48.64 | |
| E-230 | 2.72 | 278.9 | 45.26 | |

TABLE 7-continued

Biological Data for Examples E-1-E-349

| Nr. | IC$_{50}$ mTOR [nM] | IC$_{50}$ PI3K [nM] | EC$_{50}$ BT474 [nM] | EC$_{50}$ U87MG [nM] |
|---|---|---|---|---|
| E-231 | 13.62 | 184.7 | | |
| E-232 | 11.52 | 142.4 | | |
| E-233 | 1 | 89.79 | 23.04 | |
| E-234 | 0.67 | 263.2 | 21.66 | |
| E-235 | 1.24 | 178.2 | 19.16 | |
| E-236 | 0.64 | 141.3 | 18.75 | |
| E-237 | 0.96 | 120.7 | 20.61 | |
| E-238 | 0.07 | 174.6 | 19.07 | |
| E-239 | 0.26 | 46.18 | 15.16 | |
| E-240 | 0.29 | 115.4 | 16.84 | |
| E-241 | 0.25 | 91.52 | 16.6 | |
| E-242 | 0.2 | 120.1 | 18.37 | |
| E-243 | 0.73 | 109.7 | 29.82 | |
| E-245 | 0.47 | 288.2 | 21.05 | |
| E-246 | 1.13 | 81.31 | 61.41 | |
| E-247 | 0.8 | 95.37 | 19.59 | |
| E-248 | 1.18 | 50.79 | 56.1 | |
| E-249 | 1.75 | 60.47 | 22.83 | |
| E-250 | 4.36 | 92.16 | 37.88 | |
| E-251 | 7.99 | 90.72 | 588.1 | |
| E-252 | 0.57 | 48.24 | 15.22 | |
| E-253 | 1.47 | 30.6 | 64.56 | |
| E-254 | 0.97 | 31.55 | 16.6 | |
| E-255 | 0.46 | 4.83 | 43.05 | |
| E-256 | 0.67 | 22.96 | 27.94 | |
| E-257 | 2.7 | 58.26 | 43.95 | |
| E-258 | 1.55 | 110.2 | 13.1 | |
| E-259 | 1.61 | 209.2 | 13.93 | |
| E-260 | 0.81 | 63.84 | 22.95 | |
| E-261 | 1.46 | 44.34 | 11.44 | |
| E-262 | 1.63 | 133.7 | 18.79 | |
| E-263 | 2.09 | 204.4 | 22.85 | |
| E-264 | 1.39 | 61.64 | 32.3 | |
| E-265 | 1.64 | 205.6 | 24.34 | |
| E-266 | 11.46 | 560.2 | 273.2 | |
| E-267 | 9.26 | 420.9 | 168.9 | |
| E-268 | 10.44 | 242.1 | 437.7 | |
| E-269 | 15.21 | 251.8 | 59.7 | |
| E-270 | 13.23 | 328.4 | 213 | |
| E-271 | 2.75 | 113.1 | 10.3 | |
| E-272 | 24.53 | 475.3 | 107 | |
| E-273 | 4.24 | 119.3 | 14.14 | |
| E-274 | 39.77 | 444.9 | | |
| E-275 | 3.07 | 140.8 | 15.5 | |
| E-280 | 16.96 | 153.4 | 36.65 | |
| E-281 | 144.8 | 679 | | |
| E-282 | 3.83 | 173.4 | 8.61 | |
| E-283 | 40.26 | 446.5 | | |
| E-284 | 8.45 | 180.8 | 77.83 | |
| E-285 | 13.91 | 646.9 | 12.42 | |
| E-286 | 6.76 | 526.7 | 29.35 | |
| E-287 | 9.81 | 288.4 | 523 | |
| E-288 | 3.8 | 342.9 | 115.5 | |
| E-289 | 5.54 | 297.9 | 71.42 | |
| E-290 | 1.51 | 200.4 | 14.86 | |
| E-291 | 2.7 | 219.8 | 18.17 | |
| E-292 | 1.26 | 212 | 20.26 | |
| E-293 | 1.53 | 168.1 | 31.3 | |
| E-294 | 0.68 | 137.2 | 11.15 | |
| E-295 | 1.09 | 109.4 | 15.1 | |
| E-296 | 1.56 | 121.5 | 18.51 | |
| E-297 | 0.21 | 208.16 | | |
| E-298 | 0.56 | 187 | | |
| E-299 | 0.58 | 159.65 | | |
| E-300 | 0.49 | 783.3 | | |
| E-301 | 0.28 | 106.03 | | |
| E-302 | 1.66 | 112.89 | | |
| E-303 | 2.11 | 144.41 | | |
| E-304 | 1.26 | 108.17 | | |
| E-305 | 0.68 | 110.06 | | |
| E-306 | 1.01 | 108.46 | | |
| E-307 | 0.45 | 192.99 | | |
| E-308 | 0.32 | 63.43 | | |
| E-309 | 0.56 | 239.33 | | |
| E-310 | 0.76 | 86.05 | | |
| E-311 | 0.52 | 69.07 | | |
| E-312 | 0.39 | 110.31 | | |
| E-313 | 0.92 | 121.81 | | |
| E-314 | 1.68 | 76.12 | | |
| E-315 | 1.5 | 126.66 | | |
| E-316 | 1.29 | 57.12 | | |
| E-317 | 2.23 | 92.8 | | |
| E-318 | 1.28 | 107.46 | | |
| E-319 | 9.74 | 359.57 | | |
| E-320 | 5.95 | 1301.49 | | |
| E-321 | 8.92 | 412.25 | | |
| E-322 | 6.48 | 390.88 | | |
| E-323 | 9.67 | 841.74 | | |
| E-324 | 13.61 | 935.07 | | |
| E-325 | 67.77 | 1175.43 | | |
| E-326 | 11.42 | 367.08 | | |
| E-327 | 7.08 | 1356.31 | | |
| E-328 | 25.52 | 585.88 | | |
| E-329 | 4.43 | 237.84 | | |
| E-330 | 32.58 | 600.97 | | |
| E-331 | 5 | 150.52 | | |
| E-332 | 26.53 | 655.45 | | |
| E-333 | 9.74 | 599.13 | | |
| E-334 | 6.07 | 966 | | |
| E-335 | 10.6 | 2212.26 | | |
| E-336 | 5.21 | 773.45 | | |
| E-337 | 10.07 | 862.37 | | |
| E-338 | 4.85 | 634.33 | | |
| E-339 | 7.04 | 330.81 | | |
| E-340 | 5.86 | 364.04 | | |
| E-341 | 4.36 | 281.99 | | |
| E-342 | 0.66 | 137.31 | | |
| E-343 | 5.62 | 148.58 | | |
| E-344 | 2.84 | 149.4 | | |
| E-345 | 1.15 | 109.07 | | |
| E-346 | 0.45 | 167.33 | | |
| E-347 | 3.42 | 205.14 | | |
| E-348 | 5.46 | 143.82 | | |
| E-349 | 1.03 | 175.45 | | |

Analytical Method 1

HPLC: Agilent 1100 Series

MS: Agilent LC/MSD SL column: Phenomenex, Mercury Gemini C18, 3 µm, 2.0×20 mm,

Part. No. 00M-4439-B0-CE solvent A: 5 mM $NH_4HCO_3$/20 mM $NH_3$

B: acetonitrile HPLC grade detection: MS: Positive and negative mass rang: 120-700 m/z fragmentor: 70 gain EMV: 1 threshold: 0.25

UV: 315 nm bandwidth: 170 nm reference: off range: 210-400 nm range step: 2.00 nm peakwidth: <0.01 min slit: 2 nm injection: 5 µL flow: 1.00 mL/min column temperature: 40° C.

gradient: 0.00 min 5% B
   0.00-2.50 min 5%→95% B
   2.50-2.80 min 95 B
   2.81-3.10 min 95%→5% B
Analytical Method 2
Instrument: Agilent 1100-SL: incl. ELSD/DAD/MSD
Chromatography:
   Column: Phenomenex Gemini® C18, 50×2.0 mm, 3μ
Method "Acid"
   Eluent A: 0.1% formic acid in acetonitrile
   Eluent B: 0.1% formic acid in Water
   Linear Gradient program: $t_0=2\%$ A, $t_{3.5min}=98\%$ A, $t_{6min}=98\%$ A
   Flow: 1 mL/min
   Column oven temperature: 35° C.
Method "Base"
   Eluent A: 10 mM ammonia in acetonitrile
   Eluent B: 10 mM ammonia in water
   Linear Gradient program: $t_0=2\%$ A, $t_{3.5min}=98\%$ A, $t_{6min}=98\%$ A
   Flow: 1 mL/min
   Column oven temperature: 35° C.
Evaporative Light Scattering Detector (ELSD):
   Instrument: Polymer Laboratories PL-ELS 2100
   Nebuliser gas flow: 1.1 L/min $N_2$
   Nebuliser temp: 50° C.
   Evaporation temp: 80° C.
   Lamp: Blue LED 480 nm
Diode Array Detector (DAD):
   Instrument: Agilent G1316A
   Sample wavelength: 220-320 nm
   Reference wavelength: Off
Mass Spectroscopy (MSD):
   Instrument: Agilent LC/MSD-SL
   Ionisation: ESI (Positive & Negative)
   Mass range: 100-800

The Examples that follow describe the biological activity of the compounds according to the invention without restricting the invention to these Examples. All the $EC_{50}$ and $IC_{50}$ values listed herein are indicated in nM (nanomoles).

mTOR Kinase Activity Assay (Phosphorylation Status of mTOR Substrate 4E-BP1; TR-FRET)

mTOR assay described herein provides IC50 values indicating the activity of the compounds inhibiting mTOR activity Inhibition of mTOR is expected to be indicative of activity in treating conditions of excessive or anomalous cell proliferation such as cancer.

Assay Principle:

The mTOR kinase TR-FRET assay utilizes a physiologically relevant protein substrate for mTOR (4E-BP1, labeled with an acceptor fluorophore (Green Fluorescent Protein) and paired with a corresponding Tb-labeled phospho-specific antibody. The assay itself can be divided into two phases: the reaction phase and the detection phase.

In the reaction phase, all components required for the kinase reaction are added to the well, including the labeled protein substrate. The reaction is allowed to incubate for 60 minutes. After the reaction, EDTA is added to stop the kinase reaction, and terbium-labeled antibody is added to bind phosphorylated product. Because the terbium chelate is stable at the EDTA concentrations used to stop a kinase assay, the antibody and EDTA can be pre-mixed prior to addition to minimize pipetting steps. Binding of the terbium labeled antibody to the fluorophore-labeled phosphorylated product brings the terbium and GFP into proximity, resulting in an increase in TR-FRET. In the presence of an inhibitor, formation of phosphorylated product is reduced, and the TR-FRET value is decreased.

| Abbreviations used | | | |
|---|---|---|---|
| ACN | acetonitrile | min | minute(s) |
| bu | butyl | mL | millilitre |
| CDI | carbonyl diimidazole | MS | mass spectrometry |
| d | day(s) | N | normal |
| DC | thin layer chromatography | NIS | N-iodosuccinimide |
| DCM | dichloromethane | NMP | N-methylpyrrolindinone |
| DIPEA | diisopropylethyl amine | NMR | nuclear resonance spectroscopy |
| DME | dimethylether | NP | normal phase |
| DMF | N,N-dimethylformamide | ppm | part per million |
| DMSO | dimethylsulphoxide | $R_f$ | retention factor |
| eq. | equivalent | RP | reversed phase |
| EtOH | ethanol | prep | preparative |
| h | hour(s) | RT | room temperature |
| HPLC | high performance liquid chromatography | tert | tertiary |
| LC | liquid chromatography | $t_R$ | retention time |
| M | molar | THF | tetrahydrofuran |
| MeOH | methanol | TMS | Tetramethylsilanyl |
| Int. | Intermediate | PI3Ka | PI3Kalpha or PI3Kα |
| LDA | Lithiumdiisopropylamine | DIA | Diisopropylamine |
| PE | Petrolether | TLC | Thin layer chromatography |
| EtOAc | Ethylacetate | Pd(dppf)Cl$_2$ | [1,1-Bis(diphenylphosphino)ferrocene]dichloropalladium(II)] |
| [Ir(COD)(OMe)]$_2$ | (1,5-Cyclooctadiene)(methoxy)iridium(I) dimer | Pin2B2 | Bis(pinacolato)diboron |

Materials:
GFP-4E-BP1 substrate; Invitrogen order no. PV4759
Lanthascreen Tb-anti-p4E-BP1 (pThr46) Antibody Kit; Invitrogen order no. PV4758
FRAP1 (mTOR) kinase; Invitrogen order no. PV4753
ATP 10 mM
5× Assay Buffer (250 mM HEPES pH7.5, 0.05% Polysorbate 20, 5 mM EGTA, 50 mM MnCl2)
EDTA 500 mM Determining $IC_{50}$ Values for Test Compounds:

Kinase Reaction Conditions 400 nM GFP-4E-BP1, 8 nM ATP, 150 ng/mL mTOR, 50 mM HEPES pH 7.5, 0.01% Polysorbate 20, 1 mM EGTA, 10 mM MnCl2, and variable amounts of test compounds.

Preparation of Reagents

Note: Thaw and keep mTOR, the substrate, ATP, and the antibody on ice prior to making working dilutions. Working dilutions of these components can be kept at room temperature for short periods of time the day of use.

1. Add 2 ml of 5× Assay Buffer to 8 ml water to prepare 10 ml of 1× Assay Buffer, wherein the concentration of 1× Assay Buffer is 50 mM HEPES pH 7.5, 0.01% Polysorbate 20, 1 mM EGTA, and 10 mM MnCl2.
2. Prepare Antibody/EDTA Solution by first adding 2.75 µl of Tb-anti p4E-BP1 Antibody to 2397 µl of LanthaScreen™ TR-FRET Dilution Buffer. Then, add 100 µl of 0.5 M EDTA.
3. Prepare 4× Substrate/Enzyme Solution by first adding 72 µl of GFP-4E-BP1 (22 nM) to 926 µl of 1× Assay Buffer. Then, add 1.6 µl of mTOR (0.45 mg/mL).
4. Prepare ATP Solution by adding 3.2 µl of 10 mM ATP to 1997 µl of 1× Assay Buffer.

Serial Dilution of Inhibitors (16 Point Curve)

Inhibitors are serially diluted in DMSO, then diluted to a 4× working concentration with 1× Assay Buffer.

1. Dispense 40 µl of DMSO to two adjacent columns of a 96 well plate per compound (e.g. columns 1 and 2).
2. Add 10 µl of inhibitor stock (10 mM) to the first well of the first column (A1) and mix.
3. Remove 10 µl from A1 and transfer to the adjacent well in the next column (B1) and mix.
4. Remove 10 µl from B1 and transfer to the next well in the first column (B2) and mix.
5. Repeat this dilution pattern through well H1 and leave the last well (H2) as DMSO only.
6. Remove 4 µl of diluted compounds and add to 96 µl of 1× Assay Buffer in a 96-well plate making 4× compound dilutions.

Kinase Reaction

1. Add 2.5 µl of 4× compound dilutions to a 384-well plate.
2. Add 2.5 µl of 4× Enzyme/Substrate Solution.
4. Preincubate for 30 mM at RT (shaker).
5. Add 5 µl of ATP Solution to all wells to start reactions.
6. Shake the assay plate on a plate shaker for 30 seconds.
7. Incubate the assay plate for one hour at room temperature (20-25° C.).

Stop Step and Fluorescence Detection

1. Add 10 µl of Antibody/EDTA Solution to each well in columns 1-9.
2. Shake the assay plate on a plate shaker for 30 seconds.
3. Incubate the assay plate for one hour at room temperature (20-25° C.).
4. Measure the GFP (FRET) and terbium (reference) emission signals on a fluorescence plate reader (e.g. Perkin Elmer Envision).

Data Analysis

1. Calculate the emission ratio for each sample by dividing the GFP (FRET) signal by the terbium (reference) signal.
2. Plot the concentration of each compound versus the emission ratio. Determine the concentration of compound required to reach 50% of the maximum signal ($IC_{50}$). Determination of $IC_{50}$ values can be obtained by curve fitting (sigmoidal dose response, variable slope) using Prism software from GraphPad).

Inhibition of PI3Kalpha-induced PIP-2 phosphorylation

PI3Kalpha assay described herein provides $IC_{50}$ values indicating the activity of the compounds inhibiting PI3 kinase alpha activity Inhibition of PI3 kinase is expected to be indicative of activity in treating conditions of excessive or anomalous cell proliferation, such as cancers. See also J. A. Engelman, Nature Reviews Cancer, 2009, 9, 550-562; A. Carnero, Expert Opin. Investig. Drugs, 2009, 18, 1265-1277 and P. Liu et al., Nature Reviews Drug Discovery, 2009, 8, 627-64.

Method Type: Filter-Binding-Assay

1. Materials

Assay buffer: 40 mM HEPES pH 7.5 SIGMA H-3375
100 mM NaCl Merck 1.064.041.000
1 mM EGTA SIGMA E-4378
1 mM β-Glycerophosphate SIGMA G-6253
7 mM MgC12 Merck 58.331.000
1 mM DTT SIGMA D-0632
(0.1% BSA only during preparation of Lipidmix after ultrasonication)

Phospholipid blend mix (=substrate) from Avanti Polar Lipids (#790770):
Phosphatidylinositol-4,5-biphosphate (#840046) 3,665%
Phosphatidylethanolamine (#83022) 39,26%
Phosphatidylserine (#830032) 36,66%
Sphingomyeline (#860062) 3,665%
Phosphatidylcholine (#830053) 16,75%

Per aliquot lipid (16.6 mg): 26 ml assay buffer+520 µl BSA (5%)

PI3 Kinase alpha is expressed in SF9 insect cells, coinfected with viruses encoding p85alpha and His-p110alpha, purified by combined Ni-affinity and anion exchange chromatography). Aliquoted in desired amounts and stored at −80° C. Final assay concentration 25 ng/well Phosphotyrosin PDGFRbeta-peptide H-CGG-pY-MDMSKDESVD-pY-VP-MLDM-$NH_2$ was synthesized by Jerini Peptide Technologies (JPT) and used in a final conc. of 1.7 µM (stock 100 µM prepared in Assay buffer with DTT, aliquoted in desired amounts and stored at −80° C.)

Cold ATP (from Sigma; A-7699), 100 µM stock solution in H2O, use 1 µM final concentration in assay

[33P]-ATP, 370 MBq/ml from Amersham (#AH9968), use 0.5 µCi/well (10mCi/ml)

Clear 96-well plates from Greiner (#655 162)
Filter plates: Perkin Elmer UniFilter GF/B #6005177
Microscint 0 (from Perkin Elmer, #6013611)

2. Assay Procedure

The substrate-containing lipid vesicles are dissolved to a concentration of 0.637 mg lipid blend/ml assay buffer (with BSA, freshly added) in 50 ml Falcon→keep on ice, followed by ultrasonication (pulse of 15 sec followed by a pause of 10 sec, 4×). Compounds are serially diluted in assay buffer+6% DMSO and 10 µl of each dilution is added per well of a 96-well plate (compounds are tested in duplicates) and mixed with 30 µl of the lipid vesicles containing PDGFR-Peptide (0.5 µM final) and PI3K alpha (25 ng/well final). The mixture is then incubated for 20 minutes at room temperature. Subsequently, 20 µl of assay buffer containing 3 µM cold ATP and 0.5 µCi/20 µl 33P-ATP are added. The plates are then incubated at room temperature for 120 minutes (shaking with 300 rpm). The reaction mix is transferred onto filter plates using "filtermate harvester" from Packard: filter plates are rinsed with PBS, then the reaction mix is filtered onto the filter plate, washed 5 times with PBS and are allowed to dry for 30-60 minutes at 50° C.

The plate bottom is sealed with Perkin Elmer white adhesive foil and 25 µl/well Microscint0 are added, the top is covered with transparent adhesive foil and the plate is measured with Wallac Trilux 1450 Microbeta Counter.

As positive control serve wells containing vehicle controls (1% DMSO in assay buffer), showing non-inhibited kinase activity (high values). Wells containing assay buffer instead of enzyme can serve as control for background activity (low values).

3. Evaluation

Calculate $IC_{50}$ values using the Smiley program (based on GrapPad Prism)

PC3 Proliferation Test

The test is based on measurement of cellular DNA content via fluorescent dye binding. Because cellular DNA content is highly regulated, it is closely proportional to cell number. The extent of proliferation is determined by comparing cell counts for samples treated with drugs with untreated controls.

PC3 (human prostate carcinoma cell line) cells are sown in microtitre plates and incubated overnight in culture medium at 37° C. and 5% $CO_2$. The test substances are diluted stepwise and added to the cells such that the total volume is 200 µL/well. Cells to which diluent, but not substance, is added serve as controls. After an incubation time of 3 days, the medium is replaced by 100 µL/well dye-binding solution and the cells are incubated at 37° C. in the dark for a further 60 min. For measuring the fluorescence, excitation takes place at a wavelength of 485 nm and the emission is measured at 530 nm $EC_{50}$ values are calculated using the GraphPad Prism program.

AlamarBlue Assay in AN3 CA Cells

The alamarBlue cell assay provides $EC_{50}$ values indicative of the antiproliferative or cytotoxic effects of the compounds on the AN3 CA human endometrial cancer cell line.

1. Description alamarBlue® is designed to provide a rapid and sensitive measure of cell proliferation and cytotoxicity in various human and animal cell lines. The assay is based on the reduction of alamarBlue in the reducing environment of living (metabolically active) cells. In the presence of added cytotoxic or antiproliferative compounds, the innate metabolic activity ceases.

AlamarBlue is soluble and stable in culture medium. Measurements are made fluorometrically by exciting at 530-560 nm and measuring emission at 590 nm. In reporting percent alamarBlue reduction by monitoring fluorescence, data are expressed as fluorescence emission intensity units as a function of time of incubation.

2. Cells and Reagents

| | |
|---|---|
| AN3 CA cells | Human endometrial cancer cells (ATCC HTB-111) |
| alamarBlue | Serotec Ltd |
| PBS (w/o Ca, Mg) | Life Technologies, Gibco BRL (Cat. No. 4190-094) |
| DMEM Medium | Lonza (Cat. No. BE-12-604F) |
| Fetal calf serum | Life Technologies, Gibco BRL (Cat. No. 10270-106) |

3. Equipment 96-well plates, flat bottom (Falcon, Cat. No.: 353072)
96-well plates, U-shaped (Costar, Cat. No.: 3799)
$CO_2$-Incubator
Microplate Reader, Spectramax Plus, Molecular Devices 4. Typical Procedure Day 0: Seed 3000 AN3 CA cells (DMEM/10% FCS) in 180 µl medium into a 96-well plate, flat bottom (include medium blank). Incubate plates at 37° C. in a $CO_2$ incubator overnight.

Day 1: Dilute compounds to a concentration 100 µM→1:5, 10 dilution steps, in 96-well plates.
Add 20 µl per well of each dilution to cells (total volume per well 200 µl; final conc. of cpds: 10 µM→1:5; 0.5% DMSO final). If required, test further dilutions.
All concentrations are tested in duplicates.
Controls: Cells w/o cpd. (+20 µl medium/DMSO).
Cells are incubated with compounds for 3 days.

Day 4: Add 25 µl of alamarBlue solution to each well and incubate for 5-8 hours at 37° C. Measure fluorescence by exciting at 530-560 nm and measuring emission at 590 nm 5. Evaluation Calculate $EC_{50}$ using GraphPad Prism (Fifty).

alamarBlue® assay can be used to measure the inhibition of mTOR as well as PI3Kalpha in vitro.

CyQuant Assay in U87MG Cells

The CyQuant assay provides $EC_{50}$ values indicative of the antiproliferative or cytotoxic effects of the compounds on the U87MG human glioblastoma cell line.

1. Description

The test is based on measurement of cellular DNA content via fluorescent dye binding. Because cellular DNA content is highly regulated, it is closely proportional to cell number. The extent of proliferation is determined by comparing cell counts for samples treated with drugs with untreated controls. In the assay, a DNA-binding dye in combination with a plasma membrane permeabilization reagent is used. The medium is aspirated, replaced with dye binding solution, cells are incubated for 30-60 min, then fluorescence is measured (excitation at 485 nm, emission detection at 530 nm). Data are expressed as fluorescence emission intensity units as a function of time of incubation.

2. Cells and Reagents

| | |
|---|---|
| U-87MG cells | Human glioblastoma cells (ATCC HTB-14) |
| CyQuant NF assay | Invitrogen Cat.# C35006 |
| PBS (w/o Ca, Mg) | Life Technologies, Gibco BRL (Cat. No. 4190-094) |
| RPMI1640 Medium | Life Technologies, Gibco BRL (Cat. No. 61870-010) |
| Fetal calf serum | Life Technologies, Gibco BRL (Cat. No. 10270-106) |

3. Equipment 96-well plates, flat bottom (Falcon, Cat. No.: 353072)
96-well plates, U-shaped (Costar, Cat. No.: 3799)
$CO_2$-Incubator
Microplate Reader, Wallac Victor 4. Typical Procedure Day 0: Seed 3000 U-87MG cells (cultured in RPMI/10% FCS) in 150 lA medium into a 96-well plate, flat bottom (include mediumblank). Incubate plates at 37° C. in a $CO_2$ incubator overnight.

Day 1: Dilute compounds to a concentration 80 µM→1:5 in medium, 7 dilution steps, in 96-well plates.
Add 50 µl per well of each dilution (total volume per well 200 µl; final conc. of cpds: 20 µM→1:5). If required, test further dilutions.
All concentrations are tested in duplicates or triplicates.
Controls: Cells w/o cpd. (+50 µl medium+DMSO).
Cells are incubated with compounds for 3 days.

Day 4: Aspirate off medium and replace with 100 µl of 1× dye binding solution (22 µl CyQuant NF dye reagent added to 11 ml of 1×HBSS buffer). Cover the microplate and incubate for 30-60 min for equilibration of dye-DNA binding. Measure the fluorescence intensity in a microplate reader (excitation at 485 nm, emission detection at 530 nm).

5. Evaluation

Calculate $EC_{50}$ using GraphPad Prism (Fifty)

The substances of the present invention are PI3 kinase pathway inhibitors, in particular of the serine/threonine kinase mTOR and/or members of the lipid kinase family Pi3K. On account of their biological properties, the novel compounds of the general formula (1) and their isomers and their physiologically tolerated salts are suitable for treating diseases which are characterized by excessive or anomalous cell proliferation.

These diseases include, for example: viral infections (e.g. HIV and Kaposi's sarcoma); inflammation and autoimmune diseases (e.g. colitis, arthritis, Alzheimer's disease, glomerulonephritis and wound healing); bacterial, fungal and/or parasitic infections; leukaemias, lymphomas and solid tumours; skin diseases (e.g. psoriasis); bone diseases; cardiovascular diseases (e.g. restenosis and hypertrophy). In addition, the compounds are useful for protecting proliferating cells (e.g. hair cells, intestinal cells, blood cells and progenitor cells) from DNA damage due to irradiation, UV treatment and/or cytostatic treatment (Davis et al., 2001).

For example, the following cancer diseases can be treated with compounds according to the invention, without, however, being restricted thereto: brain tumours, such as acoustic neurinoma, astrocytomas such as piloid astrocytomas, fibrillary astrocytoma, protoplasmic astrocytoma, gemistocytic astrocytoma, anaplastic astrocytoma and glioblastomas, brain lymphomas, brain metastases, hypophyseal tumour such as prolactinoma, HGH (human growth hormone) producing tumour and ACTH-producing tumour (adrenocorticotrophic hormone), craniopharyngiomas, medulloblastomas, meningiomas and oligodendrogliomas; nerve tumours (neoplasms) such as tumours of the vegetative nervous system such as neuroblastoma sympathicum, ganglioneuroma, paraganglioma (phaeochromocytoma and chromaffinoma) and glomus caroticum tumour, tumours in the peripheral nervous system such as amputation neuroma, neurofibroma, neurinoma (neurilemoma, schwannoma) and malignant schwannoma, as well as tumours in the central nervous system such as brain and spinal cord tumours; intestinal cancer such as rectal carcinoma, colon carcinoma, anal carcinoma, small intestine tumours and duodenal tumours; eyelid tumours such as basalioma or basal cell carcinoma; pancreatic gland cancer or pancreatic carcinoma; bladder cancer or bladder carcinoma; lung cancer (bronchial carcinoma) such as small-cell bronchial carcinomas (oat cell carcinomas) and non-small-cell bronchial carcinomas such as squamous epithelium carcinomas, adenocarcinomas and large-cell bronchial carcinomas; breast cancer such as mammary carcinoma, such as infiltrating ductal carcinoma, colloid carcinoma, lobular invasive carcinoma, tubular carcinoma, adenoid cystic carcinoma, and papillary carcinoma; non-Hodgkin's lymphomas (NHL) such as Burkitt's lymphoma, low-malignancy non-Hodgkin's lymphomas (NHL) and mucosis fungoides; uterine cancer or endometrial carcinoma or corpus carcinoma; CUP syndrome (cancer of unknown primary); ovarian cancer or ovarian carcinoma such as mucinous, endometrial or serous cancer; gall bladder cancer; bile duct cancer such as Klatskin's tumour; testicular cancer such as seminomas and non-seminomas; lymphoma (lymphosarcoma) such as malignant lymphoma, Hodgkin's disease, non-Hodgkin's lymphomas (NHL) such as chronic lymphatic leukaemia, hair cell leukaemia, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as vocal cord tumours, supraglottal, glottal and subglottal laryngeal tumours; bone cancer such as osteochondroma, chondroma, chrondoblastoma, chondromyxoidfibroma, osteoma, osteoid-osteoma, osteoblastoma, eosinophilic granuloma, giant cell tumour, chondrosarcoma, osteosarcoma, Ewing's sarcoma, reticulosarcoma, plasmocytoma, fibrous dysplasia, juvenile bone cyst and aneurysmatic bone cyst; head/neck tumours such as tumours of the lips, tongue, floor of the mouth, oral cavity, gingiva, pallet, salivary glands, pharynx, nasal cavities, paranasal sinuses, larynx and middle ear; liver cancer such as liver cell carcinoma or hepatocellular carcinoma (HCC); leukaemias, such as acute leukaemias, such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or stomach carcinoma such as papillary, tubular and mucinous adenocarcinoma, signet ring cell carcinoma, adenoid squamous cell carcinoma, small-cell carcinoma and undifferentiated carcinoma; melanomas such as superficially spreading, nodular malignant lentigo and acral lentiginous melanoma; renal cancer, such as kidney cell carcinoma or hypernephroma or Grawitz's tumour; oesophageal cancer or oesophageal carcinoma; cancer of the penis; prostate cancer; pharyngeal cancer or pharyngeal carcinomas such as nasopharyngeal carcinomas, oropharyngeal carcinomas and hypopharyngeal carcinomas; retinoblastoma; vaginal cancer or vaginal carcinoma; squamous epithelium carcinomas, adeno carcinomas, in situ carcinomas, malignant melanomas and sarcomas; thyroid gland carcinomas such as papillary, follicular and medullary thyroid gland carcinoma, and also anaplastic carcinomas; spinalioma, prickle cell carcinoma and squamous epithelium carcinoma of the skin; thymomas, urethral cancer and vulvar cancer.

The novel compounds can be used for the prevention or short-term or long-term treatment of the abovementioned diseases including, where appropriate, in combination with other state-of-the-art compounds such as other anti-tumour substances, cytotoxic substances, cell proliferation inhibitors, antiangiogenic substances, steroids or antibodies.

The compounds of the general formula (1) can be used on their own or in combination with other active compounds according to the invention and, where appropriate, in combination with other pharmacologically active compounds as well. Chemotherapeutic agents which can be administered in combination with the compounds according to the invention include, without being restricted thereto, hormones, hormone analogs and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone and octreotide), aromatase inhibitors (e.g. anastrozole, letrozole, liarozole, vorozole, exemestane and atamestane), LHRH agonists and antagonists (e.g. goserelin acetate and luprolide), inhibitors of growth factors (growth factors such as platelet-derived growth factor and hepatocyte growth factor, examples of inhibitors are growth factor antibodies, growth factor receptor antibodies and tyrosine kinase inhibitors, such as gefitinib, imatinib, lapatinib, Erbitux® and trastuzumab); antimetabolites (e.g. antifolates such as methotrexate and raltitrexed, pyrimidine analogs such as 5-fluorouracil, capecitabine and gemcitabine, purine and adenosine analogs such as mercaptopurine, thioguanine, cladribine and pentostatin, cytarabine and fludarabine); antitumour antibiotics (e.g. anthracyclines, such as doxorubicin, daunorubicin, epirubicin and idarubicin, mitomycin C, bleomycin, dactinomycin, plicamycin and streptozocin); platinum derivatives (e.g. cisplatin, oxaliplatin and carboplatin); alkylating agents (e.g. estramustine, meclorethamine, melphalan, chlorambucil, busulphan, dacarbazine, cyclophosphamide, ifosfamide and temozolomide, nitrosoureas such as carmustine and lomustine and thiotepa); antimitotic agents (e.g. vinca alkaloids such as vinblastine, vindesine, vinorelbine and vincristine; and taxans such as paclitaxel and docetaxel); topoisomerase inhibitors (e.g. epipodophyllotoxins such as etoposide and etopophos, teniposide, amsacrine, topotecan, irinotecan and mitoxantrone) and various chemotherapeutic agents such as amifostin, anagrelide, clodronate, filgrastin, interferon alpha, leucovorin, rituximab, procarbazine, levamisole, mesna, mitotan, pamidronate and porfimer.

Examples of suitable forms for use are tablets, capsules, suppositories, solutions, in particular solutions for injection (s.c., i.v., i.m.) and infusion, syrups, emulsions or dispersible powders. In this connection, the proportion of the pharmaceutically active compound(s) should in each case be in the range of 0.1-90% by weight, preferably 0.5-50% by weight, of the total composition, that is in quantities which are sufficient to achieve the dosage range which is specified below. If necessary, the doses mentioned can be given several times a day.

Appropriate tablets can be obtained, for example, by mixing the active compound(s) with known auxiliary substances, for example inert diluents, such as calcium carbonate, calcium phosphate or lactose, disintegrants, such as maize starch or alginic acid, binders, such as starch or gelatine, lubricants, such as magnesium stearate or talc, and/or agents for achieving a depot effect, such as carboxymethyl cellulose, cellulose acetate phthalate or polyvinyl acetate. The tablets can also comprise several layers.

Correspondingly, sugar-coated tablets can be produced by coating cores, which have been prepared in analogy with tablets, with agents which are customarily used in sugar coatings, for example collidone or shellac, gum arabic, talc, titanium dioxide or sugar. The core can also comprise several layers in order to achieve a depot effect or to avoid incompatibilities. In the same way, the sugar coating can also comprise several layers in order to achieve a depot effect, with it being possible to use the auxiliary substances which are mentioned above in the case of the tablets.

Syrups of the active compounds or active compound combinations according to the invention can additionally comprise a sweetening agent, such as saccharine, cyclamate, glycerol or sugar as well as a taste-improving agent, e.g. flavouring agents such as vanillin or orange extract. They can also comprise suspension aids or thickeners, such as sodium carboxymethyl cellulose, wetting agents, for example condensation products of fatty alcohols and ethylene oxide, or protectants such as p-hydroxybenzoates.

Injection and infusion solutions are produced in a customary manner, e.g. while adding isotonizing agents, preservatives, such as p-hydroxybenzoates, or stabilizers, such as alkali to metal salts of ethylenediaminetetraacetic acid, where appropriate using emulsifiers and/or dispersants, with it being possible, for example, to employ, where appropriate, organic solvents as solubilizing agents or auxiliary solvents when using water as diluent, and aliquoted into injection bottles or ampoules or infusion bottles.

The capsules, which comprise one or more active compounds or active compound combinations, can, for example, be produced by mixing the active compounds with inert carriers, such as lactose or sorbitol, and encapsulating the mixture in gelatine capsules. Suitable suppositories can be produced, for example, by mixing with excipients which are envisaged for this purpose, such as neutral fats or polyethylene glycol, or their derivatives.

Auxiliary substances which may be mentioned by way of example are water, pharmaceutically unobjectionable organic solvents, such as paraffins (e.g. petroleum fractions), oils of vegetable origin (e.g. groundnut oil or sesame oil), monofunctional or polyfunctional alcohols (e.g. EtOH or glycerol), carrier substances such as natural mineral powders (e.g. kaolins, argillaceous earths, talc and chalk), synthetic mineral powders (e.g. highly disperse silicic acid and silicates), sugars (e.g. cane sugar, lactose and grape sugar), emulsifiers (e.g. lignin, sulphite waste liquors, methyl cellulose, starch and polyvinylpyrrolidone) and glidants (e.g. magnesium stearate, talc, stearic acid and sodium lauryl sulphate).

Administration is effected in a customary manner, preferably orally or transdermally, in particular and preferably orally. In the case of oral use, the tablets can naturally also comprise, in addition to the abovementioned carrier substances, additives such as sodium citrate, calcium carbonate and dicalcium phosphate together with a variety of further substances such as starch, preferably potato starch, gelatine and the like. It is furthermore also possible to use glidants, such as magnesium stearate, sodium lauryl sulphate and talc, for the tableting. In the case of aqueous suspensions, a variety of taste improvers or dyes can also be added to the active compounds in addition to the abovementioned auxiliary substances.

For parenteral administration, it is possible to employ solutions of the active compounds to while using suitable liquid carrier materials. The dosage for intravenous administration is 1-1000 mg per hour, preferably between 5 and 500 mg per hour.

Despite this, it may be necessary, where appropriate, to diverge from the above-mentioned quantities, depending on the body weight or the nature of the route of administration, on the individual response to the medicament, on the nature of its formulation and on the time or interval at which the administration is effected. Thus, it may, in some cases, be sufficient to make do with less than the previously mentioned lowest quantity whereas, in other cases, the abovementioned upper limit has to be exceeded. When relatively large quantities are being administered, it may be advisable to divide these into several single doses which are given over the course of the day.

The following formulation examples illustrate the present invention without, however, restricting its scope:

Pharmaceutical Formulation Examples

| A) Tablets | per tablet |
|---|---|
| Active compound in accordance with formula (1) | 100 mg |
| Lactose | 140 mg |
| Maize starch | 240 mg |
| Polyvinylpyrrolidone | 15 mg |
| Magnesium stearate | 5 mg |
| | 500 mg |

The finely ground active compound, lactose and a part of the maize starch are mixed with each other. The mixture is sieved, after which it is moistened with a solution of polyvinylpyrrolidone in water, kneaded, wet-granulated and dried.

The granular material, the remainder of the maize starch and the magnesium stearate are sieved and mixed with each other. The mixture is pressed into tablets of suitable shape and size.

| B) Tablets | per tablet |
| --- | --- |
| Active compound in accordance with formula (1) | 80 mg |
| Lactose | 55 mg |
| Maize starch | 190 mg |
| Microcrystalline cellulose | 35 mg |
| Polyvinylpyrrolidone | 15 mg |
| Sodium carboxymethyl starch | 23 mg |
| Magnesium stearate | 2 mg |
| | 400 mg |

The finely ground active compound, a part of the maize starch, the lactose, microcrystalline cellulose and polyvinylpyrrolidone are mixed with each other, after which the mixture is sieved and worked, together with the remainder of the maize starch and water, into a granular material, which is dried and sieved. The sodium carboxymethyl starch and the magnesium stearate are then added to the granular material and mixed with it, and the mixture is pressed into tablets of suitable size.

| C) Ampoule solution | |
| --- | --- |
| Active compound in accordance with formula (1) | 50 mg |
| Sodium chloride | 50 mg |
| Water for injection | 5 mL |

The active compound is dissolved, either at its intrinsic pH or, where appropriate, at pH 5.5-6.5, in water after which sodium chloride is added as isotonizing agent. The resulting solution is rendered pyrogen-free by filtration and the filtrate is aliquoted, under aseptic conditions, into ampoules, which are then sterilized and sealed by melting. The ampoules contain 5 mg, 25 mg and 50 mg of active compound.

The invention claimed is:

1. A method of treating a disease, wherein the disease is cancer selected from a group consisting of prostrate, breast and ovarian cancer, comprising administering an effective amount of a compound of formula 1 or a pharmaceutically acceptable salt thereof, to a patient in need thereof, wherein:

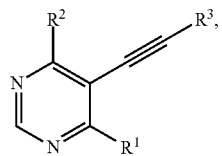

(1)

$R^3$ denotes a group selected from among 3-8 membered heterocycloalkyl, $C_{6-10}$aryl and 5-12 membered heteroaryl, optionally substituted by one or more identical or different $R^4$; and $R^1$ denotes a group selected from among $C_{6-10}$aryl and 5-12 membered heteroaryl, optionally substituted by one or more identical or different $R^5$ and $R^2$ denotes a group selected from among hydrogen, $C_{1-4}$alkyl, $C_{3-8}$cycloalkyl, 3-8 membered heteroalkyl, 3-8 membered heterocycloalkyl, —OR$^v$, —SR$^v$, —CF$_3$, —CN, —NC and —NO$_2$, and each $R^4$ denotes a group selected from among $R^a$ and $R^b$; and each $R^a$ independently of one another denotes hydrogen or a group selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, $R^a$ optionally being substituted by one or more identical or different $R^b$ and/or $R^{c4}$, each $R^b$ denotes a suitable group and is selected independently of one another from among =O, —OR$^c$, $C_{1-3}$haloalkyloxy, —OCF$_3$, —OCHF$_2$, =S, —SR$^c$, =NR$^c$, =NOR$^c$, =NNR$^c$R$^{c1}$, =NN(R$^g$)C(O)NR$^c$R$^{c1}$, —NR$^c$R$^{c1}$, —ONR$^c$R$^{c1}$, —N(OR$^c$)R$^{c1}$, —N(R$^g$)NR$^c$R$^{c1}$, halogen, —CF$_3$, —CN, —NC, —OCN, —SCN, —NO, —NO$_2$, =N$_2$, —N$_3$, —S(O)R$^c$, —S(O)OR$^c$, —S(O)$_2$R$^c$, —S(O)$_2$OR$^c$, —S(O)NR$^c$R$^{c1}$, —S(O)$_2$NR$^c$R$^{c1}$, —OS(O)R$^c$, —OS(O)$_2$R$^c$, —OS(O)$_2$OR$^c$, —OS(O)NR$^c$R$^{c1}$, —OS(O)$_2$NR$^c$R$^{c1}$, —C(O)R$^c$, —C(O)OR$^c$, —C(O)SR$^c$, —C(O)NR$^c$R$^{c1}$, —C(O)N(R$^g$)NR$^c$R$^{c1}$, —C(O)N(R$^g$)OR$^c$, —C(NR$^g$)NR$^c$R$^{c1}$, —C(NOH)R$^c$, —C(NOH)NR$^c$R$^{c1}$, —OC(O)R$^c$, —OC(O)OR$^c$, —OC(O)SR$^c$, —OC(O)NR$^c$R$^{c1}$, —OC(NR$^g$)NR$^c$R$^{c1}$, —SC(O)R$^c$, —SC(O)OR$^c$, —SC(O)NR$^c$R$^{c1}$, —SC(NR$^g$)NR$^c$R$^{c1}$, —N(R$^g$)C(O)R$^c$, —N[C(O)R$^c$][C(O)R$^{c1}$], —N(OR$^g$)C(O)R$^c$, —N(R$^g$)C(NR$^{g1}$)R$^c$, —N(R$^g$)N(R$^{g1}$)C(O)R$^c$, —N[C(O)R$^{c2}$]NR$^c$R$^{c1}$, —N(R$^g$)C(S)R$^c$, —N(R$^g$)S(O)R$^c$, —N(R$^g$)S(O)OR$^c$, —N(R$^g$)S(O)$_2$R$^c$, —N[S(O)$_2$R$^c$][S(O)$_2$R$^{c1}$], —N(R$^g$)S(O)$_2$OR$^c$, —N(R$^g$)S(O)$_2$NR$^c$R$^{c1}$, —N(R$^g$)[S(O)$_2$]$_2$R$^c$, —N(R$^g$)C(O)OR$^c$, —N(R$^g$)C(O)SR$^c$, —N(R$^g$)C(O)NR$^c$R$^{c1}$, —N(R$^g$)C(O)NR$^{g1}$NR$^c$R$^{c1}$, —N(R$^g$)N(R$^{g1}$)C(O)NR$^c$R$^{c1}$, —N(R$^g$)C(S)NR$^c$R$^{c1}$, —[N(R$^g$)C(O)]$_2$R$^c$, —N(R$^g$)[C(O)]$_2$R$^c$, —N{[C(O)]$_2$R$^c$}{[C(O)]$_2$R$^{c1}$}, —N(R$^g$)[C(O)]$_2$OR$^c$, —N(R$^g$)[C(O)]$_2$NR$^c$R$^{c1}$, —N{[C(O)]$_2$OR$^c$}{[C(O)]$_2$OR$^{c1}$}, —N{[C(O)]$_2$NR$^c$R$^{c1}$}{[C(O)]$_2$NR$^{c2}$R$^{c3}$}, —[N(R$^g$)C(O)]$_2$OR$^c$, —N(R$^g$)C(NR$^{g1}$)OR$^c$, —N(R$^g$)C(NOH)R$^c$, —N(R$^g$)C(NR$^{g1}$)SR$^c$, —N(R$^g$)C(NR$^{g1}$)NR$^c$R$^{c1}$, —N(R$^g$)C(=N—CN)NR$^c$R$^{c1}$ and —N=C(R$^g$)NR$^c$R$^{c1}$ and each $R^c$, $R^d$, $R^{c2}$, $R^{c3}$ and $R^{c4}$ independently of one another denotes hydrogen or a group selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered hetero-aryl, 6-18 membered heteroarylalkyl, 3-14 membered heterocycloalkyl and 4-14 membered heterocycloalkylalkyl, $R^c$, $R^{c1}$, $R^{c2}$, $R^{c3}$ and $R^{c4}$ independently optionally being substituted by one or more identical or different $R^d$ and/or $R^{e4}$, where $R^c$ together with $R^g$ and/or $R^{c1}$ and/or $R^{c2}$ and/or $R^{c3}$ or $R^{c2}$ together with $R^{c3}$ may form a 3-8 membered heterocyclalkyl residue via a shared C-, N- O- or S-atom, and each $R^d$ denotes a suitable group and is selected independently of one another from among =O, —OR$^e$, $C_{1-3}$haloalkyloxy, —OCF$_3$, —OCHF2, =S, —SR$^e$, =NR$^e$, =NOR$^e$, =NNR$^e$R$^{e1}$, =NN(R$^{g2}$)C(O)NR$^e$R$^{e1}$, —NR$^e$R$^{e1}$, —ONR$^e$R$^{e1}$, —N(R$^{g2}$)NR$^e$R$^{e1}$, halogen, —CF$_3$, —CN, —NC, —OCN, —SCN, —NO, —NO$_2$, =N$_2$, —N$_3$, —S(O)R$^e$, —S(O)OR$^e$, —S(O)$_2$R$^e$, —S(O)$_2$OR$^e$, —S(O)NR$^e$R$^{e1}$, —S(O)$_2$NR$^e$R$^{e1}$, —OS(O)R$^e$, —OS(O)$_2$R$^e$, —OS(O)$_2$OR$^e$, —OS(O)NR$^e$R$^{e1}$, —OS(O)$_2$NR$^e$R$^{e1}$, —C(O)R$^e$, —C(O)OR$^e$, —C(O)SR$^e$, —C(O)NR$^e$R$^{e1}$, —C(O)N(R$^{g2}$)NR$^e$R$^{e1}$, —C(O)N(R$^{g2}$)OR$^e$, —C(NR$^{g2}$)NR$^e$R$^{e1}$, —C(NOH)R$^e$, —C(NOH)NR$^e$R$^{e1}$, —OC(O)R$^e$, —OC(O)OR$^e$, —OC (O)SR$^e$, —OC(O)NR$^e$R$^{e1}$, —OC(NR$^{g2}$)NR$^e$R$^{e1}$, —SC(O)R$^e$, —SC(O)OR$^e$, —SC(O)NR$^e$R$^{e1}$, —SC(NR$^{g2}$)NR$^e$R$^{e1}$, —N(R$^{g2}$)C(O)R$^e$, —N[C(O)R$^e$][C(O)R$^{e1}$], —N(OR$^{g2}$)C(O)R$^e$, —N(R$^{g2}$)C(NR$^{g3}$)R$^e$, —N(R$^{g2}$)N(R$^{g3}$)C(O)R$^e$, —N[C(O)R$^{e2}$]NR$^e$R$^{e1}$, —N(R$^{g2}$)C(S)R$^e$, —N(R$^{g2}$)S(O)R$^e$, —N(R$^{g2}$)S(O)OR$^e$—N(R$^{g2}$)S(O)$_2$R$^e$, —N[S(O)$_2$R$^e$][S(O)$_2$R$^{e1}$], —N(R$^{g2}$)S(O)$_2$OR$^e$, —N(R$^{g2}$)S(O)$_2$NR$^e$R$^{e1}$, —N(R$^{g2}$)[S(O)$_2$]$_2$R$^e$, —N(R$^{g2}$)C(O)OR$^e$, —N(R$^{g2}$)C(O)SR$^e$, —N(R$^{g2}$)C(O)NR$^e$R$^{e1}$, —N(R$^{g2}$)C(O)NR$^{g3}$NR$^e$R$^{e1}$, —N(R$^{g2}$)N(R$^{g3}$)C(O)NR$^e$R$^{e1}$, —N(R$^{g2}$)C(S)NR$^e$R$^{e1}$, —[N(R$^{g2}$)C(O)][N(R$^{g3}$)C(O)]R$^e$, —N(R$^{g2}$)[C(O)]$_2$R$^e$, —N{[C(O)]$_2$R$^e$}{[C(O)]$_2$R$^{e1}$}, —N(R$^{g2}$)[C(O)]$_2$OR$^e$, —N(R$^{g2}$)[C(O)]$_2$NR$^e$R$^{e1}$, —N{[C(O)]$_2$OR$^e$}{[C(O)]$_2$OR$^e$}, —N{[C(O)]$_2$NR$^e$R$^{e1}$}{[C(O)]$_2$NR$^{e2}$R$^{e3}$}, —[N(R$^{g3}$)C(O)][N(R$^{g3}$)C(O)]OR$^e$, —N(R$^{g2}$)C(NR$^{g3}$)OR$^e$, —N(R$^{g2}$)C(NOH)R$^e$, —N(R$^{g2}$)C(NR$^{g3}$)SR$^e$, —N(R$^{g2}$)C(NR$^{g3}$)NR$^e$R$^{e1}$, —N(R$^{g2}$)C(=N—CN)NR$^e$R$^{e1}$ and —N=C(R$^{g2}$)NR$^e$R$^{e1}$ each R$^e$, R$^{e1}$, R$^{e2}$, R$^{e3}$ and R$^{e4}$ independently of one another denotes hydrogen or a group selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered hetero-aryl, 6-18 membered heteroarylalkyl, 3-14 membered heterocycloalkyl and 4-14 membered heterocycloalkylalkyl, where R$^e$ together with R$^{g2}$ and/or R$^{e1}$ and/or R$^{e2}$ and/or R$^{e3}$ or R$^{e2}$ together with R$^{e3}$ may form a 3-8 membered heterocyclalkyl residue via a shared C-, N-, O- or S-atom, and where R$^e$, R$^{e1}$, R$^{e2}$, R$^{e3}$ and R$^{e4}$ independently optionally being substituted by one or more identical or different R$^f$ and/or R$^{g6}$, and each R$^f$ denotes a suitable group and in each case is selected independently of one another from among =O, —OR$^g$, C$_{1-3}$haloalkyloxy, —OCF$_3$, —OCHF$_2$, =S, —SR$^g$, =NR$^{g4}$, =NOR$^{g4}$, =NNR$^{g4}$R$^{g5}$, =NN(R$^h$)C(O)NR$^{g4}$R$^{g5}$, —NR$^{g4}$R$^{g5}$, —ONR$^{g4}$R$^{g5}$, —N(R$^h$)NR$^{g4}$R$^{g5}$, halogen, —CF$_3$, —CN, —NC, —OCN, —SCN, —NO, —NO$_2$, =N$_2$, —N$_3$, —S(O)R$^{g4}$, —S(O)OR$^{g4}$, —S(O)$_2$R$^{g4}$, —S(O)$_2$OR$^{g4}$, —S(O)NR$^{g4}$R$^{g5}$, —S(O)$_2$NR$^{g4}$R$^{g5}$, —OS(O)R$^{g4}$, —OS(O)$_2$R$^{g4}$, —OS(O)$_2$OR$^{g4}$, —OS(O)NR$^{g4}$R$^{g5}$, —OS(O)$_2$NR$^{g4}$R$^{g5}$, —C(O)R$^{g4}$, —C(O)OR$^{g4}$, —C(O)SR$^{g4}$, —C(O)NR$^{g4}$R$^{g5}$, —C(O)N(R$^h$)NR$^{g4}$R$^{g5}$, —C(O)N(R$^h$)OR$^{g4}$, —C(NR$^h$)NR$^{g4}$R$^{g5}$, —C(NOH)R$^{g4}$, —C(NOH)NR$^{g4}$R$^{g5}$, —OC(O)R$^{g4}$, —OC(O)OR$^{g4}$, —OC(O)SR$^{g4}$, —OC(O)NR$^{4g}$R$^{g5}$, —OC(NR$^h$)NR$^{g4}$R$^{g5}$, —SC(O)R$^{g4}$, —SC(O)OR$^{g4}$, —SC(O)NR$^{g4}$R$^{g5}$, —SC(NR$^h$)NR$^{g4}$R$^{g5}$, —N(R$^h$)C(O)R$^{g4}$, —N[C(O)R$^{g4}$]$_2$, —N(OR$^h$)C(O)R$^{g4}$, —N(R$^h$)C(NR$^{h1}$)R$^{g4}$, —N(R$^h$)N(R$^{h1}$)C(O)R$^{g4}$, —N[C(O)R$^{g6}$]NR$^{g4}$R$^{g5}$, —N(R$^h$)C(S)R$^{g4}$, —N(R$^h$)S(O)R$^{g4}$, —N(R$^h$)S(O)OR$^{g4}$, —N(R$^h$)S(O)$_2$R$^{g4}$, —N[S(O)$_2$R$^{g4}$][S(O)$_2$R$^{g5}$], —N(R$^h$)S(O)$_2$OR$^{g4}$, —N(R$^h$)S(O)$_2$NR$^{g4}$R$^{g5}$, —N(R$^h$)[S(O)$_2$]$_2$R$^{g4}$, —N(R$^h$)C(O)OR$^{g4}$, —N(R$^h$)C(O)SR$^{g4}$, —N(R$^h$)C(O)NR$^{g4}$R$^{g5}$, —N(R$^h$)C(O)NR$^{h1}$NR$^{g4}$R$^{g5}$, —N(R$^h$)N(R$^{h1}$)C(O)NR$^{g4}$R$^{g5}$, —N(R$^h$)C(S)NR$^{g4}$R$^{g5}$, —[N(R$^h$)C(O)][N(R$^{h1}$)C(O)]R$^{g4}$, —N(R$^h$)[C(O)]$_2$R$^{g4}$, —N{[C(O)]$_2$R$^{g4}$}{[C(O)]$_2$R$^{g5}$}, —N(R$^h$)[C(O)]$_2$OR$^{g4}$, —N(R$^h$)[C(O)]$_2$NR$^{g4}$R$^{g5}$, —N{[C(O)]$_2$OR$^{g4}$}{[C(O)]$_2$OR$^{g4}$}, —N{[C(O)]$_2$NR$^{g4}$R$^{g5}$}{[C(O)]$_2$NR$^{g4}$R$^{g5}$}, —[N(R$^h$)C(O)][N(R$^{h1}$)C(O)]OR$^{g4}$, —N(R$^h$)C(NR$^{h1}$)OR$^{g4}$, —N(R$^h$)C(NOH)R$^{g4}$, —N(R$^h$)C(NR$^{h1}$)SR$^{g4}$, —N(R$^h$)C(NR$^{h1}$)NR$^{g4}$R$^{g5}$, —N(R$^h$)C(=N—CN)NR$^{g4}$R$^{g5}$ and —N=C(R$^h$)NR$^{g4}$R$^{g5}$; and each R$^g$, R$^{g1}$, R$^{g2}$, R$^{g3}$, R$^{g4}$, R$^{g5}$ and R$^{g6}$ independently of one another denotes hydrogen or a group selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered hetero-aryl, 6-18 membered heteroarylalkyl, 3-14 membered heterocycloalkyl and 4-14 membered heterocycloalkylalkyl, where R$^g$ together with R$^{g1}$ and/or R$^h$ may form a 3-8 membered cycloalkyl or a 3-8 membered heterocyclalkyl residue via a shared C-, N- O- or S-atom, and where R$^g$, R$^{g1}$, R$^{g2}$, R$^{g3}$, R$^{g4}$, R$^{g5}$ and R$^{g6}$ independently optionally being substituted by one or more identical or different R$^{h2}$; and each R$^h$, R$^{h1}$ and R$^{h2}$ is selected independently of one another from among hydrogen, C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl, where R$^h$ together with R$^{h1}$ may form a 3-8 membered cycloalkyl or a 3-8 membered heterocyclalkyl residue via a shared C-, N- O- or S-atom, and each R$^5$ denotes a group selected from among R$^m$ and R$^n$; and each R$^m$ independently of one another denotes hydrogen or a group selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl, and R$^m$ optionally substituted by one or more identical or different R$^n$ and/or R$^{o4}$, each R$^n$ denotes a suitable group and is selected independently of one another from among =O, —OR$^o$, C$_{1-3}$haloalkyloxy, —OCF$_3$, —OCHF$_2$, =S, —SR$^o$, =NR$^o$, =NOR$^o$, =NNR$^o$R$^{o1}$, =NN(R$^s$)C(O)NR$^o$R$^{o1}$, —NR$^o$R$^{o1}$, —ONR$^o$R$^{o1}$, —N(OR$^o$R$^{o1}$), —N(Rs)NR$^o$R$^{o1}$, halogen, —CF$_3$, —CN, —NC, —OCN, —SCN, —NO, —NO$_2$, =N$_2$, —N$_3$, —S(O)R$^o$, —S(O)OR$^o$, —S(O)$_2$R$^o$, —S(O)$_2$OR$^o$, —S(O)NR$^o$R$^{o1}$, —S(O)$_2$NR$^o$R$^{o1}$, —OS(O)R$^o$, —OS(O)$_2$R$^o$, —OS(O)$_2$OR$^o$, —OS(O)NR$^o$R$^{o1}$, —OS(O)$_2$NR$^o$R$^{o1}$, —C(O)R$^o$, —C(O)OR$^o$, —C(O)SR$^o$, —C(O)NR$^o$R$^{o1}$, —C(O)N(R$^s$)NR$^o$R$^{o1}$, —C(O)N(R$^s$)OR$^o$, —C(NR$^s$)NR$^o$R$^{o1}$, —C(NOH)R$^o$, —C(NOH)NR$^o$R$^{o1}$, —OC(O)R$^o$, —OC(O)OR$^o$, —OC(O)SR$^o$, —OC(O)NR$^o$R$^{o1}$, —OC(NR$^s$)NR$^o$R$^{o1}$, —SC(O)R$^o$, —SC(O)OR$^o$, —SC(O)NR$^o$R$^{o1}$, —SC(NR$^s$)NR$^o$R$^{o1}$, —N(R$^s$)C(O)R$^o$, —N[C(O)R$^o$][C(O)R$^{o1}$], —N(OR$^s$)C(O)R$^o$, —N(R$^s$)C(NR$^{s1}$) R$^o$, —N(R$^s$)N(R$^{s1}$)C(O)R$^o$, —N[C(O)R$^{o2}$]NR$^o$R$^{o1}$, —N(R$^s$)C(S)R$^o$, —N(R$^s$)S(O)R$^o$, —N(R$^s$)S(O)OR$^o$, —N(R$^s$)S(O)$_2$R$^o$, —N[S(O)$_2$R$^o$][S(O)$_2$R$^{o1}$], —N(R$^s$)S(O)$_2$OR$^o$, —N(R$^s$)S(O)$_2$NR$^o$R$^{o1}$, —N(R$^s$)[S(O)$_2$]$_2$R$^o$, —N(R$^s$)C(O)OR$^o$, —N(R$^s$)C(O)SR$^o$, —N(R$^s$)C(O)NR$^o$R$^{o1}$, —N(R$^s$)C(O)NR$^{s1}$NR$^o$R$^{o1}$, —N(R$^s$)N(R$^{s1}$)C(O)NR$^o$R$^{o1}$, —N(R$^s$)C(S)NR$^o$R$^{o1}$, —[N(R$^s$)C(O)]$_2$R$^o$, —N(R$^s$)C(O)]$_2$R$^o$, —N{[C(O)]$_2$R$^o$}{[C(O)]$_2$R$^{o1}$}, —N(R$^s$)[C(O)]$_2$OR$^o$, —N(R$^s$)[C(O)]$_2$NR$^o$R$^{o1}$, —N{[C(O)]$_2$OR$^o$}{[C(O)]$_2$OR$^{o1}$}, —N{[C(O)]$_2$NR$^o$R$^{o1}$}{[C(O)]$_2$NR$^{o2}$R$^{o3}$}, —[N(R$^s$)C(O)]$_2$OR$^o$, —N(R$^s$)C(NRs$^1$)OR$^o$, —N(R$^s$)C(NOH)R$^o$, —N(R$^s$)C(NR$^{s1}$)SR$^o$, —N(R$^s$)C(NR$^{s1}$)NR$^o$R$^{o1}$ and —N=C(R$^s$)NR$^o$R$^{o1}$ and each R$^o$, R$^{o1}$, R$^{o2}$ and R$^{o3}$ independently of one another denotes hydrogen or a group selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered hetero-aryl, 6-18 membered heteroarylalkyl, 3-14 membered heterocycloalkyl and 4-14 membered heterocycloalkylalkyl, where $R^o$ together with $R^{o1}$ and/or $R^s$ and/or $R^{c1}$ and/or $R^{c2}$ and/or $R^{c3}$ or $R^{c2}$ together with $R^{c3}$ may form a 3-8 membered mono- or bicyclic heterocyclalkyl residue via a shared C-, N- O- or S-atom, or where $R^o$ together with $R^{o1}$ may form a 3-14 membered spirocyclic heterocyclalkyl residue via a shared C-, N-, O- or S-atom and where $R^o$, $R^{o1}$, $R^{o2}$ and $R^{o3}$ independently optionally being substituted by one or more identical or different $R^p$ and/or $R^{q4}$, and each $R^p$ denotes a suitable group and is selected independently of one another from among =O, —$OR^q$, $C_{1-3}$haloalkyloxy, —$OCF_3$, —$OCHF_2$, =S, —$SR^q$, =$NR^q$, =$NOR^q$, =$NNR^qR^{q1}$, =$NN(R^s)C(O)NR^qR^{q1}$, —$NR^qR^{q1}$, —$ONR^qR^{q1}$, —$N(R^s)NR^qR^{q1}$, halogen, —$CF_3$, —CN, —NC, —OCN, —SCN, —NO, —$NO_2$, =$N_2$, —$N_3$, —$S(O)R^q$, —$S(O)OR^q$, —$S(O)_2R^q$, —$S(O)_2OR^q$, —$S(O)NR^qR^{q1}$, —$S(O)_2NR^qR^{q1}$, —$OS(O)R^q$, —$OS(O)_2R^q$, —$OS(O)_2OR^q$, —$OS(O)NR^qR^{q1}$, —$OS(O)_2NR^qR^{q1}$, —$C(O)R^q$, —$C(O)OR^q$, —$C(O)SR^q$, —$C(O)NR^qR^{q1}$, —$C(O)N(R^s)NR^qR^{q1}$, —$C(O)N(R^s)OR^q$, —$C(NR^s)NR^qR^{q1}$, —$C(NOH)R^q$, —$C(NOH)NR^qR^{q1}$, —$OC(O)R^q$, —$OC(O)OR^q$, —$OC(O)SR^q$, —$OC(O)NR^qR^{q1}$, —$OC(NR^s)NR^qR^{q1}$, —$SC(O)R^q$, —$SC(O)OR^q$, —$SC(O)NR^qR^{q1}$, —$SC(NR^s)NR^qR^{q1}$, —$N(R^s)C(O)R^q$, —$N[C(O)R^q][C(O)R^{q1}]$, —$N(OR^s)C(O)R^q$, —$N(R^s)C(R^{s1})R^q$, —$N(R^s)N(R^{s1})C(O)R^q$, —$N[C(O)R^{q2}]NR^qR^{q1}$, —$N(R^s)C(S)R^q$, —$N(R^s)S(O)R^q$, —$N(R^s)S(O)OR^q$, —$N(R^s)S(O)_2R^q$, —$N[S(O)_2R^q][S(O)_2R^{q1}]$, —$N(R^s)S(O)_2OR^q$, —$N(R^s)S(O)_2NR^qR^{q1}$, —$N(R^s)[S(O)_2]_2R^q$, —$N(R^s)C(O)OR^q$, —$N(R^s)C(O)SR^q$, —$N(R^s)C(O)NR^qR^{q1}$, —$N(R^s)C(O)NR^{s1}NR^qR^{q1}$, —$N(R^s)N(R^{s1})C(O)NR^qR^{q1}$, —$N(R^s)C(S)NR^{q1}$, —$N[R^s)C(O)][N(R^{g1})C(O)]R^q$, —$N(R^s)[C(O)]_2R^q$, —$N\{[C(O)]_2R^q\}\{[C(O)]_2R^{q1}\}$, —$N(R^s)[C(O)]_2OR^q$, —$N(R^s)[C(O)]_2NR^qR^{q1}$, —$N\{[C(O)]_2OR^q\}\{[C(O)]_2OR^{q1}\}$, —$N\{[C(O)]_2NR^qR^{q1}\}\{[C(O)]_2NR^{q2}R^{q3}\}$, —$[N(R^s)C(O)][N(R^{s1})C(O)]OR^q$, —$N(R^s)C(NR^{s1})OR^q$, —$N(R^s)C(NOH) R^q$, —$N(R^s)C(NR^{s1})SR^q$, —$N(R^s)C(NR^{s1})NR^qR^{q1}$, —$N(R^s)C(=N-CN)NR^qR^{q1}$ and —$N=C(R^s)NR^qR^{q1}$, and each $R^q$, $R^{q1}$, $R^{q2}$, $R^{q3}$ and $R^{q4}$ independently of one another denotes hydrogen or a group selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered hetero-aryl, 6-18 membered heteroarylalkyl, 3-14 membered heterocycloalkyl and 4-14 membered heterocycloalkylalkyl, where $R^q$ together with $R^{q1}$ and/or $R^{q2}$ and/or $R^{q3}$ and/or $R^s$ may form a 3-8 membered heterocyclalkyl residue via a shared C-, N- O- or S-atom, wherein $R^q$, $R^{q1}$, $R^{q2}$, $R^{q3}$ and $R^{q4}$ are optionally independently substituted by one or more identical or different $R^r$ and/or $R^{s4}$, and each $R^r$ denotes a suitable group and in each case is selected independently of one another from among =O, —$OR^s$, $C_{1-3}$haloalkyloxy, —$OCF_3$, —$OCHF_2$, =S, —$SR^s$, =$NR^s$, =$NOR^s$, =$NNR^sR^{s1}$, =$NN(R^t)C(O)NR^sR^{s1}$, —$NR^sR^{s1}$, —$ONR^sR^{s1}$, —$N(R^h)NR^sR^{s1}$, halogen, —$CF_3$, —CN, —NC, —OCN, —SCN, —NO, —$NO_2$, =$N_2$, —$N_3$, —$S(O)R^s$, —$S(O)OR^s$, —$S(O)_2R^s$, —$S(O)_2OR^s$, —$S(O)NR^sR^{s1}$, —$S(O)_2NR^sR^{s1}$, —$OS(O)R^s$, —$OS(O)_2R^s$, —$OS(O)OR^s$, —$OS(O)NR^sR^{s1}$, —$OS(O)_2NR^sR^{s1}$, —$C(O)R^s$, —$C(O)OR^s$, —$C(O)SR^s$, —$C(O)NR^sR^{s1}$, —$C(O)N(R^t)NR^sR^{s1}$, —$C(O)N(R^t)OR^s$, —$C(NR^t)NR^sR^{s1}$, —$C(NOH) R^s$, —$C(NOH)NR^sR^{s1}$, —$OC(O)R^s$, —$OC(O)OR^s$, —$OC(O)SR^s$, —$OC(O)NR^sR^{s1}$, —$OC(NR^t)NR^sR^{s1}$, —$SC(O)R^s$, —$SC(O)OR^s$, —$SC(O)NR^sR^{s1}$, —$SC(NR^t)NR^sR^{s1}$, —$N(R^t)C(O) R^s$, —$N[C(O)R^s][C(O)R^{s1}]$, —$N(OR^t)C(O)R^s$, —$N(R^t)C(NR^{t1})R^s$, —$N(R^t)N(R^{t1})C(O)R^s$, —$N[C(O)R^{g2}]NR^sR^{s1}$, —$N(R^t)C(S)R^s$, —$N(R^t)S(O)R^s$, —$N(R^t)S(O)OR^s$, —$N(R^t)S(O)_2R^s$, —$N[S(O)_2R^s][S(O)_2R^{s1}]$, —$N(R^t)S(O)_2OR^s$, —$N(R^t)S(O)_2NR^sR^{s1}$, —$N(R^t)[S(O)_2]_2R^s$, —$N(R^t)C(O)OR^s$, —$N(R^t)C(O)SR^s$, —$N(R^t)C(O)NR^sR^{s1}$, —$N(R^t)C(O)NR^{t1}NR^sR^{s1}$, —$N(R^t)N(R^{t1})C(O)NR^sR^{s1}$, —$N(R^t)C(S)NR^sR^{s1}$, —$[N(R^t)C(O)][N(R^{h1})C(O)]R^s$, —$N(R^t)[C(O)]_2R^s$, —$N\{[C(O)]_2R^s\}\{[C(O)]_2R^{s1}\}$, —$N(R^t)[C(O)]_2OR^s$, —$N(R^t)[C(O)]_2NR^sR^{s1}$, —$N\{[C(O)]_2OR^s\}\{[C(O)]_2OR^{s1}\}$, —$N\{[C(O)]_2NR^sR^{s1}\}\{[C(O)]_2NR^{s2}R^{s3}\}$, —$[N(R^t)C(O)][N(R^{t1})C(O)]OR^s$, —$N(R^t)C(NR^{t1})OR^s$, —$N(R^t)C(NOH) R^s$, —$N(R^t)C(NR^{t1})SR^s$, —$N(R^t)C(NR^{t1})NR^sR^{s1}$, —$N(R^t)C(=N-CN)NR^sR^{s1}$ and —$N=C(R^t)NR^sR^{s1}$; and each $R^s$, $R^{s1}$, $R^{s2}$, $R^{s3}$ and $R^{s4}$ independently of one another denotes hydrogen or a group selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered hetero-aryl, 6-18 membered heteroarylalkyl, 3-14 membered heterocycloalkyl and 4-14 membered heterocycloalkylalkyl, where $R^s$ together with $R^{s1}$ and/or $R^{s2}$ and/or $R^{s3}$ and/or $R^t$ may form a 3-8 membered heterocyclalkyl residue via a shared C-, N- O- or S-atom, $R^s$, $R^{s1}$, $R^{s2}$, $R^{s3}$ and $R^{s4}$ independently optionally being substituted by one or more identical or different $R^{t2}$; and each $R^t$, $R^{t1}$ and $R^{t2}$ is selected independently of one another from among hydrogen, $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, where $R^t$ together with $R^{t1}$ may form a 3-8 membered heterocyclalkyl residue via a shared C-, N-, O- or S-atom, and each $R^v$ is selected independently of one another from among hydrogen, $C_{1-6}$alkyl, 2-6 membered heteroalkyl, $C_{1-6}$haloalkyl, optionally in the form of the tautomers, the racemates, the enantiomers, the diastereomers, and optionally the pharmacologically acceptable salts thereof.

2. The method of treating cancer, comprising administering an effective amount of a compound of formula 1 of claim 1, or a pharmaceutically acceptable salt thereof and pharmaceutically acceptable excipients and/or carriers, to a patient in need thereof.

* * * * *